US012121563B2

(12) United States Patent
Mich et al.

(10) Patent No.: US 12,121,563 B2
(45) Date of Patent: Oct. 22, 2024

(54) RESCUING VOLTAGE-GATED SODIUM CHANNEL FUNCTION IN INHIBITORY NEURONS

(71) Applicants: ALLEN INSTITUTE, Seattle, WA (US); SEATTLE CHILDREN'S HOSPITAL, Seattle, WA (US)

(72) Inventors: John K. Mich, Seattle, WA (US); Edward Sebastian Lein, Mercer Island, WA (US); Jonathan Ting, Lake Forest Park, WA (US); Boaz P. Levi, Seattle, WA (US); Erik Hess, Issaquah, WA (US); Franck Kalume, Bothell, WA (US)

(73) Assignees: Allen Institute, Seattle, WA (US); Seattle Children's Hospital, Seattle, WA (US)

( * ) Notice: Subject to any disclaimer, the term of this patent is extended or adjusted under 35 U.S.C. 154(b) by 1058 days.

(21) Appl. No.: 17/044,232

(22) PCT Filed: Apr. 9, 2019

(86) PCT No.: PCT/US2019/026638

§ 371 (c)(1),
(2) Date: Sep. 30, 2020

(87) PCT Pub. No.: WO2019/199867

PCT Pub. Date: Oct. 17, 2019

(65) Prior Publication Data

US 2021/0015898 A1 Jan. 21, 2021

Related U.S. Application Data

(60) Provisional application No. 62/810,281, filed on Feb. 25, 2019, provisional application No. 62/742,835, filed on Oct. 8, 2018, provisional application No. 62/655,043, filed on Apr. 9, 2018.

(51) Int. Cl.

| | |
|---|---|
| ***A61K 38/17*** | (2006.01) |
| ***A61K 9/00*** | (2006.01) |
| ***A61K 48/00*** | (2006.01) |
| ***C07K 14/705*** | (2006.01) |
| ***C12N 15/86*** | (2006.01) |

(52) U.S. Cl.

CPC .......... *A61K 38/177* (2013.01); *A61K 9/0019* (2013.01); *A61K 48/0058* (2013.01); *C07K 14/705* (2013.01); *C12N 15/86* (2013.01); *C12N 2750/14143* (2013.01); *C12N 2830/008* (2013.01)

(58) Field of Classification Search

CPC ..................................................... C12N 15/86

See application file for complete search history.

(56) References Cited

U.S. PATENT DOCUMENTS

| | | | | |
|---|---|---|---|---|
| 7,125,676 | B2 | 10/2006 | George, Jr. et al. | |
| 7,129,343 | B2 | 10/2006 | Li et al. | |
| 9,579,399 | B2 | 2/2017 | Roska et al. | |
| 10,287,607 | B2 * | 5/2019 | Tagliatela ............ | C07K 14/705 |
| 2004/0087028 | A1 | 5/2004 | Cunningham | |
| 2005/0260576 | A1 | 11/2005 | George et al. | |
| 2009/0162332 | A1 | 6/2009 | Davidson et al. | |
| 2015/0044667 | A1 | 2/2015 | Crino | |
| 2017/0029464 | A1 | 2/2017 | Korbelin et al. | |
| 2017/0166926 | A1 | 6/2017 | Deverman et al. | |
| 2018/0078658 | A1 | 3/2018 | Fishell et al. | |
| 2021/0348195 | A1 | 11/2021 | Ting et al. | |

FOREIGN PATENT DOCUMENTS

| | | | |
|---|---|---|---|
| WO | WO2016059162 | 4/2016 | |
| WO | WO-2016161124 A1 * | 10/2016 | ......... A61K 38/1796 |
| WO | WO2016186772 | 11/2016 | |
| WO | WO2017100671 | 6/2017 | |
| WO | 2020076614 A1 | 4/2020 | |

OTHER PUBLICATIONS

Bazylinski et al.*Magnetococcus marinus* gen. nov., sp. nov., a marine, magnetotactic bacterium that represents a novel lineage ( Magnetococcaceae fam. nov., Magnetococcales ord. nov.) at the base of the Alphaproteobacteria. International J of Systematic and Evolutionary Microbiology 2013, 63;3:801-808. (Year: 2013).*

Bagneris et al. Prokaryotic NavMs channel as a structural and functional model for eukaryotic sodium channel antagonism. Proceedings of the National Academy of Sciences 2014, 111;23:8428-8433. (Year: 2014).*

Korbelin et al. A brain microvasculature endothelial cell-specific viral vector with the potential to treat neurovascular and neurological diseases. EMBO Molecular Medicine 2016, 8:609-625. (Year: 2016).*

Chan, et al., "Engineered AAVs for efficient non invasive gene delivery to the central and peripheral nervous systems", Nature Neuroscience Techinal Reports, vol. 20, No. 8, Jun. 26, 2017, pp. 1172-1179.

Extended European Search Report Dated Jan. 4, 2022 for European Application No. 19785199.1, 8 pages.

(Continued)

*Primary Examiner* — Allison M Fox
*Assistant Examiner* — Jennifer S Spence
(74) *Attorney, Agent, or Firm* — Lee & Hayes PC; C. Rachal Winger; Chrystal Quisenberry

(57) ABSTRACT

Selectively providing voltage-gated sodium channel function sufficient to rescue impaired Nav1.1 function to inhibitory neurons is described. Provided voltage-gated sodium channel function sufficient to rescue impaired Nav1.1 function in inhibitory neurons can be used to treat disorders such as epilepsy, and more particularly, Dravet Syndrome.

20 Claims, 72 Drawing Sheets

Specification includes a Sequence Listing.

(56) References Cited

OTHER PUBLICATIONS

Nathanson, "Short promoters in viral vectors drive selective expression in mammalian inhibitory neurons, but do not restrict activity to specific inhibitory cell-types", Frontiers in Neural Circuits, vol. 3, Nov. 9, 2009, pp. 1-24.
Japanese Office Action mailed Sep. 12, 2023 for Japanese Patent Application No. 2020-555346, a foreign counterpart to U.S. Appl. No. 17/044,232, 5 pages.
Choi, et al., "Optimization of AAV expression cassettes to improve packaging capacity and transgene expression on neurons", Molecular brain, vol. 7, No. 17, 2014, 10 pages.
Hawkins, et al., "Fine Mapping of a Dravet Syndrome Modifier Locus on Mouse Chromosome 5 and Candidate Gene Analysis by RNA-Seq," PLoS Genetics, vol. 12, No. 10, 2016, pp. 1-15.
Search Report and Written Opinion Dated Jul. 19, 2019, for International Application No. PCT/US2019/026638, 12 pages.
Stern, et al., "Impaired intracortical inhibition demonstrated in vivo in people with Dravet syndrome," Neurology, vol. 88, 2017, pp. 1659-1665.
Stuhmer, et al., "Expression from a Dlx gene enhancer marks adult mouse cortical GABAergic neurons," Cereb Cortex, vol. 12, No. 1, 2002, pp. 75-85.
Sula & Wallace, "Interpreting the functional role of a novel interaction motif in prokaryotic sodium channels," Journal of General Physiology, vol. 149, No. 6, 2017, pp. 613-622.
Tai, et al., "Impaired excitability of somatostatin- and parvalbumin-expressing cortical interneurons in a mouse model of Dravet syndrome," PNAS USA, vol. 111, No. 30, 2014, pp. E3139-E3148.
Ting, et al., "A robust ex vivo experimental platform for molecular-genetic dissection of adult human neocortical cell types and circuits," Scientific Reports, vol. 8, No. 1, 2018, 13 pages.
Verbeek, et al., "Seizure precipitants in Dravet syndrome: What events and activities are specifically provocative compared with other epilepsies?," Epilepsy & Behavior, vol. 47, 2015, pp. 39-44.
Weiss, et al., "Sodium channels SCN1A, SCN2A and SCN3A in familial autism," Molecular Psychiatry, vol. 8, No. 2, 2003, pp. 186-194.
Wu, et al., "Incidence of Dravet Syndrome in a US Population," Pediatrics, vol. 136, No. 5, 2015, pp. e1310-e1315.
Yang, et al., "Global CNS Transduction of Adult Mice by Intravenously Delivered rAAVrh.8 and rAAVrh. 10 and Nonhuman Primates by rAAVrh. 10," Molecular Therapy, vol. 22, No. 7, 2014, pp. 1299-1309.
Yao, et al., "Differential pattern of expression of voltage-gated sodium channel genes following ischemic brain injury in rats," Neurotoxicity Research, vol. 4, No. 1, 2002, pp. 67-75.
Yu, et al., "Reduced sodium current in GABAergic interneurons in a mouse model of severe myoclonic epilepsy in infancy," Nature Neuroscience, vol. 9, No. 9, 2006, pp. 1142-1149.
Yu, et al., "Sodium channel beta4, a new disulfide-linked auxiliary subunit with similarity to beta2," Journal of Neuroscience, vol. 23, No. 20, 2003, pp. 7577-7585.
Zerucha, et al., "A Highly Conserved Enhancer in the DIx5/DIx6Intergenic Region is the Site of Cross-Regulatory Interactions betweenDlx Genes in the Embryonic Forebrain," Journal of Neuroscience, vol. 20, No. 2, 2000, pp. 709-721.
Zufferey, et al., "Woodchuck Hepatitis Virus Posttranscriptional Regulatory Element Enhances Expression of Transgenes Delivered by Retroviral Vectors," Journal of Virology, vol. 73, No. 4, 1999, pp. 2886-2892.
"Predicted: Panthera pardus uncharacterized LOC109263725 (LOC109263725), transcript variant X2, ncRNA, Accession XR_002078354", retrieved on Jan. 27, 2020 from <<https://www.ncbi.nlm.nih.gov/nucleotide/XR_002078354.1?report=genbank&log$=nucltop&blast_rank=17 &RI D=30VXJA38016>>, Dec. 5, 2016, 2 pages.
Canadian Office Action mailed on Oct. 10, 2023 for Canadian Patent Application No. 3,115,652, a foreign counterpart to U.S. Appl. No. 17/283,232, 3 pages.
Canadian Office Action mailed on Oct. 18, 2023, for Canadian Patent Application No. 3,096,407, a foreign counterpart to U.S. Appl. No. 17/044,232, 8 pages.
Search Report and Written Opinion Dated Feb. 14, 2020 for PCT Application No. PCT/US19/54539, 13 pages.
Invitation to Pay Fees Dated Dec. 23, 2019 in International Application No. PCT/US19/54539, 2 pages.
Japanese Office Action mailed Oct. 3, 2023 for Japanese Application No. 2021-543981, a foreign counterpart to U.S. Appl. No. 17/283,232, 7 pages.
Mendell, et al., "Single-Dose Gene-Replacement Therapy for Spinal Muscular Atrophy," N. Engl. J. Med., vol. 377, No. 18, 2017, pp. 1713-1722.
Albright, et al., "Mapping the Structural Determinants Required for AAVrh.10 Transport across the Blood-Brain Barrier," Molecular Therapy, vol. 26, No. 2, 2018, pp. 510-523.
Catterall, et al., "NaV1.1 channels and epilepsy," Journal of Physiology, vol. 588, No. 11, 2010, pp. 1849-1859.
Chan, et al., "Engineered AAVs for efficient noninvasive gene delivery to the central and peripheral nervous systems," Nature Neuroscience, vol. 20, No. 8, 2017, pp. 1172-1179.
Cheah, et al., "Specific deletion of NaV1.1 sodium channels in inhibitory interneurons causes seizures and premature death in a mouse model of Dravet syndrome," PNAS USA, vol. 109, No. 36, 2012, pp. 14646-14651.
Chen, et al., "Molecular signatures of disease brain endothelia provide new sites for CNS-directed enzyme therapy," Nature Medicine, vol. 15, 2009, pp. 1215-1218.
Claes, et al., "De novo SCN1A mutations are a major cause of severe myoclonic epilepsy of infancy," Human Mutation, vol. 21, No. 6, 2003, pp. 615-621.
Deverman, et al., "Cre-dependent selection yields AAV variants for widespread gene transfer to the adult brain," Nature Biotechnology, vol. 34, No. 2, 2016, pp. 204-209.
Dimidschstein, et al., "A viral strategy for targeting and manipulating interneurons across vertebrate species," Nature Neuroscience, vol. 19, No. 12, 2016, pp. 1743-1749.
Dutton, et al., "Preferential inactivation of Scn1a in parvalbumin interneurons increases seizure susceptibility," Neurobiology of Disease, vol. 49, 2013, pp. 211-220.
Fujiwara, "Clinical spectrum of mutations in SCN1A gene: severe myoclonic epilepsy in infancy and related epilepsies," Epilepsy Res., vol. 70, No. 1, 2006, pp. 223-230.
Gambardella & Marini, "Clinical spectrum of SCN1A mutations," Epilepsia, vol. 50, No. 5, 2009, pp. 20-23.
Gersbach, et al., "Synthetic zinc finger proteins: the advent of targeted gene regulation and genome modification technologies," Accounts of Chemical Research, vol. 47, No. 8, 2014, pp. 2309-2318.
Goldin, "Resurgence of sodium channel research," Annual Review of Physiology, vol. 63, 2001, pp. 871-894.
Gombash, et al., "Intravenous AAV9 efficiently transduces myenteric neurons in neonate and juvenile mice," Frontiers in Molecular Neuroscience, vol. 7, No. 81, 2014, 11 pages.
Han, et al., "Autistic-like behaviour in Scn1a+/− mice and rescue by enhanced GABA-mediated neurotransmission," Nature, vol. 489, 2012, pp. 385-390.
Han, et al., "NaV1.1 channels are critical for intercellular communication in the suprachiasmatic nucleus and for normal circadian rhythms," PNAS USA, vol. 109, No. 6, 2012, pp. 368-377.
Harkin, et al., "The spectrum of SCN1A-related infantile epileptic encephalopathies," Brain, vol. 130, No. 3, 2007, pp. 843-852.
Hsiao, et al., "Upregulation of Haploinsufficient Gene Expression in the Brain by Targeting a Long Non-coding RNA Improves Seizure Phenotype in a Model of Dravet Syndrome," EBioMedicine, vol. 9, 2016, pp. 257-277.
Huang, et al., "Role of the Hepatitis B Virus Posttranscriptional Regulatory Element in Export of Intronless Transcripts," Molecular and Cellular Biology, vol. 15, No. 7, 1995, pp. 3864-3869.
Kalume, et al., "Reduced Sodium Current in Purkinje Neurons from NaV1.1 Mutant Mice: Implications for Ataxia in Severe Myoclonic Epilepsy in Infancy," Journal of Neuroscience, vol. 27, No. 41, 2007, pp. 11065-11074.

(56) References Cited

OTHER PUBLICATIONS

Kalume, et al., "Sleep Impairment and Reduced Interneuron Excitability in a Mouse Model of Dravet Syndrome," Neurobiology of Disease, vol. 77, 2015, pp. 141-154.
Kalume, et al., "Sudden unexpected death in a mouse model of Dravet syndrome," Journal of Clinical Investigation, vol. 123, No. 4, 2013, pp. 1798-1808.
Kalume, "Sudden unexpected death in Dravet syndrome: Respiratory and other physiological dysfunctions," Respiratory Physiology & Neurobiology, vol. 189, No. 2, 2013, pp. 324-328.
Kepecs & Fishell, "Interneuron cell types are fit to function," Nature, vol. 505, 2014, pp. 318-326.
Korbelin, et al., "A brain microvasculature endothelial cell-specific viral vector with the potential to treat neurovascular and neurological diseases," EMBO Molecular Medicine, vol. 8, No. 6, 2016, pp. 609-625.
Liu & Mertz, "HnRNP L binds a cis-acting RNA sequence element that enables intron-dependent gene expression," Genes & Development, vol. 9, 1995, pp. 1766-1780.
Livingston, et al., "A novel inherited mutation in the voltage sensor region of SCN1A is associated with Panayiotopoulos syndrome in siblings and generalized epilepsy with febrile seizures plus," Journal of Child Neurology, vol. 24, No. 4, 2009, pp. 503-508.
Marchio, et al., "Brain endothelial cell-targeted gene therapy of neurovascular disorders," EMBO Molecular Medicine, vol. 8, No. 6, 2016, pp. 592-594.
Matharu, et al., "CRISPR-mediated activation of a promoter or enhancer rescues obesity caused by haploinsufficiency," Science, vol. 363, No. 6424, 2019, pp. 186-194.
McClements & MacLaren, "Adeno-associated Virus (AAV) Dual Vector Strategies for Gene Therapy Encoding Large Transgenes," Yale Journal of Biology and Medicine, vol. 90, No. 4, 2017, pp. 611-623.
Mistry, et al., "Strain- and age-dependent hippocampal neuron sodium currents correlate with epilepsy severity in Dravet syndrome mice," Neurobiology of Disease, vol. 65, 2014, 11 pages.
Miyoshi, et al., "Genetic fate mapping reveals that the caudal ganglionic eminence produces a large and diverse population of superficial cortical interneurons," Journal of Neuroscience, vol. 30, No. 5, 2010, pp. 1582-1592.
Monory, et al., "The endocannabinoid system controls key epileptogenic circuits in the hippocampus," Neuron, vol. 51, No. 4, 2006, pp. 455-466.
Morbitzer, et al., "Regulation of selected genome loci using de novo-engineered transcription activator-like effector (TALE)-type transcription factors," Pnas USA, vol. 107, No. 50, 2010, pp. 21617-21622.
Naso, et al., "Adeno-Associated Virus (AAV) as a Vector for Gene Therapy," BioDrugs, vol. 31, No. 4, 2017, pp. 317-334.
ClinicalTrials.gov [Internet]. Bethesda (MD): National Library of Medicine (US). Apr. 23, 2018—Identifier NCT03505099, Pre-Symptomatic Study of Intravenous Onasemnogene Abeparvovec-xioi in Spinal Muscular Atrophy (SMA) for Patients With Multiple Copies of SMN2 (Sprint); Apr. 13, 2018; [8 screens]. Available from: https://clinicaltrials.gov/ct2/show/NCT03505099.
ClinicalTrials.gov [Internet]. Bethesda (MD): National Library of Medicine (US). Aug. 2, 2018—Identifier NCT03612869, Study of AAVrh10-h.SGSH Gene Therapy in Patients With Mucopolysaccharidosis Type IIIA (MPS IIA) (AAVance); Jul. 4, 2018; [8 screens]. Available from: https://clinicaltrials.gov/ct2/show/NCT03612869.
ClinicalTrials.gov [Internet]. Bethesda (MD): National Library of Medicine (US). Dec. 10, 2018—Identifier NCT03770572, Gene Therapy for Children With CLN3 Batten Disease; Dec. 7, 2018; [9 screens]. Available from: https://clinicaltrials.gov/ct2/show/NCT03770572.
Nguyen, et al., "Engineering prokaryotic channels for control of mammalian tissue excitability," Nature Communications, vol. 7, 2016, 11 pages.
O'Roak, et al., "Exome sequencing in sporadic autism spectrum disorders identifies severe de novo mutations," Nature Genetics, vol. 43, No. 6, 2011, pp. 585-589.
Oakley, et al., "Temperature- and age-dependent seizures in a mouse model of severe myoclonic epilepsy in infancy," PNAS USA, vol. 106, No. 10, 2009, pp. 3994-3999.
Ogiwara, et al., "Nav1.1 Localizes to Axons of Parvalbumin-Positive Inhibitory Interneurons: A Circuit Basis for Epileptic Seizures in Mice Carrying an Scn1a Gene Mutation," Journal of Neuroscience, vol. 27, No. 22, 2007, pp. 5903-5914.
Ohmori, et al., "Rasmussen encephalitis associated with SCN1A mutation," Epilepsia, vol. 49, No. 3, 2007, pp. 521-526.
Peron, et al., "A Cellular Resolution Map of Barrel Cortex Activity during Tactile Behavior," Neuron, vol. 86, No. 3, 2015, pp. 783-799.
Rubinstein, et al., "Dissecting the phenotypes of Dravet syndrome by gene deletion," Brain, vol. 138, Part 8, 2015, pp. 2219-2233.
Rudy, et al., "Three groups of interneurons account for nearly 100% of neocortical GABAergic neurons," Development Neurobiology, vol. 71, No. 1, 2011, pp. 45-61.
Scharfman, "Untangling" Alzheimer's Disease and Epilepsy: "Untangling" Alzheimer's Disease and Epilepsy, Epilepsy Currents, vol. 12, No. 5, 2012, pp. 178-183.
Selot, et al., "Optimized AAV rh.10 Vectors That Partially Evade Neutralizing Antibodies during Hepatic Gene Transfer," Frontiers in Pharmacology, vol. 8, No. 441, 2017, 10 pages.
Shen, et al., "Structures of human Nav1.7 channel in complex with auxiliary subunits and animal toxins," Science, vol. 363, No. 6433, 2019, pp. 1303-1308.
Stenman, et al., "Identification of Two Distinct Progenitor Populations in the Lateral Ganglionic Eminence: Implications for Striatal and Olfactory Bulb Neurogenesis," Journal of Neuroscience, vol. 23, No. 1, 2003, pp. 167-174.
Office Action Dated Apr. 18, 2023 in Japanese Application No. 2020-555346, 7 pages.
Lipinski, et al., "Clinical applications of retinal gene therapy," Prog. Retin. Eye Res., 2013, vol. 32, pp. 22-47.

* cited by examiner

FIG. 11 hDLX I56i enhancer:
TATGCACTCACAGTGGTTTGGCATGCATCTGGTGAATTTTTTTAACGAAAAATTAGTGTTG
GTTTCGATGTATGGTAGCATTCTCCCTAACGTAATTTGAATAATTCAGCAAAGCCCCACTAC
CAGCTGTACTTCTGCAGCCTCTTCCATTCTTTTCAGCATTATAATTTTGGTTAATTTTCAATT
TTAGGTCCTACGTCTCTGCAATTTGTGTATGAATAACAGAATAATTTCCCTCTTTTGTTTCGC
CTTTCCTGTTCCTGAATCTAAATAAAGATGGCTTTTTAGTATTAAAAGTGGAAGAAAATTACA
GGTAATTATCTTTGACGGTAAAAACGCTGTAATCAGCGGGCTACATGAAAAATTACTCTAAT
TATGGCTGCATTTAAGAGAATGGAAAAAAACCTTCTTGTGGATAAAAACCTTAAATTGTCCC
CAATGTCTGCTTCAAATTGGATGGCACTGCAGCTGGAGGCTTTGTTCAGAATTGATCCTGG
GGAGCTACGAACCCAAAGTTTCACAGTAGG (SEQ ID NO: 1)

Core of the hDLX I56i enhancer:
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGG (SEQ ID NO: 2)

3xhI56iCore, Triply Concatamerized Core of the hDLX I56i enhancer:
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGGCTAAATAAAGATGGCTTTTTAGTATTAAAAGTGGAAGAAAATTACAGGTAATTATC
TTTGACGGTAAAAACGCTGTAATCAGCGGGCTACATGAAAAATTACTCTAATTATGGCTGCA
TTTAAGAGAATGGCTAAATAAAGATGGCTTTTTAGTATTAAAAGTGGAAGAAAATTACAGGT
AATTATCTTTGACGGTAAAAACGCTGTAATCAGCGGGCTACATGAAAAATTACTCTAATTAT
GGCTGCATTTAAGAGAATGG (SEQ ID NO: 3)

Murine I56i Enhancer (core is the same as human):
TATACACTCACAGTGGTTTGGCATATATTTGGTGAAATTTTTTAAGGAAAAATTAGTGTTGGT
TTCGATATATGGTAGCTTTTTCTCTAACATAATTTGAATAATTCAGCAAAGCCCTACTACCAG
CTGTACTTCTGCAGCCTCTTCCATTCTTTCCAGCATTATAATTTTGGTTAATTTTCAATTTTA
GGTCCTACGTCTCTGCAATTTGTGTATGAATAACAGAATAATTTCCCTCTTTTGTTTCGCCTT
TCCTGTTCCTGAATCTAAATAAAGATGGCTTTTTAGTATTAAAAGTGGAAGAAAATTACAGG
TAATTATCTTTGACGGTAAAAACGCTGTAATCAGCGGGCTACATGAAAAATTACTCTAATTA
TGGCTGCATTTAAGAGAATGGAAAAAAACCTTCTTGTGGATAAAAACCTTAAATTGTCCCCA
ATGTCTGCTTCAAATTGGATGGCACTGCAGCTGGAGGCTTTGTTCAGAATTGATCCTGGGG
AGCTACGAACCCAAAGTTTCACAGTAGG (SEQ ID NO: 4)

Zebrafish I56i Enhancer:
ACATTGTAATTTTAGATAATATCCCAAGCGTTCACTCTCCTCGGCAATTTGTACATGAATAAC
CGAATAATTTCATCTTTTGTTTCGTCTTTGCCACTTCAAATCCAAATAAAGATGCCTTTTAGT
ATTAAAAGTGGTAGAAAATTACAGGTAATTATCTTTGACGGTAAAAACGCTGTAATCAGCGG
GCTACATCAAAAATTACCCTAATTATGTCTGCATTTATGAGAATGGAAAAAAACCCTCTCTT
GGATAAAACCCATAAATTGTCCCAAATATCT (SEQ ID NO: 5)

Core of the Zebrafish I56i Enhancer:
CCAAATAAAGATGCCTTTTAGTATTAAAAGTGGTAGAAAATTACAGGTAATTATCTTTGACG
GTAAAAACGCTGTAATCAGCGGGCTACATCAAAAATTACCCTAATTATGTCTGCATTTATGA
GAATGG (SEQ ID NO: 6)

FIG. 11, cont'd

3x Concatamerized Core of the Zebrafish I56i Enhancer:
CCAAATAAAGATGCCTTTTAGTATTAAAAGTGGTAGAAAATTACAGGTAATTATCTTTGACG
GTAAAAACGCTGTAATCAGCGGGCTACATCAAAAATTACCCTAATTATGTCTGCATTTATGA
GAATGGCCAAATAAAGATGCCTTTTAGTATTAAAAGTGGTAGAAAATTACAGGTAATTATCT
TTGACGGTAAAAACGCTGTAATCAGCGGGCTACATCAAAAATTACCCTAATTATGTCTGCAT
TTATGAGAATGGCCAAATAAAGATGCCTTTTAGTATTAAAAGTGGTAGAAAATTACAGGTAA
TTATCTTTGACGGTAAAAACGCTGTAATCAGCGGGCTACATCAAAAATTACCCTAATTATGT
CTGCATTTATGAGAATGG (SEQ ID NO: 7)

hDLX I12b enhancer:
CAGCTGCAAACCCAAGAGGGTCAGCATCATTTCACTGTATTCTCTTCTTGATTACAAGCCG
GGCCCATCAAACACAACATAATTACAGTAATTTCAGGTTTATTTATTCTAATGCAGTTTCCCC
ATCTCTCTGGTAATTATGAGCAATTTTTTCGCCCAGGGAATCTTTTTGCATTAACAAAAGAG
ATAACGCACTGAAAGCCAAATTTGCTGTGCATTGAGAAAAGGAAAAAAAAAAATCAAATAGG
TGCGAGCTGCCATCTCTGCAATTCTCTGGTACCGGAGCCGGCAAATTGCTTGCAGGTGTAT
GGAGCAAGCTTGTCAATGGCCAGGCCTCCAAATTAGCAAATGCACAGCAGCAAAGTAATG
AAGACAG (SEQ ID NO: 8)

NavSheP-D60N, codon optimized, with N-terminal 3x HA tag:
ATGGTTTACCCGTATGATGTCCCGGATTACGCTGGCAGCTACCCATACGATGTACCCGACT
ATGCCGGCAGTTATCCCTACGACGTCCCTGACTACGCATCTACGTCCCTTTTGAATGCGCC
TACCGGCCTTCAAGCTAGAGTCATTAATCTCGTCGAACAAAACTGGTTTGGACACTTTATAC
TGACTCTCATACTCATTAATGCTGTGCAGCTTGGAATGGAAACTAGCGCCAGCCTCATGGC
ACAATATGGCGCGCTGCTTATGTCCTTGAATAAGGTCCTTCTCTCTGTGTTCGTGGTCGAA
CTGCTGCTCCGGATTTATGCGTATCGGGGCAAGTTTTTTAAGGACCCGTGGAATGTGTTTG
ACTTCACTGTTATTGTTATTGCTCTGATTCCTGCATCTGGCCCATTGGCTGTCCTCCGCTCC
CTCCGAGTTCTCCGCGTCTTGAGGGTTCTGACGATTGTCCCCAGCATGAAAAGAGTAGTGT
CAGCACTGCTTGGGAGCTTGCCCGGGTTGGCCTCCATTGCAACCGTGCTTCTGTTGATCT
ATTACGTTTTCGCTGTGATCGCCACTAAAATTTTCGGGGATGCTTTTCCGGAATGGTTCGG
GACGATAGCGGACTCCTTCTATACCCTTTTTCAAATTATGACCTTGGAAAGTTGGTCTATGG
GGATCTCTAGGCCAGTGATGGAGGTGTACCCTTACGCTTGGGTATTCTTTGTGCCCTTTAT
TCTTGTTGCTACTTTTACCATGCTTAACCTTTTCATCGCCATCATAGTGAATACTATGCAGAC
ATTCTCTGACGAGGAACATGCTCTGGAGCGAGAGCAAGATAAACAGATCTTGGAACAGGA
GCAGAGACAAATGCACGAGGAACTGAAGGCCATTCGACTCGAGCTTCAGCAACTCCAAAC
CCTTTTGCGAAATGCGGCTGGGGACTCCTCCAATGTCTCCACAAAGGGCAATATCGGCTC
AGACTAA (SEQ ID NO: 9)

NavSheP endogenous sequence:
ATGAGTACATCTTTACTTAACGCGCCAACGGGTTTGCAGGCACGAGTGATTAACTTGGTTG
AGCAAAACTGGTTTGGTCATTTTATTTTGACATTGATTTTAATCAACGCGGTGCAGTTAGGT
ATGGAGACCTCAGCCAGCCTGATGGCGCAATACGGTGCTTTGTTGATGAGTCTTGATAAG
GTGCTGCTGAGTGTATTTGTGGTGGAGTTATTGCTGCGGATTTATGCCTACAGGGGGAAAT
TTTTTAAAGACCCTTGGAACGTGTTCGATTTTACCGTGATAGTGATAGCACTGATCCCTGCA
TCTGGGCCATTGGCTGTCCTGCGTTCGCTCAGGGTATTGCGGGTGCTGAGAGTGTTAACA
ATTGTGCCATCAATGAAACGGGTGGTGTCTGCGCTGTTGGGATCACTTCCTGGATTGGCAT
CGATCGCCACAGTATTACTGCTGATTTATTATGTGTTTGCGGTGATCGCTACCAAAATTTTT
GGCGATGCATTCCCTGAATGGTTTGGCACTATTGCTGACTCATTTTATACCCTATTTCAAAT
AATGACGCTTGAAAGCTGGTCTATGGGAATTTCGCGGCCAGTGATGGAAGTCTACCCTTAT
GCTTGGGTATTTTTCGTACCATTTATTCTGGTAGCGACTTTCACAATGCTAAATTTGTTTATT

FIG. 11, cont'd

GCGATTATCGTCAATACCATGCAAACCTTCAGCGACGAAGAGCATGCATTAGAGCGTGAGC
AAGACAAACAAATCTTAGAGCAGGAACAAAGACAAATGCACGAGGAGTTGAAAGCCATCAG
ACTCGAGCTACAACAATTACAAACCTTGCTGCGCAATGCTGCTGGTGATTCTTCTAATGTGT
CGACAAAGGGAAACATTGGTTCTGACTAA (SEQ ID NO: 10)

NavBp, endogenous sequence:
ATGGAAAACAATCCAGCCGAACAACAAGTTCCACCATTAGTAGCCTTAGCTCAGCGTATCG
TCTTTCATAAGGCCTTTACCCCAACTATTATTACCTTGATTATCATTAATGCCATTATTGTAG
GCCTTGAAACATATCCTACTGTTTATCAAGGTTATAATGATTGGTTCTACGCAGCAGATTTA
GCCTTACTTTGGATTTTTACAATTGAGATTACACTGCGTTTTATCGCAGCGAGACCGACTAA
ATCTTTTTTTAAAAGCAGCTGGAACTGGTTTGATTTATTAATCGTTCTTGCCGGTCATGTCTT
TGCCGGTGCTCATTTTGTAACGGTTCTTCGTATCCTGCGCGTTCTTCGCGTATTACGTGCC
ATTTCTGTCATTCCTTCTCTGCGTCGTTTAGTCGATGCTTTGCTGATGACCATCCCGGCTTT
AGGAAACATTATGATCCTGATGGGAATTATTTTCTATATTTTCGCTGTGATTGGAACGATGT
TATTTGCTTCTGTAGCACCTGAGTACTTTGGTAACTTACAGCTTTCTTTATTAACATTATTCC
AAGTTGTTACACTTGAATCTTGGGCAAGCGGTGTCATGAGGCCGATTTTTGCAGAGGTTTG
GTGGTCTTGGATTTATTTTGTCATCTTTATTTTAGTAGGGACATTTATTGTCTTTAACTTATTT
ATCGGTGTTATCGTTAATAACGTTGAAAAAGCAAACGAAGAAGAACTCAAATCAGAATTAGA
TGATAAAGAGGCAGATACAAAAGAAGAGCTTGCTTCTCTGCGTAATGAAGTAGCAGAGATG
AAAGACCTCATTAAACAAATGCATAAACAGCAAACAAAAAAAGGGTAA (SEQ ID NO: 11)

NavBp, codon optimized, with N-terminal 3x HA tag:
ATGGTTTACCCGTATGATGTCCCGGATTACGCTGGCAGCTACCCATACGATGTACCCGACT
ATGCCGGCAGTTATCCCTACGACGTCCCTGACTACGCAGAAAACAACCCAGCCGAACAGC
AAGTCCCACCCCTCGTGGCGCTCGCCCAACGCATAGTATTTCACAAGGCGTTTACGCCGA
CGATAATCACCCTCATCATTATTAATGCGATCATTGTGGGACTCGAGACATACCCAACGGTT
TACCAGGGTTACAATGATTGGTTCTATGCTGCCGACCTTGCTTTGTTGTGGATATTCACTAT
TGAAATCACGCTCCGATTCATCGCCGCCCGACCGACGAAGAGTTTCTTCAAGTCTAGCTGG
AACTGGTTTGATCTGCTTATCGTATTGGCGGGCCACGTCTTCGCTGGCGCCCATTTTGTTA
CGGTGCTTAGGATCCTCCGCGTCCTGAGGGTCCTCAGAGCTATCTCAGTCATACCCAGTC
TCCGGCGGCTGGTTGACGCACTTTTGATGACAATCCCAGCACTCGGTAACATCATGATACT
GATGGGGATTATTTTTTACATATTCGCGGTTATCGGGACGATGCTCTTTGCATCAGTAGCG
CCAGAATACTTTGGCAATTTGCAGCTGTCTCTGCTTACACTGTTCCAAGTGGTTACGCTGG
AAAGTTGGGCTAGTGGGGTTATGCGACCTATTTTTGCCGAAGTCTGGTGGTCTTGGATCTA
TTTTGTAATCTTTATTCTCGTGGGAACTTTCATAGTATTTAACCTTTTCATTGGCGTCATCGT
GAACAATGTGGAAAAAGCTAACGAAGAGGAACTGAAAAGCGAACTGGATGATAAAGAGGC
TGATACAAAAGAAGAACTGGCATCATTGCGAAACGAGGTGGCAGAAATGAAGGATCTCATA
AAACAGATGCATAAACAGCAAACAAAAAAGGGTTAA (SEQ ID NO: 12)

NavMs, endogenous sequence:
ATGTCACGCAAAATAAGAGATTTAATCGAATCCAAACGCTTTCAAAACGTCATCACCGCCAT
TATTGTGCTCAATGGCGCTGTGCTGGGTCTGCTGACCGATACAACCCTATCGGCCTCCAG
CCAAAACCTGCTGGAGCGTGTGGATCAACTTTGTCTGACTATCTTTATTGTTGAAATATCCC
TGAAAATATACGCCTATGGCGTGCGAGGCTTTTTCCGCAGCGGCTGGAATCTGTTTGATTT
TGTGATTGTGGCCATCGCGCTTATGCCCGCCCAGGGTAGCCTATCGGTGCTGCGAACCTT
CCGTATATTCCGCGTCATGCGGCTCGTATCGGTCATACCAACCATGCGAAGAGTGGTGCA
AGGCATGCTCTTGGCACTGCCCGGCGTGGGATCGGTAGCGGCACTGTTGACGGTGGTCT
TCTATATTGCGGCTGTCATGGCCACCAATCTCTACGGGGCAACCTTCCCTGAATGGTTTGG
TGATCTTAGCAAGAGCCTGTACACACTATTTCAGGTGATGACCTTAGAGTCATGGTCTATG

FIG. 11, cont'd

GGCATTGTGCGTCCAGTGATGAACGTTCATCCCAACGCATGGGTTTTTTCATCCCCTTCA
TCATGCTCACCACCTTTACCGTGCTCAACCTGTTTATTGGCATTATTGTAGATGCCATGGCC
ATCACCAAGGAACAGGAGGAAGAGGCCAAAACCGGCCACCACCAAGAGCCTATTAGCCAA
ACATTGCTCCATCTGGGAGATCGCCTAGATAGGATCGAAAAGCAGCTTGCGCAAAACAAC
GAGCTCTTACAACGACAACAGCCGCAAAAAAAATAG (SEQ ID NO: 13)

NavMs, codon optimized, with N-terminal 3x HA tag and linker:
ATGGTTTATCCGTATGATGTTCCTGACTATGCAGGATCCTATCCTTATGATGTTCCCGATTA
CGCTGGTTCTTACCCTTACGATGTTCCCGATTATGCCAGTTCTGGATTGGTGCCACGAGGC
AGCCACATGAGCCGGAAGATCAGAGATCTTATCGAATCTAAGAGATTTCAGAATGTTATTAC
CGCGATAATCGTACTCAACGGGGCGGTGCTCGGTCTCCTCACCGATACCACATTGAGCGC
TTCTAGCCAGAACCTGCTCGAAAGGGTTGACCAACTGTGCCTGACAATTTTTATCGTGGAA
ATTAGCTTGAAAATTTACGCCTACGGCGTTCGCGGTTTTTTCCGGAGCGGTTGGAATCTTTT
TGACTTCGTTATCGTTGCCATCGCGCTCATGCCCGCACAGGGTTCTTTGTCTGTGTTGAGG
ACATTCCGAATATTTCGCGTGATGCGCTTGGTATCCGTGATCCCTACGATGCGCCGCGTCG
TACAAGGAATGTTGCTGGCTCTCCCCGGCGTCGGGAGCGTTGCTGCCCTCCTTACCGTGG
TATTTTACATAGCGGCGGTTATGGCTACTAATCTTTACGGAGCTACCTTCCCGGAGTGGTT
CGGGGATTTGTCCAAGAGCCTCTATACATTGTTTCAAGTTATGACCCTGGAGTCCTGGTCT
ATGGGCATTGTCCGGCCCGTAATGAACGTACACCCAAATGCGTGGGTGTTTTTCATTCCAT
TCATCATGCTGACTACCTTTACCGTGCTGAACTTGTTCATTGGGATTATCGTGGATGCGATG
GCCATCACTAAGGAGCAAGAAGAAGAGGCTAAAACTGGCCACCACCAAGAGCCAATTTCT
CAAACCCTCTTGCATCTCGGGGACCGACTGGACCGCATTGAGAAGCAACTCGCGCAGAAC
AATGAGCTGTTGCAGCGACAGCAACCTCAAAAAAAATAA (SEQ ID NO: 14)

NavMs, codon optimized, with N-terminal His tag and linker:
ATGGGCAGCAGCCATCATCATCATCATCACAGCAGCGGCCTGGTGCCGCGCGGCAGCCA
TATGTCACGCAAAATCCGCGATTTAATCGAATCCAAACGCTTTCAAAACGTCATCACCGCCA
TTATTGTGCTCAATGGCGCTGTGCTGGGTCTGCTGACCGATACAACCCTGTCGGCCTCCA
GCCAAAACCTGCTGGAGCGTGTGGATCAACTTTGTCTGACTATCTTTATTGTTGAAATCTCC
CTGAAAATCTACGCCTATGGCGTGCGCGGCTTTTTCCGCAGCGGCTGGAATCTGTTTGATT
TTGTGATTGTGGCCATCGCGCTTATGCCGGCCCAGGGTAGCCTGTCGGTGCTGCGTACCT
TCCGTATCTTCCGCGTCATGCGCCTCGTATCGGTCATCCCAACCATGCGCCGTGTGGTGC
AAGGCATGCTCTTGGCACTGCCGGGCGTGGGCTCGGTAGCGGCACTGTTGACGGTGGTC
TTCTATATTGCGGCTGTCATGGCCACCAATCTCTACGGGGCAACCTTCCCTGAATGGTTTG
GTGATCTTAGCAAGAGCCTGTACACACTGTTTCAGGTGATGACCTTAGAGTCATGGTCTAT
GGGCATTGTGCGTCCAGTGATGAACGTTCATCCGAACGCATGGGTTTTTTTCATCCCGTTC
ATCATGCTCACCACCTTTACCGTGCTCAACCTGTTTATTGGCATTATTGTAGATGCAATGGC
AATCACCAAGGAACAGGAGGAAGAGGCCAAAACCGGTCACCATCAAGAACCTATTTCTCAA
ACTCTTCTTCATCTTGGTGATCGTCTTGATCGTATTGAAAAACAACTTGCTCAAAATAATGAA
CTTCTTCAACGTCAACAACCTCAAAAAAAATAA (SEQ ID NO: 15)

Human SCN1A:
ATGGAGCAAACAGTGCTTGTACCACCAGGACCTGACAGCTTCAACTTCTTCACCAGAGAAT
CTCTTGCGGCTATTGAAAGACGCATTGCAGAAGAAAAGGCAAAGAATCCCAAACCAGACAA
AAAAGATGACGACGAAAATGGCCCAAAGCCAAATAGTGACTTGGAAGCTGGAAAGAACCTT
CCATTTATTTATGGAGACATTCCTCCAGAGATGGTGTCAGAGCCCCTGGAGGACCTGGACC
CCTACTATATCAATAAGAAAACTTTTATAGTATTGAATAAAGGGAAGGCCATCTTCCGGTTC
AGTGCCACCTCTGCCCTGTACATTTTAACTCCCTTCAATCCTCTTAGGAAAATAGCTATTAA
GATTTTGGTACATTCATTATTCAGCATGCTAATTATGTGCACTATTTTGACAAACTGTGTGTT

FIG. 11, cont'd

TATGACAATGAGTAACCCTCCTGATTGGACAAAGAATGTAGAATACACCTTCACAGGAATAT
ATACTTTTGAATCACTTATAAAAATTATTGCAAGGGGATTCTGTTTAGAAGATTTTACTTTCC
TTCGGGATCCATGGAACTGGCTCGATTTCACTGTCATTACATTTGCGTACGTCACAGAGTTT
GTGGACCTGGGCAATGTCTCGGCATTGAGAACATTCAGAGTTCTCCGAGCATTGAAGACG
ATTTCAGTCATTCCAGGCCTGAAAACCATTGTGGGAGCCCTGATCCAGTCTGTGAAGAAGC
TCTCAGATGTAATGATCCTGACTGTGTTCTGTCTGAGCGTATTTGCTCTAATTGGGCTGCAG
CTGTTCATGGGCAACCTGAGGAATAAATGTATACAATGGCCTCCCACCAATGCTTCCTTGG
AGGAACATAGTATAGAAAAGAATATAACTGTGAATTATAATGGTACACTTATAAATGAAACT
GTCTTTGAGTTTGACTGGAAGTCATATATTCAAGATTCAAGATATCATTATTTCCTGGAGGG
TTTTTTAGATGCACTACTATGTGGAAATAGCTCTGATGCAGGCCAATGTCCAGAGGGATATA
TGTGTGTGAAAGCTGGTAGAAATCCCAATTATGGCTACACAAGCTTTGATACCTTCAGTTG
GGCTTTTTTGTCCTTGTTTCGACTAATGACTCAGGACTTCTGGGAAAATCTTTATCAACTGA
CATTACGTGCTGCTGGGAAAACGTACATGATATTTTTTGTATTGGTCATTTTCTTGGGCTCA
TTCTACCTAATAAATTTGATCCTGGCTGTGGTGGCCATGGCCTACGAGGAACAGAATCAGG
CCACCTTGGAAGAAGCAGAACAGAAAGAGGCCGAATTTCAGCAGATGATTGAACAGCTTAA
AAAGCAACAGGAGGCAGCTCAGCAGGCAGCAACGGCAACTGCCTCAGAACATTCCAGAGA
GCCCAGTGCAGCAGGCAGGCTCTCAGACAGCTCATCTGAAGCCTCTAAGTTGAGTTCCAA
GAGTGCTAAGGAAAGAAGAAATCGGAGGAAGAAAAGAAAACAGAAAGAGCAGTCTGGTGG
GGAAGAGAAAGATGAGGATGAATTCCAAAAATCTGAATCTGAGGACAGCATCAGGAGGAA
AGGTTTTCGCTTCTCCATTGAAGGGAACCGATTGACATATGAAAAGAGGTACTCCTCCCCA
CACCAGTCTTTGTTGAGCATCCGTGGCTCCCTATTTTCACCAAGGCGAAATAGCAGAACAA
GCCTTTTCAGCTTTAGAGGGCGAGCAAAGGATGTGGGATCTGAGAACGACTTCGCAGATG
ATGAGCACAGCACCTTTGAGGATAACGAGAGCCGTAGAGATTCCTTGTTTGTGCCCCGAC
GACACGGAGAGAGACGCAACAGCAACCTGAGTCAGACCAGTAGGTCATCCCGGATGCTG
GCAGTGTTTCCAGCGAATGGGAAGATGCACAGCACTGTGGATTGCAATGGTGTGGTTTCC
TTGGTTGGTGGACCTTCAGTTCCTACATCGCCTGTTGGACAGCTTCTGCCAGAGGTGATAA
TAGATAAGCCAGCTACTGATGACAATGGAACAACCACTGAAACTGAAATGAGAAAGAGAAG
GTCAAGTTCTTTCCACGTTTCCATGGACTTTCTAGAAGATCCTTCCCAAAGGCAACGAGCA
ATGAGTATAGCCAGCATTCTAACAAATACAGTAGAAGAACTTGAAGAATCCAGGCAGAAAT
GCCCACCCTGTTGGTATAAATTTTCCAACATATTCTTAATCTGGGACTGTTCTCCATATTGG
TTAAAAGTGAAACATGTTGTCAACCTGGTTGTGATGGACCCATTTGTTGACCTGGCCATCA
CCATCTGTATTGTCTTAAATACTCTTTTCATGGCCATGGAGCACTATCCAATGACGGACCAT
TTCAATAATGTGCTTACAGTAGGAAACTTGGTTTTCACTGGGATCTTTACAGCAGAAATGTT
TCTGAAAATTATTGCCATGGATCCTTACTATTATTTCCAAGAAGGCTGGAATATCTTTGACG
GTTTTATTGTGACGCTTAGCCTGGTAGAACTTGGACTCGCCAATGTGGAAGGATTATCTGT
TCTCCGTTCATTTCGATTGCTGCGAGTTTTCAAGTTGGCAAAATCTTGGCCAACGTTAAATA
TGCTAATAAAGATCATCGGCAATTCCGTGGGGGCTCTGGGAAATTTAACCCTCGTCTTGGC
CATCATCGTCTTCATTTTTGCCGTGGTCGGCATGCAGCTCTTTGGTAAAAGCTACAAAGATT
GTGTCTGCAAGATCGCCAGTGATTGTCAACTCCCACGCTGGCACATGAATGACTTCTTCCA
CTCCTTCCTGATTGTGTTCCGCGTGCTGTGTGGGGAGTGGATAGAGACCATGTGGGACTG
TATGGAGGTTGCTGGTCAAGCCATGTGCCTTACTGTCTTCATGATGGTCATGGTGATTGGA
AACCTAGTGGTCCTGAATCTCTTTCTGGCCTTGCTTCTGAGCTCATTTAGTGCAGACAACCT
TGCAGCCACTGATGATGATAATGAAATGAATAATCTCCAAATTGCTGTGGATAGGATGCAC
AAAGGAGTAGCTTATGTGAAAAGAAAAATATATGAATTTATTCAACAGTCCTTCATTAGGAA
ACAAAAGATTTTAGATGAAATTAAACCACTTGATGATCTAAACAACAAGAAAGACAGTTGTA
TGTCCAATCATACAGCAGAAATTGGGAAAGATCTTGACTATCTTAAAGATGTAAATGGAACT
ACAAGTGGTATAGGAACTGGCAGCAGTGTTGAATACATTATTGATGAAAGTGATTACATGTC
ATTCATAAACAACCCCAGTCTTACTGTGACTGTACCAATTGCTGTAGGAGAATCTGACTTTG
AAAATTTAAACACGGAAGACTTTAGTAGTGAATCGGATCTGGAAGAAAGCAAAGAGAAACT

FIG. 11, cont'd

GAATGAAAGCAGTAGCTCATCAGAAGGTAGCACTGTGGACATCGGCGCACCTGTAGAAGA
ACAGCCCGTAGTGGAACCTGAAGAAACTCTTGAACCAGAAGCTTGTTTCACTGAAGGCTGT
GTACAAAGATTCAAGTGTTGTCAAATCAATGTGGAAGAAGGCAGAGGAAAACAATGGTGGA
ACCTGAGAAGGACGTGTTTCCGAATAGTTGAACATAACTGGTTTGAGACCTTCATTGTTTTC
ATGATTCTCCTTAGTAGTGGTGCTCTGGCATTTGAAGATATATATATTGATCAGCGAAAGAC
GATTAAGACGATGTTGGAATATGCTGACAAGGTTTTCACTTACATTTTCATTCTGGAAATGC
TTCTAAAATGGGTGGCATATGGCTATCAAACATATTTCACCAATGCCTGGTGTTGGCTGGA
CTTCTTAATTGTTGATGTTTCATTGGTCAGTTTAACAGCAAATGCCTTGGGTTACTCAGAAC
TTGGAGCCATCAAATCTCTCAGGACACTAAGAGCTCTGAGACCTCTAAGAGCCTTATCTCG
ATTTGAAGGGATGAGGGTGGTTGTGAATGCCCTTTTAGGAGCAATTCCATCCATCATGAAT
GTGCTTCTGGTTTGTCTTATATTCTGGCTAATTTTCAGCATCATGGGCGTAAATTTGTTTGCT
GGCAAATTCTACCACTGTATTAACACCACAACTGGTGACAGGTTTGACATCGAAGACGTGA
ATAATCATACTGATTGCCTAAAACTAATAGAAAGAAATGAGACTGCTCGATGGAAAAATGTG
AAAGTAAACTTTGATAATGTAGGATTTGGGTATCTCTCTTTGCTTCAAGTTGCCACATTCAAA
GGATGGATGGATATAATGTATGCAGCAGTTGATTCCAGAAATGTGGAACTCCAGCCTAAGT
ATGAAGAAAGTCTGTACATGTATCTTTACTTTGTTATTTTCATCATCTTTGGGTCCTTCTTCA
CCTTGAACCTGTTTATTGGTGTCATCATAGATAATTTCAACCAGCAGAAAAAGAAGTTTGGA
GGTCAAGACATCTTTATGACAGAAGAACAGAAGAAATACTATAATGCAATGAAAAAATTAGG
ATCGAAAAAACCGCAAAAGCCTATACCTCGACCAGGAAACAAATTTCAAGGAATGGTCTTT
GACTTCGTAACCAGACAAGTTTTTGACATAAGCATCATGATTCTCATCTGTCTTAACATGGT
CACAATGATGGTGGAAACAGATGACCAGAGTGAATATGTGACTACCATTTTGTCACGCATC
AATCTGGTGTTCATTGTGCTATTTACTGGAGAGTGTGTACTGAAACTCATCTCTCTACGCCA
TTATTATTTTACCATTGGATGGAATATTTTTGATTTTGTGGTTGTCATTCTCTCCATTGTAGG
TATGTTTCTTGCCGAGCTGATAGAAAAGTATTTCGTGTCCCCTACCCTGTTCCGAGTGATCC
GTCTTGCTAGGATTGGCCGAATCCTACGTCTGATCAAAGGAGCAAAGGGGATCCGCACGC
TGCTCTTTGCTTTGATGATGTCCCTTCCTGCGTTGTTTAACATCGGCCTCCTACTCTTCCTA
GTCATGTTCATCTACGCCATCTTTGGGATGTCCAACTTTGCCTATGTTAAGAGGGAAGTTG
GGATCGATGACATGTTCAACTTTGAGACCTTTGGCAACAGCATGATCTGCCTATTCCAAATT
ACAACCTCTGCTGGCTGGGATGGATTGCTAGCACCCATTCTCAACAGTAAGCCACCCGACT
GTGACCCTAATAAAGTTAACCCTGGAAGCTCAGTTAAGGGAGACTGTGGGAACCCATCTGT
TGGAATTTTCTTTTTTGTCAGTTACATCATCATATCCTTCCTGGTTGTGGTGAACATGTACAT
CGCGGTCATCCTGGAGAACTTCAGTGTTGCTACTGAAGAAAGTGCAGAGCCTCTGAGTGA
GGATGACTTTGAGATGTTCTATGAGGTTTGGGAGAAGTTTGATCCCGATGCAACTCAGTTC
ATGGAATTTGAAAAATTATCTCAGTTTGCAGCTGCGCTTGAACCGCCTCTCAATCTGCCACA
ACCAAACAAACTCCAGCTCATTGCCATGGATTTGCCCATGGTGAGTGGTGACCGGATCCAC
TGTCTTGATATCTTATTTGCTTTTACAAAGCGGGTTCTAGGAGAGAGTGGAGAGATGGATG
CTCTACGAATACAGATGGAAGAGCGATTCATGGCTTCCAATCCTTCCAAGGTCTCCTATCA
GCCAATCACTACTACTTTAAAACGAAAACAAGAGGAAGTATCTGCTGTCATTATTCAGCGTG
CTTACAGACGCCACCTTTTAAAGCGAACTGTAAAACAAGCTTCCTTTACGTACAATAAAAAC
AAAATCAAAGGTGGGGCTAATCTTCTTATAAAAGAAGACATGATAATTGACAGAATAAATGA
AAACTCTATTACAGAAAAAACTGATCTGACCATGTCCACTGCAGCTTGTCCACCTTCCTATG
ACCGGGTGACAAAGCCAATTGTGGAAAAACATGAGCAAGAAGGCAAAGATGAAAAAGCCA
AAGGGA (SEQ ID NO: 16)

FIG. 11, cont'd

SYFP2:
ATGGTCAGCAAGGGCGAGGAGCTGTTCACCGGGGTGGTGCCCATCCTGGTCGAGCTGGA
CGGCGACGTCAATGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAAGACGACGGCAACTACAAGACCCGCGCCGAGGTGAAGTTCGAGGGCGACAC
CCTGGTGAACCGCATCGAGCTGAAGGGCATCGACTTCAAGGAGGACGGCAACATCCTGG
GGCACAAGCTGGAGTACAACTACAACAGCCACAACGTCTATATCACCGCCGACAAGCAGA
AGAACGGCATCAAGGCCAACTTCAAGATCCGCCACAACATCGAGGACGGCGGCGTGCAG
CTCGCCGACCACTACCAGCAGAACACCCCCATCGGCGACGGCCCCGTGCTGCTGCCCGA
CAACCACTACCTGAGCTACCAGTCCAAGCTGAGCAAAGACCCCAACGAGAAGCGCGATCA
CATGGTCCTGCTGGAGTTCGTGACCGCCGCCGGGATCACTCTCGGCATGGACGAGCTGTA
CAAA (SEQ ID NO: 17)

P2A Encoding Sequence:
GGCAGCGGCGCCACCAACTTCAGCCTGCTGAAGCAGGCCGGCGACGTGGAGGAGAACCC
CGGCCCCGGAGCTAGCGGA (SEQ ID NO: 18)

WPRE3:
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTAGTTCTTGCCACGGCGGAACTCATCGC
CGCCTGCCTTGCCCGCTGCTGGACAGGGGCTCGGCTGTTGGGCACTGACAATTCCGTGG
(SEQ ID NO: 19)

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 20)

N-terminal 3XHA tag (Protein):
MVYPYDVPDYAGSYPYDVPDYAGSYPYDVPDYA (SEQ ID NO: 21)

N-terminal 3XHA tag (DNA):
ATGGTTTACCCGTATGATGTCCCGGATTACGCTGGCAGCTACCCATACGATGTACCCGACT
ATGCCGGCAGTTATCCCTACGACGTCCCTGACTACGCA (SEQ ID NO: 22)

hSCN1A N-term of two-part expression system:
ATGGAGCAAACAGTGCTTGTACCACCAGGACCTGACAGCTTCAACTTCTTCACCAGAGAAT
CTCTTGCGGCTATTGAAAGACGCATTGCAGAAGAAAAGGCAAAGAATCCCAAACCAGACAA
AAAAGATGACGACGAAAATGGCCCAAAGCCAAATAGTGACTTGGAAGCTGGAAAGAACCTT
CCATTTATTTATGGAGACATTCCTCCAGAGATGGTGTCAGAGCCCCTGGAGGACCTGGACC
CCTACTATATCAATAAGAAAACTTTTATAGTATTGAATAAAGGGAAGGCCATCTTCCGGTTC
AGTGCCACCTCTGCCCTGTACATTTTAACTCCCTTCAATCCTCTTAGGAAAATAGCTATTAA
GATTTTGGTACATTCATTATTCAGCATGCTAATTATGTGCACTATTTTGACAAACTGTGTGTT
TATGACAATGAGTAACCCTCCTGATTGGACAAAGAATGTAGAATACACCTTCACAGGAATAT
ATACTTTTGAATCACTTATAAAAATTATTGCAAGGGGATTCTGTTTAGAAGATTTTACTTTCC

FIG. 11, cont'd

TTCGGGATCCATGGAACTGGCTCGATTTCACTGTCATTACATTTGCGTACGTCACAGAGTTT
GTGGACCTGGGCAATGTCTCGGCATTGAGAACATTCAGAGTTCTCCGAGCATTGAAGACG
ATTTCAGTCATTCCAGGCCTGAAAACCATTGTGGGAGCCCTGATCCAGTCTGTGAAGAAGC
TCTCAGATGTAATGATCCTGACTGTGTTCTGTCTGAGCGTATTTGCTCTAATTGGGCTGCAG
CTGTTCATGGGCAACCTGAGGAATAAATGTATACAATGGCCTCCCACCAATGCTTCCTTGG
AGGAACATAGTATAGAAAAGAATATAACTGTGAATTATAATGGTACACTTATAAATGAAACT
GTCTTTGAGTTTGACTGGAAGTCATATATTCAAGATTCAAGATATCATTATTTCCTGGAGGG
TTTTTTAGATGCACTACTATGTGGAAATAGCTCTGATGCAGGCCAATGTCCAGAGGGATATA
TGTGTGTGAAAGCTGGTAGAAATCCCAATTATGGCTACACAAGCTTTGATACCTTCAGTTG
GGCTTTTTTGTCCTTGTTTCGACTAATGACTCAGGACTTCTGGGAAAATCTTTATCAACTGA
CATTACGTGCTGCTGGGAAAACGTACATGATATTTTTTGTATTGGTCATTTTCTTGGGCTCA
TTCTACCTAATAAATTTGATCCTGGCTGTGGTGGCCATGGCCTACGAGGAACAGAATCAGG
CCACCTTGGAAGAAGCAGAACAGAAAGAGGCCGAATTTCAGCAGATGATTGAACAGCTTAA
AAAGCAACAGGAGGCAGCTCAGCAGGCAGCAACGGCAACTGCCTCAGAACATTCCAGAGA
GCCCAGTGCAGCAGGCAGGCTCTCAGACAGCTCATCTGAAGCCTCTAAGTTGAGTTCCAA
GAGTGCTAAGGAAAGAAGAAATCGGAGGAAGAAAAGAAAACAGAAAGAGCAGTCTGGTGG
GGAAGAGAAAGATGAGGATGAATTCCAAAAATCTGAATCTGAGGACAGCATCAGGAGGAA
AGGTTTTCGCTTCTCCATTGAAGGGAACCGATTGACATATGAAAAGAGGTACTCCTCCCCA
CACCAGTCTTTGTTGAGCATCCGTGGCTCCCTATTTTCACCAAGGCGAAATAGCAGAACAA
GCCTTTTCAGCTTTAGAGGGCGAGCAAAGGATGTGGGATCTGAGAACGACTTCGCAGATG
ATGAGCACAGCACCTTTGAGGATAACGAGAGCCGTAGAGATTCCTTGTTTGTGCCCCGAC
GACACGGAGAGAGACGCAACAGCAACCTGAGTCAGACCAGTAGGTCATCCCGGATGCTG
GCAGTGTTTCCAGCGAATGGGAAGATGCACAGCACTGTGGATTGCAATGGTGTGGTTTCC
TTGGTTGGTGGACCTTCAGTTCCTACATCGCCTGTTGGACAGCTTCTGCCAGAGGTGATAA
TAGATAAGCCAGCTACTGATGACAATGGAACAACCACTGAAACTGAAATGAGAAAGAGAAG
GTCAAGTTCTTTCCACGTTTCCATGGACTTTCTAGAAGATCCTTCCCAAAGGCAACGAGCA
ATGAGTATAGCCAGCATTCTAACAAATACAGTAGAAGAACTTGAAGAATCCAGGCAGAAAT
GCCCACCCTGTTGGTATAAATTTTCCAACATATTCTTAATCTGGGACTGTTCTCCATATTGG
TTAAAAGTGAAACATGTTGTCAACCTGGTTGTGATGGACCCATTTGTTGACCTGGCCATCA
CCATCTGTATTGTCTTAAATACTCTTTTCATGGCCATGGAGCACTATCCAATGACGGACCAT
TTCAATAATGTGCTTACAGTAGGAAACTTGGTTTTCACTGGGATCTTTACAGCAGAAATGTT
TCTGAAAATTATTGCCATGGATCCTTACTATTATTTCCAAGAAGGCTGGAATATCTTTGACG
GTTTTATTGTGACGCTTAGCCTGGTAGAACTTGGACTCGCCAATGTGGAAGGATTATCTGT
TCTCCGTTCATTTCGATTGCTGCGAGTTTTCAAGTTGGCAAAATCTTGGCCAACGTTAAATA
TGCTAATAAAGATCATCGGCAATTCCGTGGGGGCTCTGGGAAATTTAACCCTCGTCTTGGC
CATCATCGTCTTCATTTTTGCCGTGGTCGGCATGCAGCTCTTTGGTAAAAGCTACAAAGATT
GTGTCTGCAAGATCGCCAGTGATTGTCAACTCCCACGCTGGCACATGAATGACTTCTTCCA
CTCCTTCCTGATTGTGTTCCGCGTGCTGTGTGGGGAGTGGATAGAGACCATGTGGGACTG
TATGGAGGTTGCTGGTCAAGCCATGTGCCTTACTGTCTTCATGATGGTCATGGTGATTGGA
AACCTAGTGGTCCTGAATCTCTTTCTGGCCTTGCTTCTGAGCTCATTTAGTGCAGACAACCT
TGCAGCCACTGATGATGATAATGAAATGAATAATCTCCAAATTGCTGTGGATAGGATGCAC
AAAGGAGTAGCTTATGTGAAAAGAAAAATATATGAATTTATTCAACAGTCCTTCATTAGGAA
ACAAAAGATTT (SEQ ID NO: 23)

hSCN1A C-term of two-part expression system with c-terminal 3XHA sequence:
CTGGTAGAACTTGGACTCGCCAATGTGGAAGGATTATCTGTTCTCCGTTCATTTCGATTGCT
GCGAGTTTTCAAGTTGGCAAAATCTTGGCCAACGTTAAATATGCTAATAAAGATCATCGGCA
ATTCCGTGGGGGCTCTGGGAAATTTAACCCTCGTCTTGGCCATCATCGTCTTCATTTTTGC
CGTGGTCGGCATGCAGCTCTTTGGTAAAAGCTACAAAGATTGTGTCTGCAAGATCGCCAGT

FIG. 11, cont'd

GATTGTCAACTCCCACGCTGGCACATGAATGACTTCTTCCACTCCTTCCTGATTGTGTTCC
GCGTGCTGTGTGGGGAGTGGATAGAGACCATGTGGGACTGTATGGAGGTTGCTGGTCAA
GCCATGTGCCTTACTGTCTTCATGATGGTCATGGTGATTGGAAACCTAGTGGTCCTGAATC
TCTTTCTGGCCTTGCTTCTGAGCTCATTTAGTGCAGACAACCTTGCAGCCACTGATGATGAT
AATGAAATGAATAATCTCCAAATTGCTGTGGATAGGATGCACAAAGGAGTAGCTTATGTGAA
AAGAAAAATATATGAATTTATTCAACAGTCCTTCATTAGGAAACAAAAGATTTTAGATGAAAT
TAAACCACTTGATGATCTAAACAACAAGAAAGACAGTTGTATGTCCAATCATACAGCAGAAA
TTGGGAAAGATCTTGACTATCTTAAAGATGTAAATGGAACTACAAGTGGTATAGGAACTGG
CAGCAGTGTTGAATACATTATTGATGAAAGTGATTACATGTCATTCATAAACAACCCCAGTC
TTACTGTGACTGTACCAATTGCTGTAGGAGAATCTGACTTTGAAAATTTAAACACGGAAGAC
TTTAGTAGTGAATCGGATCTGGAAGAAAGCAAAGAGAAACTGAATGAAAGCAGTAGCTCAT
CAGAAGGTAGCACTGTGGACATCGGCGCACCTGTAGAAGAACAGCCCGTAGTGGAACCTG
AAGAAACTCTTGAACCAGAAGCTTGTTTCACTGAAGGCTGTGTACAAAGATTCAAGTGTTGT
CAAATCAATGTGGAAGAAGGCAGAGGAAAACAATGGTGGAACCTGAGAAGGACGTGTTTC
CGAATAGTTGAACATAACTGGTTTGAGACCTTCATTGTTTTCATGATTCTCCTTAGTAGTGG
TGCTCTGGCATTTGAAGATATATATATTGATCAGCGAAAGACGATTAAGACGATGTTGGAAT
ATGCTGACAAGGTTTTCACTTACATTTTCATTCTGGAAATGCTTCTAAAATGGGTGGCATAT
GGCTATCAAACATATTTCACCAATGCCTGGTGTTGGCTGGACTTCTTAATTGTTGATGTTTC
ATTGGTCAGTTTAACAGCAAATGCCTTGGGTTACTCAGAACTTGGAGCCATCAAATCTCTCA
GGACACTAAGAGCTCTGAGACCTCTAAGAGCCTTATCTCGATTTGAAGGGATGAGGGTGG
TTGTGAATGCCCTTTTAGGAGCAATTCCATCCATCATGAATGTGCTTCTGGTTTGTCTTATA
TTCTGGCTAATTTTCAGCATCATGGGCGTAAATTTGTTTGCTGGCAAATTCTACCACTGTAT
TAACACCACAACTGGTGACAGGTTTGACATCGAAGACGTGAATAATCATACTGATTGCCTA
AAACTAATAGAAAGAAATGAGACTGCTCGATGGAAAAATGTGAAAGTAAACTTTGATAATGT
AGGATTTGGGTATCTCTCTTTGCTTCAAGTTGCCACATTCAAAGGATGGATGGATATAATGT
ATGCAGCAGTTGATTCCAGAAATGTGGAACTCCAGCCTAAGTATGAAGAAAGTCTGTACAT
GTATCTTTACTTTGTTATTTTCATCATCTTTGGGTCCTTCTTCACCTTGAACCTGTTTATTGG
TGTCATCATAGATAATTTCAACCAGCAGAAAAAGAAGTTTGGAGGTCAAGACATCTTTATGA
CAGAAGAACAGAAGAAATACTATAATGCAATGAAAAAATTAGGATCGAAAAAACCGCAAAA
GCCTATACCTCGACCAGGAAACAAATTTCAAGGAATGGTCTTTGACTTCGTAACCAGACAA
GTTTTTGACATAAGCATCATGATTCTCATCTGTCTTAACATGGTCACAATGATGGTGGAAAC
AGATGACCAGAGTGAATATGTGACTACCATTTTGTCACGCATCAATCTGGTGTTCATTGTGC
TATTTACTGGAGAGTGTGTACTGAAACTCATCTCTCTACGCCATTATTATTTTACCATTGGAT
GGAATATTTTTGATTTTGTGGTTGTCATTCTCTCCATTGTAGGTATGTTTCTTGCCGAGCTG
ATAGAAAAGTATTTCGTGTCCCCTACCCTGTTCCGAGTGATCCGTCTTGCTAGGATTGGCC
GAATCCTACGTCTGATCAAAGGAGCAAAGGGGATCCGCACGCTGCTCTTTGCTTTGATGAT
GTCCCTTCCTGCGTTGTTTAACATCGGCCTCCTACTCTTCCTAGTCATGTTCATCTACGCCA
TCTTTGGGATGTCCAACTTTGCCTATGTTAAGAGGGAAGTTGGGATCGATGACATGTTCAA
CTTTGAGACCTTTGGCAACAGCATGATCTGCCTATTCCAAATTACAACCTCTGCTGGCTGG
GATGGATTGCTAGCACCCATTCTCAACAGTAAGCCACCCGACTGTGACCCTAATAAAGTTA
ACCCTGGAAGCTCAGTTAAGGGAGACTGTGGGAACCCATCTGTTGGAATTTTCTTTTTTGT
CAGTTACATCATCATATCCTTCCTGGTTGTGGTGAACATGTACATCGCGGTCATCCTGGAG
AACTTCAGTGTTGCTACTGAAGAAAGTGCAGAGCCTCTGAGTGAGGATGACTTTGAGATGT
TCTATGAGGTTTGGGAGAAGTTTGATCCCGATGCAACTCAGTTCATGGAATTTGAAAAATTA
TCTCAGTTTGCAGCTGCGCTTGAACCGCCTCTCAATCTGCCACAACCAAACAAACTCCAGC
TCATTGCCATGGATTTGCCCATGGTGAGTGGTGACCGGATCCACTGTCTTGATATCTTATTT
GCTTTTACAAAGCGGGTTCTAGGAGAGAGTGGAGAGATGGATGCTCTACGAATACAGATG
GAAGAGCGATTCATGGCTTCCAATCCTTCCAAGGTCTCCTATCAGCCAATCACTACTACTTT
AAAACGAAAACAAGAGGAAGTATCTGCTGTCATTATTCAGCGTGCTTACAGACGCCACCTT

FIG. 11, cont'd

TTAAAGCGAACTGTAAAACAAGCTTCCTTTACGTACAATAAAAACAAAATCAAAGGTGGGGC TAATCTTCTTATAAAAGAAGACATGATAATTGACAGAATAAATGAAAACTCTATTACAGAAAA AACTGATCTGACCATGTCCACTGCAGCTTGTCCACCTTCCTATGACCGGGTGACAAAGCCA ATTGTGGAAAAACATGAGCAAGAAGGCAAAGATGAAAAAGCCAAAGGGAAAGGAGGTGGT GGTTCAGGTGGGGGCGGCTCAGAGTACCCCTATGATGTCCCTGATTATGCGGCGGAATAC CCCTATGACGTGCCGGACTACGCGGCTGAATATCCGTATGACGTTCCCGATTATGCGGCT AAGCTCGAATAATGA (SEQ ID NO: 24)

604 bp homology region of hSCN1A N term and C term that can be used in two-part expression system:
CTGGTAGAACTTGGACTCGCCAATGTGGAAGGATTATCTGTTCTCCGTTCATTTCGATTGCT GCGAGTTTTCAAGTTGGCAAAATCTTGGCCAACGTTAAATATGCTAATAAAGATCATCGGCA ATTCCGTGGGGGCTCTGGGAAATTTAACCCTCGTCTTGGCCATCATCGTCTTCATTTTTGC CGTGGTCGGCATGCAGCTCTTTGGTAAAAGCTACAAAGATTGTGTCTGCAAGATCGCCAGT GATTGTCAACTCCCACGCTGGCACATGAATGACTTCTTCCACTCCTTCCTGATTGTGTTCC GCGTGCTGTGTGGGGAGTGGATAGAGACCATGTGGGACTGTATGGAGGTTGCTGGTCAA GCCATGTGCCTTACTGTCTTCATGATGGTCATGGTGATTGGAAACCTAGTGGTCCTGAATC TCTTTCTGGCCTTGCTTCTGAGCTCATTTAGTGCAGACAACCTTGCAGCCACTGATGATGAT AATGAAATGAATAATCTCCAAATTGCTGTGGATAGGATGCACAAAGGAGTAGCTTATGTGAA AAGAAAAATATATGAATTTATTCAACAGTCCTTCATTAGGAAACAAAAGATTT (SEQ ID NO: 25)

P2A Translation from CN1498:
(GSG)ATNFSLLKQAGDVEENPGPGASG (SEQ ID NO: 26)

T2A:
(GSG)EGRGSLLTCGDVEENPGP (SEQ ID NO: 27)

E2A:
(GSG)QCTNYALLKLAGDVESNPGPP (SEQ ID NO: 28)

F2A:
(GSG)VKQTLNFDLLKLAGDVESNPGP (SEQ ID NO: 29)

MinBglobin:
GGGCTGGGCATAAAAGTCAGGGCAGAGCCATCTATTGCTTACATTTGCTTCTG (SEQ ID NO: 30)

minCMV:
GAGGTAGGCGTGTACGGTGGGAGGCCTATATAAGCAGAGCTCGTTTAGTGAACCGTCAGA TCGCCTGG (SEQ ID NO: 31)

PHP.eB capsid:
AAV9 capsid except that amino acids starting at residue 586: SAQA are changed to SDGTLAVPFKA (SEQ ID NO: 32)

FIG. 11, cont'd

CN1367 - The portion between L-ITR and R-ITR: positions 142-2984:
GCGGCCGCACGCGTATAGGTACCGAGCTCTATGCACTCACAGTGGTTTGGCATGCATCTG
GTGAATTTTTTTAACGAAAAATTAGTGTTGGTTTCGATGTATGGTAGCATTCTCCCTAACGT
AATTTGAATAATTCAGCAAAGCCCCACTACCAGCTGTACTTCTGCAGCCTCTTCCATTCTTT
TCAGCATTATAATTTTGGTTAATTTTCAATTTTAGGTCCTACGTCTCTGCAATTTGTGTATGA
ATAACAGAATAATTTCCCTCTTTTGTTTCGCCTTTCCTGTTCCTGAATCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGAAAAAAACC
TTCTTGTGGATAAAAACCTTAAATTGTCCCCAATGTCTGCTTCAAATTGGATGGCACTGCAG
CTGGAGGCTTTGTTCAGAATTGATCCTGGGGAGCTACGAACCCAAAGTTTCACAGTAGGGA
GCTCGGGCTGGGCATAAAAGTCAGGGCAGAGCCATCTATTGCTTACATTTGCTTCTGGGAT
CCAGATCTTTCGAAGCTAGCGCTACCGGTCGCCACCATGGGCAGCAGCCATCATCATCAT
CATCACAGCAGCGGCCTGGTGCCGCGCGGCAGCCATATGTCACGCAAAATCCGCGATTTA
ATCGAATCCAAACGCTTTCAAAACGTCATCACCGCCATTATTGTGCTCAATGGCGCTGTGC
TGGGTCTGCTGACCGATACAACCCTGTCGGCCTCCAGCCAAAACCTGCTGGAGCGTGTGG
ATCAACTTTGTCTGACTATCTTTATTGTTGAAATCTCCCTGAAAATCTACGCCTATGGCGTG
CGCGGCTTTTTCCGCAGCGGCTGGAATCTGTTTGATTTTGTGATTGTGGCCATCGCGCTTA
TGCCGGCCCAGGGTAGCCTGTCGGTGCTGCGTACCTTCCGTATCTTCCGCGTCATGCGCC
TCGTATCGGTCATCCCAACCATGCGCCGTGTGGTGCAAGGCATGCTCTTGGCACTGCCGG
GCGTGGGCTCGGTAGCGGCACTGTTGACGGTGGTCTTCTATATTGCGGCTGTCATGGCCA
CCAATCTCTACGGGGCAACCTTCCCTGAATGGTTTGGTGATCTTAGCAAGAGCCTGTACAC
ACTGTTTCAGGTGATGACCTTAGAGTCATGGTCTATGGGCATTGTGCGTCCAGTGATGAAC
GTTCATCCGAACGCATGGGTTTTTTTCATCCCGTTCATCATGCTCACCACCTTTACCGTGCT
CAACCTGTTTATTGGCATTATTGTAGATGCAATGGCAATCACCAAGGAACAGGAGGAAGAG
GCCAAAACCGGTCACCATCAAGAACCTATTTCTCAAACTCTTCTTCATCTTGGTGATCGTCT
TGATCGTATTGAAAAACAACTTGCTCAAAATAATGAACTTCTTCAACGTCAACAACCTCAAA
AAAAAGGCAGCGGCGCCACCAACTTCAGCCTGCTGAAGCAGGCCGGCGACGTGGAGGAG
AACCCCGGCCCCATGGTGAGCAAGGGCGAGGAGCTGTTCACCGGGGTGGTGCCCATCCT
GGTCGAGCTGGACGGCGACGTAAACGGCCACAAGTTCAGCGTGTCCGGCGAGGGCGAG
GGCGATGCCACCTACGGCAAGCTGACCCTGAAGCTGATCTGCACCACCGGCAAGCTGCC
CGTGCCCTGGCCCACCCTCGTGACCACCCTGGGCTACGGCGTGCAGTGCTTCGCCCGCT
ACCCCGACCACATGAAGCAGCACGACTTCTTCAAGTCCGCCATGCCCGAAGGCTACGTCC
AGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCACC
GCCGACAAGCAGAAGAACGGCATCAAGGCCAACTTCAAGATCCGCCACAACATCGAGGAC
GGCGGCGTGCAGCTCGCCGACCACTACCAGCAGAACACCCCCATCGGCGACGGCCCCGT
GCTGCTGCCCGACAACCACTACCTGAGCTACCAGTCCAAGCTGAGCAAAGACCCCAACGA
GAAGCGCGATCACATGGTCCTGCTGGAGTTCGTGACCGCCGCCGGGATCACTCTCGGCAT
GGACGAGCTGTACAAGTAAGTCGACGGCGCGCCGCGGCCGCGAATTCGATATCATAATCA
ACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCA
TTTTCTCCTCCTTGTATAAATCCTGGTTAGTTCTTGCCACGGCGGAACTCATCGCCGCCTG
CCTTGCCCGCTGCTGGACAGGGGCTCGGCTGTTGGGCACTGACAATTCCGTGGCTCGAG
AGATCTTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGG
GGGAGGATTGGGAAGACAATAGCAGGCATGCACGTGCGGACCGAGCGGCCGC (SEQ ID
NO: 33)

FIG. 11, cont'd

CN1500 - The portion between L-ITR and R-ITR: positions 142-2976:
GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAAGGCAGCGG
CGCCACCAACTTCAGCCTGCTGAAGCAGGCCGGCGACGTGGAGGAGAACCCCGGCCCCG
GAGCTAGCGGAATGGTTTACCCGTATGATGTCCCGGATTACGCTGGCAGCTACCCATACG
ATGTACCCGACTATGCCGGCAGTTATCCCTACGACGTCCCTGACTACGCATCTACGTCCCT
TTTGAATGCGCCTACCGGCCTTCAAGCTAGAGTCATTAATCTCGTCGAACAAAACTGGTTT
GGACACTTTATACTGACTCTCATACTCATTAATGCTGTGCAGCTTGGAATGGAAACTAGCG
CCAGCCTCATGGCACAATATGGCGCGCTGCTTATGTCCTTGAATAAGGTCCTTCTCTCTGT
GTTCGTGGTCGAACTGCTGCTCCGGATTTATGCGTATCGGGGCAAGTTTTTTAAGGACCCG
TGGAATGTGTTTGACTTCACTGTTATTGTTATTGCTCTGATTCCTGCATCTGGCCCATTGGC
TGTCCTCCGCTCCCTCCGAGTTCTCCGCGTCTTGAGGGTTCTGACGATTGTCCCCAGCAT
GAAAAGAGTAGTGTCAGCACTGCTTGGGAGCTTGCCCGGGTTGGCCTCCATTGCAACCGT
GCTTCTGTTGATCTATTACGTTTTCGCTGTGATCGCCACTAAAATTTTCGGGGATGCTTTTC
CGGAATGGTTCGGGACGATAGCGGACTCCTTCTATACCCTTTTTCAAATTATGACCTTGGA
AAGTTGGTCTATGGGGATCTCTAGGCCAGTGATGGAGGTGTACCCTTACGCTTGGGTATTC
TTTGTGCCCTTTATTCTTGTTGCTACTTTTACCATGCTTAACCTTTTCATCGCCATCATAGTG
AATACTATGCAGACATTCTCTGACGAGGAACATGCTCTGGAGCGAGAGCAAGATAAACAGA
TCTTGGAACAGGAGCAGAGACAAATGCACGAGGAACTGAAGGCCATTCGACTCGAGCTTC
AGCAACTCCAAACCCTTTTGCGAAATGCGGCTGGGGACTCCTCCAATGTCTCCACAAAGG
GCAATATCGGCTCAGACTAATGACCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGAGATCTCACGTGCGGACCGAGCGGCCGC (SEQ ID NO: 34)

FIG. 11, cont'd

CN1498 - The portion between L-ITR and R-ITR: positions 142-2943:
GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAGGCAGCGG
CGCCACCAACTTCAGCCTGCTGAAGCAGGCCGGCGACGTGGAGGAGAACCCCGGCCCCG
GAGCTAGCGGAATGGTTTACCCGTATGATGTCCCGGATTACGCTGGCAGCTACCCATACG
ATGTACCCGACTATGCCGGCAGTTATCCCTACGACGTCCCTGACTACGCAGAAAACAACCC
AGCCGAACAGCAAGTCCCACCCCTCGTGGCGCTCGCCCAACGCATAGTATTTCACAAGGC
GTTTACGCCGACGATAATCACCCTCATCATTATTAATGCGATCATTGTGGGACTCGAGACAT
ACCCAACGGTTTACCAGGGTTACAATGATTGGTTCTATGCTGCCGACCTTGCTTTGTTGTG
GATATTCACTATTGAAATCACGCTCCGATTCATCGCCGCCCGACCGACGAAGAGTTTCTTC
AAGTCTAGCTGGAACTGGTTTGATCTGCTTATCGTATTGGCGGGCCACGTCTTCGCTGGCG
CCCATTTTGTTACGGTGCTTAGGATCCTCCGCGTCCTGAGGGTCCTCAGAGCTATCTCAGT
CATACCCAGTCTCCGGCGGCTGGTTGACGCACTTTTGATGACAATCCCAGCACTCGGTAA
CATCATGATACTGATGGGGATTATTTTTACATATTCGCGGTTATCGGGACGATGCTCTTTG
CATCAGTAGCGCCAGAATACTTTGGCAATTTGCAGCTGTCTCTGCTTACACTGTTCCAAGT
GGTTACGCTGGAAAGTTGGGCTAGTGGGGTTATGCGACCTATTTTTGCCGAAGTCTGGTG
GTCTTGGATCTATTTTGTAATCTTTATTCTCGTGGGAACTTTCATAGTATTTAACCTTTTCATT
GGCGTCATCGTGAACAATGTGGAAAAAGCTAACGAAGAGGAACTGAAAAGCGAACTGGAT
GATAAAGAGGCTGATACAAAAGAAGAACTGGCATCATTGCGAAACGAGGTGGCAGAAATG
AAGGATCTCATAAAACAGATGCATAAACAGCAAACAAAAAAGGGTTAATGACCGCGGCCGC
GAATTCGATATCATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGC (SEQ ID NO: 35)

FIG. 11, cont'd

CN1499 - The portion between L-ITR and R-ITR: positions 142-2946:
GCGGCCGCACGCGTGGTACCCTAAATAAAGATGGCTTTTTAGTATTAAAAGTGGAAGAAAA
TTACAGGTAATTATCTTTGACGGTAAAAACGCTGTAATCAGCGGGCTACATGAAAAATTACT
CTAATTATGGCTGCATTTAAGAGAATGGCTAAATAAAGATGGCTTTTTAGTATTAAAAGTGG
AAGAAAATTACAGGTAATTATCTTTGACGGTAAAAACGCTGTAATCAGCGGGCTACATGAAA
AATTACTCTAATTATGGCTGCATTTAAGAGAATGGCTAAATAAAGATGGCTTTTTAGTATTAA
AAGTGGAAGAAAATTACAGGTAATTATCTTTGACGGTAAAAACGCTGTAATCAGCGGGCTA
CATGAAAAATTACTCTAATTATGGCTGCATTTAAGAGAATGGAGCTCGGGCTGGTCGACAC
AATTGGAGGTAGGCGTGTACGGTGGGAGGCCTATATAAGCAGAGCTCGTTTAGTGAACCG
TCAGATCGCCTGGAGGATCCTTCGAAAAGCTTGCTACCGGTCGCCACCATGGTCAGCAAG
GGCGAGGAGCTGTTCACCGGGGTGGTGCCCATCCTGGTCGAGCTGGACGGCGACGTCAA
TGGCCACAAGTTCAGCGTGTCCGGCGAGGGCGAGGGCGATGCCACCTACGGCAAGCTGA
CCCTGAAGCTGATCTGCACCACCGGCAAGCTGCCCGTGCCCTGGCCCACCCTCGTGACC
ACCCTGGGCTACGGCGTGCAGTGCTTCGCCCGCTACCCCGACCACATGAAGCAGCACGA
CTTCTTCAAGTCCGCCATGCCCGAAGGCTACGTCCAGGAGCGCACCATCTTCTTCAAAGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACTACAACAGCCACAACGTCTATATCACCGCCGACAAGCAGAAGAACGGCATCAA
GGCCAACTTCAAGATCCGCCACAACATCGAGGACGGCGGCGTGCAGCTCGCCGACCACT
ACCAGCAGAACACCCCCATCGGCGACGGCCCCGTGCTGCTGCCCGACAACCACTACCTG
AGCTACCAGTCCAAGCTGAGCAAAGACCCCAACGAGAAGCGCGATCACATGGTCCTGCTG
GAGTTCGTGACCGCCGCCGGGATCACTCTCGGCATGGACGAGCTGTACAAAGGCAGCGG
CGCCACCAACTTCAGCCTGCTGAAGCAGGCCGGCGACGTGGAGGAGAACCCCGGCCCCG
GAGCTAGCGGAATGGTTTATCCGTATGATGTTCCTGACTATGCAGGATCCTATCCTTATGAT
GTTCCCGATTACGCTGGTTCTTACCCTTACGATGTTCCCGATTATGCCAGTTCTGGATTGGT
GCCACGAGGCAGCCACATGAGCCGGAAGATCAGAGATCTTATCGAATCTAAGAGATTTCA
GAATGTTATTACCGCGATAATCGTACTCAACGGGGCGGTGCTCGGTCTCCTCACCGATACC
ACATTGAGCGCTTCTAGCCAGAACCTGCTCGAAAGGGTTGACCAACTGTGCCTGACAATTT
TTATCGTGGAAATTAGCTTGAAAATTTACGCCTACGGCGTTCGCGGTTTTTTCCGGAGCGG
TTGGAATCTTTTTGACTTCGTTATCGTTGCCATCGCGCTCATGCCCGCACAGGGTTCTTTGT
CTGTGTTGAGGACATTCCGAATATTTCGCGTGATGCGCTTGGTATCCGTGATCCCTACGAT
GCGCCGCGTCGTACAAGGAATGTTGCTGGCTCTCCCCGGCGTCGGGAGCGTTGCTGCCC
TCCTTACCGTGGTATTTTACATAGCGGCGGTTATGGCTACTAATCTTTACGGAGCTACCTTC
CCGGAGTGGTTCGGGGATTTGTCCAAGAGCCTCTATACATTGTTTCAAGTTATGACCCTGG
AGTCCTGGTCTATGGGCATTGTCCGGCCCGTAATGAACGTACACCCAAATGCGTGGGTGT
TTTTCATTCCATTCATCATGCTGACTACCTTTACCGTGCTGAACTTGTTCATTGGGATTATCG
TGGATGCGATGGCCATCACTAAGGAGCAAGAAGAAGAGGCTAAAACTGGCCACCACCAAG
AGCCAATTTCTCAAACCCTCTTGCATCTCGGGGACCGACTGGACCGCATTGAGAAGCAACT
CGCGCAGAACAATGAGCTGTTGCAGCGACAGCAACCTCAAAAAAAATAATGACCGCGGCC
GCGAATTCGATATCATAATCAACCTCTGGATTACAAAATTTGTGAAAGATTGACTGGTATTC
TTAACTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTAGTTCTTGCCACG
GCGGAACTCATCGCCGCCTGCCTTGCCCGCTGCTGGACAGGGGCTCGGCTGTTGGGCAC
TGACAATTCCGTGGCTCGAGAGATCTTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCTGGGGGGTGGGG
TGGGGCAGGACAGCAAGGGGGAGGATTGGGAAGACAATAGCAGGCATGAGATCTCACGT
GCGGACCGAGCGGCCGC (SEQ ID NO: 36)

FIG. 11, cont'd

CN1244 - The portion between L-ITR and R-ITR: positions 142-2042:
GCGGCCGCACGCGTATAGGTACCGAGCTCTATGCACTCACAGTGGTTTGGCATGCATCTG
GTGAATTTTTTTAACGAAAAATTAGTGTTGGTTTCGATGTATGGTAGCATTCTCCCTAACGT
AATTTGAATAATTCAGCAAAGCCCCACTACCAGCTGTACTTCTGCAGCCTCTTCCATTCTTT
TCAGCATTATAATTTTGGTTAATTTTCAATTTTAGGTCCTACGTCTCTGCAATTTGTGTATGA
ATAACAGAATAATTTCCCTCTTTTGTTTCGCCTTTCCTGTTCCTGAATCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGAAAAAAACC
TTCTTGTGGATAAAAACCTTAAATTGTCCCCAATGTCTGCTTCAAATTGGATGGCACTGCAG
CTGGAGGCTTTGTTCAGAATTGATCCTGGGGAGCTACGAACCCAAAGTTTCACAGTAGGGA
GCTCGGGCTGGGCATAAAAGTCAGGGCAGAGCCATCTATTGCTTACATTTGCTTCTGGGAT
CCAGATCTTTCGAAGCTAGCGCTACCGGTCGCCACCATGGTGAGCAAGGGCGAGGAGCT
GTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGCTG
ATCTGCACCACCGGCAAGCTGCCCGTGCCCTGGCCCACCCTCGTGACCACCCTGGGCTA
CGGCGTGCAGTGCTTCGCCCGCTACCCCGACCACATGAAGCAGCACGACTTCTTCAAGTC
CGCCATGCCCGAAGGCTACGTCCAGGAGCGCACCATCTTCTTCAAGGACGACGGCAACTA
CAAGACCCGCGCCGAGGTGAAGTTCGAGGGCGACACCCTGGTGAACCGCATCGAGCTGA
AGGGCATCGACTTCAAGGAGGACGGCAACATCCTGGGGCACAAGCTGGAGTACAACTACA
ACAGCCACAACGTCTATATCACCGCCGACAAGCAGAAGAACGGCATCAAGGCCAACTTCA
AGATCCGCCACAACATCGAGGACGGCGGCGTGCAGCTCGCCGACCACTACCAGCAGAAC
ACCCCCATCGGCGACGGCCCCGTGCTGCTGCCCGACAACCACTACCTGAGCTACCAGTC
CAAGCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGTCGACGGCGCGCCGC
GGCCGCGAATTCGATATCATAATCAACCTCTGGATTACAAAATTTGTGAAAGATTGACTGGT
ATTCTTAACTATGTTGCTCCTTTTACGCTATGTGGATACGCTGCTTTAATGCCTTTGTATCAT
GCTATTGCTTCCCGTATGGCTTTCATTTTCTCCTCCTTGTATAAATCCTGGTTAGTTCTTGCC
ACGGCGGAACTCATCGCCGCCTGCCTTGCCCGCTGCTGGACAGGGGCTCGGCTGTTGGG
CACTGACAATTCCGTGGCTCGAGAGATCTTCGACTGTGCCTTCTAGTTGCCAGCCATCTGT
TGTTTGCCCCTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTGGGGGGTG
GGGTGGGGCAGGACAGCAAGGGGGAGGATTGGGAAGACAATAGCAGGCATGAGATCTCA
CGTGCGGACCGAGCGGCCGC (SEQ ID NO: 37)

CN1389 - The portion between L-ITR and R-ITR corresponds to positions 142-1897:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCGGTCGCCACCATGGTGAGCAAGGGCGAG
GAGCTGTTCACCGGGGTGGTGCCCATCCTGGTCGAGCTGGACGGCGACGTAAACGGCCA
CAAGTTCAGCGTGTCCGGCGAGGGCGAGGGCGATGCCACCTACGGCAAGCTGACCCTGA
AGCTGATCTGCACCACCGGCAAGCTGCCCGTGCCCTGGCCCACCCTCGTGACCACCCTG

FIG. 11, cont'd

GGCTACGGCGTGCAGTGCTTCGCCCGCTACCCCGACCACATGAAGCAGCACGACTTCTTC
AAGTCCGCCATGCCCGAAGGCTACGTCCAGGAGCGCACCATCTTCTTCAAGGACGACGGC
AACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACA
ACTACAACAGCCACAACGTCTATATCACCGCCGACAAGCAGAAGAACGGCATCAAGGCCA
ACTTCAAGATCCGCCACAACATCGAGGACGGCGGCGTGCAGCTCGCCGACCACTACCAG
CAGAACACCCCCATCGGCGACGGCCCCGTGCTGCTGCCCGACAACCACTACCTGAGCTA
CCAGTCCAAGCTGAGCAAAGACCCCAACGAGAAGCGCGATCACATGGTCCTGCTGGAGTT
CGTGACCGCCGCCGGGATCACTCTCGGCATGGACGAGCTGTACAAGTAAGTCGACGGCG
CGCCGCGGCCGCGAATTCGATATCATAATCAACCTCTGGATTACAAAATTTGTGAAAGATT
GACTGGTATTCTTAACTATGTTGCTCCTTTTACGCTATGTGGATACGCTGCTTTAATGCCTT
TGTATCATGCTATTGCTTCCCGTATGGCTTTCATTTTCTCCTCCTTGTATAAATCCTGGTTAG
TTCTTGCCACGGCGGAACTCATCGCCGCCTGCCTTGCCCGCTGCTGGACAGGGGCTCGG
CTGTTGGGCACTGACAATTCCGTGGCTCGAGAGATCTTCGACTGTGCCTTCTAGTTGCCAG
CCATCTGTTGTTTGCCCCTCCCCCGTGCCTTCCTTGACCCTGGAAGGTGCCACTCCCACTG
TCCTTTCCTAATAAAATGAGGAAATTGCATCGCATTGTCTGAGTAGGTGTCATTCTATTCTG
GGGGGTGGGGTGGGGCAGGACAGCAAGGGGGAGGATTGGGAAGACAATAGCAGGCATG
AGATCTCACGTGCGGACCGAGCGGCCGCAGGAACCCCTAGTGATGGAGTTGGCCACTCC
CTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGGGGCGCCT
GATGCGGTATTTTCTCCTTACGCATCTGTGCGGTATTTCACACCGCATACGTCAAAGCAAC
CATAGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCCTTTC
TCGCCACGTTCGCCGGCTTTCCCCGTCAAGCTCTAAATCGGGGGCTCCCTTTAGGGTTCC
GATTTAGTGCTTTACGGCACCTCGACCCCAAAAAACTTGATTTGGGTGATGGTTCACGTAG
TGGGCCATCGCCCTGATAGACGGTTTTTCGCCCTTTGACGTTGGAGTCCACGTTCTTTAAT
AGTGGACTCTTGTTCCAAACTGGAACAACACTCAACCCTATCTCGGGCTATTCTTTTGATTT
ATAAGGGATTTTGCCGATTTCGGCCTATTGGTTAAAAAATGAGCTGATTTAACAAAAATTTA
ACGCGAATTTTAACAAAATATTAACGTTTACAATTTTATGGTGCACTCTCAGTACAATCTGCT
CTGATGCCGCATAGTTAAGCCAGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGACGAAAGGGCCTCGTGATA
CGCCTATTTTTATAGGTTAATGTCATGATAATAATGGTTTCTTAGACGTCAGGTGGCACTTTT
CGGGGAAATGTGCGCGGAACCCCTATTTGTTTATTTTTCTAAATACATTCAAATATGTATCC
GCTCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGACGCC
GGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCAT
AACCATGAGTGATAACACTGCGGCCAACTTACTTCTGACAACGATCGGAGGACCGAAGGA
GCTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGAGTCAGG
CAACTATGGATGAACGAAATAGACAGATCGCTGAGATAGGTGCCTCACTGATTAAGCATTG

FIG. 11, cont'd

GTAACTGTCAGACCAAGTTTACTCATATATACTTTAGATTGATTTAAAACTTCATTTTTAATTT
AAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGT (SEQ ID NO: 38)

CN1390 - The portion between L-ITR and R-ITR corresponds to positions 142-1660:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTTCGCCTTTCCTGTTCCTGAAT
CTAAATAAAGATGGCTTTTTAGTATTAAAAGTGGAAGAAAATTACAGGTAATTATCTTTGACG
GTAAAAACGCTGTAATCAGCGGGCTACATGAAAAATTACTCTAATTATGGCTGCATTTAAGA
GAATGGACCTGCAGGGAGCTCGGGCTGGGCATAAAAGTCAGGGCAGAGCCATCTATTGCT
TACATTTGCTTCTGGGATCCAGATCTTTCGAAGCTAGCGCTACCGGTCGCCACCATGGTGA
GCAAGGGCGAGGAGCTGTTCACCGGGGTGGTGCCCATCCTGGTCGAGCTGGACGGCGAC
GTAAACGGCCACAAGTTCAGCGTGTCCGGCGAGGGCGAGGGCGATGCCACCTACGGCAA
GCTGACCCTGAAGCTGATCTGCACCACCGGCAAGCTGCCCGTGCCCTGGCCCACCCTCG
TGACCACCCTGGGCTACGGCGTGCAGTGCTTCGCCCGCTACCCCGACCACATGAAGCAG
CACGACTTCTTCAAGTCCGCCATGCCCGAAGGCTACGTCCAGGAGCGCACCATCTTCTTC
AAGGACGACGGCAACTACAAGACCCGCGCCGAGGTGAAGTTCGAGGGCGACACCCTGGT
GAACCGCATCGAGCTGAAGGGCATCGACTTCAAGGAGGACGGCAACATCCTGGGGCACA
AGCTGGAGTACAACTACAACAGCCACAACGTCTATATCACCGCCGACAAGCAGAAGAACG
GCATCAAGGCCAACTTCAAGATCCGCCACAACATCGAGGACGGCGGCGTGCAGCTCGCC
GACCACTACCAGCAGAACACCCCCATCGGCGACGGCCCCGTGCTGCTGCCCGACAACCA
CTACCTGAGCTACCAGTCCAAGCTGAGCAAAGACCCCAACGAGAAGCGCGATCACATGGT
CCTGCTGGAGTTCGTGACCGCCGCCGGGATCACTCTCGGCATGGACGAGCTGTACAAGTA
AGTCGACGGCGCGCCGCGGCCGCGAATTCGATATCATAATCAACCTCTGGATTACAAAATT
TGTGAAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGTATAA
ATCCTGGTTAGTTCTTGCCACGGCGGAACTCATCGCCGCCTGCCTTGCCCGCTGCTGGAC
AGGGGCTCGGCTGTTGGGCACTGACAATTCCGTGGCTCGAGAGATCTTCGACTGTGCCTT
CTAGTTGCCAGCCATCTGTTGTTTGCCCCTCCCCCGTGCCTTCCTTGACCCTGGAAGGTGC
CACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAAT
AGCAGGCATGAGATCTCACGTGCGGACCGAGCGGCCGCAGGAACCCCTAGTGATGGAGT
TGGCCACTCCCTCTCTGCGCGCTCGCTCGCTCACTGAGGCCGGGCGACCAAAGGTCGCC
CGACGCCCGGGCTTTGCCCGGGCGGCCTCAGTGAGCGAGCGAGCGCGCAGCTGCCTGC
AGGGGCGCCTGATGCGGTATTTTCTCCTTACGCATCTGTGCGGTATTTCACACCGCATACG
TCAAAGCAACCATAGTACGCGCCCTGTAGCGGCGCATTAAGCGCGGCGGGTGTGGTGGTT
ACGCGCAGCGTGACCGCTACACTTGCCAGCGCCCTAGCGCCCGCTCCTTTCGCTTTCTTC

FIG. 11, cont'd

CCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTTGGGTGATGG
TTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGCTGATTTAACA
AAAATTTAACGCGAATTTTAACAAAATATTAACGTTTACAATTTTATGGTGCACTCTCAGTAC
AATCTGCTCTGATGCCGCATAGTTAAGCCAGCCCCGACACCCGCCAACACCCGCTGACGC
GCCCTGACGGGCTTGTCTGCTCCCGGCATCCGCTTACAGACAAGCTGTGACCGTCTCCGG
GAGCTGCATGTGTCAGAGGTTTTCACCGTCATCACCGAAACGCGCGAGACGAAAGGGCCT
CGTGATACGCCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATACATTCAAAT
ATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAG
AACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGG
GAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAA
GCATTGGTAACTGTCAGACCAAGTTTACTCATATATACTTTAGATTGATTTAAAACTTCATTT
TTAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCT
GTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC
GGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTC
GATTTTTGTGATGCTCGTCAGGGGGGCGGAGCCTATGGAAAAACGCCAGCAACGCGGCCT
TTTTACGGTTCCTGGCCTTTTGCTGGCCTTTTGCTCACATGT (SEQ ID NO: 39)

CN1203 - The portion between L-ITR and R-ITR corresponds to positions 183-2052:
AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTATAGGTACCGAGCTCTATGCACTCACAGTGGTTTGGCATGCAT
CTGGTGAATTTTTTTTAACGAAAAATTAGTGTTGGTTTCGATGTATGGTAGCATTCTCCCTAA
CGTAATTTGAATAATTCAGCAAAGCCCCACTACCAGCTGTACTTCTGCAGCCTCTTCCATTC
TTTTCAGCATTATAATTTTGGTTAATTTTCAATTTTAGGTCCTACGTCTCTGCAATTTGTGTAT

FIG. 11, cont'd

GAATAACAGAATAATTTCCCTCTTTTGTTTCGCCTTTCCTGTTCCTGAATCTAAATAAAGATG
GCTTTTTAGTATTAAAAGTGGAAGAAAATTACAGGTAATTATCTTTGACGGTAAAAACGCTG
TAATCAGCGGGCTACATGAAAAATTACTCTAATTATGGCTGCATTTAAGAGAATGGAAAAAA
ACCTTCTTGTGGATAAAAACCTTAAATTGTCCCCAATGTCTGCTTCAAATTGGATGGCACTG
CAGCTGGAGGCTTTGTTCAGAATTGATCCTGGGGAGCTACGAACCCAAAGTTTCACAGTAG
GGAGCTCGGGCTGGGCATAAAAGTCAGGGCAGAGCCATCTATTGCTTACATTTGCTTCTG
GGATCCAGATCTTTCGAAGCTAGCGCTACCGGTCGCCACCATGGTGAGCAAGGGCGAGG
AGCTGTTCACCGGGGTGGTGCCCATCCTGGTCGAGCTGGACGGCGACGTAAACGGCCAC
AAGTTCAGCGTGTCCGGCGAGGGCGAGGGCGATGCCACCTACGGCAAGCTGACCCTGAA
GCTGATCTGCACCACCGGCAAGCTGCCCGTGCCCTGGCCCACCCTCGTGACCACCCTGG
GCTACGGCGTGCAGTGCTTCGCCCGCTACCCCGACCACATGAAGCAGCACGACTTCTTCA
AGTCCGCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCATCGAG
CTGAAGGGCATCGACTTCAAGGAGGACGGCAACATCCTGGGGCACAAGCTGGAGTACAAC
TACAACAGCCACAACGTCTATATCACCGCCGACAAGCAGAAGAACGGCATCAAGGCCAAC
TTCAAGATCCGCCACAACATCGAGGACGGCGGCGTGCAGCTCGCCGACCACTACCAGCA
GAACACCCCCATCGGCGACGGCCCCGTGCTGCTGCCCGACAACCACTACCTGAGCTACC
AGTCCAAGCTGAGCAAAGACCCCAACGAGAAGCGCGATCACATGGTCCTGCTGGAGTTCG
TGACCGCCGCCGGGATCACTCTCGGCATGGACGAGCTGTACAAGTAAGTCGACGGCGCG
CCGCGGCCGCGAATTCGATATCATAATCAACCTCTGGATTACAAAATTTGTGAAAGATTGA
CTGGTATTCTTAACTATGTTGCTCCTTTTACGCTATGTGGATACGCTGCTTTAATGCCTTTGT
ATCATGCTATTGCTTCCCGTATGGCTTTCATTTTCTCCTCCTTGTATAAATCCTGGTTAGTTC
TTGCCACGGCGGAACTCATCGCCGCCTGCCTTGCCCGCTGCTGGACAGGGGCTCGGCTG
TTGGGCACTGACAATTCCGTGGCTCGAGCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGACTAGTCCAC
TCCCTCTCTGCGCGCTCGCTCGCTCACTGAGGCCGGGCGACCAAAGGTCGCCCGACGCC
CGGGCTTTGCCCGGGCGGCCTCAGTGAGCGAGCGAGCGCGCAGAGAGGGACAGATCCG
GGCCCGCATGCGTCGACAATTCACTGGCCGTCGTTTTACAACGTCGTGACTGGGAAAACC
CTGGCGTTACCCAACTTAATCGCCTTGCAGCACATCCCCCTTTCGCCAGCTGGCGTAATAG
CGAAGAGGCCCGCACCGATCGCCCTTCCCAACAGTTGCGCAGCCTGAATGGCGAATGGC
GCCTGATGCGGTATTTTCTCCTTACGCATCTGTGCGGTATTTCACACCGCATATGGTGCAC
TCTCAGTACAATCTGCTCTGATGCCGCATAGTTAAGCCAGCCCCGACACCCGCCAACACC
CGCTGACGCGCCCTGACGGGCTTGTCTGCTCCCGGCATCCGCTTACAGACAAGCTGTGAC
CGTCTCCGGGAGCTGCATGTGTCAGAGGTTTTCACCGTCATCACCGAAACGCGCGAGACG
AAAGGGCCTCGTGATACGCCTATTTTTATAGGTTAATGTCATGATAATAATGGTTTCTTAGA
CGTCAGGTGGCACTTTTCGGGGAAATGTGCGCGGAACCCCTATTTGTTTATTTTTCTAAATA
CATTCAAATATGTATCCGCTCATGAGACAATAACCCTGATAAATGCTTCAATAATATTGAAAA
AGGAAGAGTATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAGATCAGTTG
GGTGCACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGA
TGCCTGTAGCAATGGCAACAACGTTGCGCAAACTATTAACTGGCGAACTACTTACTCTAGC

FIG. 11, cont'd

TTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTAC
ACGACGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGATTTA
AAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGTAACTGGCT
TCAGCAGAGCGCAGATACCAAATACTGTTCTTCTAGTGTAGCCGTAGTTAGGCCACCACTT
CAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCTCTG
ACTTGAGCGTCGATTTTTGTGATGCTCGTCAGGGGGGCGGAGCCTATGGAAAAACGCCAG
CAACGCGGCCTTTTTACGGTTCCTGGCCTTTTGCTGGCCTTTTGCTCACATGTTCTTTCCTG
CGTTATCCCCTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAGAGCGCCCA
ATACGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTGTGAGCGG
ATAACAATTTCACACAGGAAACAGCTATGACCATGATTACGCCAAGCTCTCGAGATCTAG
(SEQ ID NO: 40)

CN1180 - The portion between L-ITR and R-ITR corresponds to positions 183-1891:
AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTCAGCTGCAAACCCAAGAGGGTCAGCATCATTTCACTGTATTCT
CTTCTTGATTACAAGCCGGGCCCATCAAACACAACATAATTACAGTAATTTCAGGTTTATTT
ATTCTAATGCAGTTTCCCCATCTCTCTGGTAATTATGAGCAATTTTTTCGCCCAGGGAATCT
TTTTGCATTAACAAAAGAGATAACGCACTGAAAGCCAAATTTGCTGTGCATTGAGAAAAGGA
AAAAAAAAAATCAAATAGGTGCGAGCTGCCATCTCTGCAATTCTCTGGTACCGGAGCCGGC
AAATTGCTTGCAGGTGTATGGAGCAAGCTTGTCAATGGCCAGGCCTCCAAATTAGCAAATG
CACAGCAGCAAAGTAATGAAGACAGGAGCTCGGGCTGGGCATAAAAGTCAGGGCAGAGC
CATCTATTGCTTACATTTGCTTCTGGGATCCAGATCTTTCGAAGCTAGCGCTACCGGTCGC
CACCATGGTGAGCAAGGGCGAGGAGCTGTTCACCGGGGTGGTGCCCATCCTGGTCGAGC
TGGACGGCGACGTAAACGGCCACAAGTTCAGCGTGTCCGGCGAGGGCGAGGGCGATGCC
ACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA

FIG. 11, cont'd

TCACATGGTCCTGCTGGAGTTCGTGACCGCCGCCGGGATCACTCTCGGCATGGACGAGCT
GTACAAGTAAGTCGACGGCGCGCCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGCGACTGTGCC
TTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGT
GTCATTCTATTCTGGGGGGTGGGGTGGGGCAGGACAGCAAGGGGGAGGATTGGGAAGAC
AATAGCAGGCATGACTAGTGCATGCCCACTCCCTCTCTGCGCGCTCGCTCGCTCACTGAG
GCCGGGCGACCAAAGGTCGCCCGACGCCCGGGCTTTGCCCGGGCGGCCTCAGTGAGCG
AGCGAGCGCGCAGAGAGGGACAGATCCGGGCCCGCATGCGTCGACAATTCACTGGCCGT
CGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAA
CAGTTGCGCAGCCTGAATGGCGAATGGCGCCTGATGCGGTATTTTCTCCTTACGCATCTGT
GCGGTATTTCACACCGCATATGGTGCACTCTCAGTACAATCTGCTCTGATGCCGCATAGTT
AAGCCAGCCCCGACACCCGCCAACACCCGCTGACGCGCCCTGACGGGCTTGTCTGCTCC
CGGCATCCGCTTACAGACAAGCTGTGACCGTCTCCGGGAGCTGCATGTGTCAGAGGTTTT
CACCGTCATCACCGAAACGCGCGAGACGAAAGGGCCTCGTGATACGCCTATTTTTATAGG
TTAATGTCATGATAATAATGGTTTCTTAGACGTCAGGTGGCACTTTTCGGGGAAATGTGCG
CGGAACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAGAAACGCTG
GTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATGAGCA
CTTTTAAAGTTCTGCTATGTGGCGCGGTATTATCCCGTATTGACGCCGGGCAAGAGCAACT
CGGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGC
CATACCAAACGACGAGCGTGACACCACGATGCCTGTAGCAATGGCAACAACGTTGCGCAA
ACTATTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTGCT
GATAAATCTGGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACC
AAGTTTACTCATATATACTTTAGATTGATTTAAAACTTCATTTTTAATTTAAAAGGATCTAGGT
GAAGATCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTTCTT
CTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGC
TATGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGC

FIG. 11, cont'd

TGGCCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGTCAG
TGAGCGAGGAAGCGGAAGAGCGCCCAATACGCAAACCGCCTCTCCCCGCGCGTTGGCCG
ATTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCGG
CTCGTATGTTGTGTGGAATTGTGAGCGGATAACAATTTCACACAGGAAACAGCTATGACCA
TGATTACGCCAAGCTCTCGAGATCTAG (SEQ ID NO: 41)

CN2001 - The portion between L-ITR and R-ITR corresponds to positions 142-2023:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGGAAAACAACCCAGCCGAACAGCA
AGTCCCACCCCTCGTGGCGCTCGCCCAACGCATAGTATTTCACAAGGCGTTTACGCCGAC
GATAATCACCCTCATCATTATTAATGCGATCATTGTGGGACTCGAGACATACCCAACGGTTT
ACCAGGGTTACAATGATTGGTTCTATGCTGCCGACCTTGCTTTGTTGTGGATATTCACTATT
GAAATCACGCTCCGATTCATCGCCGCCCGACCGACGAAGAGTTTCTTCAAGTCTAGCTGG
AACTGGTTTGATCTGCTTATCGTATTGGCGGGCCACGTCTTCGCTGGCGCCCATTTTGTTA
CGGTGCTTAGGATCCTCCGCGTCCTGAGGGTCCTCAGAGCTATCTCAGTCATACCCAGTC
TCCGGCGGCTGGTTGACGCACTTTTGATGACAATCCCAGCACTCGGTAACATCATGATACT
GATGGGGATTATTTTTTACATATTCGCGGTTATCGGGACGATGCTCTTTGCATCAGTAGCG
CCAGAATACTTTGGCAATTTGCAGCTGTCTCTGCTTACACTGTTCCAAGTGGTTACGCTGG
AAAGTTGGGCTAGTGGGGTTATGCGACCTATTTTTGCCGAAGTCTGGTGGTCTTGGATCTA
TTTTGTAATCTTTATTCTCGTGGGAACTTTCATAGTATTTAACCTTTTCATTGGCGTCATCGT
GAACAATGTGGAAAAAGCTAACGAAGAGGAACTGAAAAGCGAACTGGATGATAAAGAGGC
TGATACAAAAGAAGAACTGGCATCATTGCGAAACGAGGTGGCAGAAATGAAGGATCTCATA
AAACAGATGCATAAACAGCAAACAAAAAAGGGTTAATGACGGCGCGCCGCGGCCGCGAAT
TCGATATCATAATCAACCTCTGGATTACAAAATTTGTGAAAGATTGACTGGTATTCTTAACTA
TGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTAGTTCTTGCCACGGCGGAA
CTCATCGCCGCCTGCCTTGCCCGCTGCTGGACAGGGGCTCGGCTGTTGGGCACTGACAA
TTCCGTGGCTCGAGAGATCTTCGACTGTGCCTTCTAGTTGCCAGCCATCTGTTGTTTGCCC
CTCCCCCGTGCCTTCCTTGACCCTGGAAGGTGCCACTCCCACTGTCCTTTCCTAATAAAAT
GAGGAAATTGCATCGCATTGTCTGAGTAGGTGTCATTCTATTCTGGGGGGTGGGGTGGGG
CAGGACAGCAAGGGGGAGGATTGGGAAGACAATAGCAGGCATGAGATCTCACGTGCGGA
CCGAGCGGCCGCAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGGGGCGCCTGATGCGGTATTTTCTC
CTTACGCATCTGTGCGGTATTTCACACCGCATACGTCAAAGCAACCATAGTACGCGCCCTG
TAGCGGCGCATTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGCCACGTTCGCCGG
CTTTCCCCGTCAAGCTCTAAATCGGGGGCTCCCTTTAGGGTTCCGATTTAGTGCTTTACGG

FIG. 11, cont'd

CACCTCGACCCCAAAAAACTTGATTTGGGTGATGGTTCACGTAGTGGGCCATCGCCCTGAT
AGACGGTTTTTCGCCCTTTGACGTTGGAGTCCACGTTCTTTAATAGTGGACTCTTGTTCCAA
ACTGGAACAACACTCAACCCTATCTCGGGCTATTCTTTTGATTTATAAGGGATTTTGCCGAT
TTCGGCCTATTGGTTAAAAAATGAGCTGATTTAACAAAAATTTAACGCGAATTTTAACAAAAT
ATTAACGTTTACAATTTTATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTTTCA
CCGTCATCACCGAAACGCGCGAGACGAAAGGGCCTCGTGATACGCCTATTTTTATAGGTTA
ATGTCATGATAATAATGGTTTCTTAGACGTCAGGTGGCACTTTTCGGGGAAATGTGCGCGG
AACCCCTATTTGTTTATTTTTCTAAATACATTCAAATATGTATCCGCTCATGAGACAATAACC
CTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGAACTGGATCTCA
ACAGCGGTAAGATCCTTGAGAGTTTTCGCCCCGAAGAACGTTTTCCAATGATGAGCACTTT
TAAAGTTCTGCTATGTGGCGCGGTATTATCCCGTATTGACGCCGGGCAAGAGCAACTCGG
TCGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTTTGCA
CAACATGGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCGCAAACT
ATTAACTGGCGAACTACTTACTCTAGCTTCCCGGCAACAATTAATAGACTGGATGGAGGCG
GATAAAGTTGCAGGACCACTTCTGCGCTCGGCCCTTCCGGCTGGCTGGTTTATTGCTGATA
AATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAG
TTTACTCATATATACTTTAGATTGATTTAAAACTTCATTTTTAATTTAAAAGGATCTAGGTGAA
GATCCTTTTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGTAATCTGC
TGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTCCTTCT
AGTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTG
CACACAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGGTATCTTTAT
AGTCCTGTCGGGTTTCGCCACCTCTGACTTGAGCGTCGATTTTTGTGATGCTCGTCAGGGG
GGCGGAGCCTATGGAAAAACGCCAGCAACGCGGCCTTTTTACGGTTCCTGGCCTTTTGCT
GGCCTTTTGCTCACATGT (SEQ ID NO: 42)

CN2002 - The portion between L-ITR and R-ITR corresponds to positions 142-1993:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT

FIG. 11, cont'd

AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGAGCCGGAAGATCAGAGATCTTATC
GAATCTAAGAGATTTCAGAATGTTATTACCGCGATAATCGTACTCAACGGGGCGGTGCTCG
GTCTCCTCACCGATACCACATTGAGCGCTTCTAGCCAGAACCTGCTCGAAAGGGTTGACCA
ACTGTGCCTGACAATTTTTATCGTGGAAATTAGCTTGAAAATTTACGCCTACGGCGTTCGCG
GTTTTTTCCGGAGCGGTTGGAATCTTTTTGACTTCGTTATCGTTGCCATCGCGCTCATGCC
CGCACAGGGTTCTTTGTCTGTGTTGAGGACATTCCGAATATTTCGCGTGATGCGCTTGGTA
TCCGTGATCCCTACGATGCGCCGCGTCGTACAAGGAATGTTGCTGGCTCTCCCCGGCGTC
GGGAGCGTTGCTGCCCTCCTTACCGTGGTATTTTACATAGCGGCGGTTATGGCTACTAATC
TTTACGGAGCTACCTTCCCGGAGTGGTTCGGGGATTTGTCCAAGAGCCTCTATACATTGTT
TCAAGTTATGACCCTGGAGTCCTGGTCTATGGGCATTGTCCGGCCCGTAATGAACGTACAC
CCAAATGCGTGGGTGTTTTTCATTCCATTCATCATGCTGACTACCTTTACCGTGCTGAACTT
GTTCATTGGGATTATCGTGGATGCGATGGCCATCACTAAGGAGCAAGAAGAAGAGGCTAA
AACTGGCCACCACCAAGAGCCAATTTCTCAAACCCTCTTGCATCTCGGGGACCGACTGGA
CCGCATTGAGAAGCAACTCGCGCAGAACAATGAGCTGTTGCAGCGACAGCAACCTCAAAA
AAAATAATGACGGCGCGCCGCGGCCGCGAATTCGATATCATAATCAACCTCTGGATTACAA
AATTTGTGAAAGATTGACTGGTATTCTTAACTATGTTGCTCCTTTTACGCTATGTGGATACG
CTGCTTTAATGCCTTTGTATCATGCTATTGCTTCCCGTATGGCTTTCATTTTCTCCTCCTTGT
ATAAATCCTGGTTAGTTCTTGCCACGGCGGAACTCATCGCCGCCTGCCTTGCCCGCTGCT
GGACAGGGGCTCGGCTGTTGGGCACTGACAATTCCGTGGCTCGAGAGATCTTCGACTGTG
CCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGAGATCTCACGTGCGGACCGAGCGGCCGCAGGAACCCCTAGTGAT
GGAGTTGGCCACTCCCTCTCTGCGCGCTCGCTCGCTCACTGAGGCCGGGCGACCAAAGG
TCGCCCGACGCCCGGGCTTTGCCCGGGCGGCCTCAGTGAGCGAGCGAGCGCGCAGCTG
CCTGCAGGGGCGCCTGATGCGGTATTTTCTCCTTACGCATCTGTGCGGTATTTCACACCGC
ATACGTCAAAGCAACCATAGTACGCGCCCTGTAGCGGCGCATTAAGCGCGGCGGGTGTG
GTGGTTACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTTGGG
TGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGG
CTATTCTTTTGATTTATAAGGGATTTTGCCGATTTCGGCCTATTGGTTAAAAAATGAGCTGAT
TTAACAAAAATTTAACGCGAATTTTAACAAAATATTAACGTTTACAATTTTATGGTGCACTCT
CAGTACAATCTGCTCTGATGCCGCATAGTTAAGCCAGCCCCGACACCCGCCAACACCCGC
TGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAAAAG
GAAGAGTATGAGTATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCG

FIG. 11, cont'd

GAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACAC
GACGGGGAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATTGATTTAA
ACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCT
TCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGT (SEQ ID NO: 43)

CN2003 - The portion between L-ITR and R-ITR corresponds to positions 142-2056:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGTCTACGTCCCTTTTGAATGCGCCT
ACCGGCCTTCAAGCTAGAGTCATTAATCTCGTCGAACAAAACTGGTTTGGACACTTTATACT
GACTCTCATACTCATTAATGCTGTGCAGCTTGGAATGGAAACTAGCGCCAGCCTCATGGCA
CAATATGGCGCGCTGCTTATGTCCTTGAATAAGGTCCTTCTCTCTGTGTTCGTGGTCGAAC
TGCTGCTCCGGATTTATGCGTATCGGGGCAAGTTTTTTAAGGACCCGTGGAATGTGTTTGA
CTTCACTGTTATTGTTATTGCTCTGATTCCTGCATCTGGCCCATTGGCTGTCCTCCGCTCCC
TCCGAGTTCTCCGCGTCTTGAGGGTTCTGACGATTGTCCCCAGCATGAAAAGAGTAGTGTC
AGCACTGCTTGGGAGCTTGCCCGGGTTGGCCTCCATTGCAACCGTGCTTCTGTTGATCTAT
TACGTTTTCGCTGTGATCGCCACTAAAATTTTCGGGGATGCTTTTCCGGAATGGTTCGGGA
CGATAGCGGACTCCTTCTATACCCTTTTTCAAATTATGACCTTGGAAAGTTGGTCTATGGGG
ATCTCTAGGCCAGTGATGGAGGTGTACCCTTACGCTTGGGTATTCTTTGTGCCCTTTATTCT
TGTTGCTACTTTTACCATGCTTAACCTTTTCATCGCCATCATAGTGAATACTATGCAGACATT
CTCTGACGAGGAACATGCTCTGGAGCGAGAGCAAGATAAACAGATCTTGGAACAGGAGCA
GAGACAAATGCACGAGGAACTGAAGGCCATTCGACTCGAGCTTCAGCAACTCCAAACCCT
TTTGCGAAATGCGGCTGGGGACTCCTCCAATGTCTCCACAAAGGGCAATATCGGCTCAGA
CTAATGACGGCGCGCCGCGGCCGCGAATTCGATATCATAATCAACCTCTGGATTACAAAAT

FIG. 11, cont'd

TTGTGAAAGATTGACTGGTATTCTTAACTATGTTGCTCCTTTTACGCTATGTGGATACGCTG
CTTTAATGCCTTTGTATCATGCTATTGCTTCCCGTATGGCTTTCATTTTCTCCTCCTTGTATA
AATCCTGGTTAGTTCTTGCCACGGCGGAACTCATCGCCGCCTGCCTTGCCCGCTGCTGGA
CAGGGGCTCGGCTGTTGGGCACTGACAATTCCGTGGCTCGAGAGATCTTCGACTGTGCCT
TCTAGTTGCCAGCCATCTGTTGTTTGCCCCTCCCCCGTGCCTTCCTTGACCCTGGAAGGTG
CCACTCCCACTGTCCTTTCCTAATAAAATGAGGAAATTGCATCGCATTGTCTGAGTAGGTGT
CATTCTATTCTGGGGGGTGGGGTGGGGCAGGACAGCAAGGGGGAGGATTGGGAAGACAA
TAGCAGGCATGAGATCTCACGTGCGGACCGAGCGGCCGCAGGAACCCCTAGTGATGGAG
TTGGCCACTCCCTCTCTGCGCGCTCGCTCGCTCACTGAGGCCGGGCGACCAAAGGTCGC
CCGACGCCCGGGCTTTGCCCGGGCGGCCTCAGTGAGCGAGCGAGCGCGCAGCTGCCTG
CAGGGGCGCCTGATGCGGTATTTTCTCCTTACGCATCTGTGCGGTATTTCACACCGCATAC
GTCAAAGCAACCATAGTACGCGCCCTGTAGCGGCGCATTAAGCGCGGCGGGTGTGGTGG
TTACGCGCAGCGTGACCGCTACACTTGCCAGCGCCCTAGCGCCCGCTCCTTTCGCTTTCT
TCCCTTCCTTTCTCGCCACGTTCGCCGGCTTTCCCCGTCAAGCTCTAAATCGGGGGCTCCC
TTTAGGGTTCCGATTTAGTGCTTTACGGCACCTCGACCCCAAAAAACTTGATTTGGGTGAT
GGTTCACGTAGTGGGCCATCGCCCTGATAGACGGTTTTTCGCCCTTTGACGTTGGAGTCC
ACGTTCTTTAATAGTGGACTCTTGTTCCAAACTGGAACAACACTCAACCCTATCTCGGGCTA
TTCTTTTGATTTATAAGGGATTTTGCCGATTTCGGCCTATTGGTTAAAAAATGAGCTGATTTA
ACAAAAATTTAACGCGAATTTTAACAAAATATTAACGTTTACAATTTTATGGTGCACTCTCAG
TACAATCTGCTCTGATGCCGCATAGTTAAGCCAGCCCCGACACCCGCCAACACCCGCTGA
CGCGCCCTGACGGGCTTGTCTGCTCCCGGCATCCGCTTACAGACAAGCTGTGACCGTCTC
CGGGAGCTGCATGTGTCAGAGGTTTTCACCGTCATCACCGAAACGCGCGAGACGAAAGGG
CCTCGTGATACGCCTATTTTTATAGGTTAATGTCATGATAATAATGGTTTCTTAGACGTCAG
GTGGCACTTTTCGGGGAAATGTGCGCGGAACCCCTATTTGTTTATTTTTCTAAATACATTCA
AATATGTATCCGCTCATGAGACAATAACCCTGATAAATGCTTCAATAATATTGAAAAAGGAA
GAGTATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGGGTGC
ACGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCCC
GTATTGACGCCGGGCAAGAGCAACTCGGTCGCCGCATACACTATTCTCAGAATGACTTGG
TTGAGTACTCACCAGTCACAGAAAAGCATCTTACGGATGGCATGACAGTAAGAGAATTATG
CAGTGCTGCCATAACCATGAGTGATAACACTGCGGCCAACTTACTTCTGACAACGATCGGA
GGACCGAAGGAGCTAACCGCTTTTTTGCACAACATGGGGGATCATGTAACTCGCCTTGATC
GTTGGGAACCGGAGCTGAATGAAGCCATACCAAACGACGAGCGTGACACCACGATGCCTG
TAGCAATGGCAACAACGTTGCGCAAACTATTAACTGGCGAACTACTTACTCTAGCTTCCCG
GCAACAATTAATAGACTGGATGGAGGCGGATAAAGTTGCAGGACCACTTCTGCGCTCGGC
CCTTCCGGCTGGCTGGTTTATTGCTGATAAATCTGGAGCCGGTGAGCGTGGGTCTCGCGG
TATCATTGCAGCACTGGGGCCAGATGGTAAGCCCTCCCGTATCGTAGTTATCTACACGACG
GGGAGTCAGGCAACTATGGATGAACGAAATAGACAGATCGCTGAGATAGGTGCCTCACTG
ATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCT
TAACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCAGC
GGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGA
ACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCA
GCGGTCGGGCTGAACGGGGGGTTCGTGCACACAGCCCAGCTTGGAGCGAACGACCTACA
CCGAACTGAGATACCTACAGCGTGAGCTATGAGAAAGCGCCACGCTTCCCGAAGGGAGAA

FIG. 11, cont'd

AGGCGGACAGGTATCCGGTAAGCGGCAGGGTCGGAACAGGAGAGCGCACGAGGGAGCT
TCCAGGGGGAAACGCCTGGTATCTTTATAGTCCTGTCGGGTTTCGCCACCTCTGACTTGAG
CGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGT (SEQ ID NO: 44)

CN1504 - The portion between L-ITR and R-ITR corresponds to positions 142-4489:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGTCGACACAATTGGAGGTAGGCGTGTACGGTGGGAGGCCTATATA
AGCAGAGCTCGTTTAGTGAACCGTCAGATCGCCTGGAGGATCCTTCGAAAAGCTTGCTAC
CGGTGCCACCATGGTCAGCAAGGGCGAGGAGCTGTTCACCGGGGTGGTGCCCATCCTGG
TCGAGCTGGACGGCGACGTCAATGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAAGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGGCAGCGGCGCCACCAACTTCAGCCTGCTGAAGCAGGCCGGCGACG
TGGAGGAGAACCCCGGCCCCGGAACTAGTGGTATGGAGCAAACAGTGCTTGTACCACCAG
GACCTGACAGCTTCAACTTCTTCACCAGAGAATCTCTTGCGGCTATTGAAAGACGCATTGC
AGAAGAAAAGGCAAAGAATCCCAAACCAGACAAAAAAGATGACGACGAAAATGGCCCAAA
GCCAAATAGTGACTTGGAAGCTGGAAAGAACCTTCCATTTATTTATGGAGACATTCCTCCA
GAGATGGTGTCAGAGCCCCTGGAGGACCTGGACCCCTACTATATCAATAAGAAAACTTTTA
TAGTATTGAATAAAGGGAAGGCCATCTTCCGGTTCAGTGCCACCTCTGCCCTGTACATTTT
AACTCCCTTCAATCCTCTTAGGAAAATAGCTATTAAGATTTTGGTACATTCATTATTCAGCAT
GCTAATTATGTGCACTATTTTGACAAACTGTGTGTTTATGACAATGAGTAACCCTCCTGATT
GGACAAAGAATGTAGAATACACCTTCACAGGAATATATACTTTTGAATCACTTATAAAAATTA
TTGCAAGGGGATTCTGTTTAGAAGATTTTACTTTCCTTCGGGATCCATGGAACTGGCTCGAT
TTCACTGTCATTACATTTGCGTACGTCACAGAGTTTGTGGACCTGGGCAATGTCTCGGCAT
TGAGAACATTCAGAGTTCTCCGAGCATTGAAGACGATTTCAGTCATTCCAGGCCTGAAAAC
CATTGTGGGAGCCCTGATCCAGTCTGTGAAGAAGCTCTCAGATGTAATGATCCTGACTGTG
TTCTGTCTGAGCGTATTTGCTCTAATTGGGCTGCAGCTGTTCATGGGCAACCTGAGGAATA
AATGTATACAATGGCCTCCCACCAATGCTTCCTTGGAGGAACATAGTATAGAAAAGAATATA
ACTGTGAATTATAATGGTACACTTATAAATGAAACTGTCTTTGAGTTTGACTGGAAGTCATAT
ATTCAAGATTCAAGATATCATTATTTCCTGGAGGGTTTTTTAGATGCACTACTATGTGGAAAT
AGCTCTGATGCAGGCCAATGTCCAGAGGGATATATGTGTGTGAAAGCTGGTAGAAATCCCA
ATTATGGCTACACAAGCTTTGATACCTTCAGTTGGGCTTTTTTGTCCTTGTTTCGACTAATG

FIG. 11, cont'd

ACTCAGGACTTCTGGGAAAATCTTTATCAACTGACATTACGTGCTGCTGGGAAAACGTACA
TGATATTTTTTGTATTGGTCATTTTCTTGGGCTCATTCTACCTAATAAATTTGATCCTGGCTG
TGGTGGCCATGGCCTACGAGGAACAGAATCAGGCCACCTTGGAAGAAGCAGAACAGAAAG
AGGCCGAATTTCAGCAGATGATTGAACAGCTTAAAAAGCAACAGGAGGCAGCTCAGCAGG
CAGCAACGGCAACTGCCTCAGAACATTCCAGAGAGCCCAGTGCAGCAGGCAGGCTCTCAG
ACAGCTCATCTGAAGCCTCTAAGTTGAGTTCCAAGAGTGCTAAGGAAAGAAGAAATCGGAG
GAAGAAAAGAAAACAGAAAGAGCAGTCTGGTGGGGAAGAGAAAGATGAGGATGAATTCCA
AAAATCTGAATCTGAGGACAGCATCAGGAGGAAAGGTTTTCGCTTCTCCATTGAAGGGAAC
CGATTGACATATGAAAAGAGGTACTCCTCCCCACACCAGTCTTTGTTGAGCATCCGTGGCT
CCCTATTTTCACCAAGGCGAAATAGCAGAACAAGCCTTTTCAGCTTTAGAGGGCGAGCAAA
GGATGTGGGATCTGAGAACGACTTCGCAGATGATGAGCACAGCACCTTTGAGGATAACGA
GAGCCGTAGAGATTCCTTGTTTGTGCCCCGACGACACGGAGAGAGACGCAACAGCAACCT
GAGTCAGACCAGTAGGTCATCCCGGATGCTGGCAGTGTTTCCAGCGAATGGGAAGATGCA
CAGCACTGTGGATTGCAATGGTGTGGTTTCCTTGGTTGGTGGACCTTCAGTTCCTACATCG
CCTGTTGGACAGCTTCTGCCAGAGGTGATAATAGATAAGCCAGCTACTGATGACAATGGAA
CAACCACTGAAACTGAAATGAGAAAGAGAAGGTCAAGTTCTTTCCACGTTTCCATGGACTTT
CTAGAAGATCCTTCCCAAAGGCAACGAGCAATGAGTATAGCCAGCATTCTAACAAATACAG
TAGAAGAACTTGAAGAATCCAGGCAGAAATGCCCACCCTGTTGGTATAAATTTTCCAACATA
TTCTTAATCTGGGACTGTTCTCCATATTGGTTAAAAGTGAAACATGTTGTCAACCTGGTTGT
GATGGACCCATTTGTTGACCTGGCCATCACCATCTGTATTGTCTTAAATACTCTTTTCATGG
CCATGGAGCACTATCCAATGACGGACCATTTCAATAATGTGCTTACAGTAGGAAACTTGGT
TTTCACTGGGATCTTTACAGCAGAAATGTTTCTGAAAATTATTGCCATGGATCCTTACTATTA
TTTCCAAGAAGGCTGGAATATCTTTGACGGTTTTATTGTGACGCTTAGCCTGGTAGAACTTG
GACTCGCCAATGTGGAAGGATTATCTGTTCTCCGTTCATTTCGATTGCTGCGAGTTTTCAAG
TTGGCAAAATCTTGGCCAACGTTAAATATGCTAATAAAGATCATCGGCAATTCCGTGGGGG
CTCTGGGAAATTTAACCCTCGTCTTGGCCATCATCGTCTTCATTTTTGCCGTGGTCGGCAT
GCAGCTCTTTGGTAAAAGCTACAAAGATTGTGTCTGCAAGATCGCCAGTGATTGTCAACTC
CCACGCTGGCACATGAATGACTTCTTCCACTCCTTCCTGATTGTGTTCCGCGTGCTGTGTG
GGGAGTGGATAGAGACCATGTGGGACTGTATGGAGGTTGCTGGTCAAGCCATGTGCCTTA
CTGTCTTCATGATGGTCATGGTGATTGGAAACCTAGTGGTCCTGAATCTCTTTCTGGCCTT
GCTTCTGAGCTCATTTAGTGCAGACAACCTTGCAGCCACTGATGATGATAATGAAATGAATA
ATCTCCAAATTGCTGTGGATAGGATGCACAAAGGAGTAGCTTATGTGAAAAGAAAAATATAT
GAATTTATTCAACAGTCCTTCATTAGGAAACAAAAGATCTCACGTGCGGACCGAGCGGCCG
CAGGAACCCCTAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTCAGTGAGCG
AGCGAGCGCGCAGCTGCCTGCAGGGGCGCCTGATGCGGTATTTTCTCCTTACGCATCTGT
GCGGTATTTCACACCGCATACGTCAAAGCAACCATAGTACGCGCCCTGTAGCGGCGCATT
AAGCGCGGCGGGTGTGGTGGTTACGCGCAGCGTGACCGCTACACTTGCCAGCGCCCTAG
CGCCCGCTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACCTCGACCCC
AAAAAACTTGATTTGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAACAAC
ACTCAACCCTATCTCGGGCTATTCTTTTGATTTATAAGGGATTTTGCCGATTTCGGCCTATT
GGTTAAAAAATGAGCTGATTTAACAAAAATTTAACGCGAATTTTAACAAAATATTAACGTTTA
CAATTTTATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGCTTA
CAGACAAGCTGTGACCGTCTCCGGGAGCTGCATGTGTCAGAGGTTTTCACCGTCATCACC
GAAACGCGCGAGACGAAAGGGCCTCGTGATACGCCTATTTTTATAGGTTAATGTCATGATA
ATAATGGTTTCTTAGACGTCAGGTGGCACTTTTCGGGGAAATGTGCGCGGAACCCCTATTT

FIG. 11, cont'd

GTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAA
GATCCTTGAGAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTAACTGGC
GAACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAG
CCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGACCCCGTA
GAAAAGATCAAAGGATCTTCTTGAGATCCTTTTTTTCTGCGCGTAATCTGCTGCTTGCAAAC
AAAAAAACCACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAGTGTAGCCGT
AGTTAGGCCACCACTTCAAGAACTCTGTAGCACCGCCTACATACCTCGCTCTGCTAATCCT
GTTACCAGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTGCT
CACATGT (SEQ ID NO: 45)

CN1512 - The portion between L-ITR and R-ITR corresponds to positions 142-4165:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAGGTACCCTGGTAGAACTT
GGACTCGCCAATGTGGAAGGATTATCTGTTCTCCGTTCATTTCGATTGCTGCGAGTTTTCAA
GTTGGCAAAATCTTGGCCAACGTTAAATATGCTAATAAAGATCATCGGCAATTCCGTGGGG
GCTCTGGGAAATTTAACCCTCGTCTTGGCCATCATCGTCTTCATTTTTGCCGTGGTCGGCA
TGCAGCTCTTTGGTAAAAGCTACAAAGATTGTGTCTGCAAGATCGCCAGTGATTGTCAACT
CCCACGCTGGCACATGAATGACTTCTTCCACTCCTTCCTGATTGTGTTCCGCGTGCTGTGT
GGGGAGTGGATAGAGACCATGTGGGACTGTATGGAGGTTGCTGGTCAAGCCATGTGCCTT
ACTGTCTTCATGATGGTCATGGTGATTGGAAACCTAGTGGTCCTGAATCTCTTTCTGGCCTT
GCTTCTGAGCTCATTTAGTGCAGACAACCTTGCAGCCACTGATGATGATAATGAAATGAATA
ATCTCCAAATTGCTGTGGATAGGATGCACAAAGGAGTAGCTTATGTGAAAAGAAAAATATAT
GAATTTATTCAACAGTCCTTCATTAGGAAACAAAAGATTTTAGATGAAATTAAACCACTTGAT
GATCTAAACAACAAGAAAGACAGTTGTATGTCCAATCATACAGCAGAAATTGGGAAAGATCT
TGACTATCTTAAAGATGTAAATGGAACTACAAGTGGTATAGGAACTGGCAGCAGTGTTGAA
TACATTATTGATGAAAGTGATTACATGTCATTCATAAACAACCCCAGTCTTACTGTGACTGTA
CCAATTGCTGTAGGAGAATCTGACTTTGAAAATTTAAACACGGAAGACTTTAGTAGTGAATC

FIG. 11, cont'd

GGATCTGGAAGAAAGCAAAGAGAAACTGAATGAAAGCAGTAGCTCATCAGAAGGTAGCAC
TGTGGACATCGGCGCACCTGTAGAAGAACAGCCCGTAGTGGAACCTGAAGAAACTCTTGA
ACCAGAAGCTTGTTTCACTGAAGGCTGTGTACAAAGATTCAAGTGTTGTCAAATCAATGTG
GAAGAAGGCAGAGGAAAACAATGGTGGAACCTGAGAAGGACGTGTTTCCGAATAGTTGAA
CATAACTGGTTTGAGACCTTCATTGTTTTCATGATTCTCCTTAGTAGTGGTGCTCTGGCATT
TGAAGATATATATATTGATCAGCGAAAGACGATTAAGACGATGTTGGAATATGCTGACAAG
GTTTTCACTTACATTTTCATTCTGGAAATGCTTCTAAAATGGGTGGCATATGGCTATCAAAC
ATATTTCACCAATGCCTGGTGTTGGCTGGACTTCTTAATTGTTGATGTTTCATTGGTCAGTT
TAACAGCAAATGCCTTGGGTTACTCAGAACTTGGAGCCATCAAATCTCTCAGGACACTAAG
AGCTCTGAGACCTCTAAGAGCCTTATCTCGATTTGAAGGGATGAGGGTGGTTGTGAATGCC
CTTTTAGGAGCAATTCCATCCATCATGAATGTGCTTCTGGTTTGTCTTATATTCTGGCTAATT
TTCAGCATCATGGGCGTAAATTTGTTTGCTGGCAAATTCTACCACTGTATTAACACCACAAC
TGGTGACAGGTTTGACATCGAAGACGTGAATAATCATACTGATTGCCTAAAACTAATAGAAA
GAAATGAGACTGCTCGATGGAAAAATGTGAAAGTAAACTTTGATAATGTAGGATTTGGGTAT
CTCTCTTTGCTTCAAGTTGCCACATTCAAAGGATGGATGGATATAATGTATGCAGCAGTTGA
TTCCAGAAATGTGGAACTCCAGCCTAAGTATGAAGAAAGTCTGTACATGTATCTTTACTTTG
TTATTTTCATCATCTTTGGGTCCTTCTTCACCTTGAACCTGTTTATTGGTGTCATCATAGATA
ATTTCAACCAGCAGAAAAAGAAGTTTGGAGGTCAAGACATCTTTATGACAGAAGAACAGAA
GAAATACTATAATGCAATGAAAAAATTAGGATCGAAAAAACCGCAAAAGCCTATACCTCGAC
CAGGAAACAAATTTCAAGGAATGGTCTTTGACTTCGTAACCAGACAAGTTTTTGACATAAGC
ATCATGATTCTCATCTGTCTTAACATGGTCACAATGATGGTGGAAACAGATGACCAGAGTG
AATATGTGACTACCATTTTGTCACGCATCAATCTGGTGTTCATTGTGCTATTTACTGGAGAG
TGTGTACTGAAACTCATCTCTCTACGCCATTATTATTTTACCATTGGATGGAATATTTTTGAT
TTTGTGGTTGTCATTCTCTCCATTGTAGGTATGTTTCTTGCCGAGCTGATAGAAAAGTATTT
CGTGTCCCCTACCCTGTTCCGAGTGATCCGTCTTGCTAGGATTGGCCGAATCCTACGTCTG
ATCAAAGGAGCAAAGGGGATCCGCACGCTGCTCTTTGCTTTGATGATGTCCCTTCCTGCGT
TGTTTAACATCGGCCTCCTACTCTTCCTAGTCATGTTCATCTACGCCATCTTTGGGATGTCC
AACTTTGCCTATGTTAAGAGGGAAGTTGGGATCGATGACATGTTCAACTTTGAGACCTTTG
GCAACAGCATGATCTGCCTATTCCAAATTACAACCTCTGCTGGCTGGGATGGATTGCTAGC
ACCCATTCTCAACAGTAAGCCACCCGACTGTGACCCTAATAAAGTTAACCCTGGAAGCTCA
GTTAAGGGAGACTGTGGGAACCCATCTGTTGGAATTTTCTTTTTTGTCAGTTACATCATCAT
ATCCTTCCTGGTTGTGGTGAACATGTACATCGCGGTCATCCTGGAGAACTTCAGTGTTGCT
ACTGAAGAAAGTGCAGAGCCTCTGAGTGAGGATGACTTTGAGATGTTCTATGAGGTTTGGG
AGAAGTTTGATCCCGATGCAACTCAGTTCATGGAATTTGAAAAATTATCTCAGTTTGCAGCT
GCGCTTGAACCGCCTCTCAATCTGCCACAACCAAACAAACTCCAGCTCATTGCCATGGATT
TGCCCATGGTGAGTGGTGACCGGATCCACTGTCTTGATATCTTATTTGCTTTTACAAAGCG
GGTTCTAGGAGAGAGTGGAGAGATGGATGCTCTACGAATACAGATGGAAGAGCGATTCAT
GGCTTCCAATCCTTCCAAGGTCTCCTATCAGCCAATCACTACTACTTTAAAACGAAAACAAG
AGGAAGTATCTGCTGTCATTATTCAGCGTGCTTACAGACGCCACCTTTTAAAGCGAACTGT
AAAACAAGCTTCCTTTACGTACAATAAAAACAAAATCAAAGGTGGGGCTAATCTTCTTATAA
AAGAAGACATGATAATTGACAGAATAAATGAAAACTCTATTACAGAAAAAACTGATCTGACC
ATGTCCACTGCAGCTTGTCCACCTTCCTATGACCGGGTGACAAAGCCAATTGTGGAAAAAC
ATGAGCAAGAAGGCAAAGATGAAAAAGCCAAAGGGAAAGGAGGTGGTGGTTCAGGTGGG
GGCGGCTCAGAGTACCCCTATGATGTCCCTGATTATGCGGCGGAATACCCCTATGACGTG
CCGGACTACGCGGCTGAATATCCGTATGACGTTCCCGATTATGCGGCTAAGCTCGAATAAT
GATGAGAATTCATCATAATCAACCTCTGGATTACAAAATTTGTGAAAGATTGACTGGTATTC
TTAACTATGTTGCTCCTTTTACGCTATGTGGATACGCTGCTTTAATGCCTTTGTATCATGCTA
TTGCTTCCCGTATGGCTTTCATTTTCTCCTCCTTGTATAAATCCTGGTTAGTTCTTGCCACG
GCGGAACTCATCGCCGCCTGCCTTGCCCGCTGCTGGACAGGGGCTCGGCTGTTGGGCAC

FIG. 11, cont'd

TGACAATTCCGTGGCTCGAGAGATCTTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAA
TAAAATGAGGAAATTGCATCGCATTGTCTGAGTAGGTGTCATTCTATTCTGGGGGGTGGGG
TGGGGCAGGACAGCAAGGGGGAGGATTGGGAAGACAATAGCAGGCATGAGATCTCACGT
GCGGACCGAGCGGCCGCAGGAACCCCTAGTGATGGAGTTGGCCACTCCCTCTCTGCGCG
CTCGCTCGCTCACTGAGGCCGGGCGACCAAAGGTCGCCCGACGCCCGGGCTTTGCCCGG
GCGGCCTCAGTGAGCGAGCGAGCGCGCAGCTGCCTGCAGGGGCGCCTGATGCGGTATTT
TCTCCTTACGCATCTGTGCGGTATTTCACACCGCATACGTCAAAGCAACCATAGTACGCGC
CCTGTAGCGGCGCATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTTT
ACGGCACCTCGACCCCAAAAAACTTGATTTGGGTGATGGTTCACGTAGTGGGCCATCGCC
CTGATAGACGGTTTTTCGCCCTTTGACGTTGGAGTCCACGTTCTTTAATAGTGGACTCTTGT
TCCAAACTGGAACAACACTCAACCCTATCTCGGGCTATTCTTTTGATTTATAAGGGATTTTG
CCGATTTCGGCCTATTGGTTAAAAAATGAGCTGATTTAACAAAAATTTAACGCGAATTTTAA
CAAAATATTAACGTTTACAATTTTATGGTGCACTCTCAGTACAATCTGCTCTGATGCCGCAT
AGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGG
TTTTCACCGTCATCACCGAAACGCGCGAGACGAAAGGGCCTCGTGATACGCCTATTTTTAT
AGGTTAATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACG
CTGGTGAAAGTAAAAGATGCTGAAGATCAGTTGGGTGCACGAGTGGGTTACATCGAACTG
GATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAA
AAGCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTGCGC
AAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCA

FIG. 11, cont'd

GGGGGGCGGAGCCTATGGAAAAACGCCAGCAACGCGGCCTTTTTACGGTTCCTGGCCTTT
TGCTGGCCTTTTGCTCACATGT (SEQ ID NO: 46)

CN2004 - The portion between L-ITR and R-ITR corresponds to positions 142-3792:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTAATGGAGCAAACAGTGCTTGTACCACCAGGAC
CTGACAGCTTCAACTTCTTCACCAGAGAATCTCTTGCGGCTATTGAAAGACGCATTGCAGA
AGAAAAGGCAAAGAATCCCAAACCAGACAAAAAAGATGACGACGAAAATGGCCCAAAGCC
AAATAGTGACTTGGAAGCTGGAAAGAACCTTCCATTTATTTATGGAGACATTCCTCCAGAGA
TGGTGTCAGAGCCCCTGGAGGACCTGGACCCCTACTATATCAATAAGAAAACTTTTATAGT
ATTGAATAAAGGGAAGGCCATCTTCCGGTTCAGTGCCACCTCTGCCCTGTACATTTTAACT
CCCTTCAATCCTCTTAGGAAAATAGCTATTAAGATTTTGGTACATTCATTATTCAGCATGCTA
ATTATGTGCACTATTTTGACAAACTGTGTGTTTATGACAATGAGTAACCCTCCTGATTGGAC
AAAGAATGTAGAATACACCTTCACAGGAATATATACTTTTGAATCACTTATAAAAATTATTGC
AAGGGGATTCTGTTTAGAAGATTTTACTTTCCTTCGGGATCCATGGAACTGGCTCGATTTCA
CTGTCATTACATTTGCGTACGTCACAGAGTTTGTGGACCTGGGCAATGTCTCGGCATTGAG
AACATTCAGAGTTCTCCGAGCATTGAAGACGATTTCAGTCATTCCAGGCCTGAAAACCATT
GTGGGAGCCCTGATCCAGTCTGTGAAGAAGCTCTCAGATGTAATGATCCTGACTGTGTTCT
GTCTGAGCGTATTTGCTCTAATTGGGCTGCAGCTGTTCATGGGCAACCTGAGGAATAAATG
TATACAATGGCCTCCCACCAATGCTTCCTTGGAGGAACATAGTATAGAAAAGAATATAACTG
TGAATTATAATGGTACACTTATAAATGAAACTGTCTTTGAGTTTGACTGGAAGTCATATATTC
AAGATTCAAGATATCATTATTTCCTGGAGGGTTTTTTAGATGCACTACTATGTGGAAATAGC
TCTGATGCAGGCCAATGTCCAGAGGGATATATGTGTGTGAAAGCTGGTAGAAATCCCAATT
ATGGCTACACAAGCTTTGATACCTTCAGTTGGGCTTTTTTGTCCTTGTTTCGACTAATGACT
CAGGACTTCTGGGAAAATCTTTATCAACTGACATTACGTGCTGCTGGGAAAACGTACATGA
TATTTTTTGTATTGGTCATTTTCTTGGGCTCATTCTACCTAATAAATTTGATCCTGGCTGTGG
TGGCCATGGCCTACGAGGAACAGAATCAGGCCACCTTGGAAGAAGCAGAACAGAAAGAGG
CCGAATTTCAGCAGATGATTGAACAGCTTAAAAAGCAACAGGAGGCAGCTCAGCAGGCAG
CAACGGCAACTGCCTCAGAACATTCCAGAGAGCCCAGTGCAGCAGGCAGGCTCTCAGACA
GCTCATCTGAAGCCTCTAAGTTGAGTTCCAAGAGTGCTAAGGAAAGAAGAAATCGGAGGAA
GAAAAGAAAACAGAAAGAGCAGTCTGGTGGGGAAGAGAAAGATGAGGATGAATTCCAAAA
ATCTGAATCTGAGGACAGCATCAGGAGGAAAGGTTTTCGCTTCTCCATTGAAGGGAACCGA
TTGACATATGAAAAGAGGTACTCCTCCCCACACCAGTCTTTGTTGAGCATCCGTGGCTCCC
TATTTTCACCAAGGCGAAATAGCAGAACAAGCCTTTTCAGCTTTAGAGGGCGAGCAAAGGA
TGTGGGATCTGAGAACGACTTCGCAGATGATGAGCACAGCACCTTTGAGGATAACGAGAG
CCGTAGAGATTCCTTGTTTGTGCCCCGACGACACGGAGAGAGACGCAACAGCAACCTGAG
TCAGACCAGTAGGTCATCCCGGATGCTGGCAGTGTTTCCAGCGAATGGGAAGATGCACAG
CACTGTGGATTGCAATGGTGTGGTTTCCTTGGTTGGTGGACCTTCAGTTCCTACATCGCCT
GTTGGACAGCTTCTGCCAGAGGTGATAATAGATAAGCCAGCTACTGATGACAATGGAACAA
CCACTGAAACTGAAATGAGAAAGAGAAGGTCAAGTTCTTTCCACGTTTCCATGGACTTTCTA

FIG. 11, cont'd

GAAGATCCTTCCCAAAGGCAACGAGCAATGAGTATAGCCAGCATTCTAACAAATACAGTAG
AAGAACTTGAAGAATCCAGGCAGAAATGCCCACCCTGTTGGTATAAATTTTCCAACATATTC
TTAATCTGGGACTGTTCTCCATATTGGTTAAAAGTGAAACATGTTGTCAACCTGGTTGTGAT
GGACCCATTTGTTGACCTGGCCATCACCATCTGTATTGTCTTAAATACTCTTTTCATGGCCA
TGGAGCACTATCCAATGACGGACCATTTCAATAATGTGCTTACAGTAGGAAACTTGGTTTTC
ACTGGGATCTTTACAGCAGAAATGTTTCTGAAAATTATTGCCATGGATCCTTACTATTATTTC
CAAGAAGGCTGGAATATCTTTGACGGTTTTATTGTGACGCTTAGCCTGGTAGAACTTGGAC
TCGCCAATGTGGAAGGATTATCTGTTCTCCGTTCATTTCGATTGCTGCGAGTTTTCAAGTTG
GCAAAATCTTGGCCAACGTTAAATATGCTAATAAAGATCATCGGCAATTCCGTGGGGGCTC
TGGGAAATTTAACCCTCGTCTTGGCCATCATCGTCTTCATTTTTGCCGTGGTCGGCATGCA
GCTCTTTGGTAAAAGCTACAAAGATTGTGTCTGCAAGATCGCCAGTGATTGTCAACTCCCA
CGCTGGCACATGAATGACTTCTTCCACTCCTTCCTGATTGTGTTCCGCGTGCTGTGTGGGG
AGTGGATAGAGACCATGTGGGACTGTATGGAGGTTGCTGGTCAAGCCATGTGCCTTACTG
TCTTCATGATGGTCATGGTGATTGGAAACCTAGTGGTCCTGAATCTCTTTCTGGCCTTGCTT
CTGAGCTCATTTAGTGCAGACAACCTTGCAGCCACTGATGATGATAATGAAATGAATAATCT
CCAAATTGCTGTGGATAGGATGCACAAAGGAGTAGCTTATGTGAAAAGAAAAATATATGAAT
TTATTCAACAGTCCTTCATTAGGAAACAAAAGATCTGTGCGGACCGAGCGGCCGCAGGAAC
CCCTAGTGATGGAGTTGGCCACTCCCTCTCTGCGCGCTCGCTCGCTCACTGAGGCCGGG
CGACCAAAGGTCGCCCGACGCCCGGGCTTTGCCCGGGCGGCCTCAGTGAGCGAGCGAG
CGCGCAGCTGCCTGCAGGGGCGCCTGATGCGGTATTTTCTCCTTACGCATCTGTGCGGTA
TTTCACACCGCATACGTCAAAGCAACCATAGTACGCGCCCTGTAGCGGCGCATTAAGCGC
GGCGGGTGTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCAAGCTCTA
AATCGGGGGCTCCCTTTAGGGTTCCGATTTAGTGCTTTACGGCACCTCGACCCCAAAAAAC
TTGATTTGGGTGATGGTTCACGTAGTGGGCCATCGCCCTGATAGACGGTTTTTCGCCCTTT
GACGTTGGAGTCCACGTTCTTTAATAGTGGACTCTTGTTCCAAACTGGAACAACACTCAAC
CCTATCTCGGGCTATTCTTTTGATTTATAAGGGATTTTGCCGATTTCGGCCTATTGGTTAAA
AAATGAGCTGATTTAACAAAAATTTAACGCGAATTTTAACAAAATATTAACGTTTACAATTTTA
TGGTGCACTCTCAGTACAATCTGCTCTGATGCCGCATAGTTAAGCCAGCCCCGACACCCG
CCAACACCCGCTGACGCGCCCTGACGGGCTTGTCTGCTCCCGGCATCCGCTTACAGACAA
GCTGTGACCGTCTCCGGGAGCTGCATGTGTCAGAGGTTTTCACCGTCATCACCGAAACGC
GCGAGACGAAAGGGCCTCGTGATACGCCTATTTTTATAGGTTAATGTCATGATAATAATGG
TTTCTTAGACGTCAGGTGGCACTTTTCGGGGAAATGTGCGCGGAACCCCTATTTGTTTATTT
TTCTAAATACATTCAAATATGTATCCGCTCATGAGACAATAACCCTGATAAATGCTTCAATAA
TATTGAAAAAGGAAGAGTATGAGTATTCAACATTTCCGTGTCGCCCTTATTCCCTTTTTTGC
GGCATTTTGCCTTCCTGTTTTTGCTCACCCAGAAACGCTGGTGAAAGTAAAAGATGCTGAA
GATCAGTTGGGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTTCTGCTATGTG
GCGCGGTATTATCCCGTATTGACGCCGGGCAAGAGCAACTCGGTCGCCGCATACACTATT
CTCAGAATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACTTACTT
CTGACAACGATCGGAGGACCGAAGGAGCTAACCGCTTTTTTGCACAACATGGGGGATCAT
GTAACTCGCCTTGATCGTTGGGAACCGGAGCTGAATGAAGCCATACCAAACGACGAGCGT
GACACCACGATGCCTGTAGCAATGGCAACAACGTTGCGCAAACTATTAACTGGCGAACTAC
TTACTCTAGCTTCCCGGCAACAATTAATAGACTGGATGGAGGCGGATAAAGTTGCAGGACC
ACTTCTGCGCTCGGCCCTTCCGGCTGGCTGGTTTATTGCTGATAAATCTGGAGCCGGTGA
GCGTGGGTCTCGCGGTATCATTGCAGCACTGGGGCCAGATGGTAAGCCCTCCCGTATCGT
AGTTATCTACACGACGGGGAGTCAGGCAACTATGGATGAACGAAATAGACAGATCGCTGA
GATAGGTGCCTCACTGATTAAGCATTGGTAACTGTCAGACCAAGTTTACTCATATATACTTT

FIG. 11, cont'd

AGATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAG
GTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGC
TTCCCGAAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCTATGGAAA
AACGCCAGCAACGCGGCCTTTTTACGGTTCCTGGCCTTTTGCTGGCCTTTTGCTCACATGT
(SEQ ID NO: 47)

CN2005 - The portion between L-ITR and R-ITR corresponds to positions 142-4160:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAGGTACCCTGGTAGAACTT
GGACTCGCCAATGTGGAAGGATTATCTGTTCTCCGTTCATTTCGATTGCTGCGAGTTTTCAA
GTTGGCAAAATCTTGGCCAACGTTAAATATGCTAATAAAGATCATCGGCAATTCCGTGGGG
GCTCTGGGAAATTTAACCCTCGTCTTGGCCATCATCGTCTTCATTTTTGCCGTGGTCGGCA
TGCAGCTCTTTGGTAAAAGCTACAAAGATTGTGTCTGCAAGATCGCCAGTGATTGTCAACT
CCCACGCTGGCACATGAATGACTTCTTCCACTCCTTCCTGATTGTGTTCCGCGTGCTGTGT
GGGGAGTGGATAGAGACCATGTGGGACTGTATGGAGGTTGCTGGTCAAGCCATGTGCCTT
ACTGTCTTCATGATGGTCATGGTGATTGGAAACCTAGTGGTCCTGAATCTCTTTCTGGCCTT
GCTTCTGAGCTCATTTAGTGCAGACAACCTTGCAGCCACTGATGATGATAATGAAATGAATA
ATCTCCAAATTGCTGTGGATAGGATGCACAAAGGAGTAGCTTATGTGAAAAGAAAAATATAT
GAATTTATTCAACAGTCCTTCATTAGGAAACAAAAGATTTTAGATGAAATTAAACCACTTGAT
GATCTAAACAACAAGAAAGACAGTTGTATGTCCAATCATACAGCAGAAATTGGGAAAGATCT
TGACTATCTTAAAGATGTAAATGGAACTACAAGTGGTATAGGAACTGGCAGCAGTGTTGAA
TACATTATTGATGAAAGTGATTACATGTCATTCATAAACAACCCCAGTCTTACTGTGACTGTA
CCAATTGCTGTAGGAGAATCTGACTTTGAAAATTTAAACACGGAAGACTTTAGTAGTGAATC
GGATCTGGAAGAAAGCAAAGAGAAACTGAATGAAAGCAGTAGCTCATCAGAAGGTAGCAC
TGTGGACATCGGCGCACCTGTAGAAGAACAGCCCGTAGTGGAACCTGAAGAAACTCTTGA
ACCAGAAGCTTGTTTCACTGAAGGCTGTGTACAAAGATTCAAGTGTTGTCAAATCAATGTG
GAAGAAGGCAGAGGAAAACAATGGTGGAACCTGAGAAGGACGTGTTTCCGAATAGTTGAA
CATAACTGGTTTGAGACCTTCATTGTTTTCATGATTCTCCTTAGTAGTGGTGCTCTGGCATT
TGAAGATATATATATTGATCAGCGAAAGACGATTAAGACGATGTTGGAATATGCTGACAAG
GTTTTCACTTACATTTTCATTCTGGAAATGCTTCTAAAATGGGTGGCATATGGCTATCAAAC
ATATTTCACCAATGCCTGGTGTTGGCTGGACTTCTTAATTGTTGATGTTTCATTGGTCAGTT
TAACAGCAAATGCCTTGGGTTACTCAGAACTTGGAGCCATCAAATCTCTCAGGACACTAAG
AGCTCTGAGACCTCTAAGAGCCTTATCTCGATTTGAAGGGATGAGGGTGGTTGTGAATGCC
CTTTTAGGAGCAATTCCATCCATCATGAATGTGCTTCTGGTTTGTCTTATATTCTGGCTAATT
TTCAGCATCATGGGCGTAAATTTGTTTGCTGGCAAATTCTACCACTGTATTAACACCACAAC
TGGTGACAGGTTTGACATCGAAGACGTGAATAATCATACTGATTGCCTAAAACTAATAGAAA
GAAATGAGACTGCTCGATGGAAAAATGTGAAAGTAAACTTTGATAATGTAGGATTTGGGTAT
CTCTCTTTGCTTCAAGTTGCCACATTCAAAGGATGGATGGATATAATGTATGCAGCAGTTGA
TTCCAGAAATGTGGAACTCCAGCCTAAGTATGAAGAAAGTCTGTACATGTATCTTTACTTTG

FIG. 11, cont'd

TTATTTTCATCATCTTTGGGTCCTTCTTCACCTTGAACCTGTTTATTGGTGTCATCATAGATA
ATTTCAACCAGCAGAAAAAGAAGTTTGGAGGTCAAGACATCTTTATGACAGAAGAACAGAA
GAAATACTATAATGCAATGAAAAAATTAGGATCGAAAAAACCGCAAAAGCCTATACCTCGAC
CAGGAAACAAATTTCAAGGAATGGTCTTTGACTTCGTAACCAGACAAGTTTTTGACATAAGC
ATCATGATTCTCATCTGTCTTAACATGGTCACAATGATGGTGGAAACAGATGACCAGAGTG
AATATGTGACTACCATTTTGTCACGCATCAATCTGGTGTTCATTGTGCTATTTACTGGAGAG
TGTGTACTGAAACTCATCTCTCTACGCCATTATTATTTTACCATTGGATGGAATATTTTTGAT
TTTGTGGTTGTCATTCTCTCCATTGTAGGTATGTTTCTTGCCGAGCTGATAGAAAAGTATTT
CGTGTCCCCTACCCTGTTCCGAGTGATCCGTCTTGCTAGGATTGGCCGAATCCTACGTCTG
ATCAAAGGAGCAAAGGGGATCCGCACGCTGCTCTTTGCTTTGATGATGTCCCTTCCTGCGT
TGTTTAACATCGGCCTCCTACTCTTCCTAGTCATGTTCATCTACGCCATCTTTGGGATGTCC
AACTTTGCCTATGTTAAGAGGGAAGTTGGGATCGATGACATGTTCAACTTTGAGACCTTTG
GCAACAGCATGATCTGCCTATTCCAAATTACAACCTCTGCTGGCTGGGATGGATTGCTAGC
ACCCATTCTCAACAGTAAGCCACCCGACTGTGACCCTAATAAAGTTAACCCTGGAAGCTCA
GTTAAGGGAGACTGTGGGAACCCATCTGTTGGAATTTTCTTTTTTGTCAGTTACATCATCAT
ATCCTTCCTGGTTGTGGTGAACATGTACATCGCGGTCATCCTGGAGAACTTCAGTGTTGCT
ACTGAAGAAAGTGCAGAGCCTCTGAGTGAGGATGACTTTGAGATGTTCTATGAGGTTTGGG
AGAAGTTTGATCCCGATGCAACTCAGTTCATGGAATTTGAAAAATTATCTCAGTTTGCAGCT
GCGCTTGAACCGCCTCTCAATCTGCCACAACCAAACAAACTCCAGCTCATTGCCATGGATT
TGCCCATGGTGAGTGGTGACCGGATCCACTGTCTTGATATCTTATTTGCTTTTACAAAGCG
GGTTCTAGGAGAGAGTGGAGAGATGGATGCTCTACGAATACAGATGGAAGAGCGATTCAT
GGCTTCCAATCCTTCCAAGGTCTCCTATCAGCCAATCACTACTACTTTAAAACGAAAACAAG
AGGAAGTATCTGCTGTCATTATTCAGCGTGCTTACAGACGCCACCTTTTAAAGCGAACTGT
AAAACAAGCTTCCTTTACGTACAATAAAAACAAAATCAAAGGTGGGGCTAATCTTCTTATAA
AAGAAGACATGATAATTGACAGAATAAATGAAAACTCTATTACAGAAAAAACTGATCTGACC
ATGTCCACTGCAGCTTGTCCACCTTCCTATGACCGGGTGACAAAGCCAATTGTGGAAAAAC
ATGAGCAAGAAGGCAAAGATGAAAAAGCCAAAGGGAAATAATGACATCATAATCAACCTCT
GGATTACAAAATTTGTGAAAGATTGACTGGTATTCTTAACTATGTTGCTCCTTTTACGCTATG
TGGATACGCTGCTTTAATGCCTTTGTATCATGCTATTGCTTCCCGTATGGCTTTCATTTTCTC
CTCCTTGTATAAATCCTGGTTAGTTCTTGCCACGGCGGAACTCATCGCCGCCTGCCTTGCC
CGCTGCTGGACAGGGGCTCGGCTGTTGGGCACTGACAATTCCGTGGCTCGAGAGATCTTC
GACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGAT
TGGGAAGACAATAGCAGGCATGAGATCTCACGTGCGGACCGAGCGGCCGCAGGAACCCC
TAGTGATGGAGTTGGCCACTCCCTCTCTGCGCGCTCGCTCGCTCACTGAGGCCGGGCGA
CCAAAGGTCGCCCGACGCCCGGGCTTTGCCCGGGCGGCCTCAGTGAGCGAGCGAGCGC
GCAGCTGCCTGCAGGGGCGCCTGATGCGGTATTTTCTCCTTACGCATCTGTGCGGTATTT
CACACCGCATACGTCAAAGCAACCATAGTACGCGCCCTGTAGCGGCGCATTAAGCGCGGC
GGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAAT
CGGGGGCTCCCTTTAGGGTTCCGATTTAGTGCTTTACGGCACCTCGACCCCAAAAAACTTG
ATTTGGGTGATGGTTCACGTAGTGGGCCATCGCCCTGATAGACGGTTTTTCGCCCTTTGAC
GTTGGAGTCCACGTTCTTTAATAGTGGACTCTTGTTCCAAACTGGAACAACACTCAACCCTA
TCTCGGGCTATTCTTTTGATTTATAAGGGATTTTGCCGATTTCGGCCTATTGGTTAAAAAAT
GAGCTGATTTAACAAAAATTTAACGCGAATTTTAACAAAATATTAACGTTTACAATTTTATGG
TGCACTCTCAGTACAATCTGCTCTGATGCCGCATAGTTAAGCCAGCCCCGACACCCGCCAA
CACCCGCTGACGCGCCCTGACGGGCTTGTCTGCTCCCGGCATCCGCTTACAGACAAGCTG
TGACCGTCTCCGGGAGCTGCATGTGTCAGAGGTTTTCACCGTCATCACCGAAACGCGCGA

FIG. 11, cont'd

GACGAAAGGGCCTCGTGATACGCCTATTTTTATAGGTTAATGTCATGATAATAATGGTTTCT
TAGACGTCAGGTGGCACTTTTCGGGGAAATGTGCGCGGAACCCCTATTTGTTTATTTTTCT
AAATACATTCAAATATGTATCCGCTCATGAGACAATAACCCTGATAAATGCTTCAATAATATT
GAAAAAGGAAGAGTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGATGCTGAAGATCA
GTTGGGTGCACGAGTGGGTTACATCGAACTGGATCTCAACAGCGGTAAGATCCTTGAGAG
TTTTCGCCCCGAAGAACGTTTTCCAATGATGAGCACTTTTAAAGTTCTGCTATGTGGCGCG
GTATTATCCCGTATTGACGCCGGGCAAGAGCAACTCGGTCGCCGCATACACTATTCTCAGA
ATGACTTGGTTGAGTACTCACCAGTCACAGAAAAGCATCTTACGGATGGCATGACAGTAAG
AGAATTATGCAGTGCTGCCATAACCATGAGTGATAACACTGCGGCCAACTTACTTCTGACA
ACGATCGGAGGACCGAAGGAGCTAACCGCTTTTTTGCACAACATGGGGGATCATGTAACT
CGCCTTGATCGTTGGGAACCGGAGCTGAATGAAGCCATACCAAACGACGAGCGTGACACC
ACGATGCCTGTAGCAATGGCAACAACGTTGCGCAAACTATTAACTGGCGAACTACTTACTC
TAGCTTCCCGGCAACAATTAATAGACTGGATGGAGGCGGATAAAGTTGCAGGACCACTTCT
GCGCTCGGCCCTTCCGGCTGGCTGGTTTATTGCTGATAAATCTGGAGCCGGTGAGCGTGG
GTCTCGCGGTATCATTGCAGCACTGGGGCCAGATGGTAAGCCCTCCCGTATCGTAGTTAT
CTACACGACGGGGAGTCAGGCAACTATGGATGAACGAAATAGACAGATCGCTGAGATAGG
TGCCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTCATGA
CCAAAATCCCTTAACGTGAGTTTTCGTTCCACTGAGCGTCAGACCCCGTAGAAAAGATCAA
AGGATCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGGTAAC
TGGCTTCAGCAGAGCGCAGATACCAAATACTGTCCTTCTAGTGTAGCCGTAGTTAGGCCAC
CACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGA
ACGACCTACACCGAACTGAGATACCTACAGCGTGAGCTATGAGAAAGCGCCACGCTTCCC
GAAGGGAGAAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGGTTTCGCCACC
TCTGACTTGAGCGTCGATTTTTGTGATGCTCGTCAGGGGGGCGGAGCCTATGGAAAAACG
CCAGCAACGCGGCCTTTTTACGGTTCCTGGCCTTTTGCTGGCCTTTTGCTCACATGT (SEQ ID NO: 48)

CN2006 - The portion between L-ITR and R-ITR corresponds to positions 142-4790:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGTCGACACAATTGGAGGTAGGCGTGTACGGTGGGAGGCCTATATA
AGCAGAGCTCGTTTAGTGAACCGTCAGATCGCCTGGAGGATCCTTCGAAAAGCTTGCTAC
CGGTGCCACCATGGTCAGCAAGGGCGAGGAGCTGTTCACCGGGGTGGTGCCCATCCTGG
TCGAGCTGGACGGCGACGTCAATGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC

FIG. 11, cont'd

CGACCACATGAAGCAGCACGACTTCTTCAAGTCCGCCATGCCCGAAGGCTACGTCCAGGA
GCGCACCATCTTCTTCAAAGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAAGGCAGCGGCGCCACCAACTTCAGCCTGCTGAAGCAGGCCGGCGACG
TGGAGGAGAACCCCGGCCCCGGAACTAGTGGTATGGAGCAAACAGTGCTTGTACCACCAG
GACCTGACAGCTTCAACTTCTTCACCAGAGAATCTCTTGCGGCTATTGAAAGACGCATTGC
AGAAGAAAAGGCAAAGAATCCCAAACCAGACAAAAAAGATGACGACGAAAATGGCCCAAA
GCCAAATAGTGACTTGGAAGCTGGAAAGAACCTTCCATTTATTTATGGAGACATTCCTCCA
GAGATGGTGTCAGAGCCCCTGGAGGACCTGGACCCCTACTATATCAATAAGAAAACTTTTA
TAGTATTGAATAAAGGGAAGGCCATCTTCCGGTTCAGTGCCACCTCTGCCCTGTACATTTT
AACTCCCTTCAATCCTCTTAGGAAAATAGCTATTAAGATTTTGGTACATTCATTATTCAGCAT
GCTAATTATGTGCACTATTTTGACAAACTGTGTGTTTATGACAATGAGTAACCCTCCTGATT
GGACAAAGAATGTAGAATACACCTTCACAGGAATATATACTTTTGAATCACTTATAAAAATTA
TTGCAAGGGGATTCTGTTTAGAAGATTTTACTTTCCTTCGGGATCCATGGAACTGGCTCGAT
TTCACTGTCATTACATTTGCGTACGTCACAGAGTTTGTGGACCTGGGCAATGTCTCGGCAT
TGAGAACATTCAGAGTTCTCCGAGCATTGAAGACGATTTCAGTCATTCCAGGCCTGAAAAC
CATTGTGGGAGCCCTGATCCAGTCTGTGAAGAAGCTCTCAGATGTAATGATCCTGACTGTG
TTCTGTCTGAGCGTATTTGCTCTAATTGGGCTGCAGCTGTTCATGGGCAACCTGAGGAATA
AATGTATACAATGGCCTCCCACCAATGCTTCCTTGGAGGAACATAGTATAGAAAAGAATATA
ACTGTGAATTATAATGGTACACTTATAAATGAAACTGTCTTTGAGTTTGACTGGAAGTCATAT
ATTCAAGATTCAAGATATCATTATTTCCTGGAGGGTTTTTTAGATGCACTACTATGTGGAAAT
AGCTCTGATGCAGGCCAATGTCCAGAGGGATATATGTGTGTGAAAGCTGGTAGAAATCCCA
ATTATGGCTACACAAGCTTTGATACCTTCAGTTGGGCTTTTTTGTCCTTGTTTCGACTAATG
ACTCAGGACTTCTGGGAAAATCTTTATCAACTGACATTACGTGCTGCTGGAAAACGTACA
TGATATTTTTTGTATTGGTCATTTTCTTGGGCTCATTCTACCTAATAAATTTGATCCTGGCTG
TGGTGGCCATGGCCTACGAGGAACAGAATCAGGCCACCTTGGAAGAAGCAGAACAGAAAG
AGGCCGAATTTCAGCAGATGATTGAACAGCTTAAAAAGCAACAGGAGGCAGCTCAGCAGG
CAGCAACGGCAACTGCCTCAGAACATTCCAGAGAGCCCAGTGCAGCAGGCAGGCTCTCAG
ACAGCTCATCTGAAGCCTCTAAGTTGAGTTCCAAGAGTGCTAAGGAAAGAAGAAATCGGAG
GAAGAAAAGAAAACAGAAAGAGCAGTCTGGTGGGGAAGAGAAAGATGAGGATGAATTCCA
AAAATCTGAATCTGAGGACAGCATCAGGAGGAAAGGTTTTCGCTTCTCCATTGAAGGGAAC
CGATTGACATATGAAAAGAGGTACTCCTCCCCACACCAGTCTTTGTTGAGCATCCGTGGCT
CCCTATTTTCACCAAGGCGAAATAGCAGAACAAGCCTTTTCAGCTTTAGAGGGCGAGCAAA
GGATGTGGGATCTGAGAACGACTTCGCAGATGATGAGCACAGCACCTTTGAGGATAACGA
GAGCCGTAGAGATTCCTTGTTTGTGCCCCGACGACACGGAGAGAGACGCAACAGCAACCT
GAGTCAGACCAGTAGGTCATCCCGGATGCTGGCAGTGTTTCCAGCGAATGGGAAGATGCA
CAGCACTGTGGATTGCAATGGTGTGGTTTCCTTGGTTGGTGGACCTTCAGTTCCTACATCG
CCTGTTGGACAGCTTCTGCCAGAGGTGATAATAGATAAGCCAGCTACTGATGACAATGGAA
CAACCACTGAAACTGAAATGAGAAAGAGAAGGTCAAGTTCTTTCCACGTTTCCATGGACTTT
CTAGAAGATCCTTCCCAAAGGCAACGAGCAATGAGTATAGCCAGCATTCTAACAAATACAG
TAGAAGAACTTGAAGAATCCAGGCAGAAATGCCCACCCTGTTGGTATAAATTTTCCAACATA
TTCTTAATCTGGGACTGTTCTCCATATTGGTTAAAAGTGAAACATGTTGTCAACCTGGTTGT
GATGGACCCATTTGTTGACCTGGCCATCACCATCTGTATTGTCTTAAATACTCTTTTCATGG
CCATGGAGCACTATCCAATGACGGACCATTTCAATAATGTGCTTACAGTAGGAAACTTGGT

FIG. 11, cont'd

TTTCACTGGGATCTTTACAGCAGAAATGTTTCTGAAAATTATTGCCATGGATCCTTACTATTA
TTTCCAAGAAGGCTGGAATATCTTTGACGGTTTTATTGTGACGCTTAGCCTGGTAGAACTTG
GACTCGCCAATGTGGAAGGATTATCTGTTCTCCGTTCATTTCGATTGCTGCGAGTTTTCAAG
TTGGCAAAATCTTGGCCAACGTTAAATATGCTAATAAAGATCATCGGCAATTCCGTGGGGG
CTCTGGGAAATTTAACCCTCGTCTTGGCCATCATCGTCTTCATTTTTGCCGTGGTCGTGAGT
TTGGGGACCCTTGATTGTTCTTTCTTTTTCGCTATTGTAAAATTCATGTTATATGGAGGGGG
CAAAGTTTTCAGGGTGTTGTTTAGAATGGGAAGATGTCCCTTGTATCACCATGGACCCTCA
TGATAATTTTGTTTCTTTCACTTTCTACTCTGTTGACAACCATTGTCTCCTCTTATTTTCTTTT
CATTTTCTGTAACTTTTTCGTTAAACTTTAGCTTGCATTTGTAACGAATTTTTAAATTCACTTT
TGTTTATTTGTCAGATTGTAAGTACTTTCTCTAATCACTTTTTTTTCAAGGCAATCAGGGTAT
ATTATATTGTACTTCAGCACAGTTTTAGAGAACAATTGTTATAATTAAATGATAAGGTAGAAT
ATTTCTGCATATAAATTCTGGCTGGCGTGGAAATATTCTTATTGGTAGAAACAACTACACCC
TGGTCATCATCCTGCCTTTCTCTTTATGGTTACAATGATATACACTGTTTGAGATGAGGATA
AAATACTCTGAGTCCAAACCGGGCCCCTCTGCTAACCATGTTCATGCCTTCTTCTCTTTCCT
ACTCACGTGCGGACCGAGCGGCCGCAGGAACCCCTAGTGATGGAGTTGGCCACTCCCTC
TCTGCGCGCTCGCTCGCTCACTGAGGCCGGGCGACCAAAGGTCGCCCGACGCCCGGGCT
TTGCCCGGGCGGCCTCAGTGAGCGAGCGAGCGCGCAGCTGCCTGCAGGGGCGCCTGAT
GCGGTATTTTCTCCTTACGCATCTGTGCGGTATTTCACACCGCATACGTCAAAGCAACCAT
AGTACGCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTTTCTCG
CCACGTTCGCCGGCTTTCCCCGTCAAGCTCTAAATCGGGGGCTCCCTTTAGGGTTCCGAT
TTAGTGCTTTACGGCACCTCGACCCCAAAAAACTTGATTTGGGTGATGGTTCACGTAGTGG
GCCATCGCCCTGATAGACGGTTTTTCGCCCTTTGACGTTGGAGTCCACGTTCTTTAATAGT
GGACTCTTGTTCCAAACTGGAACAACACTCAACCCTATCTCGGGCTATTCTTTTGATTTATA
AGGGATTTTGCCGATTTCGGCCTATTGGTTAAAAAATGAGCTGATTTAACAAAAATTTAACG
CGAATTTTAACAAAATATTAACGTTTACAATTTTATGGTGCACTCTCAGTACAATCTGCTCTG
ATGCCGCATAGTTAAGCCAGCCCCGACACCCGCCAACACCCGCTGACGCGCCCTGACGG
GCTTGTCTGCTCCCGGCATCCGCTTACAGACAAGCTGTGACCGTCTCCGGGAGCTGCATG
TGTCAGAGGTTTTCACCGTCATCACCGAAACGCGCGAGACGAAAGGGCCTCGTGATACGC
CTATTTTTATAGGTTAATGTCATGATAATAATGGTTTCTTAGACGTCAGGTGGCACTTTTCG
GGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATT
CAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTA
CATCGAACTGGATCTCAACAGCGGTAAGATCCTTGAGAGTTTTCGCCCCGAAGAACGTTTT
CCAATGATGAGCACTTTTAAAGTTCTGCTATGTGGCGCGGTATTATCCCGTATTGACGCCG
GGCAAGAGCAACTCGGTCGCCGCATACACTATTCTCAGAATGACTTGGTTGAGTACTCACC
AGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAATGGCAA
CAACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGG
TAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAGATCCTTTTTT

FIG. 11, cont'd

TCTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATAC
CAAATACTGTCCTTCTAGTGTAGCCGTAGTTAGGCCACCACTTCAAGAACTCTGTAGCACC
GCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGT (SEQ ID NO: 49)

CN2007 - The portion between L-ITR and R-ITR corresponds to positions 142-4671:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCAGAGTTTGGGGACCCTTGATTGTTCTTT
CTTTTTCGCTATTGTAAAATTCATGTTATATGGAGGGGGCAAAGTTTTCAGGGTGTTGTTTA
GAATGGGAAGATGTCCCTTGTATCACCATGGACCCTCATGATAATTTTGTTTCTTTCACTTT
CTACTCTGTTGACAACCATTGTCTCCTCTTATTTTCTTTTCATTTTCTGTAACTTTTTCGTTAA
ACTTTAGCTTGCATTTGTAACGAATTTTTAAATTCACTTTTGTTTATTTGTCAGATTGTAAGTA
CTTTCTCTAATCACTTTTTTTTCAAGGCAATCAGGGTATATTATATTGTACTTCAGCACAGTT
TTAGAGAACAATTGTTATAATTAAATGATAAGGTAGAATATTTCTGCATATAAATTCTGGCTG
GCGTGGAAATATTCTTATTGGTAGAAACAACTACACCCTGGTCATCATCCTGCCTTTCTCTT
TATGGTTACAATGATATACACTGTTTGAGATGAGGATAAAATACTCTGAGTCCAAACCGGGC
CCCTCTGCTAACCATGTTCATGCCTTCTTCTCTTTCCTACAGGGCATGCAGCTCTTTGGTAA
AAGCTACAAAGATTGTGTCTGCAAGATCGCCAGTGATTGTCAACTCCCACGCTGGCACATG
AATGACTTCTTCCACTCCTTCCTGATTGTGTTCCGCGTGCTGTGTGGGGAGTGGATAGAGA
CCATGTGGGACTGTATGGAGGTTGCTGGTCAAGCCATGTGCCTTACTGTCTTCATGATGGT
CATGGTGATTGGAAACCTAGTGGTCCTGAATCTCTTTCTGGCCTTGCTTCTGAGCTCATTTA
GTGCAGACAACCTTGCAGCCACTGATGATGATAATGAAATGAATAATCTCCAAATTGCTGT
GGATAGGATGCACAAAGGAGTAGCTTATGTGAAAAGAAAAATATATGAATTTATTCAACAGT
CCTTCATTAGGAAACAAAAGATTTTAGATGAAATTAAACCACTTGATGATCTAAACAACAAG
AAAGACAGTTGTATGTCCAATCATACAGCAGAAATTGGGAAAGATCTTGACTATCTTAAAGA
TGTAAATGGAACTACAAGTGGTATAGGAACTGGCAGCAGTGTTGAATACATTATTGATGAAA
GTGATTACATGTCATTCATAAACAACCCCAGTCTTACTGTGACTGTACCAATTGCTGTAGGA
GAATCTGACTTTGAAAATTTAAACACGGAAGACTTTAGTAGTGAATCGGATCTGGAAGAAAG
CAAAGAGAAACTGAATGAAAGCAGTAGCTCATCAGAAGGTAGCACTGTGGACATCGGCGC
ACCTGTAGAAGAACAGCCCGTAGTGGAACCTGAAGAAACTCTTGAACCAGAAGCTTGTTTC
ACTGAAGGCTGTGTACAAAGATTCAAGTGTTGTCAAATCAATGTGGAAGAAGGCAGAGGAA
AACAATGGTGGAACCTGAGAAGGACGTGTTTCCGAATAGTTGAACATAACTGGTTTGAGAC
CTTCATTGTTTTCATGATTCTCCTTAGTAGTGGTGCTCTGGCATTTGAAGATATATATATTGA
TCAGCGAAAGACGATTAAGACGATGTTGGAATATGCTGACAAGGTTTTCACTTACATTTTCA
TTCTGGAAATGCTTCTAAAATGGGTGGCATATGGCTATCAAACATATTTCACCAATGCCTGG
TGTTGGCTGGACTTCTTAATTGTTGATGTTTCATTGGTCAGTTTAACAGCAAATGCCTTGGG
TTACTCAGAACTTGGAGCCATCAAATCTCTCAGGACACTAAGAGCTCTGAGACCTCTAAGA
GCCTTATCTCGATTTGAAGGGATGAGGGTGGTTGTGAATGCCCTTTTAGGAGCAATTCCAT
CCATCATGAATGTGCTTCTGGTTTGTCTTATATTCTGGCTAATTTTCAGCATCATGGGCGTA
AATTTGTTTGCTGGCAAATTCTACCACTGTATTAACACCACAACTGGTGACAGGTTTGACAT
CGAAGACGTGAATAATCATACTGATTGCCTAAAACTAATAGAAAGAAATGAGACTGCTCGAT

FIG. 11, cont'd

GGAAAAATGTGAAAGTAAACTTTGATAATGTAGGATTTGGGTATCTCTCTTTGCTTCAAGTT
GCCACATTCAAAGGATGGATGGATATAATGTATGCAGCAGTTGATTCCAGAAATGTGGAAC
TCCAGCCTAAGTATGAAGAAAGTCTGTACATGTATCTTTACTTTGTTATTTTCATCATCTTTG
GGTCCTTCTTCACCTTGAACCTGTTTATTGGTGTCATCATAGATAATTTCAACCAGCAGAAA
AAGAAGTTTGGAGGTCAAGACATCTTTATGACAGAAGAACAGAAGAAATACTATAATGCAAT
GAAAAAATTAGGATCGAAAAAACCGCAAAAGCCTATACCTCGACCAGGAAACAAATTTCAA
GGAATGGTCTTTGACTTCGTAACCAGACAAGTTTTTGACATAAGCATCATGATTCTCATCTG
TCTTAACATGGTCACAATGATGGTGGAAACAGATGACCAGAGTGAATATGTGACTACCATTT
TGTCACGCATCAATCTGGTGTTCATTGTGCTATTTACTGGAGAGTGTGTACTGAAACTCATC
TCTCTACGCCATTATTATTTTACCATTGGATGGAATATTTTTGATTTTGTGGTTGTCATTCTC
TCCATTGTAGGTATGTTTCTTGCCGAGCTGATAGAAAAGTATTTCGTGTCCCCTACCCTGTT
CCGAGTGATCCGTCTTGCTAGGATTGGCCGAATCCTACGTCTGATCAAAGGAGCAAAGGG
GATCCGCACGCTGCTCTTTGCTTTGATGATGTCCCTTCCTGCGTTGTTTAACATCGGCCTC
CTACTCTTCCTAGTCATGTTCATCTACGCCATCTTTGGGATGTCCAACTTTGCCTATGTTAA
GAGGGAAGTTGGGATCGATGACATGTTCAACTTTGAGACCTTTGGCAACAGCATGATCTGC
CTATTCCAAATTACAACCTCTGCTGGCTGGGATGGATTGCTAGCACCCATTCTCAACAGTA
AGCCACCCGACTGTGACCCTAATAAAGTTAACCCTGGAAGCTCAGTTAAGGGAGACTGTG
GGAACCCATCTGTTGGAATTTTCTTTTTTGTCAGTTACATCATCATATCCTTCCTGGTTGTG
GTGAACATGTACATCGCGGTCATCCTGGAGAACTTCAGTGTTGCTACTGAAGAAAGTGCAG
AGCCTCTGAGTGAGGATGACTTTGAGATGTTCTATGAGGTTTGGGAGAAGTTTGATCCCGA
TGCAACTCAGTTCATGGAATTTGAAAAATTATCTCAGTTTGCAGCTGCGCTTGAACCGCCTC
TCAATCTGCCACAACCAAACAAACTCCAGCTCATTGCCATGGATTTGCCCATGGTGAGTGG
TGACCGGATCCACTGTCTTGATATCTTATTTGCTTTTACAAAGCGGGTTCTAGGAGAGAGT
GGAGAGATGGATGCTCTACGAATACAGATGGAAGAGCGATTCATGGCTTCCAATCCTTCCA
AGGTCTCCTATCAGCCAATCACTACTACTTTAAAACGAAAACAAGAGGAAGTATCTGCTGTC
ATTATTCAGCGTGCTTACAGACGCCACCTTTTAAAGCGAACTGTAAAACAAGCTTCCTTTAC
GTACAATAAAAACAAAATCAAAGGTGGGGCTAATCTTCTTATAAAAGAAGACATGATAATTG
ACAGAATAAATGAAAACTCTATTACAGAAAAAACTGATCTGACCATGTCCACTGCAGCTTGT
CCACCTTCCTATGACCGGGTGACAAAGCCAATTGTGGAAAAACATGAGCAAGAAGGCAAA
GATGAAAAAGCCAAAGGGAAAGGAGGTGGTGGTTCAGGTGGGGGCGGCTCAGAGTACCC
CTATGATGTCCCTGATTATGCGGCGGAATACCCCTATGACGTGCCGGACTACGCGGCTGA
ATATCCGTATGACGTTCCCGATTATGCGGCTAAGCTCGAATAATGATGAGAATTCATCATAA
TCAACCTCTGGATTACAAAATTTGTGAAAGATTGACTGGTATTCTTAACTATGTTGCTCCTTT
TACGCTATGTGGATACGCTGCTTTAATGCCTTTGTATCATGCTATTGCTTCCCGTATGGCTT
TCATTTTCTCCTCCTTGTATAAATCCTGGTTAGTTCTTGCCACGGCGGAACTCATCGCCGCC
TGCCTTGCCCGCTGCTGGACAGGGGCTCGGCTGTTGGGCACTGACAATTCCGTGGCTCG
AGAGATCTTCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCAT
CGCATTGTCTGAGTAGGTGTCATTCTATTCTGGGGGGTGGGGTGGGGCAGGACAGCAAG
GGGGAGGATTGGGAAGACAATAGCAGGCATGAGATCTCACGTGCGGACCGAGCGGCCGC
AGGAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGCTGCCTGCAGGGGCGCCTGATGCGGTATTTTCTCCTTACGCATCTGTG
CGGTATTTCACACCGCATACGTCAAAGCAACCATAGTACGCGCCCTGTAGCGGCGCATTAA
GCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAG
CTCTAAATCGGGGGCTCCCTTTAGGGTTCCGATTTAGTGCTTTACGGCACCTCGACCCCAA
AAAACTTGATTTGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGGAACAACACT

FIG. 11, cont'd

CAACCCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGTTTACAA
TTTTATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATCACCGA
AACGCGCGAGACGAAAGGGCCTCGTGATACGCCTATTTTTATAGGTTAATGTCATGATAAT
AATGGTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAAATGCTT
CAATAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGTTCTGCTA
TGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCA
TGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGA
TCATGTAACTCGCCTTGATCGTTGGGAACCGGAGCTGAATGAAGCCATACCAAACGACGA
GCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCG
TATCGTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCATATAT
ACTTTAGATTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTAGTGTAGCCGTA
GTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCA
CATGT (SEQ ID NO: 50)

CN2008 - The portion between L-ITR and R-ITR corresponds to positions 142-3995:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGTCGACACAATTGGAGGTAGGCGTGTACGGTGGGAGGCCTATATA

FIG. 11, cont'd

AGCAGAGCTCGTTTAGTGAACCGTCAGATCGCCTGGAGGATCCTTCGAAAAGCTTGCTAC
CGGTGCCACCATGGAGCAAACAGTGCTTGTACCACCAGGACCTGACAGCTTCAACTTCTTC
ACCAGAGAATCTCTTGCGGCTATTGAAAGACGCATTGCAGAAGAAAAGGCAAAGAATCCCA
AACCAGACAAAAAAGATGACGACGAAAATGGCCCAAAGCCAAATAGTGACTTGGAAGCTG
GAAAGAACCTTCCATTTATTTATGGAGACATTCCTCCAGAGATGGTGTCAGAGCCCCTGGA
GGACCTGGACCCCTACTATATCAATAAGAAAACTTTTATAGTATTGAATAAAGGGAAGGCCA
TCTTCCGGTTCAGTGCCACCTCTGCCCTGTACATTTTAACTCCCTTCAATCCTCTTAGGAAA
ATAGCTATTAAGATTTTGGTACATTCATTATTCAGCATGCTAATTATGTGCACTATTTTGACA
AACTGTGTGTTTATGACAATGAGTAACCCTCCTGATTGGACAAAGAATGTAGAATACACCTT
CACAGGAATATATACTTTTGAATCACTTATAAAAATTATTGCAAGGGGATTCTGTTTAGAAGA
TTTTACTTTCCTTCGGGATCCATGGAACTGGCTCGATTTCACTGTCATTACATTTGCGTACG
TCACAGAGTTTGTGGACCTGGGCAATGTCTCGGCATTGAGAACATTCAGAGTTCTCCGAGC
ATTGAAGACGATTTCAGTCATTCCAGGCCTGAAAACCATTGTGGGAGCCCTGATCCAGTCT
GTGAAGAAGCTCTCAGATGTAATGATCCTGACTGTGTTCTGTCTGAGCGTATTTGCTCTAAT
TGGGCTGCAGCTGTTCATGGGCAACCTGAGGAATAAATGTATACAATGGCCTCCCACCAAT
GCTTCCTTGGAGGAACATAGTATAGAAAAGAATATAACTGTGAATTATAATGGTACACTTAT
AAATGAAACTGTCTTTGAGTTTGACTGGAAGTCATATATTCAAGATTCAAGATATCATTATTT
CCTGGAGGGTTTTTTAGATGCACTACTATGTGGAAATAGCTCTGATGCAGGCCAATGTCCA
GAGGGATATATGTGTGTGAAAGCTGGTAGAAATCCCAATTATGGCTACACAAGCTTTGATA
CCTTCAGTTGGGCTTTTTTGTCCTTGTTTCGACTAATGACTCAGGACTTCTGGGAAAATCTT
TATCAACTGACATTACGTGCTGCTGGGAAAACGTACATGATATTTTTTGTATTGGTCATTTTC
TTGGGCTCATTCTACCTAATAAATTTGATCCTGGCTGTGGTGGCCATGGCCTACGAGGAAC
AGAATCAGGCCACCTTGGAAGAAGCAGAACAGAAAGAGGCCGAATTTCAGCAGATGATTG
AACAGCTTAAAAAGCAACAGGAGGCAGCTCAGCAGGCAGCAACGGCAACTGCCTCAGAAC
ATTCCAGAGAGCCCAGTGCAGCAGGCAGGCTCTCAGACAGCTCATCTGAAGCCTCTAAGT
TGAGTTCCAAGAGTGCTAAGGAAAGAAGAAATCGGAGGAAGAAAAGAAAACAGAAAGAGC
AGTCTGGTGGGGAAGAGAAAGATGAGGATGAATTCCAAAAATCTGAATCTGAGGACAGCAT
CAGGAGGAAAGGTTTTCGCTTCTCCATTGAAGGGAACCGATTGACATATGAAAAGAGGTAC
TCCTCCCCACACCAGTCTTTGTTGAGCATCCGTGGCTCCCTATTTTCACCAAGGCGAAATA
GCAGAACAAGCCTTTTCAGCTTTAGAGGGCGAGCAAAGGATGTGGGATCTGAGAACGACT
TCGCAGATGATGAGCACAGCACCTTTGAGGATAACGAGAGCCGTAGAGATTCCTTGTTTGT
GCCCCGACGACACGGAGAGAGACGCAACAGCAACCTGAGTCAGACCAGTAGGTCATCCC
GGATGCTGGCAGTGTTTCCAGCGAATGGGAAGATGCACAGCACTGTGGATTGCAATGGTG
TGGTTTCCTTGGTTGGTGGACCTTCAGTTCCTACATCGCCTGTTGGACAGCTTCTGCCAGA
GGTGATAATAGATAAGCCAGCTACTGATGACAATGGAACAACCACTGAAACTGAAATGAGA
AAGAGAAGGTCAAGTTCTTTCCACGTTTCCATGGACTTTCTAGAAGATCCTTCCCAAAGGC
AACGAGCAATGAGTATAGCCAGCATTCTAACAAATACAGTAGAAGAACTTGAAGAATCCAG
GCAGAAATGCCCACCCTGTTGGTATAAATTTTCCAACATATTCTTAATCTGGGACTGTTCTC
CATATTGGTTAAAAGTGAAACATGTTGTCAACCTGGTTGTGATGGACCCATTTGTTGACCTG
GCCATCACCATCTGTATTGTCTTAAATACTCTTTTCATGGCCATGGAGCACTATCCAATGAC
GGACCATTTCAATAATGTGCTTACAGTAGGAAACTTGGTTTTCACTGGGATCTTTACAGCAG
AAATGTTTCTGAAAATTATTGCCATGGATCCTTACTATTATTTCCAAGAAGGCTGGAATATCT
TTGACGGTTTTATTGTGACGCTTAGCCTGGTAGAACTTGGACTCGCCAATGTGGAAGGATT
ATCTGTTCTCCGTTCATTTCGATTGCTGCGAGTTTTCAAGTTGGCAAAATCTTGGCCAACGT
TAAATATGCTAATAAAGATCATCGGCAATTCCGTGGGGGCTCTGGGAAATTTAACCCTCGT
CTTGGCCATCATCGTCTTCATTTTTGCCGTGGTCGTGAGTTTGGGGACCCTTGATTGTTCTT
TCTTTTTCGCTATTGTAAAATTCATGTTATATGGAGGGGGCAAAGTTTTCAGGGTGTTGTTT
AGAATGGGAAGATGTCCCTTGTATCACCATGGACCCTCATGATAATTTTGTTTCTTTCACTT
TCTACTCTGTTGACAACCATTGTCTCCTCTTATTTTCTTTTCATTTTCTGTAACTTTTTCGTTA

FIG. 11, cont'd

AACTTTAGCTTGCATTTGTAACGAATTTTTAAATTCACTTTTGTTTATTTGTCAGATTGTAAGT
ACTTTCTCTAATCACTTTTTTTTCAAGGCAATCAGGGTATATTATATTGTACTTCAGCACAGT
TTTAGAGAACAATTGTTATAATTAAATGATAAGGTAGAATATTTCTGCATATAAATTCTGGCT
GGCGTGGAAATATTCTTATTGGTAGAAACAACTACACCCTGGTCATCATCCTGCCTTTCTCT
TTATGGTTACAATGATATACACTGTTTGAGATGAGGATAAAATACTCTGAGTCCAAACCGGG
CCCCTCTGCTAACCATGTTCATGCCTTCTTCTCTTTCCTACTCACGTGCGGACCGAGCGGC
CGCAGGAACCCCTAGTGATGGAGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTGAG
CGAGCGAGCGCGCAGCTGCCTGCAGGGGCGCCTGATGCGGTATTTTCTCCTTACGCATCT
GTGCGGTATTTCACACCGCATACGTCAAAGCAACCATAGTACGCGCCCTGTAGCGGCGCA
TTAAGCGCGGCGGGTGTGGTGGTTACGCGCAGCGTGACCGCTACACTTGCCAGCGCCCT
AGCGCCCGCTCCTTTCGCTTTCTTCCCTTCCTTTCTCGCCACGTTCGCCGGCTTTCCCCGT
CAAGCTCTAAATCGGGGGCTCCCTTTAGGGTTCCGATTTAGTGCTTTACGGCACCTCGACC
CCAAAAAACTTGATTTGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAACAA
CACTCAACCCTATCTCGGGCTATTCTTTTGATTTATAAGGGATTTTGCCGATTTCGGCCTAT
TGGTTAAAAAATGAGCTGATTTAACAAAAATTTAACGCGAATTTTAACAAAATATTAACGTTT
ACAATTTTATGGTGCACTCTCAGTACAATCTGCTCTGATGCCGCATAGTTAAGCCAGCCCC
GACACCCGCCAACACCCGCTGACGCGCCCTGACGGGCTTGTCTGCTCCCGGCATCCGCT
TACAGACAAGCTGTGACCGTCTCCGGGAGCTGCATGTGTCAGAGGTTTTCACCGTCATCA
CCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATAAAT
GCTTCAATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGT
AAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTTACGGAT
GGCATGACAGTAAGAGAATTATGCAGTGCTGCCATAACCATGAGTGATAACACTGCGGCCA
ACTTACTTCTGACAACGATCGGAGGACCGAAGGAGCTAACCGCTTTTTTGCACAACATGGG
GGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGG
CGAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTT
TTGATAATCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAA
GCGCCACGCTTCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTTATAGTCCTGTC

FIG. 11, cont'd

GGGTTTCGCCACCTCTGACTTGAGCGTCGATTTTTGTGATGCTCGTCAGGGGGGCGGAGC
CTATGGAAAAACGCCAGCAACGCGGCCTTTTTACGGTTCCTGGCCTTTTGCTGGCCTTTTG
CTCACATGT (SEQ ID NO: 51)

CN2009 - The portion between L-ITR and R-ITR corresponds to positions 142-4525:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCAGAGTTTGGGGACCCTTGATTGTTCTTT
CTTTTTCGCTATTGTAAAATTCATGTTATATGGAGGGGGCAAAGTTTTCAGGGTGTTGTTTA
GAATGGGAAGATGTCCCTTGTATCACCATGGACCCTCATGATAATTTTGTTTCTTTCACTTT
CTACTCTGTTGACAACCATTGTCTCCTCTTATTTTCTTTTCATTTTCTGTAACTTTTTCGTTAA
ACTTTAGCTTGCATTTGTAACGAATTTTTAAATTCACTTTTGTTTATTTGTCAGATTGTAAGTA
CTTTCTCTAATCACTTTTTTTTCAAGGCAATCAGGGTATATTATATTGTACTTCAGCACAGTT
TTAGAGAACAATTGTTATAATTAAATGATAAGGTAGAATATTTCTGCATATAAATTCTGGCTG
GCGTGGAAATATTCTTATTGGTAGAAACAACTACACCCTGGTCATCATCCTGCCTTTCTCTT
TATGGTTACAATGATATACACTGTTTGAGATGAGGATAAAATACTCTGAGTCCAAACCGGGC
CCCTCTGCTAACCATGTTCATGCCTTCTTCTCTTTCCTACAGGGCATGCAGCTCTTTGGTAA
AAGCTACAAAGATTGTGTCTGCAAGATCGCCAGTGATTGTCAACTCCCACGCTGGCACATG
AATGACTTCTTCCACTCCTTCCTGATTGTGTTCCGCGTGCTGTGTGGGGAGTGGATAGAGA
CCATGTGGGACTGTATGGAGGTTGCTGGTCAAGCCATGTGCCTTACTGTCTTCATGATGGT
CATGGTGATTGGAAACCTAGTGGTCCTGAATCTCTTTCTGGCCTTGCTTCTGAGCTCATTTA
GTGCAGACAACCTTGCAGCCACTGATGATGATAATGAAATGAATAATCTCCAAATTGCTGT
GGATAGGATGCACAAAGGAGTAGCTTATGTGAAAAGAAAAATATATGAATTTATTCAACAGT
CCTTCATTAGGAAACAAAAGATTTTAGATGAAATTAAACCACTTGATGATCTAAACAACAAG
AAAGACAGTTGTATGTCCAATCATACAGCAGAAATTGGGAAAGATCTTGACTATCTTAAAGA
TGTAAATGGAACTACAAGTGGTATAGGAACTGGCAGCAGTGTTGAATACATTATTGATGAAA
GTGATTACATGTCATTCATAAACAACCCCAGTCTTACTGTGACTGTACCAATTGCTGTAGGA
GAATCTGACTTTGAAAATTTAAACACGGAAGACTTTAGTAGTGAATCGGATCTGGAAGAAAG
CAAAGAGAAACTGAATGAAAGCAGTAGCTCATCAGAAGGTAGCACTGTGGACATCGGCGC
ACCTGTAGAAGAACAGCCCGTAGTGGAACCTGAAGAAACTCTTGAACCAGAAGCTTGTTTC
ACTGAAGGCTGTGTACAAAGATTCAAGTGTTGTCAAATCAATGTGGAAGAAGGCAGAGGAA
AACAATGGTGGAACCTGAGAAGGACGTGTTTCCGAATAGTTGAACATAACTGGTTTGAGAC
CTTCATTGTTTTCATGATTCTCCTTAGTAGTGGTGCTCTGGCATTTGAAGATATATATATTGA
TCAGCGAAAGACGATTAAGACGATGTTGGAATATGCTGACAAGGTTTTCACTTACATTTTCA
TTCTGGAAATGCTTCTAAAATGGGTGGCATATGGCTATCAAACATATTTCACCAATGCCTGG
TGTTGGCTGGACTTCTTAATTGTTGATGTTTCATTGGTCAGTTTAACAGCAAATGCCTTGGG
TTACTCAGAACTTGGAGCCATCAAATCTCTCAGGACACTAAGAGCTCTGAGACCTCTAAGA
GCCTTATCTCGATTTGAAGGGATGAGGGTGGTTGTGAATGCCCTTTTAGGAGCAATTCCAT
CCATCATGAATGTGCTTCTGGTTTGTCTTATATTCTGGCTAATTTTCAGCATCATGGGCGTA
AATTTGTTTGCTGGCAAATTCTACCACTGTATTAACACCACAACTGGTGACAGGTTTGACAT
CGAAGACGTGAATAATCATACTGATTGCCTAAAACTAATAGAAAGAAATGAGACTGCTCGAT
GGAAAAATGTGAAAGTAAACTTTGATAATGTAGGATTTGGGTATCTCTCTTTGCTTCAAGTT
GCCACATTCAAAGGATGGATGGATATAATGTATGCAGCAGTTGATTCCAGAAATGTGGAAC
TCCAGCCTAAGTATGAAGAAAGTCTGTACATGTATCTTTACTTTGTTATTTTCATCATCTTTG
GGTCCTTCTTCACCTTGAACCTGTTTATTGGTGTCATCATAGATAATTTCAACCAGCAGAAA
AAGAAGTTTGGAGGTCAAGACATCTTTATGACAGAAGAACAGAAGAAATACTATAATGCAAT
GAAAAAATTAGGATCGAAAAAACCGCAAAAGCCTATACCTCGACCAGGAAACAAATTTCAA
GGAATGGTCTTTGACTTCGTAACCAGACAAGTTTTTGACATAAGCATCATGATTCTCATCTG
TCTTAACATGGTCACAATGATGGTGGAAACAGATGACCAGAGTGAATATGTGACTACCATTT

FIG. 11, cont'd

TGTCACGCATCAATCTGGTGTTCATTGTGCTATTTACTGGAGAGTGTGTACTGAAACTCATC
TCTCTACGCCATTATTATTTTACCATTGGATGGAATATTTTTGATTTTGTGGTTGTCATTCTC
TCCATTGTAGGTATGTTTCTTGCCGAGCTGATAGAAAAGTATTTCGTGTCCCCTACCCTGTT
CCGAGTGATCCGTCTTGCTAGGATTGGCCGAATCCTACGTCTGATCAAAGGAGCAAAGGG
GATCCGCACGCTGCTCTTTGCTTTGATGATGTCCCTTCCTGCGTTGTTTAACATCGGCCTC
CTACTCTTCCTAGTCATGTTCATCTACGCCATCTTTGGGATGTCCAACTTTGCCTATGTTAA
GAGGGAAGTTGGGATCGATGACATGTTCAACTTTGAGACCTTTGGCAACAGCATGATCTGC
CTATTCCAAATTACAACCTCTGCTGGCTGGGATGGATTGCTAGCACCCATTCTCAACAGTA
AGCCACCCGACTGTGACCCTAATAAAGTTAACCCTGGAAGCTCAGTTAAGGGAGACTGTG
GGAACCCATCTGTTGGAATTTTCTTTTTTGTCAGTTACATCATCATATCCTTCCTGGTTGTG
GTGAACATGTACATCGCGGTCATCCTGGAGAACTTCAGTGTTGCTACTGAAGAAAGTGCAG
AGCCTCTGAGTGAGGATGACTTTGAGATGTTCTATGAGGTTTGGGAGAAGTTTGATCCCGA
TGCAACTCAGTTCATGGAATTTGAAAAATTATCTCAGTTTGCAGCTGCGCTTGAACCGCCTC
TCAATCTGCCACAACCAAACAAACTCCAGCTCATTGCCATGGATTTGCCCATGGTGAGTGG
TGACCGGATCCACTGTCTTGATATCTTATTTGCTTTTACAAAGCGGGTTCTAGGAGAGAGT
GGAGAGATGGATGCTCTACGAATACAGATGGAAGAGCGATTCATGGCTTCCAATCCTTCCA
AGGTCTCCTATCAGCCAATCACTACTACTTTAAAACGAAAACAAGAGGAAGTATCTGCTGTC
ATTATTCAGCGTGCTTACAGACGCCACCTTTTAAAGCGAACTGTAAAACAAGCTTCCTTTAC
GTACAATAAAAACAAAATCAAAGGTGGGGCTAATCTTCTTATAAAAGAAGACATGATAATTG
ACAGAATAAATGAAAACTCTATTACAGAAAAAACTGATCTGACCATGTCCACTGCAGCTTGT
CCACCTTCCTATGACCGGGTGACAAAGCCAATTGTGGAAAAACATGAGCAAGAAGGCAAA
GATGAAAAAGCCAAAGGGAAATAATGACATCATAATCAACCTCTGGATTACAAAATTTGTGA
AAGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTAGTTCTTGCCACGGCGGAACTCATCGCCGCCTGCCTTGCCCGCTGCTGGACAGGGG
CTCGGCTGTTGGGCACTGACAATTCCGTGGCTCGAGAGATCTTCGACTGTGCCTTCTAGTT
GCCAGCCATCTGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGTAGGTGTCATTCT
ATTCTGGGGGGTGGGGTGGGGCAGGACAGCAAGGGGGAGGATTGGGAAGACAATAGCA
GGCATGAGATCTCACGTGCGGACCGAGCGGCCGCAGGAACCCCTAGTGATGGAGTTGGC
CACTCCCTCTCTGCGCGCTCGCTCGCTCACTGAGGCCGGGCGACCAAAGGTCGCCCGAC
GCCCGGGCTTTGCCCGGGCGGCCTCAGTGAGCGAGCGAGCGCGCAGCTGCCTGCAGGG
GCGCCTGATGCGGTATTTTCTCCTTACGCATCTGTGCGGTATTTCACACCGCATACGTCAA
AGCAACCATAGTACGCGCCCTGTAGCGGCGCATTAAGCGCGGCGGGTGTGGTGGTTACG
CGCAGCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTTGGGTGATGGTTC
ACGTAGTGGGCCATCGCCCTGATAGACGGTTTTTCGCCCTTTGACGTTGGAGTCCACGTTC
TTTAATAGTGGACTCTTGTTCCAAACTGGAACAACACTCAACCCTATCTCGGGCTATTCTTT
TGATTTATAAGGGATTTTGCCGATTTCGGCCTATTGGTTAAAAAATGAGCTGATTTAACAAA
AATTTAACGCGAATTTTAACAAAATATTAACGTTTACAATTTTATGGTGCACTCTCAGTACAA
TCTGCTCTGATGCCGCATAGTTAAGCCAGCCCCGACACCCGCCAACACCCGCTGACGCGC
CCTGACGGGCTTGTCTGCTCCCGGCATCCGCTTACAGACAAGCTGTGACCGTCTCCGGGA
GCTGCATGTGTCAGAGGTTTTCACCGTCATCACCGAAACGCGCGAGACGAAAGGGCCTCG
TGATACGCCTATTTTTATAGGTTAATGTCATGATAATAATGGTTTCTTAGACGTCAGGTGGC
ACTTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAGTAT
GAGTATTCAACATTTCCGTGTCGCCCTTATTCCCTTTTTTGCGGCATTTTGCCTTCCTGTTTT
TGCTCACCCAGAAACGCTGGTGAAAGTAAAAGATGCTGAAGATCAGTTGGGTGCACGAGT

FIG. 11, cont'd

GGGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTATTGA
CGCCGGGCAAGAGCAACTCGGTCGCCGCATACACTATTCTCAGAATGACTTGGTTGAGTA
CTCACCAGTCACAGAAAAGCATCTTACGGATGGCATGACAGTAAGAGAATTATGCAGTGCT
GCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGG
AACCGGAGCTGAATGAAGCCATACCAAACGACGAGCGTGACACCACGATGCCTGTAGCAA
TGGCAACAACGTTGCGCAAACTATTAACTGGCGAACTACTTACTCTAGCTTCCCGGCAACA
ATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCAT
TGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAG
CATTGGTAACTGTCAGACCAAGTTTACTCATATATACTTTAGATTGATTTAAAACTTCATTTTT
AATTTAAAAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGT
TTGTTTGCCGGATCAAGAGCTACCAACTCTTTTTCCGAAGGTAACTGGCTTCAGCAGAGCG
CAGATACCAAATACTGTCCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCG
ATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAA
CTGAGATACCTACAGCGTGAGCTATGAGAAAGCGCCACGCTTCCCGAAGGGAGAAAGGCG
GACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGA
TTTTTGTGATGCTCGTCAGGGGGGCGGAGCCTATGGAAAAACGCCAGCAACGCGGCCTTT
TTACGGTTCCTGGCCTTTTGCTGGCCTTTTGCTCACATGT (SEQ ID NO: 52)

AVV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE
WELQKENSKRWNPEIQYTSNYYKSNNVEFAVNTEGVYSEPRPIGTRYLTRNL (SEQ ID NO: 57)

FIG. 11, cont'd

CN2026-rAAV-3xhI56i(core)-minBG-hSCN1A_Fragment1-WPRE3-BGHpA:
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGGAGCAAACAGTGCTTGTACCACC
AGGACCTGACAGCTTCAACTTCTTCACCAGAGAATCTCTTGCGGCTATTGAAAGACGCATT
GCAGAAGAAAAGGCAAAGAATCCCAAACCAGACAAAAAAGATGACGACGAAAATGGCCCA
AAGCCAAATAGTGACTTGGAAGCTGGAAAGAACCTTCCATTTATTTATGGAGACATTCCTCC
AGAGATGGTGTCAGAGCCCCTGGAGGACCTGGACCCCTACTATATCAATAAGAAAACTTTT
ATAGTATTGAATAAAGGGAAGGCCATCTTCCGGTTCAGTGCCACCTCTGCCCTGTACATTT
TAACTCCCTTCAATCCTCTTAGGAAAATAGCTATTAAGATTTTGGTACATTCATTATTCAGCA
TGCTAATTATGTGCACTATTTTGACAAACTGTGTGTTTATGACAATGAGTAACCCTCCTGATT
GGACAAAGAATGTAGAATACACCTTCACAGGAATATATACTTTTGAATCACTTATAAAAATTA
TTGCAAGGGGATTCTGTTTAGAAGATTTTACTTTCCTTCGGGATCCATGGAACTGGCTCGAT
TTCACTGTCATTACATTTGCGTACGTCACAGAGTTTGTGGACCTGGGCAATGTCTCGGCAT
TGAGAACATTCAGAGTTCTCCGAGCATTGAAGACGATTTCAGTCATTCCAGGCCTGAAAAC
CATTGTGGGAGCCCTGATCCAGTCTGTGAAGAAGCTCTCAGATGTAATGATCCTGACTGTG
TTCTGTCTGAGCGTATTTGCTCTAATTGGGCTGCAGCTGTTCATGGGCAACCTGAGGAATA
AATGTATACAATGGCCTCCCACCAATGCTTCCTTGGAGGAACATAGTATAGAAAAGAATATA
ACTGTGAATTATAATGGTACACTTATAAATGAAACTGTCTTTGAGTTTGACTGGAAGTCATAT
ATTCAAGATTCAAGATATCATTATTTCCTGGAGGGTTTTTTAGATGCACTACTATGTGGAAAT
AGCTCTGATGCAGGCCAATGTCCAGAGGGATATATGTGTGTGAAAGCTGGTAGAAATCCCA
ATTATGGCTACACAAGCTTTGATACCTTCAGTTGGGCTTTTTTGTCCTTGTTTCGACTAATG
ACTCAGGACTTCTGGGAAAATCTTTATCAACTGACATTACGTGCTGCTGGGAAAACGTACA
TGATATTTTTTGTGTTGGTCATTTTCTTGGGCTCATTCTACCTAATAAATTTGATCCTGGCTG
TGGTGGCCATGGCCTACGAGGAACAGAATCAGGCCACCTTGGAAGAAGCAGAACAGAAAG
AGGCCGAATTTCAGCAGATGATTGAACAGCTTAAAAAGCAACAGGAGGCAGCTCAGCAGG
CAGCAACGGCAACTGCCTCAGAACATTCCAGAGAGCCCAGTGCAGCAGGCAGGCTCTCAG
ACAGCTCATCTGAAGCCTCTAAGTTGAGTTCCAAGAGTGCTAAGGAAAGAAGAAATCGGAG
GAAGAAAAGAAAACAGAAAGAGCAGTCTGGTGGGGAAGAGAAAGATGAGGATGAATTCCA
AAAATCTGAATCTGAGGACAGCATCAGGAGGAAAGGTTTTCGCTTCTCCATTGAAGGGAAC
CGATTGACATATGAAAAGAGGTACTCCTCCCCACACCAGTCTTTGTTGAGCATCCGTGGCT
CCCTATTTTCACCAAGGCGAAATAGCAGAACAAGCCTTTTCAGCTTTAGAGGGCGAGCAAA
GGATGTGGGATCTGAGAACGACTTCGCAGATGATGAGCACAGCACCTTTGAGGATAACGA
GAGCCGTAGAGATTCCTTGTTTGTGCCCCGACGACACGGAGAGAGACGCAACAGCAACCT
GAGTCAGACCAGTAGGTCATCCCGGTGATGACGGCGCGCCGCGGCCGCGAATTCGATAT
CATAATCAACCTCTGGATTACAAAATTTGTGAAAGATTGACTGGTATTCTTAACTATGTTGCT
CCTTTTACGCTATGTGGATACGCTGCTTTAATGCCTTTGTATCATGCTATTGCTTCCCGTAT
GGCTTTCATTTTCTCCTCCTTGTATAAATCCTGGTTAGTTCTTGCCACGGCGGAACTCATCG
CCGCCTGCCTTGCCCGCTGCTGGACAGGGGCTCGGCTGTTGGGCACTGACAATTCCGTG
GCTCGAGAGATCTTCGACTGTGCCTTCTAGTTGCCAGCCATCTGTTGTTTGCCCCTCCCCC
GTGCCTTCCTTGACCCTGGAAGGTGCCACTCCCACTGTCCTTTCCTAATAAAATGAGGAAA

FIG. 11, cont'd

TTGCATCGCATTGTCTGAGTAGGTGTCATTCTATTCTGGGGGGTGGGGTGGGGCAGGACA
GCAAGGGGGAGGATTGGGAAGACAATAGCAGGCATGAGATCTCACGTGCGGACCGAGCG
GCCGCAGGAACCCCTAGTGATGGAGTTGGCCACTCCCTCTCTGCGCGCTCGCTCGCTCAC
TGAGGCCGGGCGACCAAAGGTCGCCCGACGCCCGGGCTTTGCCCGGGCGGCCTCAGTG
AGCGAGCGAGCGCGCAGCTGCCTGCAGGGGCGCCTGATGCGGTATTTTCTCCTTACGCAT
CTGTGCGGTATTTCACACCGCATACGTCAAAGCAACCATAGTACGCGCCCTGTAGCGGCG
CATTAAGCGCGGCGGGTGTGGTGGTTACGCGCAGCGTGACCGCTACACTTGCCAGCGCC
CTAGCGCCCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGGCACCTCGA
CCCCAAAAAACTTGATTTGGGTGATGGTTCACGTAGTGGGCCATCGCCCTGATAGACGGTT
TTTCGCCCTTTGACGTTGGAGTCCACGTTCTTTAATAGTGGACTCTTGTTCCAAACTGGAAC
AACACTCAACCCTATCTCGGGCTATTCTTTTGATTTATAAGGGATTTTGCCGATTTCGGCCT
ATTGGTTAAAAAATGAGCTGATTTAACAAAAATTTAACGCGAATTTTAACAAAATATTAACGT
TTACAATTTTATGGTGCACTCTCAGTACAATCTGCTCTGATGCCGCATAGTTAAGCCAGCCC
CGACACCCGCCAACACCCGCTGACGCGCCCTGACGGGCTTGTCTGCTCCCGGCATCCGC
TTACAGACAAGCTGTGACCGTCTCCGGGAGCTGCATGTGTCAGAGGTTTTCACCGTCATCA
CCGAAACGCGCGAGACGAAAGGGCCTCGTGATACGCCTATTTTTATAGGTTAATGTCATGA
TAATAATGGTTTCTTAGACGTCAGGTGGCACTTTTCGGGGAAATGTGCGCGGAACCCCTAT
TTGTTTATTTTTCTAAATACATTCAAATATGTATCCGCTCATGAGACAATAACCCTGATAAAT
GCTTCAATAATATTGAAAAAGGAAGAGTATGAGTATTCAACATTTCCGTGTCGCCCTTATTC
CCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGT
AAGATCCTTGAGAGTTTTCGCCCCGAAGAACGTTTTCCAATGATGAGCACTTTTAAAGTTCT
GCTATGTGGCGCGGTATTATCCCGTATTGACGCCGGGCAAGAGCAACTCGGTCGCCGCAT
ACACTATTCTCAGAATGACTTGGTTGAGTACTCACCAGTCACAGAAAAGCATCTTACGGAT
GGCATGACAGTAAGAGAATTATGCAGTGCTGCCATAACCATGAGTGATAACACTGCGGCCA
ACTTACTTCTGACAACGATCGGAGGACCGAAGGAGCTAACCGCTTTTTTGCACAACATGGG
GGATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTGG
CGAACTACTTACTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGATAAATCTGGA
GCCGGTGAGCGTGGGTCTCGCGGTATCATTGCAGCACTGGGGCCAGATGGTAAGCCCTC
CCGTATCGTAGTTATCTACACGACGGGGAGTCAGGCAACTATGGATGAACGAAATAGACA
GATCGCTGAGATAGGTGCCTCACTGATTAAGCATTGGTAACTGTCAGACCAAGTTTACTCA
TATATACTTTAGATTGATTTAAAACTTCATTTTTAATTTAAAAGGATCTAGGTGAAGATCCTTT
TTGATAATCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCTT
TTTCCGAAGGTAACTGGCTTCAGCAGAGCGCAGATACCAAATACTGTCCTTCTAGTGTAGC
CGTAGTTAGGCCACCACTTCAAGAACTCTGTAGCACCGCCTACATACCTCGCTCTGCTAAT
CCTGTTACCAGTGGCTGCTGCCAGTGGCGATAAGTCGTGTCTTACCGGGTTGGACTCAAG
ACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAA
GCGCCACGCTTCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTTATAGTCCTGTC
GGGTTTCGCCACCTCTGACTTGAGCGTCGATTTTTGTGATGCTCGTCAGGGGGGCGGAGC
CTATGGAAAAACGCCAGCAACGCGGCCTTTTTACGGTTCCTGGCCTTTTGCTGGCCTTTTG
CTCACATGT (SEQ ID NO: 58)

FIG. 11, cont'd

CN2027-rAAV-3xhI56i(core)-minBG-hSCN1A_Fragment2-WPRE3-BGHpA
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGCTGGCAGTGTTTCCAGCGAATGG
GAAGATGCACAGCACTGTGGATTGCAATGGTGTGGTTTCCTTGGTTGGTGGACCTTCAGTT
CCTACATCGCCTGTTGGACAGCTTCTGCCAGAGGTGATAATAGATAAGCCAGCTACTGATG
ACAATGGAACAACCACTGAAACTGAAATGAGAAAGAGAAGGTCAAGTTCTTTCCACGTTTC
CATGGACTTTCTAGAAGATCCTTCCCAAAGGCAACGAGCAATGAGTATAGCCAGCATTCTA
ACAAATACAGTAGAAGAACTTGAAGAATCCAGGCAGAAATGCCCACCCTGTTGGTATAAAT
TTTCCAACATATTCTTAATCTGGGACTGTTCTCCATATTGGTTAAAAGTGAAACATGTTGTCA
ACCTGGTCGTGATGGACCCATTTGTTGACCTGGCCATCACCATCTGTATTGTCTTAAATACT
CTTTTCATGGCCATGGAGCACTATCCAATGACGGACCATTTCAATAATGTGCTTACAGTAG
GAAACTTGGTTTTCACTGGGATCTTTACAGCAGAAATGTTTCTGAAAATTATTGCCATGGAT
CCTTACTATTATTTCCAAGAAGGCTGGAATATCTTTGACGGTTTTATTGTGACGCTTAGCCT
GGTAGAACTTGGACTCGCCAATGTGGAAGGATTATCTGTTCTCCGTTCATTTCGATTGCTG
CGAGTTTTCAAGTTGGCAAAATCTTGGCCAACGTTAAATATGCTAATAAAGATCATCGGCAA
TTCCGTGGGGGCTCTGGGAAATTTAACCCTCGTCTTGGCCATCATCGTCTTCATTTTTGCC
GTGGTCGGCATGCAGCTCTTTGGTAAAAGCTACAAAGATTGTGTCTGCAAGATCGCCAGTG
ATTGTCAACTCCCACGCTGGCACATGAATGACTTCTTCCACTCCTTCCTGATTGTGTTCCGC
GTGCTGTGTGGGGAGTGGATAGAGACCATGTGGGACTGTATGGAGGTTGCTGGTCAAGCC
ATGTGCCTTACTGTCTTCATGATGGTCATGGTGATTGGAAACCTAGTGGTCCTGAATCTCTT
TCTGGCCTTGCTTCTGAGCTCATTTAGTGCAGACAACCTTGCAGCCACTGATGATGATAAT
GAAATGAATAATCTCCAAATTGCTGTGGATAGGATGCACAAAGGAGTAGCTTATGTGAAAA
GAAAAATATATGAATTTATTCAACAGTCCTTCATTAGGAAACAAAAGATTTTAGATGAAATTA
AACCACTTGATGATCTAAACAACAAGAAAGACAGTTGTTGATGACGGCGCGCCGCGGCCG
CGAATTCGATATCATAATCAACCTCTGGATTACAAAATTTGTGAAAGATTGACTGGTATTCTT
AACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTAGTTCTTGCCACGGC
GGAACTCATCGCCGCCTGCCTTGCCCGCTGCTGGACAGGGGCTCGGCTGTTGGGCACTG
ACAATTCCGTGGCTCGAGAGATCTTCGACTGTGCCTTCTAGTTGCCAGCCATCTGTTGTTT
GCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGAGATCTCACGTGC
GGACCGAGCGGCCGCAGGAACCCCTAGTGATGGAGTTGGCCACTCCCTCTCTGCGCGCT
CGCTCGCTCACTGAGGCCGGGCGACCAAAGGTCGCCCGACGCCCGGGCTTTGCCCGGG
CGGCCTCAGTGAGCGAGCGAGCGCGCAGCTGCCTGCAGGGGCGCCTGATGCGGTATTTT
CTCCTTACGCATCTGTGCGGTATTTCACACCGCATACGTCAAAGCAACCATAGTACGCGCC
CTGTAGCGGCGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTCGCCACGTTCGC
CGGCTTTCCCCGTCAAGCTCTAAATCGGGGGCTCCCTTTAGGGTTCCGATTTAGTGCTTTA
CGGCACCTCGACCCCAAAAAACTTGATTTGGGTGATGGTTCACGTAGTGGGCCATCGCCC

FIG. 11, cont'd

TGATAGACGGTTTTTCGCCCTTTGACGTTGGAGTCCACGTTCTTTAATAGTGGACTCTTGTT
CCAAACTGGAACAACACTCAACCCTATCTCGGGCTATTCTTTTGATTTATAAGGGATTTTGC
CGATTTCGGCCTATTGGTTAAAAAATGAGCTGATTTAACAAAAATTTAACGCGAATTTTAACA
AAATATTAACGTTTACAATTTTATGGTGCACTCTCAGTACAATCTGCTCTGATGCCGCATAG
TTAAGCCAGCCCCGACACCCGCCAACACCCGCTGACGCGCCCTGACGGGCTTGTCTGCT
CCCGGCATCCGCTTACAGACAAGCTGTGACCGTCTCCGGGAGCTGCATGTGTCAGAGGTT
TTCACCGTCATCACCGAAACGCGCGAGACGAAAGGGCCTCGTGATACGCCTATTTTTATAG
GTTAATGTCATGATAATAATGGTTTCTTAGACGTCAGGTGGCACTTTTCGGGGAAATGTGC
GCGGAACCCCTATTTGTTTATTTTTCTAAATACATTCAAATATGTATCCGCTCATGAGACAAT
AACCCTGATAAATGCTTCAATAATATTGAAAAAGGAAGAGTATGAGTATTCAACATTTCCGT
GTCGCCCTTATTCCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACATCGAACTGGA
TCTCAACAGCGGTAAGATCCTTGAGAGTTTTCGCCCCGAAGAACGTTTTCCAATGATGAGC
ACTTTTAAAGTTCTGCTATGTGGCGCGGTATTATCCCGTATTGACGCCGGGCAAGAGCAAC
TCGGTCGCCGCATACACTATTCTCAGAATGACTTGGTTGAGTACTCACCAGTCACAGAAAA
GCATCTTACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACCGCTTTTT
TGCACAACATGGGGGATCATGTAACTCGCCTTGATCGTTGGGAACCGGAGCTGAATGAAG
CCATACCAAACGACGAGCGTGACACCACGATGCCTGTAGCAATGGCAACAACGTTGCGCA
AACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTT
TGCTGGCCTTTTGCTCACATGT (SEQ ID NO: 59)

CN2028-rAAV-3xhI56i(core)-minBG-hSCN1A_Fragment3-WPRE3-BGHpA
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA

FIG. 11, cont'd

ATGGAGCTCGGGCTGGGCATAAAAGTCAGGGCAGAGCCATCTATTGCTTACATTTGCTTCT
GGGATCCAGATCTTTCGAAGCTAGCGCTACCACCATGTCCAATCATACAACAGAAATTGGG
AAAGATCTTGACTATCTTAAAGATGTAAATGGAACTACAAGTGGTATAGGAACTGGCAGCA
GTGTTGAAAAATACATTATTGATGAAAGTGATTACATGTCATTCATAAACAACCCCAGTCTTA
CTGTGACTGTACCAATTGCTGTAGGAGAATCTGACTTTGAAAATTTAAACACGGAAGACTTT
AGTAGTGAATCGGATCTGGAAGAAAGCAAAGAGAAACTGAATGAAAGCAGTAGCTCATCAG
AAGGTAGCACTGTGGACATCGGCGCACCTGTAGAAGAACAGCCCGTAGTGGAACCTGAAG
AAACTCTTGAACCAGAAGCTTGTTTCACTGAAGGCTGTGTACAAAGATTCAAGTGTTGTCAA
ATCAATGTGGAAGAAGGCAGAGGAAAACAATGGTGGAACCTGAGAAGGACGTGTTTCCGA
ATAGTTGAACATAACTGGTTTGAGACCTTCATTGTTTTCATGATTCTCCTTAGTAGTGGTGC
TCTGGCATTTGAAGATATATATATTGATCAGCGAAAGACGATTAAGACGATGTTGGAATATG
CTGACAAGGTTTTCACTTACATTTTCATTCTGGAAATGCTTCTAAAATGGGTGGCATATGGC
TATCAAACATATTTCACCAATGCCTGGTGTTGGCTGGACTTCTTAATTGTTGATGTTTCATTG
GTCAGTTTAACAGCAAATGCCTTGGGTTACTCAGAACTTGGAGCCATCAAATCTCTCAGGA
CACTAAGAGCTCTGAGACCTCTAAGAGCCTTATCTCGATTTGAAGGGATGAGGGTGGTTGT
GAATGCCCTTTTAGGAGCAATTCCATCCATCATGAATGTGCTTCTGGTTTGTCTTATATTCT
GGCTAATTTTCAGCATCATGGGCGTAAATTTGTTTGCTGGCAAATTCTACCACTGTATTAAC
ACCACAACTGGTGACAGGTTTGACATCGAAGACGTGAATAATCATACTGATTGCCTAAAAC
TAATAGAAAGAAATGAGACTGCTCGATGGAAAAATGTGAAAGTAAACTTTGATAATGTAGGA
TTTGGGTATCTCTCTTTGCTTCAAGTTGCCACATTCAAAGGATGGATGGATATAATGTATGC
AGCAGTTGATTCCAGAAATGTGGAACTCCAGCCTAAGTATGAAGAAAGTCTGTACATGTAT
CTTTACTTTGTTATTTTCATCATCTTTGGGTCCTTCTTCACCTTGAACCTGTTTATTGGTGTC
ATCATAGATAATTTCAACCAGCAGAAAAAGAAGTTTGGAGGTCAAGACATCTTTTGATGACG
GCGCGCCGCGGCCGCGAATTCGATATCATAATCAACCTCTGGATTACAAAATTTGTGAAAG
ATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGT
TAGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGG
CATGAGATCTCACGTGCGGACCGAGCGGCCGCAGGAACCCCTAGTGATGGAGTTGGCCA
CTCCCTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCTGCCTGCAGGGGC
GCCTGATGCGGTATTTTCTCCTTACGCATCTGTGCGGTATTTCACACCGCATACGTCAAAG
CAACCATAGTACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCCCTTC
CTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTTGGGTGATGGTTCA
CGTAGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGGCTATTCTTTT
GATTTATAAGGGATTTTGCCGATTTCGGCCTATTGGTTAAAAAATGAGCTGATTTAACAAAA
ATTTAACGCGAATTTTAACAAAATATTAACGTTTACAATTTTATGGTGCACTCTCAGTACAAT
CTGCTCTGATGCCGCATAGTTAAGCCAGCCCCGACACCCGCCAACACCCGCTGACGCGCC
CTGACGGGCTTGTCTGCTCCCGGCATCCGCTTACAGACAAGCTGTGACCGTCTCCGGGAG
CTGCATGTGTCAGAGGTTTTCACCGTCATCACCGAAACGCGCGAGACGAAAGGGCCTCGT
GATACGCCTATTTTTATAGGTTAATGTCATGATAATAATGGTTTCTTAGACGTCAGGTGGCA
CTTTTCGGGGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGAAGAGTATG

FIG. 11, cont'd

AGTATTCAACATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACAAT
TAATAGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCA
TTGGTAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGCGAT
AAGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGAT
TTTTGTGATGCTCGTCAGGGGGGCGGAGCCTATGGAAAAACGCCAGCAACGCGGCCTTTT
TACGGTTCCTGGCCTTTTGCTGGCCTTTTGCTCACATGT (SEQ ID NO: 60)

CN2029-rAAV-3xhI56i(core)-minBG-hSCN1A_Fragment4-WPRE3-BGHpA
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGGTACCCTAAATAAAGATGGC
TTTTTAGTATTAAAAGTGGAAGAAAATTACAGGTAATTATCTTTGACGGTAAAAACGCTGTAA
TCAGCGGGCTACATGAAAAATTACTCTAATTATGGCTGCATTTAAGAGAATGGCTAAATAAA
GATGGCTTTTTAGTATTAAAAGTGGAAGAAAATTACAGGTAATTATCTTTGACGGTAAAAAC
GCTGTAATCAGCGGGCTACATGAAAAATTACTCTAATTATGGCTGCATTTAAGAGAATGGCT
AAATAAAGATGGCTTTTTAGTATTAAAAGTGGAAGAAAATTACAGGTAATTATCTTTGACGGT
AAAAACGCTGTAATCAGCGGGCTACATGAAAAATTACTCTAATTATGGCTGCATTTAAGAGA
ATGGAGCTCGGGCTGGGCATAAAAGTCAGGGCAGAGCCATCTATTGCTTACATTTGCTTCT
GGGATCCAGATCTTTCGAAGCTAGCGCTACCACCATGACAGAAGAACAGAAGAAATACTAT
AATGCAATGAAAAAATTAGGATCGAAAAAACCGCAAAAGCCTATACCTCGACCAGGAAACA
AATTTCAAGGAATGGTCTTTGACTTCGTAACCAGACAAGTTTTTGACATAAGCATCATGATT
CTCATCTGTCTTAACATGGTCACAATGATGGTGGAAACAGATGACCAGAGTGAATATGTGA
CTACCATTTTGTCACGCATCAATCTGGTGTTCATTGTGCTATTTACTGGAGAGTGTGTACTG
AAACTCATCTCTCTACGCCATTATTATTTTACCATTGGATGGAATATTTTTGATTTTGTGGTT
GTCATTCTCTCCATTGTAGGTATGTTTCTTGCCGAGCTGATAGAAAAGTATTTCGTGTCCCC
TACCCTGTTCCGAGTGATCCGTCTTGCTAGGATTGGCCGAATCCTACGTCTGATCAAAGGA
GCAAAGGGGATCCGCACGCTGCTCTTTGCTTTGATGATGTCCCTTCCTGCGTTGTTTAACA

FIG. 11, cont'd

TCGGCCTCCTACTCTTCCTAGTCATGTTCATCTACGCCATCTTTGGGATGTCCAACTTTGCC
TATGTTAAGAGGGAAGTTGGGATCGATGACATGTTCAACTTTGAGACCTTTGGCAACAGCA
TGATCTGCCTATTCCAAATTACAACCTCTGCTGGCTGGGATGGATTGCTAGCACCCATTCT
CAACAGTAAGCCACCCGACTGTGACCCTAATAAAGTTAACCCTGGAAGCTCAGTTAAGGGA
GACTGTGGGAACCCATCTGTTGGAATTTTCTTTTTTGTCAGTTACATCATCATATCCTTCCT
GGTTGTGGTGAACATGTACATCGCGGTCATCCTGGAGAACTTCAGTGTTGCTACTGAAGAA
AGTGCAGAGCCTCTGAGTGAGGATGACTTTGAGATGTTCTATGAGGTTTGGGAGAAGTTTG
ATCCCGATGCAACTCAGTTCATGGAATTTGAAAAATTATCTCAGTTTGCAGCTGCGCTTGAA
CCGCCTCTCAATCTGCCACAACCAAACAAACTCCAGCTCATTGCCATGGATTTGCCCATGG
TGAGTGGTGACCGGATCCACTGTCTTGATATCTTATTTGCTTTTACAAAGCGGGTTCTAGGA
GAGAGTGGAGAGATGGATGCTCTACGAATACAGATGGAAGAGCGATTCATGGCTTCCAAT
CCTTCCAAGGTCTCCTATCAGCCAATCACTACTACTTTAAAACGAAAACAAGAGGAAGTATC
TGCTGTCATTATTCAGCGTGCTTACAGACGCCACCTTTTAAAGCGAACTGTAAAACAAGCTT
CCTTTACGTACAATAAAAACAAAATCAAAGGTGGGGCTAATCTTCTTATAAAAGAAGACATG
ATAATTGACAGAATAAATGAAAACTCTATTACAGAAAAAACTGATCTGACCATGTCCACTGC
AGCTTGTCCACCTTCCTATGACCGGGTGACAAAGCCAATTGTGGAAAAACATGAGCAAGAA
GGCAAAGATGAAAAAGCCAAAGGGAAATAATGACGGCGCGCCGCGGCCGCGAATTCGATA
TCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTA
TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGAGATCTTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGAGATCTCACGTGCGGACCGAGC
GGCCGCAGGAACCCCTAGTGATGGAGTTGGCCACTCCCTCTCTGCGCGCTCGCTCGCTCA
CTGAGGCCGGGCGACCAAAGGTCGCCCGACGCCCGGGCTTTGCCCGGGCGGCCTCAGT
GAGCGAGCGAGCGCGCAGCTGCCTGCAGGGGCGCCTGATGCGGTATTTTCTCCTTACGC
ATCTGTGCGGTATTTCACACCGCATACGTCAAAGCAACCATAGTACGCGCCCTGTAGCGG
CGCATTAAGCGCGGCGGGTGTGGTGGTTACGCGCAGCGTGACCGCTACACTTGCCAGCG
CCCTAGCGCCCGCTCCTTTCGCTTTCTTCCCTTCCTTTCTCGCCACGTTCGCCGGCTTTCC
CCGTCAAGCTCTAAATCGGGGGCTCCCTTTAGGGTTCCGATTTAGTGCTTTACGGCACCTC
GACCCCAAAAAACTTGATTTGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACTGG
AACAACACTCAACCCTATCTCGGGCTATTCTTTTGATTTATAAGGGATTTTGCCGATTTCGG
CCTATTGGTTAAAAAATGAGCTGATTTAACAAAAATTTAACGCGAATTTTAACAAAATATTAA
CGTTTACAATTTTATGGTGCACTCTCAGTACAATCTGCTCTGATGCCGCATAGTTAAGCCAG
CCCCGACACCCGCCAACACCCGCTGACGCGCCCTGACGGGCTTGTCTGCTCCCGGCATC
CGCTTACAGACAAGCTGTGACCGTCTCCGGGAGCTGCATGTGTCAGAGGTTTTCACCGTC
ATCACCGAAACGCGCGAGACGAAAGGGCCTCGTGATACGCCTATTTTTATAGGTTAATGTC
ATGATAATAATGGTTTCTTAGACGTCAGGTGGCACTTTTCGGGGAAATGTGCGCGGAACCC
CTATTTGTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGCACTTTTAAA
GTTCTGCTATGTGGCGCGGTATTATCCCGTATTGACGCCGGGCAAGAGCAACTCGGTCGC
CGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCG

FIG. 11, cont'd

GCCAACTTACTTCTGACAACGATCGGAGGACCGAAGGAGCTAACCGCTTTTTTGCACAACA
TGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAACGAAATAGA
CAGATCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCA
AGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCAGGGGGGCGGA
GCCTATGGAAAAACGCCAGCAACGCGGCCTTTTTACGGTTCCTGGCCTTTTGCTGGCCTTT
TGCTCACATGT (SEQ ID NO: 61)

hSCN1A_Fragment1_ProteinSequence
MEQTVLVPPGPDSFNFFTRESLAAIERRIAEEKAKNPKPDKKDDDENGPKPNSDLEAGKNLPFI
YGDIPPEMVSEPLEDLDPYYINKKTFIVLNKGKAIFRFSATSALYILTPFNPLRKIAIKILVHSLFSML
IMCTILTNCVFMTMSNPPDWTKNVEYTFTGIYTFESLIKIIARGFCLEDFTFLRDPWNWLDFTVIT
FAYVTEFVDLGNVSALRTFRVLRALKTISVIPGLKTIVGALIQSVKKLSDVMILTVFCLSVFALIGLQ
LFMGNLRNKCIQWPPTNASLEEHSIEKNITVNYNGTLINETVFEFDWKSYIQDSRYHYFLEGFLD
ALLCGNSSDAGQCPEGYMCVKAGRNPNYGYTSFDTFSWAFLSLFRLMTQDFWENLYQLTLRA
AGKTYMIFFVLVIFLGSFYLINLILAVVAMAYEEQNQATLEEAEQKEAEFQQMIEQLKKQQEAAQ
QAATATASEHSREPSAAGRLSDSSSEASKLSSKSAKERRNRRKKRKQKEQSGGEEKDEDEFQ
KSESEDSIRRKGFRFSIEGNRLTYEKRYSSPHQSLLSIRGSLFSPRRNSRTSLFSFRGRAKDVG
SENDFADDEHSTFEDNESRRDSLFVPRRHGERRNSNLSQTSRSSR* (SEQ ID NO: 62)

hSCN1A_Fragment2_ProteinSequence
MLAVFPANGKMHSTVDCNGVVSLVGGPSVPTSPVGQLLPEVIIDKPATDDNGTTTETEMRKRR
SSSFHVSMDFLEDPSQRQRAMSIASILTNTVEELEESRQKCPPCWYKFSNIFLIWDCSPYWLKV
KHVVNLVVMDPFVDLAITICIVLNTLFMAMEHYPMTDHFNNVLTVGNLVFTGIFTAEMFLKIIAMD
PYYYFQEGWNIFDGFIVTLSLVELGLANVEGLSVLRSFRLLRVFKLAKSWPTLNMLIKIIGNSVGA
LGNLTLVLAIIVFIFAVVGMQLFGKSYKDCVCKIASDCQLPRWHMNDFFHSFLIVFRVLCGEWIE
TMWDCMEVAGQAMCLTVFMMVMVIGNLVVLNLFLALLLSSFSADNLAATDDDNEMNNLQIAVD
RMHKGVAYVKRKIYEFIQQSFIRKQKILDEIKPLDDLNNKKDSC* (SEQ ID NO: 63)

hSCN1A_Fragment3_ProteinSequence
MSNHTTEIGKDLDYLKDVNGTTSGIGTGSSVEKYIIDESDYMSFINNPSLTVTVPIAVGESDFENL
NTEDFSSESDLEESKEKLNESSSSSEGSTVDIGAPVEEQPVVEPEETLEPEACFTEGCVQRFK
CCQINVEEGRGKQWWNLRRTCFRIVEHNWFETFIVFMILLSSGALAFEDIYIDQRKTIKTMLEYA
DKVFTYIFILEMLLKWVAYGYQTYFTNAWCWLDFLIVDVSLVSLTANALGYSELGAIKSLRTLRAL

FIG. 11, cont'd

RPLRALSRFEGMRVVVNALLGAIPSIMNVLLVCLIFWLIFSIMGVNLFAGKFYHCINTTTGDRFDI
EDVNNHTDCLKLIERNETARWKNVKVNFDNVGFGYLSLLQVATFKGWMDIMYAAVDSRNVEL
QPKYEESLYMYLYFVIFIIFGSFFTLNLFIGVIIDNFNQQKKKFGGQDIF* (SEQ ID NO: 64)

hSCN1A_Fragment4_ProteinSequence
MTEEQKKYYNAMKKLGSKKPQKPIPRPGNKFQGMVFDFVTRQVFDISIMILICLNMVTMMVETD
DQSEYVTTILSRINLVFIVLFTGECVLKLISLRHYYFTIGWNIFDFVVVILSIVGMFLAELIEKYFVSP
TLFRVIRLARIGRILRLIKGAKGIRTLLFALMMSLPALFNIGLLLFLVMFIYAIFGMSNFAYVKREVGI
DDMFNFETFGNSMICLFQITTSAGWDGLLAPILNSKPPDCDPNKVNPGSSVKGDCGNPSVGIFF
FVSYIIISFLVVVNMYIAVILENFSVATEESAEPLSEDDFEMFYEVWEKFDPDATQFMEFEKLSQF
AAALEPPLNLPQPNKLQLIAMDLPMVSGDRIHCLDILFAFTKRVLGESGEMDALRIQMEERFMA
SNPSKVSYQPITTTLKRKQEEVSAVIIQRAYRRHLLKRTVKQASFTYNKNKIKGGANLLIKEDMII
DRINENSITEKTDLTMSTAACPPSYDRVTKPIVEKHEQEGKDEKAKGK* (SEQ ID NO: 65)

Nucleotide sequences that can result in upregulation of SCN1A expression (described in Hsiao et al., EBioMedicine 9 (2016) 257-277):

TCGACTTTGAAAA (SEQ ID NO: 66)
CCTCTCCACGCGCAGTACATT (SEQ ID NO: 67)
T•C•G•G•T•G•T•C•C•A•C•T•C•T•G•G•C•A•G•T• (SEQ ID NO: 68)
T•G•C•A•C•T•G•T•G•G•G•A•G•C•C•T•G•T•C•T (SEQ ID NO: 69)
G•T•A•G•C•A•C•T•G•T•G•G•A•C•A•T•C•G•G•C (SEQ ID NO: 70)
G•T•A•G•A•A•G•A•A•C•A•G•C•C•C•G•T•A•G•T•G (SEQ ID NO: 71)
G•T•G•G•T•C•T•C•T•G•C•A•T•T•C•T•G•T•C•A (SEQ ID NO: 72)
G•T•G•G•T•A•T•A•G•G•A•A•C•T•G•G•C•A•G•C•A (SEQ ID NO: 73)
G•T•C•C•A•A•T•C•A•T•A•C•A•G•C•A•G•A•A (SEQ ID NO: 74)
G•T•G•A•C•T•G•T•A•C•C•A•A•T•T•G•C•T•G•T (SEQ ID NO: 75)
A•C•T•T•C•T•T•C•C•A•C•T•C•C•T•T•C•C•T (SEQ ID NO: 76)
G•A•T•G•T•C•C•C•T•T•C•C•T•G•C•G•T•T•G•T (SEQ ID NO: 77)
T•G•T•G•G•A•T•G•C•T•G•G•G•T•G•T•C•T•C•T•C (SEQ ID NO: 78)
T•C•C•C•A•G•T•G•A•C•T•C•C•C•G•A•T•G•C•T (SEQ ID NO: 79)
A•G•T•C•T•C•A•G•T•T•G•T•C•A•G•T•A•C•C•T•C (SEQ ID NO: 80)
G•T•T•A•T•T•G•A•A•T•G•C•C•C•T•G•G•T•G•T (SEQ ID NO: 81)
T•C•G•G•A•T•C•A•T•C•A•G•G•G•T•T•G•T•A•G•T (SEQ ID NO: 82)
G•T•G•G•T•A•T•A•G•G•A•A•C•T•G•G•C•A•G•C•A (SEQ ID NO: 83)
T•C•T•G•C•T•C•T•T•C•C•C•T•A•C•A•T•T•G•G (SEQ ID NO: 84)
G•T•A•A•T•C•T•G•C•T•C•T•T•C•C•C•T•A•C (SEQ ID NO: 85)
G•G•G•A•G•A•A•C•T•T•G•A•G•A•G•C•A•A•C•A•G (SEQ ID NO: 86)
G•C•C•A•G•T•C•A•C•A•A•A•T•T•C•A•G•A•T•C•A (SEQ ID NO: 87)
G•T•G•G•C•A•T•A•G•G•G•A•C•G•G•G•C•A•G•C•A (SEQ ID NO: 88)
G•T•A•G•C•A•C•T•G•T•G•G•A•C•A•T•C•G•G•C (SEQ ID NO: 89)
G•T•A•G•A•A•G•A•A•C•A•G•C•C•C•G•T•A•G•T•G (SEQ ID NO: 90)
G•T•C•C•A•A•T•C•A•T•A•C•A•G•C•A•G•A•A (SEQ ID NO: 91)
G•T•G•A•C•T•G•T•A•C•C•A•A•T•T•G•C•T•G•T (SEQ ID NO: 92)
A•C•T•T•C•T•T•C•C•A•C•T•C•C•T•T•C•C•T (SEQ ID NO: 93)
G•A•T•G•T•C•C•C•T•T•C•C•T•G•C•G•T•T•G•T (SEQ ID NO: 94)
T•G•T•G•G•A•T•G•C•T•G•G•G•T•G•T•C•T•C•T•C (SEQ ID NO: 95)

FIG. 11, cont'd

T•C•C•C•A•G•T•G•A•C•T•C•C•C•G•A•T•G•C•T (SEQ ID NO: 96)
A•G•T•C•T•C•A•G•T•T•G•T•C•A•G•T•A•C•C•T•C (SEQ ID NO: 97)
T•C•G•G•A•T•C•A•T•C•A•G•G•G•T•T•G•T•A•G•T (SEQ ID NO: 98)
G•T•G•G•T•A•T•A•G•G•A•A•C•T•G•G•C•A•G•C•A (SEQ ID NO: 99)
G•T•G•GAC•AGGAT•GCAC•AAAGG•A (SEQ ID NO: 100)
T•G•G•T•A•T•A•G•G•A•A•C•T•G•G•C•A•G•C•A (SEQ ID NO: 101)
G•T•G•G•C•A•T•A•G•G•G•A•C•G•G•G•C•A•G•C•A (SEQ ID NO: 102)
G•T•G•ACTGTGCCCATTG•C•T•G (SEQ ID NO: 103)
G•C•C•ACTT•GATGAT•CTA•A•A•C (SEQ ID NO: 104)
G•T•G•GAC•AGGAT•GCAC•AAAGG•A (SEQ ID NO: 105)
T•G•G•T•A•T•A•G•G•A•A•C•T•G•G•C•A•G•C•A (SEQ ID NO: 106)
*C•*C•A•C•G•C•G•C•G•A•G•T•*A•*C•*A (SEQ ID NO: 107)
*G•*T•A•T•A•G•G•A•A•C•T•G•*G•*C•*A (SEQ ID NO: 108)
*G•*T•G•G•T•A•*T•A•G•G•A•A•*C•*T•*G (SEQ ID NO: 109)
*A•*G•A•A•C•T•T•G•A•G•A•G•*C•*A•*A (SEQ ID NO: 110)
*G•*C•C•A•G•*T•C•A•*C•A•A•A•*T•*T•*C (SEQ ID NO: 111)
*C•*A•C•A•A•A•T•T•C•A•G•A•*T•*C•*A (SEQ ID NO: 112)
*G•*T•GGTA*T•AGGAA*C•*T•*G (SEQ ID NO: 113)
*G•*T•A•T•A•G•G•A•A•C•T•G•*G•*C•*A (SEQ ID NO: 114)
*G•*T•G•G•T•A•*T•A•G•G•A•A•*C•*T•*G (SEQ ID NO: 115)
*G•*C•CAGT•C•A*C•AAA*T•*T•*C (SEQ ID NO: 116)
*C•*A•CAAATTCAGA*T•*C•*A (SEQ ID NO: 117)
*G•*C•C•A•G•xU•C•A•xC•A•A•xA•xU•*T•*C (SEQ ID NO: 118)
*G•C•C•A•G•*T•C•A•*C•A•A•A•T•*T•*C (SEQ ID NO: 119)
*G•*C•xC•A•G•xU•C•A•xC•A•xA•*A•*T (SEQ ID NO: 120)
*G•*C•C•A•G•T•C•A•C•A•*A•*A•*T (SEQ ID NO: 121)
*G•C•C•A•G•T•C•A•*C•*A•*A (SEQ ID NO: 122)
*G•*C•C•A•G•T•C•A•C•*A•*A•*A (SEQ ID NO: 123)
*A•*T•T•G•A•G•C•C•A•*G•*T•*C (SEQ ID NO: 124)
*G•*T•GGTA*T•AGGAA*C•*T•*G (SEQ ID NO: 125)
xG•xC•C•A•G•xU•C•A•xC•A•A•A•xU•T•C•xA•xG (SEQ ID NO: 126)
xG•xC•C•A•G•xU•C•A•xC•A•A•A•xU•xU•xC (SEQ ID NO: 127)
xG•xU•xG•G•xU•A•xU•A•G•G•A•A•xC•T•G•G•xC•A•xG•xC•xA (SEQ ID NO: 128)
xG•xG•xG•A•G•A•A•xC•T•xU•G•A•G•A•G•xC•A•A•xC•xA•xG (SEQ ID NO: 129)
xG•xC•xC•A•G•T•xC•A•C•A•A•A•xU•T•xC•A•G•A•xU•xC•xA (SEQ ID NO: 130)
xG•xU•xG•GxU•AxU•AGGAAxC•TGGxC•AxG•xC•xA (SEQ ID NO: 131)
xG•xG•xU•A•xU•A•G•G•xA•A•C•xU•G•G•xC•A•G•xC•A•G•xU•G•xU•xU•xG (SEQ ID NO: 132)
xU•xG•xG•T•A•xU•A•G•xG•A•A•xC•T•G•G•xC•A•G•C•xA•xG•xU (SEQ ID NO: 133)
xG•G•T•A•xU•A•G•G•A•A•xC•T•G•G•xC•A•G•xC•A•G•T•G•T•T•xG (SEQ ID NO: 134)
xA•xA•G•xC•G•G•xU•A•T•A•G•G•A•A•xC•T•G•G•xC•A•G•xC•A•xG (SEQ ID NO: 135)
xG•xA•xG•C•C•A•G•xU•C•A•xC•A•A•A•xU•T•C•A•G•xA•T•C•A•xC•xC•xC (SEQ ID NO: 136)
xA•A•xU•G•G•G•A•G•A•A•xC•xU•xU•G•A•G•A•G•xC•xA•xA (SEQ ID NO: 137)
xG•TGACxU•GTGCCxC•ATTGCTxG (SEQ ID NO: 138)
xG•ACAAxC•CTTGxC•AGCCAxC•TGAxU•GATGxA (SEQ ID NO: 139)
xU•xG•G•xU•A•xU•A•G•G•A•A•xC•T•G•G•xC•A•xG•xC•xA (SEQ ID NO: 140)
xC•xC•A•G•T•xC•A•C•A•A•A•xU•T•xC•A•G•A•xU•xC•xA (SEQ ID NO: 141)
xU•xG•GxU•AxU•AGGAAxC•TGGxC•AxG•xC•xA (SEQ ID NO: 142)
xA•xG•C•C•A•G•xU•C•A•xC•A•A•A•xU•T•C•A•G•xA•T•C•A•xC•xC•xC (SEQ ID NO: 143)

Figure 11:
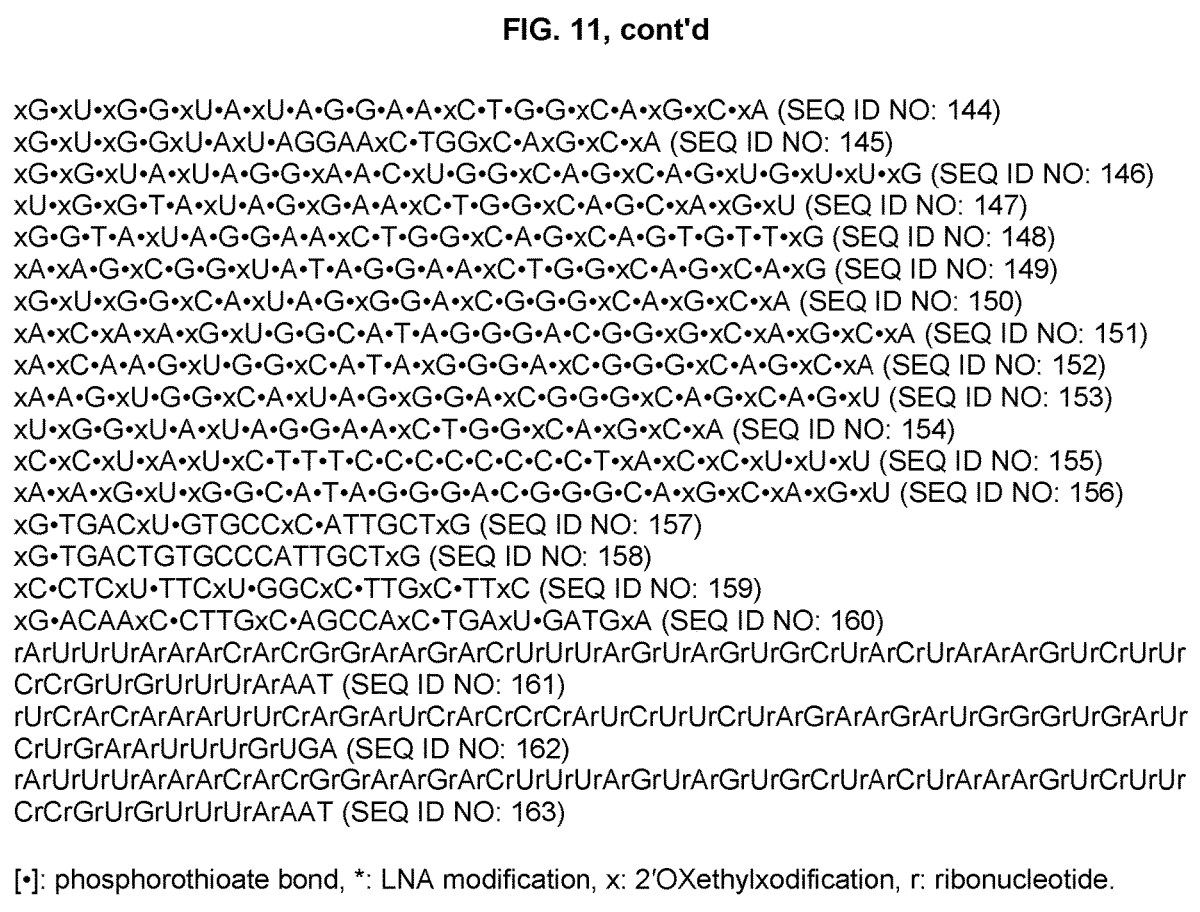

FIG. 11, cont'd xG•xU•xG•G•xU•A•xU•A•G•G•A•A•xC•T•G•G•xC•A•xG•xC•xA (SEQ ID NO: 144)
xG•xU•xG•GxU•AxU•AGGAAxC•TGGxC•AxG•xC•xA (SEQ ID NO: 145)
xG•xG•xU•A•xU•A•G•G•xA•A•C•xU•G•G•xC•A•G•xC•A•G•xU•G•xU•xU•xG (SEQ ID NO: 146)
xU•xG•xG•T•A•xU•A•G•xG•A•A•xC•T•G•G•xC•A•G•C•xA•xG•xU (SEQ ID NO: 147)
xG•G•T•A•xU•A•G•G•A•A•xC•T•G•G•xC•A•G•xC•A•G•T•G•T•T•xG (SEQ ID NO: 148)
xA•xA•G•xC•G•G•xU•A•T•A•G•G•A•A•xC•T•G•G•xC•A•G•xC•A•xG (SEQ ID NO: 149)
xG•xU•xG•G•xC•A•xU•A•G•xG•G•A•xC•G•G•G•xC•A•xG•xC•xA (SEQ ID NO: 150)
xA•xC•xA•xA•xG•xU•G•G•C•A•T•A•G•G•G•A•C•G•G•xG•xC•xA•xG•xC•xA (SEQ ID NO: 151)
xA•xC•A•A•G•xU•G•G•xC•A•T•A•xG•G•G•A•xC•G•G•G•xC•A•G•xC•xA (SEQ ID NO: 152)
xA•A•G•xU•G•G•xC•A•xU•A•G•xG•G•A•xC•G•G•G•xC•A•G•xC•A•G•xU (SEQ ID NO: 153)
xU•xG•G•xU•A•xU•A•G•G•A•A•xC•T•G•G•xC•A•xG•xC•xA (SEQ ID NO: 154)
xC•xC•xU•xA•xU•xC•T•T•T•C•C•C•C•C•C•C•C•T•xA•xC•xC•xU•xU•xU (SEQ ID NO: 155)
xA•xA•xG•xU•xG•G•C•A•T•A•G•G•G•A•C•G•G•G•C•A•xG•xC•xA•xG•xU (SEQ ID NO: 156)
xG•TGACxU•GTGCCxC•ATTGCTxG (SEQ ID NO: 157)
xG•TGACTGTGCCCATTGCTxG (SEQ ID NO: 158)
xC•CTCxU•TTCxU•GGCxC•TTGxC•TTxC (SEQ ID NO: 159)
xG•ACAAxC•CTTGxC•AGCCAxC•TGAxU•GATGxA (SEQ ID NO: 160)
rArUrUrUrArArArCrArCrGrGrArArGrArCrUrUrUrArGrUrArGrUrGrCrUrArCrUrArArArGrUrCrUrUrCrCrGrUrGrUrUrUrArAAT (SEQ ID NO: 161)
rUrCrArCrArArArUrUrCrArGrArUrCrArCrCrCrArUrCrUrUrCrUrArGrArArGrArUrGrGrGrUrGrArUrCrUrGrArArUrUrUrGrUGA (SEQ ID NO: 162)
rArUrUrUrArArArCrArCrGrGrArArGrArCrUrUrUrArGrUrArGrUrGrCrUrArCrUrArArArGrUrCrUrUrCrCrGrUrGrUrUrUrArAAT (SEQ ID NO: 163)

[•]: phosphorothioate bond, *: LNA modification, x: 2′OXethylxodification, r: ribonucleotide.

RESCUING VOLTAGE-GATED SODIUM CHANNEL FUNCTION IN INHIBITORY NEURONS

CROSS-REFERENCE TO RELATED APPLICATIONS

This application is a U.S. National Phase Application based on International Patent Application No. PCT/US2019/026638, filed Apr. 9, 2019, which claims priority to U.S. Provisional Patent Application Nos. 62/655,043, filed Apr. 9, 2018, 62/742,835, filed Oct. 8, 2018, and 62/810,281, filed Feb. 25, 2019, each of which is incorporated herein by reference in its entirety as if fully set forth herein.

STATEMENT REGARDING FEDERALLY SPONSORED RESEARCH OR DEVELOPMENT

This invention was made with government support under grant RF1MH114126 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2FZ4606_ST25.txt. The text file is 301 KB, was created on Feb. 17, 2021, and is being submitted electronically via EFS-Web.

FIELD OF THE DISCLOSURE

The current disclosure describes the rescue of voltage-gated sodium channel function selectively in inhibitory neurons in need thereof. Rescued voltage-gated sodium channel function in inhibitory neurons can be used to treat disorders such as epilepsy, and more particularly, Dravet Syndrome.

BACKGROUND OF THE DISCLOSURE

There are numerous neurological disorders for which treatments are urgently needed. One class of such disorders arise due to dysfunctional Nav1.1 sodium channels in inhibitory neurons. For example, epilepsy, infantile spasms, migraine headaches, and autism spectrum disorders are associated with dysfunctional Nav1.1 sodium channels.

Epilepsy is a neurological disorder that occurs when the brain presents an enduring predisposition to generate two or more epileptic seizures. An epileptic seizure is a temporary disruption of brain function due to abnormal excessive or synchronous neuronal activity. Its manifestation may include periods of unusual behavior, sensations and sometimes loss of consciousness.

Dravet Syndrome (DS) particularly is a rare and catastrophic form of intractable epilepsy that begins in infancy. Initially, the patient experiences prolonged seizures. In their second year, additional types of seizure begin to occur and this typically coincides with a developmental decline. This leads to poor development of language and motor skills.

Children with DS are likely to experience multiple seizures per day. Epileptic seizures are far more likely to result in death in sufferers of DS; 10 to 16% of patients diagnosed with DS die in childhood, particularly between two and four years of age. Additionally, patients are at risk of numerous associated conditions including orthopedic developmental issues, impaired growth, sleep and circadian rhythm impairments, and chronic infections.

Of particular concern, children with DS are particularly susceptible to episodes of Status epilepticus. Status epilepticus is a condition in which a seizure lasts for more than 5 minutes or multiple seizures occur close together within a 5 minute-period without recovery of consciousness between them. This severe condition is categorized as a medical emergency requiring immediate medical intervention, typically involving hospitalization. Prolonged convulsive status epilepticus lasting >30 min can be fatal and lead to substantial brain damage. Frequent hospitalizations of children with DS are clearly distressing, not only to the patient but also to family and care givers. The cost of care for DS is also high as the affected children require constant supervision and many require institutionalization.

At present, although a number of anticonvulsant therapies can be employed to reduce the instance of seizures in patients with DS, the results obtained with such therapies are typically poor and those therapies only produce partial cessation of seizures in most patients. Many of these anticonvulsants such as clobazam and clonazepam have undesirable side effects, which are particularly acute in pediatric patients. Furthermore, certain anticonvulsants (particularly the sodium-channel blockers) exacerbate the seizures.

Cell-type or cell-class specific gene delivery using non-pathogenic viral delivery is showing increasing promise for the treatment of diverse diseases. Inclusion of particular gene regulatory elements, such as specific promoters or enhancers, within the delivered vector, has been beneficial to provide specificity for gene expression within particular targeted cell types. For example, Dimidschstein and colleagues (Nat Neurosci 19(12):1743-1749, 2016) developed a viral delivery gene construct based on the adeno-associated virus (AAV) that resulted in selective expression of a gene within gamma-aminobutyric acid (GABA)ergic interneurons within the telencephalon, a cell type important in the treatment of epilepsy. This construct included a 529 base pair (bp) enhancer sequence (referred to as mI56i or mDlx).

One significant drawback to using AAV as a selective gene-delivery system is the strictly restricted packaging limit of AAVs; this is particularly limiting to the inclusion of lengthy genetic control elements. In addition, existing interneuron-specific AAV expression constructs provide weak expression in certain applications, as well as for expression of transgenes (such as therapeutic genes) that are more poorly tolerated than other more commonly used proteins. Thus, there remains a need in the art for shorter enhancer sequences that are capable of providing rapid and strong expression of functional proteins within selected cell types.

SUMMARY OF THE DISCLOSURE

The current disclosure provides expression constructs that result in unexpectedly rapid and high levels of protein expression selectively within inhibitory neurons for the purpose of rescuing defective Nav1.1 channel function. In particular embodiments, the current disclosure provides a concatemerized core of the human I56i enhancer and a gene encoding a voltage-gated sodium channel protein or nucleotide sequence that can rescue impaired Nav1.1 sodium channel function. The expression constructs can be used to reverse or ameliorate the effects of Nav1.1 voltage-gated sodium channel dysfunction in inhibitory neurons. In particular embodiments, the current disclosure provides treatment of sodium channel disorders by selectively delivering a gene allowing for a functioning voltage-gated sodium channel to inhibitory neurons. Administration of viral vectors including these enhancers and genes results in selective expression of a protein or nucleotide sequence that rescues Nav1.1 sodium channel function in inhibitory interneurons. In particular embodiments, the therapeutic voltage-gated sodium channel genes in these viral vectors can be of bacterial origin, which are small and can fit into a single AAV construct, or of human origin, which are larger and can use a dual construct AAV delivery technique, among other strategies. The Nav1.1 sodium channel disorders that can be treated include epilepsy, and more particularly, Dravet Syndrome (DS). For example, as disclosed herein, administration of the expression constructs results in therapeutic efficacy to treat DS in a well-established in vivo mouse model of the disease.

BRIEF DESCRIPTION OF THE SEVERAL VIEWS OF THE DRAWINGS

Many of the drawings submitted herein are better understood in color. Applicant considers the color versions of the drawings as part of the original submission and reserve the right to present color images of the drawings in later proceedings.

(FIG. 1A) Green fluorescence identifies cells expressing a CN1180/DJ viral vector at 7 DIV/DPI (DIV: days in vitro, DPI: days post infection). CN1180 includes a SYFP2 expression cassette under control of the human DLX (hDLX) 112b enhancer and a minimal beta-globin promoter. Neurons were patch-clamped and visualized post-hoc with Alexa 594 backfill in the red channel. (FIG. 1B) Morphologies of patched cells from one human case, categorized by presence of YFP fluorescence, suggest that SYFP2-expressing cells are largely interneurons. (FIG. 1C) Electrophysiological parameters of YFP+neurons suggest that these cells are predominantly fast-spiking interneurons. (FIG. 1D) Post-hoc immuno-histochemistry demonstrates that many YFP+ cells (arrows) express Parvalbumin (PVALB), which suggests that these cells have molecular properties of fast-spiking interneurons.

(FIG. 4A) Schematic representations of three vector constructs, CN1244, CN1389, and CN1390 (CN1203 scAAV). Key: hI56i—full-length human DlxI56i enhancer (SEQ ID NO: 1); hI56iCore—human DlxI56i enhancer core (SEQ ID NO: 2); minBG—minimal beta globin promoter; SYFP2—super yellow fluorescent protein 2; WPRE3—woodchuck hepatitis virus posttranscriptional regulatory element 3; BGHpA—bovine growth hormone polyA sequence; L-ITR and R-ITR—Adeno-associated virus-2 (AAV2) inverted terminal repeats (ITRs). (FIG. 4B) Fluorograph images showing relative expression of the SYFP2 from AAV vector constructs CN1244, CN1389, and CN1390.

(FIG. 6A) Time course of virus-mediated YFP expression following human brain slice transduction with CN1390/PHP.eB (left panel: 1 DIV/1 DPI; middle panel: 3 DIV/3 DPI; right panel: 6 DIV/6 DPI). (FIG. 6B) Expanded view of the boxed region in (FIG. 6A, right panel). (FIG. 6C) High magnification view of a virus labeled interneuron with bipolar morphology. (FIG. 6D) Example whole cell recordings from four different virus-labeled YFP+ human interneurons and demonstrating diverse firing patterns to supra-threshold current injection. (FIG. 6E) Functional analysis of human neocortical interneuron firing patterns and electrical properties by patch clamp recording was feasible as early as 40 hours post-infection with CN1390/PHP.eB virus.

FIG. 11. Exemplary sequences supporting the disclosure.

DETAILED DESCRIPTION

Figure 1A:
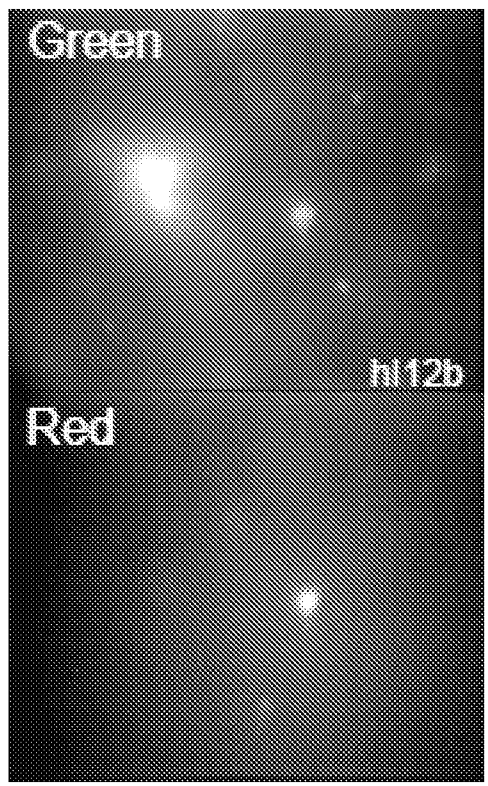
FIGS. 1A-1D. Pan-GABAergic viral enhancer labels fast spiking interneurons in human organotypic slice culture.

In vertebrates, voltage gated sodium channels (Navs) are heteromeric protein complexes including a large central pore composed of alpha subunits, and smaller auxiliary subunits composed of beta subunits which modulate the kinetics and subcellular distribution of the pores. The alpha subunits are encoded by a family of 9 different genes (from SCN1A to SCN11A), and the beta subunits are encoded by 4 different genes (SCN1B to SCN4B), and these gene members show cell- and tissue-specific expression patterns. Each of the nine different alpha subunit genes seeds a distinct Nav channel complex, making 9 different subtypes (Nav1.1-Nav1.9), and these nine Nav channels display tissue specific localization and functional differences (See, Goldin, (2001) Annu Rev Physiol 63: 871-94; and Yu et al., (2003), J. Neurosci 23: 7577-758).

Navs are central for neuron function, being responsible for initiating the rapid upstroke of action potentials in excitable nervous system cells, and Nav1.1 drives this activity in many cells. The Nav1.1 channel includes the SCN1A alpha subunit, and is expressed in nearly all neurons and at high levels in GABAergic neurons. The Nav1.2 channel includes the SCN2A subunit; the Nav1.3 channel includes the SCN3A subunit, the Nav1.4 channel includes the SCN4A subunit, the Nav1.5 channel includes the SCN5A subunit, the Nav1.6 channel includes the SCN8A subunit, the Nav1.7 channel includes the SCN9A subunit, the Nav1.8 channel includes the SCN10A subunit, and the Nav1.9 channel includes the SCN11A subunit.

There are numerous neurological disorders for which treatments are urgently needed. One class of such disorders arise due to dysfunctional Nav1.1 sodium channels in inhibitory neurons. For example, the following disorders and conditions are associated with dysfunctional Nav1.1 sodium channels: epilepsy (including Dravet syndrome (DS), generalized epilepsy with febrile seizures plus (GEFS+), borderline DS, intractable childhood epilepsy with generalized tonic-clonic seizures (ICEGTC), cryptogenic focal and generalized epilepsies, myoclonic-astatic epilepsy (Doose syndrome), Lennox Gastaut syndrome, and severe infantile multifocal epilepsy (Gambardella A et al. Epilepsia. 2009, 50 Suppl 5:20-3)), West syndrome, also known as infantile spasms (Harkin L. A. et al. Brain, 2007, 130(3) 843-852), rare cases of familiar migraine such as familial hemiplegic migraine 3 (FHM3), Panayiotopoulos syndrome (Livingston J. H. et al. J Child Neurol. 2009, 24(4):503-8), familial autism (Weiss L. A et al. 2003, Molecular Psychiatry, 8(2), 186-194), sporadic autism spectrum disorders (ASDs) (Nat Genet. 2011 43(6):585-9), Rasmussens's encephalitis, also known as chronic focal encephalitis, or CFE (Ohmori I. et al, Epilepsia. 2008 49(3):521-6), Alzheimer's disease (Scharfman H. E. Epilepsy Curr. 2012 12(5): 178-183), and cerebral ischemia-reperfusion (Yao C. et al, Neurotox Res. 2002; 4(1):67).

The underlying cause of epilepsy is believed to arise from a defect in the excitation-inhibition (E/I) balance of cortical circuits. Forebrain GABAergic interneurons are the primary source of inhibition in the telencephalon and various lines of evidence indicate their importance in epilepsy. DS particularly is a severe childhood epilepsy predominantly due to SCN1A haploinsufficiency. It is marked by severe and frequent seizures (sometimes hundreds a day), leads to developmental delay, and has a lethality rate of up to 16%. DS affects nearly 1 in 20,000 births in both the United States and Europe, and more than 10,000 people are estimated to suffer from DS on both continents (Wu et al., Pediatrics 136, e1310-e1315, 2015). Heterozygous loss-of-function mutations in SCN1A, the gene that encodes the pore forming subunit of the voltage-gated sodium channel Nav1.1 is the predominant cause of DS (Catterall et al., *J. Physiol.* 588, 1849-1859, 2010; Claes et al., *Hum. Mutat.* 21, 615-621, 2003; Fujiwara, *Epilepsy Res.* 70 Suppl 1, S223-230, 2006; Verbeek et al., *Epilepsy Behav. EB* 47, 39-44, 2015). Genetic models of DS have established the pathophysiology of this disease (Han et al., *Nature* 489, 385-390, 2012; Kalume et al., *J. Clin. Invest.* 123, 1798-1808, 2013; Kalume et al., *J. Neurosci.* 27, 11065-11074, 2007; Kalume et al., *Neurobiol.*

*Dis.* 77, 141-154, 2015; Oakley et al., *Proc. Natl. Acad. Sci.* 106, 3994-3999, 2009; Cheah et al., *Proc. Natl. Acad. Sci.* 109, 14646-14651, 2012; Han et al., *Proc. Natl. Acad. Sci.* 109, E368-E377, 2012). Mouse models of DS have reduced Nav1.1 function due to heterozygous deletion of Scn1a and exhibit the key phenotypic traits of DS including: febrile seizures, anxiety, and sleep deficits (Han et al., *Nature* 489, 385-390, 2012; Kalume et al., *J. Clin. Invest.* 123, 1798-1808, 2013; Kalume et al., *Neurobiol. Dis.* 77, 141-154, 2015; Oakley et al., *Proc. Natl. Acad. Sci.* 106, 3994-3999, 2009; Tai et al., *Proc. Natl. Acad. Sci.* 111, E3139-E3148, 2014; Yu et al., *Nat. Neurosci.* 9, 1142-1149, 2006).

DS is a disease of forebrain interneurons. Global Scn1a deletion causes reduced sodium current and excitability of GABAergic interneurons with no detectable impact on excitatory neurons (Catterall et al., *J. Physiol.* 588, 1849-1859, 2010; Kalume et al., *J. Neurosci.* 27, 11065-11074, 2007; Cheah et al., *Proc. Natl. Acad. Sci.* 109, 14646-14651, 2012; Tai et al., *Proc. Natl. Acad. Sci.* 111, E3139-E3148, 2014; Yu et al., *Nat. Neurosci.* 9, 1142-1149, 2006; Ogiwara et al., *J. Neurosci.* 27, 5903-5914, 2007 Rubinstein et al., *Brain* 138, 2219-2233, 2015; Mistry et al., *Neurobiol. Dis.* 65, 1-11, 2014). Conditional deletion of Scn1a in forebrain or interneurons using specific Cre drivers qualitatively reproduced the key symptoms of DS, whereas excitatory neuron-specific deletion caused no detectable phenotype (Cheah et al., *Proc. Natl. Acad. Sci.* 109, 14646-14651, 2012). In addition, targeted deletion of Scn1a in $Pvalb^+$ or $Sst^+$ interneuron classes (separately or in combination) revealed that dysfunction in each class separately contributes to the multifaceted phenotypes of DS, with $Pvalb^+$ cells exerting a greater effect (Rubinstein et al., *Brain* 138, 2219-2233, 2015; Dutton et al., *Neurobiol. Dis.* 49, 211-220, 2013). Consistent with these mouse models, patients with DS demonstrated a reduced GABAergic inhibition, and no change in glutamatergic neuron excitability following transcranial stimulation testing (Stern et al., *Neurology* 88, 1659-1665, 2017). Thus, studies of both mouse and human strongly indicate that DS is a disease of forebrain interneurons, caused by pathogenic loss-of-function mutations in SCN1A. Based on this insight, it was hypothesized that targeted introduction of functional voltage gated sodium channel with properties similar to Nav1.1 in forebrain GABAergic interneurons would improve or eliminate DS symptoms via rescue of their physiology. For exemplary methods to electrophysiologically and phenotypically characterize DS in a mouse model, see FIG. 1 of Rubinstein et al., *Brain* 138(Pt 8):2219-33, 2015.

Cell type- or cell class-specific gene delivery using non-pathogenic recombinant adeno-associated virus (rAAV) is showing increasing promise for the treatment of diverse diseases. Inclusion within rAAVs of one or more cis-acting DNA-control elements, such as specific promoters or enhancers, has been beneficial to provide specificity for expression within particular target cells, including specific cell types or cell classes in the brain. For example, Dimidschstein and colleagues (*Nat Neurosci* 19(12):1743-1749, 2016) developed a rAAV that results in selective expression of a gene within GABAergic interneurons within the telencephalon. The rAAV includes a 529 base pair (bp) enhancer sequence (referred to as mI56i or mDlx) from the distal-less homeobox 5 and 6 (Dlx5/6) genes, which are naturally expressed by forebrain GABAergic interneurons during embryonic development (Zerucha et al., *J. Neurosci.* 20(2):709-721, 2000). A construct developed by Dimidschstein et al. is available on Addgene as ID #83900 (in which the enhancer drives eGFP expression). Additional constructs which employ the murine or human I56i enhancer to drive various transgenes are also available through Addgene, such as Plasmid ID #s 83899 (driving GCaMP6f expression), 83898 (driving ChR2-mCherry expression), 83895 (driving Cre recombinase-dependent eGFP expression), 89897 (driving bicistronic hM3Dq and nls-dTomato expression), 83896 (driving bicistronic hM4Di and nls-dTomato expression), and 83894 (driving cre recombinase-dependent tdTomato expression). See also U.S. Patent Publication No. US2018/0078658. Additionally, the mDlx enhancer has previously been used to reliably target reporter genes in a pattern very similar to the normal patterns of Dlx5/6 expression during embryonic development (Zerucha et al., *J Neuroscience* 20:709-721, 2000; Stühmer et al., *Cerebral Cortex* 12:75-85, 2002; Stenman et al., *J Neuroscience* 23:167-174, 2003; Monory et al., *Neuron.* 51:455-455, 2006; Miyoshi et al., *J Neuroscience* 30:1532-1594, 2010).

One significant drawback to using rAAVs as a selective gene-delivery system is the strictly restricted packaging limit of AAVs; this is particularly limiting to the inclusion of lengthy genetic control elements. In addition, existing interneuron-specific rAAV expression constructs provide weak expression in certain applications, as well as for expression of transgenes (such as therapeutic genes) that are more poorly tolerated than GFP. Thus, there remains a need in the art for even shorter enhancer sequences that are capable of providing cell-specific expression of Nav1.1 function-restoring proteins particularly in neurons such as inhibitory interneurons. There also remains a need for genetic elements that provide stronger expression, and/or that work with a wider selection of reporter or other target genes and in a wider array of expression contexts.

The current disclosure provides expression constructs that result in high levels of protein expression in inhibitory neurons for the purpose of rescuing voltage-gated sodium channel function. The protein expression is selective to targeted inhibitory neurons and results in therapeutic efficacy to treat DS in a well-established in vivo mouse model of the disease, particularly that described in Kalume et al., *J. Clin. Invest.* 123, 1798-1808, 2013; and Oakley et al., *Proc. Natl. Acad. Sci.* 106, 3994-3999, 2009. In this model, mice can be implanted with electroencephalography (EEG) and electromyography (EMG) electrodes using approaches described in Kalume et al., *J. Clin. Invest.* 123, 1798-1808, 2013; Kalume et al., *Neurobiol. Dis.* 77, 141-154, 2015; and Oakley et al., *Proc. Natl. Acad. Sci.* 106, 3994-3999, 2009). After recovery, animals can be continuously monitored by video, EEG, and EMG. During testing procedures, mouse body temperature can be increased in 0.5° C. steps until either a generalized tonic-clonic seizure occurs, or a core body temperature of 42° C. is achieved. For each treatment group, a Kaplan Meier curve for seizure susceptibility due to temperature can be generated and the average temperature of seizure occurrence can be computed. Chi-squared tests can contrast Kaplan Meier plots of seizure susceptibility, and unpaired 2-tailed t-tests ascertain differences among average temperatures of seizure occurrence.

In particular embodiments, the expression constructs include non-naturally occurring enhancer element sequences that demonstrate strong and rapid interneuron-specific expression when used to drive a heterologous encoding sequence to treat Nav1.1 associated sodium channel disorders. In particular embodiments, the non-naturally occurring enhancer element includes multiple copies of a shortened, core portion of the human or murine I56i enhancer (SEQ ID NO: 3). In fact, the present disclosure can include a concatemerized core of the I56i enhancer from any species, so long as the concatemerized core results in selective expression of a functional protein in inhibitory neurons. For example, the Zebrafish I56i enhancer is provided as SEQ ID NO: 5 and the core of the Zebrafish I56i enhancer is provided as SEQ ID NO: 6. Particular embodiments provide a non-naturally occurring enhancer element including a three-copy concatemer of the human, murine, or zebrafish I56i core, such as shown in SEQ ID NO: 3 and SEQ ID NO: 7. Additional embodiments include 2×, 4×, 5×, 6×, 7×, 8×, 9×, or 10× copies of I56i core sequence of SEQ ID NO: 2 or SEQ ID NO: 6, arranged for instance in tandem. Particular embodiments can include a concatemerized hybrid of SEQ ID NO: 2 and SEQ ID NO: 6 (e.g., 2-6-2, 6-2-6, 2-2-6, 6-6-2).

In particular embodiments, a concatemerized core of the I56i enhancer is used to minimize the size required to enhance expression of proteins or nucleotide sequences that rescue voltage-gated sodium channel function. The synthetic 3× human DLX I56i core enhancer (a.k.a., 3×hI56iCore; SEQ ID NO: 3) is shorter than the original full-length enhancer sequence reported in Dimidschstein et al. (*Nat Neurosci* 19(12):1743-1749, 2016), despite being a 3× concatemer of the strongly conserved core of the enhancer. When used to construct a heterologous expression cassette driving expression of proteins rescuing Nav1.1 sodium channel function, this concatemerized core enhancer provided more room for cargo genes linked to the enhancer, which is highly desirable in gene therapy vectors.

Figure 4A:
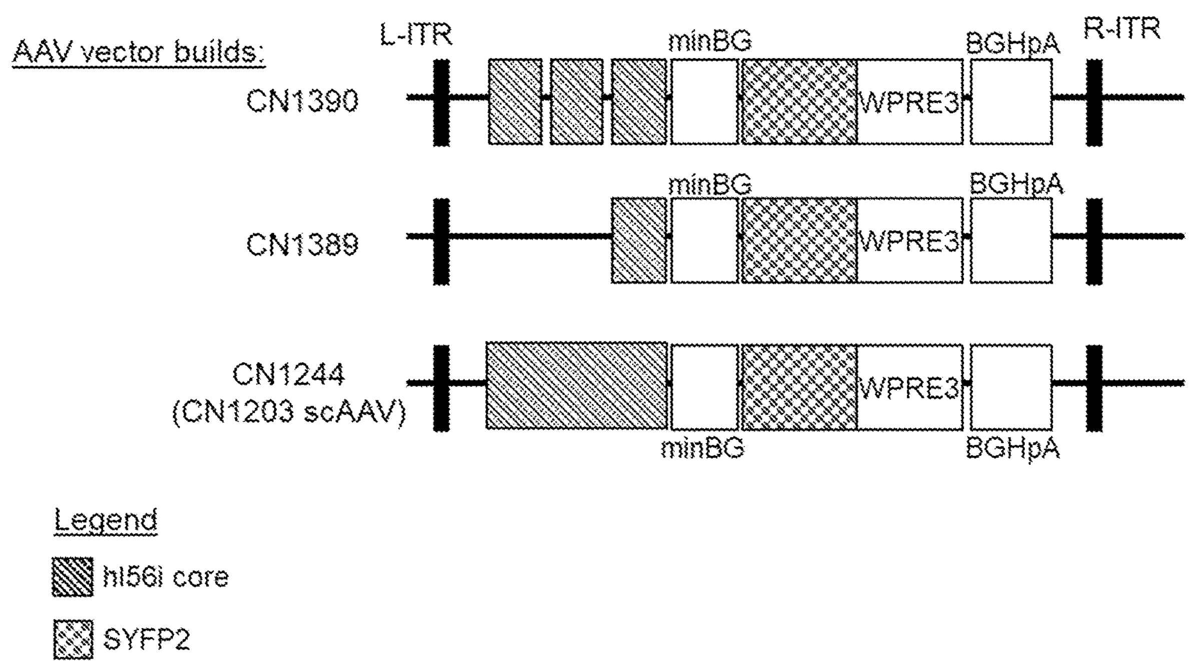
FIGS. 4A, 4B. Comparison of CN1244 vs CN1389 vs CN1390.
Figure 4B:
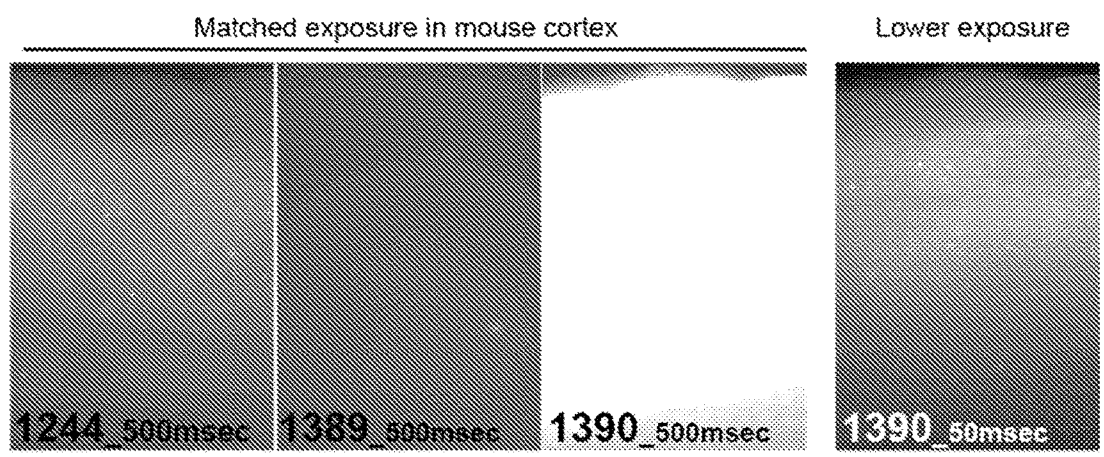
Figure 5:
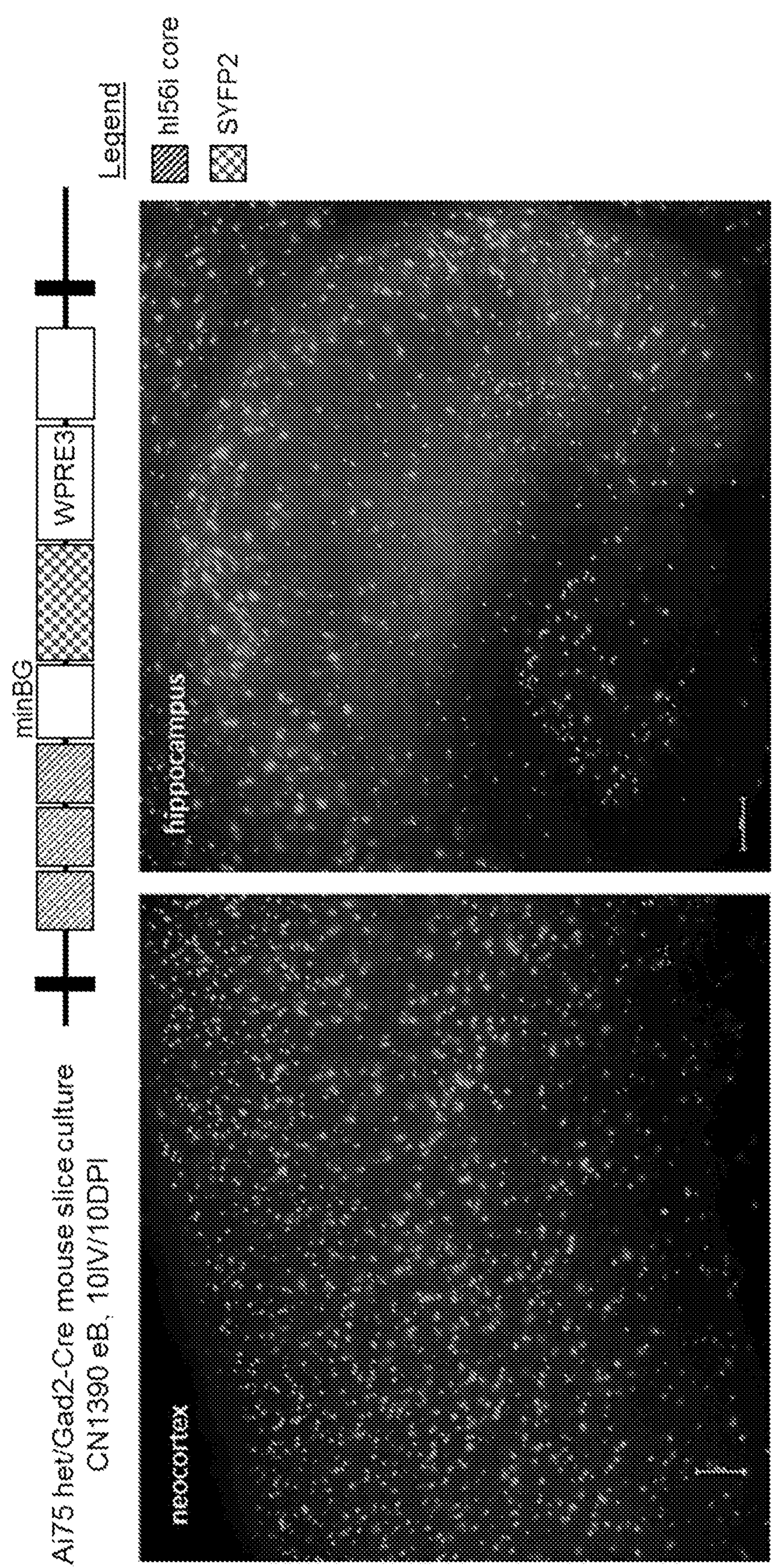
FIG. 5. CN1390 retains cell type specificity of reporter expression for the pan-GABAergic neuronal populations (marked with red fluorescence in these Ai75 het/Gad2-IRES-Cre mice) in the juvenile mouse cortex and hippocampus in slice culture. 10 DIV/10 DPI.
Figure 6A:
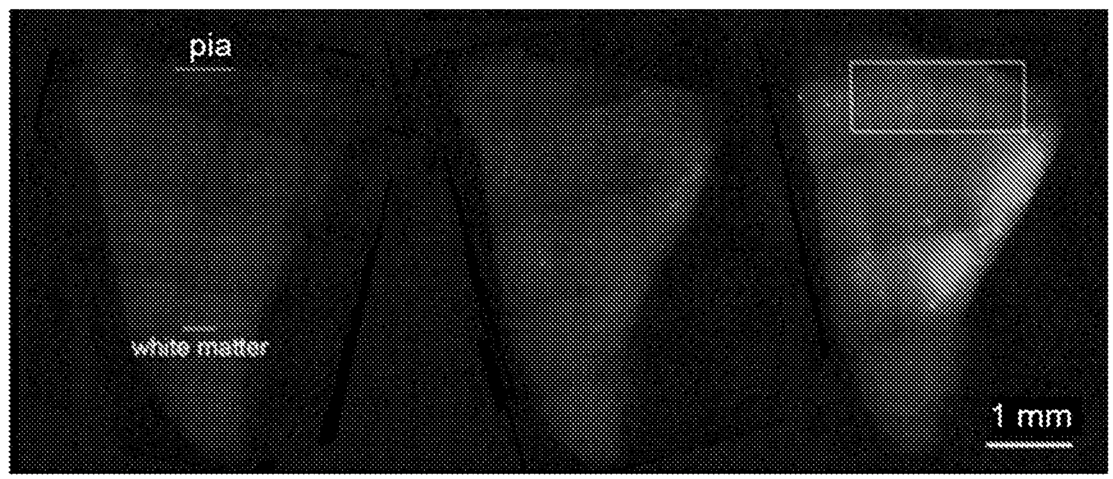
FIGS. 6A-6E. CN1390 exhibits rapid onset of transgene expression in human ex vivo brain slices.
Figure 6B:
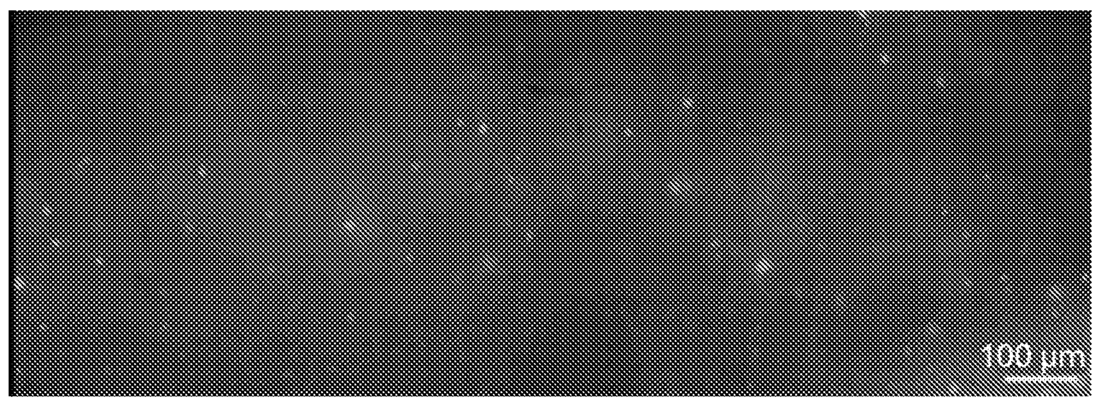
Figure 6C:
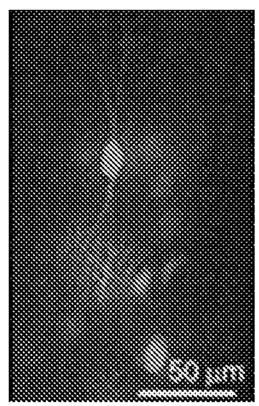
Figure 6D:
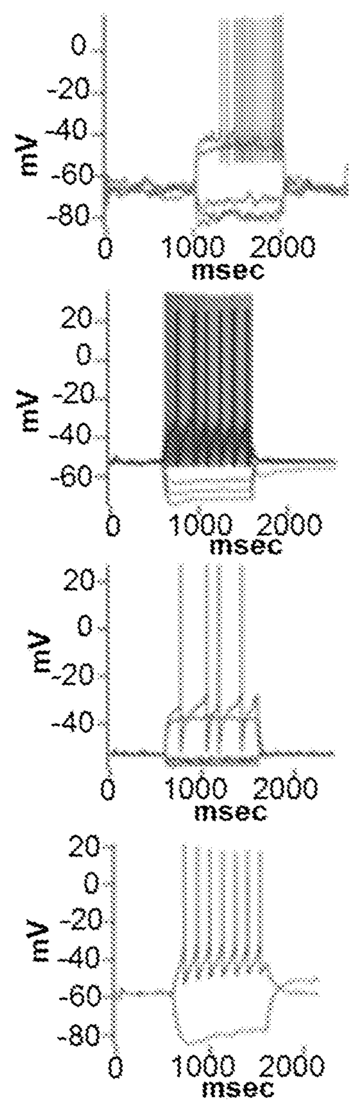
Figure 6E:
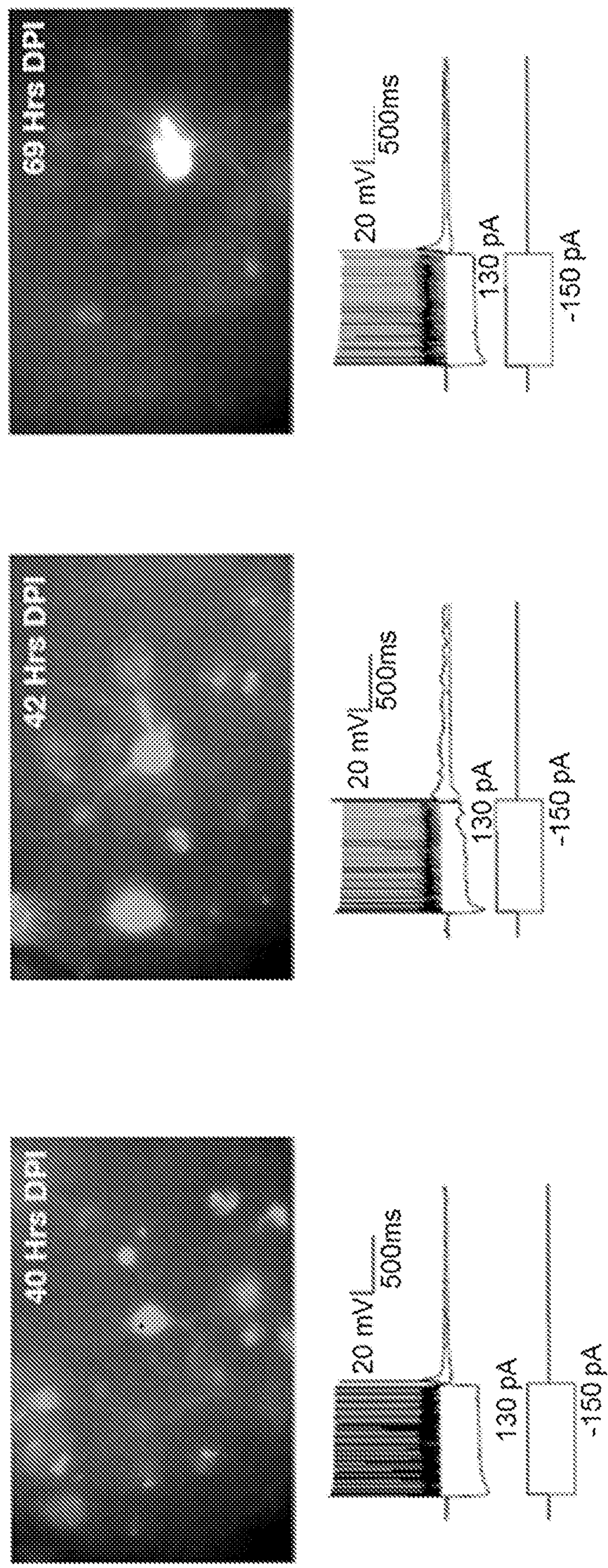
Figure 7A:
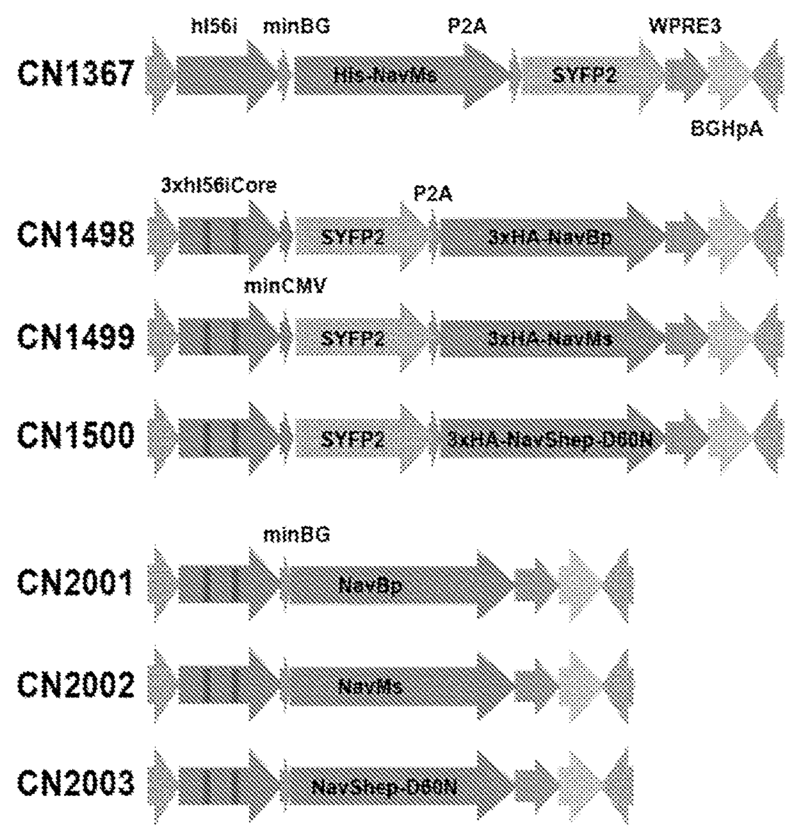
FIGS. 7A-7F. AAV vector reagents to reverse DS symptoms in $Scn1a^{+/-}$ mice. (7A) Vectors to deliver epitope-tagged Nav genes of bacterial origin (NavBacs). The Nav genes shown here are NavMs (from *Magnetococcus marinus*), NavBp (from *Bacillus pseudofirmus*), and NavSheP-D60N (from *Shewanella putrifaciens* with an engineered D60N mutation). These examples all have N-terminal epitope tags (hexahistidine in the case of CN1367, or 3×HA for CN1498, CN1499, and CN1500). hI56i refers to the full-length I56i enhancer of SEQ ID NO: 1; 3×hI56iCore refers to the concatemerized core of the I56i enhancer (SEQ ID NO: 3); (7B) Graded expression levels from NavBac vectors. (7C) Weak but detectable expression in few Pvalb interneurons from vector CN1367. (7D) Trend towards seizure protection with vector CN1367. (7E) Vector 1500 drives high-level expression in $Pvalb^+$ and $Pvalb^-$ interneurons throughout cortex. (7F) Abundant production of HA-tagged NavBacs in cell bodies and proximal processes with vectors 1498 and 1500, but not 1499.
Figure 7B:
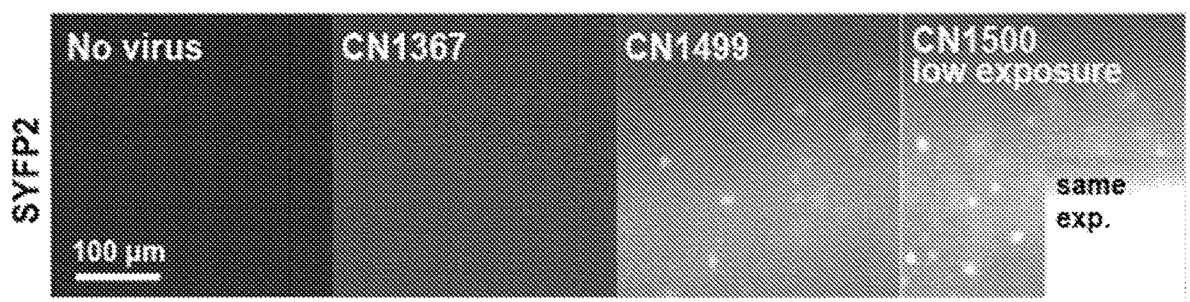
Figure 7C:
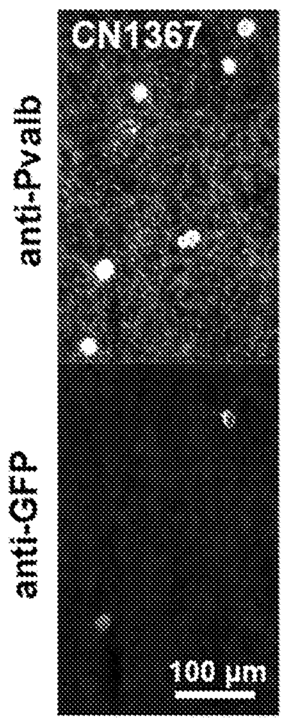
Figure 7D:
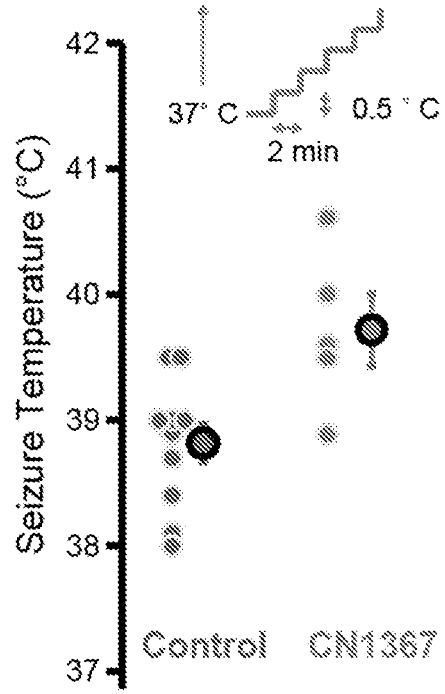
Figure 7E:
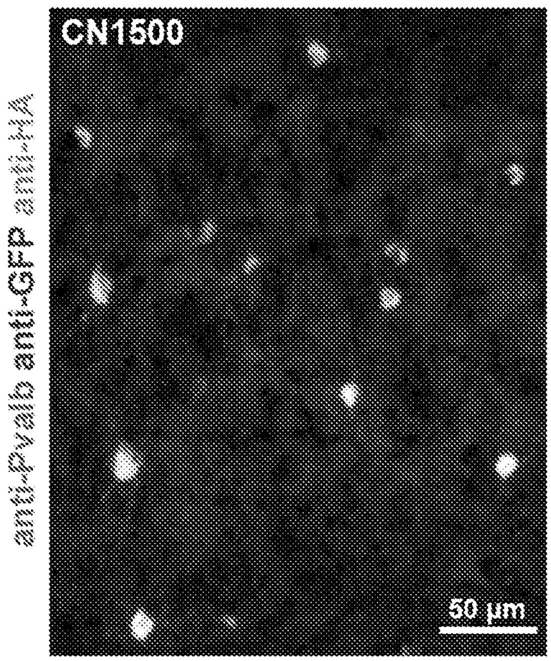
Figure 7F:
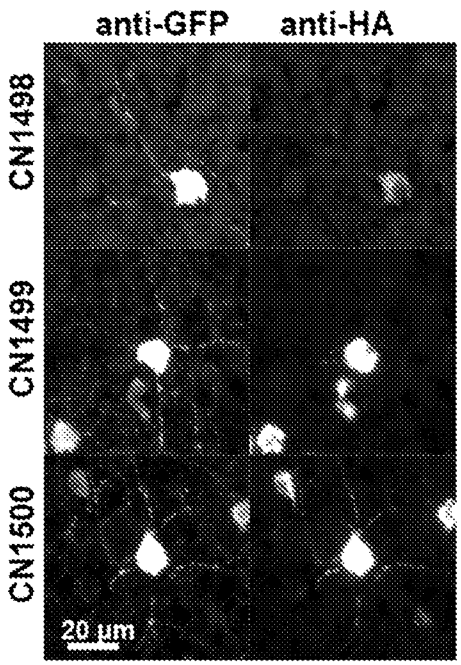

The compact size of the enhancer core, together with the multiple copies linked together as a concatemer, led to unexpectedly strong peak transgene expression in forebrain interneurons following viral transduction of mouse and human brain tissue (see FIGS. 4B & 5). The onset is also surprisingly rapid (see FIGS. 6A, 6B), leading to faster and higher expression in direct comparison to virus packaged with, for instance, the enhancer of Addgene plasmid #83900. The increase in expression is supra-linear and not simply three times the level driven by the full-length enhancer (SEQ ID NO: 1). Thus, the concatemerized I56i core enhancer also enables new and improved viral (and other) vectors such as those described herein with demonstrably better performance in the treatment of Nav1.1 sodium channel disorders. These are particularly useful for achieving transgene expression in inhibitory brain cell types such as neocortical GABAergic interneurons in diverse animal species.

Thus, the current disclosure provides expression constructs, vectors, and methods useful in reversing or ameliorating deficiency of function of the voltage-gated sodium channel Nav1.1. In particular embodiments, the current disclosure provides treatment of Nav1.1 channel disorders by selectively delivering a gene providing a protein or nucleotide sequence that allows for rescue of voltage-gated sodium channel function to inhibitory interneurons with impaired Nav1.1 activity.

In particular embodiments, genes encoding proteins that rescue voltage-gated sodium channel function when Nav1.1 is impaired, are Nav genes of bacterial origin (NavBac) that function in human cells (Nguyen et al., *Nat. Commun.* 7, 13132, 2016; Sula et al., *Nat. Commun.* 8, 14205, 2017; DeCaen et al., *eLife* 3, e04387, 2014). Particular exemplary NavBacs include NavSheP, NavBp, and NavMs, which are three Nav proteins from three separate bacterial species. For representative experimental protocols and data demonstrating that bacterial voltage-gated sodium channels can confer sodium conductance to non-excitable cells, see Nguyen et al., Nature Communications 18(7),13132, 2016 and particularly Supplemental FIG. 8.

NavBac proteins can also be engineered by mutagenesis to increase or alter activity as necessary, as in NavSheP-D60N. Additionally, these proteins can be engineered to incorporate tags or other fusion proteins for detection, as in His-NavMs (which contains an N-terminal hexahistidine tag), or with N-terminal 3×HA tags, or with other epitope tags or fluorescent protein tags or with any other protein tag as necessary. In particular embodiments, expression constructs do not encode immunogenic components. In particular embodiments, expression constructs do not include or encode immunogenic components.

In particular embodiments, the genes encoding proteins that restore voltage-gated sodium channel function are genes encoding SCNA1 (e.g., human SCNA1 or mouse Scna1).

In particular embodiments, therapeutic treatments are based on the intravenous, retro-orbital, intraspinal, and/or intrathecal administration of viral vectors result in selective expression within targeted inhibitory neurons.

In particular embodiments, provided herein is an AAV viral vector CN1500, a recombinant AAV that expresses the transgene SYFP2-P2A-NavSheP-D60N, which when translated is cleaved into two proteins: SYFP2 (reporter) and NavSheP-D60N. As indicated, NavSheP-D60N (Nguyen et al., *Nat. Comm.* 7:13132, 2016) is a modified voltage-gated sodium channel of bacterial origin that has been modified to improve the channel kinetics and codon-optimized for increased expression in mammalian cells. The transgene expression level is elevated by the addition of a WPRE3 element, and transcription is terminated with the bovine growth hormone poly adenylation sequence (BGHpA). Expression of the transgene is high and limited to inhibitory cells in forebrain structures including the cortex and the hippocampus, via the 3×hI56iCore synthetic enhancer directly 5' of a cytomegalovirus (CMV) minimal promoter. Furthermore, the therapeutic transgene NavSheP-D60N can be labeled by an HA epitope tag to verify protein expression and correct protein localization. Therapeutic efficacy in a mouse model of DS has been demonstrated. In particular embodiments, the HA epitope tag can be removed from CN1500 and other vector designs described herein.

Figure 8:
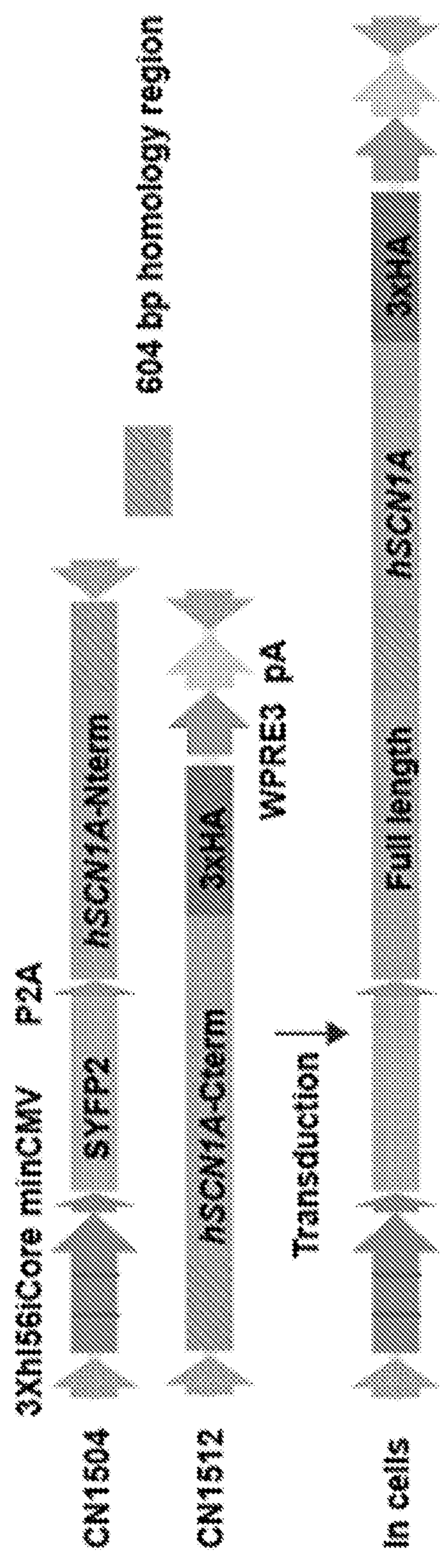
FIG. 8. Four exemplary strategies to encode and deliver full-length human SCN1A protein despite exceeding the AAV packaging limit. The human SCN1A gene (hSCN1A) has a 6030 bp open reading frame which exceeds the 4.7 kb packaging limit in AAV vectors. One approach to overcome this size limit is to split hSCN1A into two parts for delivery. Strategies 1 and 2 take advantage of homology-driven recombination between two separate AAV vector genomes (homologous regions indicated with hashed lines) to enable full open reading frame reconstitution in co-transduced cells. Strategies 3 and 4, in contrast, add trans-splicing elements (synthetic intron indicated by dots) to potentially increase the efficiency of open reading frame reconstitution and hence full-length protein expression. Strategies 1 and 3 utilize SYFP-P2A- and 3×HA-tagged hSCN1A protein to enable easy detection of both parts of the protein by fluorescence and immunohistochemistry, while strategies 2 and 4 utilize untagged hSCN1A protein and a vertebrate promoter to ensure low immunogenicity of the delivered transgene and encoded proteins. Another strategy is to utilize multiple vectors, each encoding a different segment or subunit of the SCN1A protein. Protein subunits can then self-assemble after expression naturally or through the inclusion of engineered cysteines or other linking domains.
Figure 8:
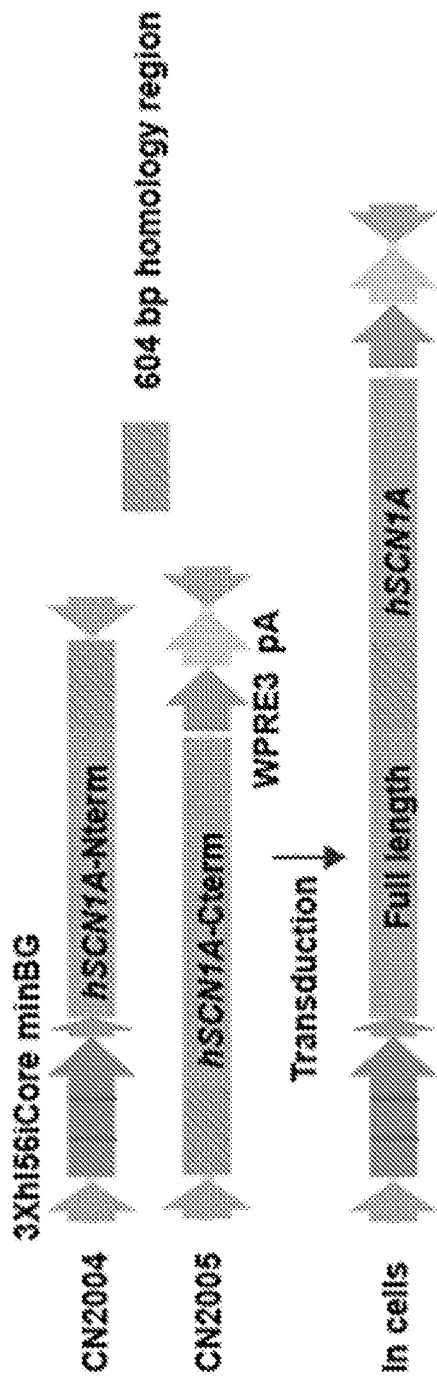
Figure 8:
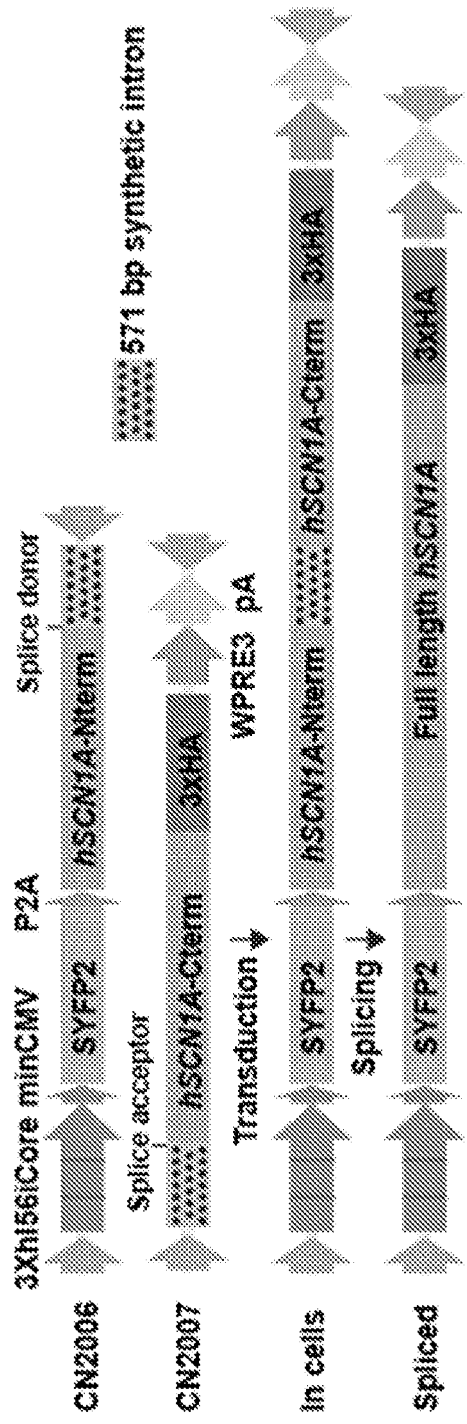
Figure 8:
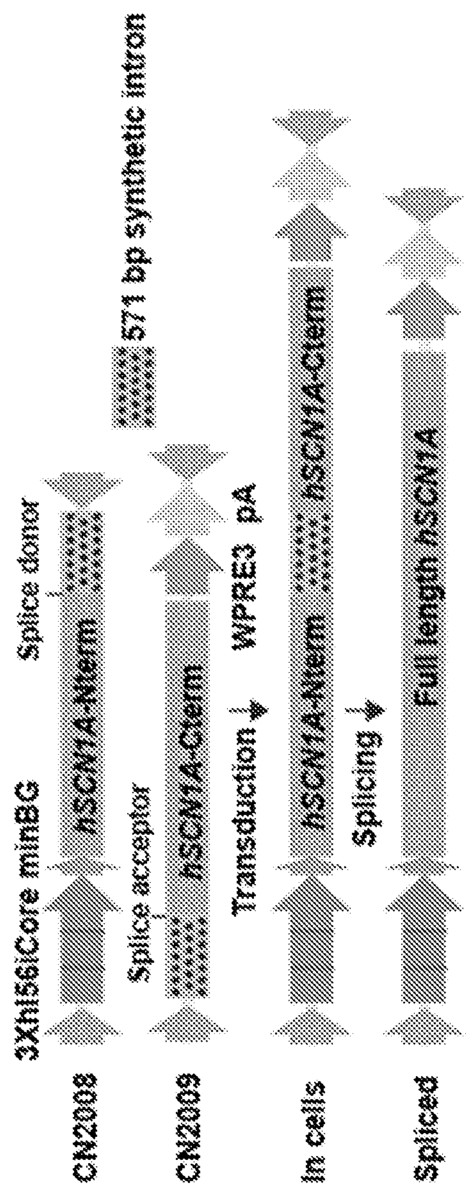

The human SCNA1 gene is relatively large and can benefit from administration from a vector that accepts a larger cargo than AAV or by using a two-AAV vector administration strategy. Multiple different strategies can be utilized in order to split a large open reading frame among two AAV vectors. Four strategies to split the large hSCN1A open reading frame are depicted in FIG. 8, but several more can be imagined.

Figure 9:
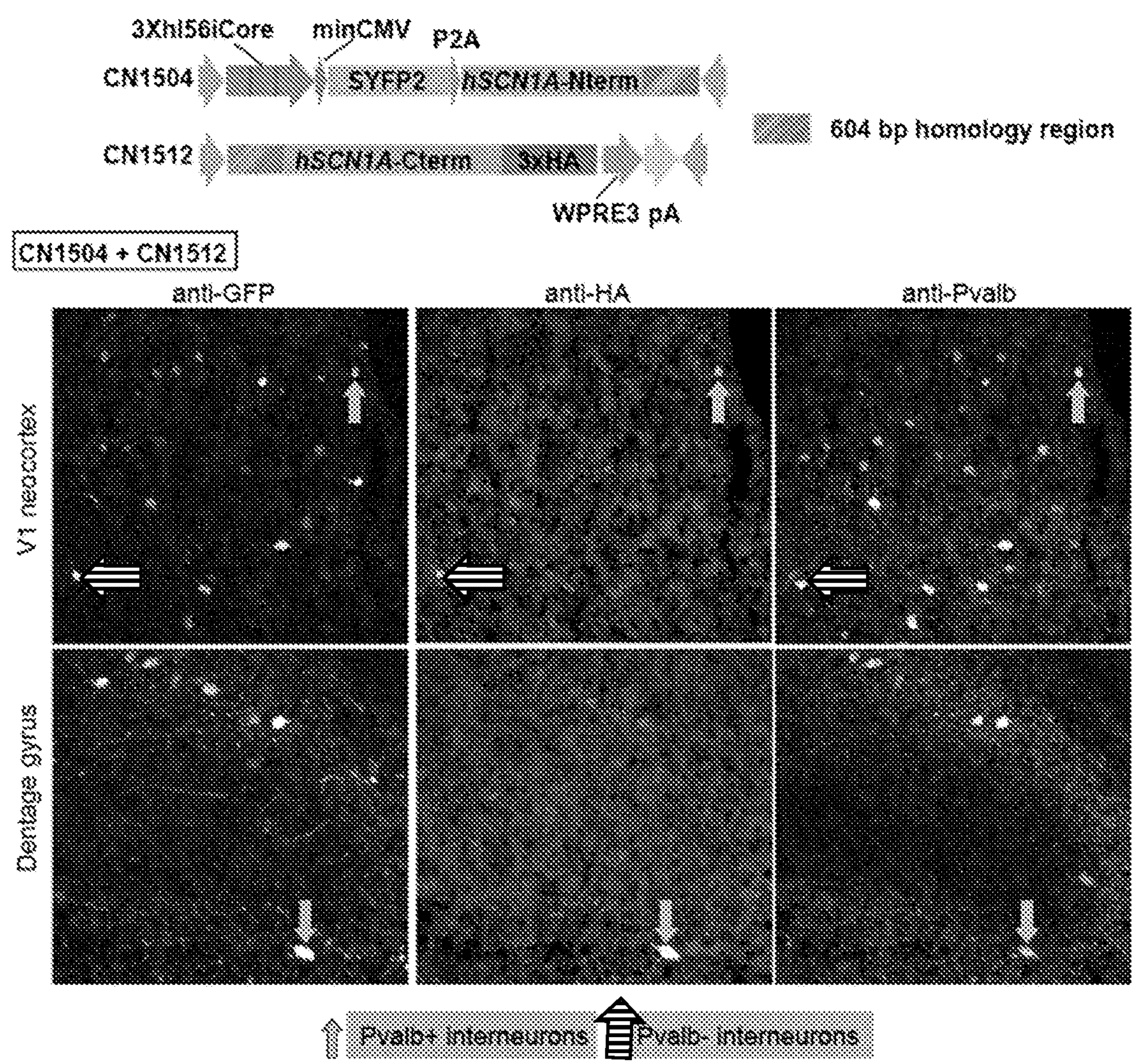
FIG. 9. Full-length human SCN1A expression driven by a two-part AAV viral vector system. (Top panel): Model of two-part vector system. The top vector (1504) includes the concatemerized 3×hI56iCore (SEQ ID NO: 3) and promoter (minCMV) elements to drive expression in all inhibitory neurons (including both Pvalb+ and Pvalb− inhibitory neurons). The driven transgene includes a SYFP2 linked by a P2A tag to the N-terminal region of human SCN1A, which includes 604 bp homology to the C-terminal region included on the bottom vector 1512. The bottom vector 1512 also includes a C-terminal 3×HA tag and 3'UTR regulatory sequences (WPRE3 and polyA sites). (Bottom panel): Both AAV viral vectors were packaged into viral particles with PHP.eB capsid and both were delivered intravenously to a C57Bl/6 mouse. After 21 days the mouse brain was harvested, fixed, and processed for immunofluorescence with anti-GFP (targeting SYFP2), anti-HA, and anti-Pvalb antibodies to detect transgene-expressing cells and their overlap with $Pvalb^{+}$ inhibitory neurons (which are cells having particular importance in DS symptomology). Many inhibitory neurons were labeled with the N-terminal $SYFP2^{+}$ tag at high level, including both $Pvalb^{+}$ and $Pvalb^{-}$ inhibitory neurons. Some of these $SYFP2^{+}$ cells also express HA which indicates fully intact SCN1A protein product being expressed in these $GFP^{+}HA^{+}$ cells (arrows). The vertical arrows indicate $Pvalb^{+}$ interneurons expressing human SCN1A and the horizontal arrows indicate $Pvalb^{-}$ interneurons expressing human SCN1A. These SCN1A-expressing cells are found throughout the forebrain (both neocortex and hippocampus [here dentate gyrus]), which includes the brain region known to be important in many epilepsies and known to be dysfunctional in DS.

In particular embodiments, a two-vector administration strategy can split a coding sequence between two vectors. In particular embodiments, the first vector can encode the N-terminal portion of a protein and include a promoter and an enhancer. The second vector can encode the C-terminal portion of the protein and include a termination signal and a polyA signal. The portions of the protein encoded by each vector overlap to create a region of homology. Example 2, FIG. 8 strategy 1, and FIG. 9 show an example of such a two-vector system that achieved selective expression of the human SCN1A protein in inhibitory neurons. The 604-base pair (bp) region of homology is depicted in FIG. 9 by diagonal hashing. However, as is understood by one of ordinary skill in the art, a wide range of number of homologous bp can be selected. In particular embodiments, bp regions of homology range from less than 75 to more than 1500 bp. Moreover, various other components and configurations can be appropriate in a two-vector system as described in relation to single vector systems in more detail elsewhere herein. Another possible configuration includes a synthetic intron element that provides a region of homology as well as splice donor and acceptor sites that make final reconstitution of the protein more efficient and lead to higher levels of protein expression.

Moreover, additional strategies can also be used to provide exogenous voltage-gated sodium channel activity to inhibitory neurons that are deficient in this activity. For example, particular embodiments can utilize expression constructs encoding an artificial transcription factor that increases the expression of the endogenous functional copy of SCN1A.

In particular embodiments, expression constructs can encode molecules that increase the prevalence of functional SCN1A mRNA molecules, for example through post-transcriptional positive regulation of splicing and or stability.

In particular embodiments, strategies can be employed that restore the full length hSCN1A transcript through trans-splicing the hSCN1A transcript separated into two parts.

In particular embodiments, expression constructs (e.g., AAV) can deliver hSCN1A protein as several (two or four) subunit ORFs delivered by two or four separate vectors.

Aspects of the disclosure are now described with the following additional options and detail: (i) Expression Constructs & Vectors; (ii) Compositions for Administration (iii) Methods of Use; (iv) Kits and Commercial Packages; (iv) Exemplary Embodiments; and (v) Experimental Examples.

(i) Expression Constructs & Vectors. Expression constructs disclosed herein include (i) a concatemerized core of the I56i enhancer sequence that leads to selective expression of a coding sequence within inhibitory neurons, (ii) a coding sequence that is expressed and results in a protein or nucleotide sequence that rescues voltage-gated sodium channel function in a cell in need thereof, and (iii) a promoter. The expression construct can also include other regulatory elements if necessary or beneficial. In particular embodiments, expression constructs are isolated polynucleotides.

In particular embodiments, an "enhancer" or an "enhancer element" is a cis-acting sequence that increases the level of transcription associated with a promoter, and can function in either orientation relative to the promoter and the coding sequence that is to be transcribed, and can be located upstream or downstream relative to the promoter or the coding sequence to be transcribed. There are art-recognized methods and techniques for measuring function(s) of enhancer element sequences. By way of example, specific methods for determining or measuring function(s) of a I56i enhancer are described in Dimidschstein et al. (Nat Neurosci 19(12):1743-1749, 2016) and U.S. Patent Publication No. US2018/0078658. Particular examples of enhancer sequences include the human full-length I56i enhancer (SEQ ID NO: 1), the h156 core (SEQ ID NO: 2), and the 3×hI56i core (SEQ ID NO: 3) as well as the murine and zebrafish orthologs thereof.

In particular embodiments, an inhibitory-neuron-specific enhancer is an enhancer that is uniquely or predominantly utilized in inhibitory neurons. An inhibitory-neuron-specific enhancer enhances expression of a gene in inhibitory neurons, but does not substantially affect expression of genes in other cell types, for example non-inhibitory neurons or glial cells, thus having neuronal specific transcriptional activity. In some instances there may be some low level expression in other cell types, but such expression is substantially lower than in inhibitory neurons, for example less than 1% or 1%, 2%, 3%, 5%, 10%, 15% or 20% of the expression levels in inhibitory neurons. In particular embodiments, interneurons are the only cell types that express the right combination of transcription factors that bind to the concatemerized core of the I56i enhancer to drive gene expression.

In particular embodiments, selective expression within inhibitory neurons is demonstrated by 10% more expression, 20% more expression, 30% more expression, 40% more expression; 50% more expression; 60% more expression, 70% more expression, 80% more expression, 90% more expression, 100% more expression or more over non-inhibitory neurons. In particular embodiments, selective expression within inhibitory neurons is demonstrated by expression within inhibitory neurons and no detectable expression within non-inhibitory neurons.

In particular embodiments, selective expression within GABAergic interneurons is demonstrated by 10% more expression, 20% more expression, 30% more expression, 40% more expression; 50% more expression; 60% more expression, 70% more expression, 80% more expression, 90% more expression, 100% more expression or more over non-GABAergic interneurons. In particular embodiments, selective expression within GABAergic interneurons is demonstrated by expression within GABAergic interneurons and no detectable expression within non-GABAergic interneurons.

In particular embodiments, one class of inhibitory neurons can be identified based on Pvalb expression as described in relation to FIGS. 1, 7C, 7E, and 8. In particular embodiments, GABAergic interneurons can be distinguished from other cell types by the expression of the genes Gad2 and Gad1; in the adult cortex, GABAergic interneurons can be distinguished from glutamatergic excitatory neurons by the presence of GABA. In the adult striatum, GABAergic interneurons can be distinguished from Medium Spiny Neurons by the expression of the gene Nkx2.1. (See, for example, Rudy et al., Devel Neurobio 71, 45-61 (2011)): Kepecs. & Fishell, Nature. 505, 318-326 (2014).

In particular embodiments, a coding sequence encodes a protein or nucleotide sequence that rescues voltage-gated sodium channel function. In particular embodiments, the coding sequence further encodes a reporter protein. If the coding sequence encodes a protein or nucleotide sequence that rescues voltage-gated sodium channel function and a reporter protein, it can further encode a skipping element such as a self-cleaving peptide or an internal ribosome entry site (IRES) sequence.

Exemplary proteins that restore voltage-gated sodium channel function include NavShep, NavShep-D60N, NavBp, NavMs, and hSCN1A, and their epitope-tagged variants 3×HA-NavShep-D60N, 3×HA-NavBp, 3×HA-NavMs, His-NavMs, and hSCN1A-3×HA.

Exemplary coding sequences that encode proteins that rescue voltage-gated sodium channel function include SEQ ID NOs: 9-16.

Further, as indicated above, there are additional strategies that can be used to provide exogenous voltage-gated sodium channel activity to inhibitory neurons that are deficient in this activity. For example, in particular embodiments, enhancer-vectors (e.g., AAV) can encode an artificial transcription factor that increases the expression of the endogenous functional copy of SCN1A (or other SCN_A family gene) in SCN1A$^{+/-}$ patients (e.g., Dravet patients) or other patients deficient in other voltage-gated sodium channels.

This artificial transcription factor can contain a specific DNA-binding domain linked to a general transcription-activating domain. The DNA-binding domain can be engineered from a Cas9-related gene using CRISPR activation technology (as in Matharu et al., 2019, Science, 363(6424), 186-194 wherein Cas proteins are engineered to lack nuclease activity), or from other custom DNA-sensing proteins such as TALE-transcription factors (TFs) (Morbitzer et al., 2010, Proc. Nat. Acad. Sci., 107(50), 21617-21622) or zinc finger TFs (Gersbach et al., 2014, Acc. Chem. Res, 47(8), 2309-2318). Additional information and options regarding CRISPR and other targeted gene binding (and optionally editing) systems and components are provided below.

In particular embodiments, enhancer-vectors can encode molecules that increase the prevalence of functional SCN1A mRNA molecules, for example through post-transcriptional positive regulation of splicing and or stability, eventually leading to increases in functional voltage-gated sodium channel activity. This could be accomplished through AAV introduction of antisense RNA oligonucleotide molecules to increase splicing (Hsiao et al., 2016, EBioMedicine. 9, 257-277), or to prevent potential microRNA negative regulation.

In particular embodiments, strategies can be employed that restore the full length hSCN1A transcript through trans-splicing the hSCN1A transcript separated into two parts. This can be accelerated through the use of strong synthetic splice donors and splice acceptors in a two vector system, and through the use of different ITRs (ITR2 and ITR5) that induce proper juxtaposition of the two different genomes in cell after transduction (McClements M E, et al., 2017, Yale J. Biol Med. 90(4):611-623).

In particular embodiments, enhancer-vectors (e.g., AAV) can deliver hSCN1A protein as several (two or four) subunit ORFs delivered by two or four separate vectors. Nav channels display pseudo-four-fold internal symmetry, due to four similar internal domains within the alpha subunit (Shen et al., Science 363(6433), 1303-1308), demonstrating that this protein can be amenable to delivery in two or four pieces. As indicated previously, assembly of sub-units can occur naturally and/or can be facilitated by the inclusion of engineered cysteines or other linking domains.

In particular embodiments, due to its internal 4-domain pseudo-symmetry, hSCN1A can be delivered in four fragments encoded on four different vectors that can self-assemble into a tetramer that is functionally and chemically equivalent to the functional NaV1.1 alpha subunit, except with breakpoints in surface loops. Alternatively, a single fragment may be delivered on a single vector that may self-assemble into a homo-tetrameric complex resembling the NaV1.1 alpha subunit which consists entirely of human sequence. Either strategy can deliver human non-immunogenic biomolecules to inhibitory cells for the purpose of rescuing Nav1.1 channel function in neurons that are deficient in voltage-gated sodium channel activity.

Additional strategies could also be used to reduce the hSCN1A ORF into a smaller (e.g., AAV-compatible) size (<4.7 kb).

Exemplary reporter proteins include fluorescent proteins such as yellow fluorescent molecules such as SYFP2, Citrine, PhiYFP and ZsYellow1; red fluorescent molecules such as mCherry, mRuby, Jred, and AsRed2; green fluorescent molecules such as green fluorescent protein (GFP), enhanced green fluorescent protein (EGFP), avGFP, ZsGreen, and mAzamiGreen; orange fluorescent molecules such as mOrange and mKusabira-Orange; blue fluorescent molecules such as Sapphire, mKalamal, EBFP2 and Azurite; cyan fluorescent molecules such as Cerulean and mTurquoise; far red proteins such as mPlum and mNeptune.

GFP is composed of 238 amino acids (26.9 kDa), originally isolated from the jellyfish Aequorea victoria/Aequorea aequorea/Aequorea forskalea that fluoresces green when exposed to blue light. The GFP from A. victoria has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of 9.13E-21 $m^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from Aequorea victoria. Its excitation peak is 514 nm and its emission peak is 527 nm.

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the expression constructs include an internal ribosome entry site (IRES) sequence. IRES allow ribosomes to initiate translation at a second internal site on a mRNA molecule, leading to production of two proteins from one mRNA.

Coding sequences encoding proteins described herein can be obtained from publicly available databases and publications. Coding sequences can further include various sequence polymorphisms, mutations, and/or sequence variants wherein such alterations do not affect the function of the encoded protein. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, and termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin, CMV, minCMV, SV40 immediately early promoter, and the Rous Sarcoma Virus (RSV) long-terminal repeat (LTR) promoter.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell, or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived nucleic acid elements that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus. "Adenovirus vectors" refer to those constructs containing adenovirus sequences sufficient to (a) support packaging of an expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5'-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replication, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and rare integration into genomic DNA, and because their capsids and genomes can be tailored to allow expression in selected cell populations. scAAV refers to a self-complementary AAV. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retrovirus. Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

"Self-inactivating" (SIN) vectors refer to replication-defective vectors in which the right (3') LTR enhancer-promoter region, known as the U3 region, has been modified (e.g., by deletion or substitution) to prevent viral transcription beyond the first round of viral replication. This is because the right (3') LTR U3 region is used as a template for the left (5') LTR U3 region during viral replication and, thus, the viral transcript cannot be made without the U3 enhancer-promoter. In a further embodiment, the 3' LTR is modified such that the U5 region is replaced, for example, with an ideal poly(A) sequence. It should be noted that modifications to the LTRs such as modifications to the 3' LTR, the 5' LTR, or both 3' and 5' LTRs, are also included in particular embodiments.

In particular embodiments, viral vectors include a TAR element. The term "TAR" refers to the "trans-activation response" genetic element located in the R region of lentiviral (e.g., HIV) LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, J. Virol., 73:2886); the posttranscriptional regulatory element present in hepatitis B virus (HPRE) (Huang et al., Mol. Cell. Biol., 5:3864); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation sequence 3' of a polynucleotide encoding a polypeptide to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA or SV40pA. In particular embodiments, a preferred embodiment of an expression construct includes a terminator element. These elements can serve to enhance transcript levels and to minimize read through from the construct into other plasmid sequences.

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

Particular embodiments include:

| Vector Name | Features |
|---|---|
| CN1367 | rAAV2: hI56i-minBglobin-His-NavMs-P2A-SYFP2-WPRE3-BGHpA |
| CN1244 | rAAV2: hI56i-minBglobin-SYFP2-WPRE3-BGHpA |
| CN1389 | rAAV2: 1xhI56iCore-minBglobin-SYFP2-WPRE3-BGHpA |
| CN1390 | rAAV2: 3xhI56iCore-minBglobin-SYFP2-WPRE3-BGHpA |
| CN1203 | scAAV: hI56i-minBglobin-SYFP2-WPRE3-BGHpA |
| CN1180 | scAAV: hI12b-minBglobin-SYFP2-WPRE3-BGHpA |
| CN1498 | rAAV2: 3xhI56iCore-minCMV-SYFP2-P2A-3xHA-NavBp-WPRE3-BGHpA |
| CN1499 | rAAV2: 3xhI56iCore-minCMV-SYFP2-P2A-3xHA-NavMs-WPRE3-BGHpA |
| CN1500 | rAAV2: 3xhI56iCore-minCMV-SYFP2-P2A-3xHA-NavSheP-D60N-WPRE3-BGHpA |
| CN1504 | rAAV2: 3xhII56iCore-minCMV-SYFP2-P2A-hSCN1A-Nterm |
| CN1512 | rAAV2: hSCN1A-Cterm-3xHA-WPRE3-BGHpA |
| CN2001 | rAAV2: 3xhI56iCore-minBG-NavBp-WPRE3-BGHpA |
| CN2002 | rAAV2: 3xhI56iCore-minBG-NavMs-WPRE3-BGHpA |
| CN2003 | rAAV2: 3xhI56iCore-minBG-NavSheP-D60N-WPRE3-BGHpA |

-continued

| Vector Name | Features |
|---|---|
| CN2004 | rAAV2: 3xhl56iCore-minBG-hSCN1AFrontEnd |
| CN2005 | rAAV2: hSCN1ABackEnd-WPRE3-BGHpA |
| CN2006 | rAAV2: 3xhl56iCore-minBG-SYFP2ns-P2A-hSCN1AFrontEnd-IntronBridge |
| CN2007 | rAAV2: IntronBridge-hSCN1ABackEnd-3xHA-WPRE3-BGHpA |
| CN2008 | rAAV2: 3xhl56iCore-minBG-hSCN1AFrontEnd-IntronBridge |
| CN2009 | rAAV2: IntronBridge-hSCN1ABackEnd-WPRE3-BGHpA |
| CN2026 | rAAV-3xhl56i(core)-minBG-hSCN1A_Fragment1-WPRE3-BGHpA |
| CN2027 | rAAV-3xhl56i(core)-minBG-hSCN1A_Fragment2-WPRE3-BGHpA |
| CN2028 | rAAV-3xhl56i(core)-minBG-hSCN1A_Fragment3-WPRE3-BGHpA |
| CN2029 | rAAV-3xhl56i(core)-minBG-hSCN1A_Fragment4-WPRE3-BGHp |

In particular embodiments viral vectors with capsids that cross the blood-brain barrier (BBB) are selected. In particular embodiments, AAV are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1(Marchio et al., EMBO Mol Med. 2016; 8(6): 592), AAV-PHP.S (Chan et al., Nat Neurosci. 2017; 20(8): 1172), AAV-PHP.B (Deverman et al., Nat Biotechnol. 2016; 34(2): 204), and AAV-PPS (Chen et al., Nat Med. 2009; 15: 1215).

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to the ongoing clinical trials for the treatment of spinal muscular atrophy (SMA) syndrome by AveXis (AVXS-101, NCT03505099) and the treatment of CLN3 gene-Related Neuronal Ceroid-Lipofuscinosis (NCT03770572). In particular embodiments, a representative AAV9 capsid protein sequence can include the AAV9 VP1 capsid protein sequence (UniProt Accession number Q6JC40, SEQ ID NO: 57).

AAVrh.10, was originally isolated from rhesus macaques and shows low seropositivity in humans when compared with other common serotypes used for gene delivery applications (Selot et al., Front Pharmacol. 2017; 8: 441) and is currently being evaluated in clinical trials LYS-SAF302, LYSOGENE, and NCT03612869.

AAV1R6 and AAV1R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 53) epitope that was isolated during in vivo screening of a random AAV display peptide library. It shows high specificity accompanied by high transgene expression in the brain with minimal off-target affinity (including for the liver) (Körbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 54), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 55). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 56) epitope into the capsid of AAV2, shows a dramatically improved brain tropism relative to AAV2.

In particular embodiments, a capsid that results in brain-wide transduction of inhibitory cells in a primate following administration (e.g., i.v. administration) is chosen. In particular embodiments, a capsid that results in widespread transduction of tissue and cell types impacted by the loss of Scn1a following administration is chosen.

Compositions for Administration. Expression constructs and vectors of the present disclosure (referred to herein as physiologically active components) can be formulated with a carrier that is suitable for administration to human or animal subjects. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously.

In particular embodiments, compositions can be formulated for intravenous, intraocular, intravitreal, parenteral, subcutaneous, intracerebro-ventricular, intramuscular, intrathecal, intraspinal, oral, intraperitoneal, oral or nasal inhalation, or by direct injection to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are widely suitable as both water- and lipid-soluble substances can be entrapped, i.e. in the aqueous spaces and within the bilayer itself, respectively.

Liposomes may also be employed for site-specific delivery of active agents by selectively modifying the liposomal formulation. Should specific targeting be desired, methods are available for this to be accomplished. For example, binding domains of antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types.

In addition to the teachings of Couvreur et al. (*FEBS Lett.* 84(2):323-326, 1977; *Crit Rev Ther Drug Carrier Syst.* 5(1)1-20, 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

Alternatively, the disclosure provides for pharmaceutically acceptable nanocapsule formulations of the physiologically active components of the present disclosure. Nanocapsules can generally entrap compounds in a stable and reproducible way (Quintanar-Guerrero et al., *Drug Dev Ind Pharm* 24(12):1113-1128, 1998; Quintanar-Guerrero et al., *Pharm Res.* 15(7):1056-1062, 1998; Quintanar-Guerrero et al., J. *Microencapsul.* 15(1):107-119, 1998; Douglas et al., *Crit Rev Ther Drug Carrier Syst* 3(3):233-261, 1987). To avoid side effects due to intracellular polymeric overloading, ultrafine particles can be designed using polymers able to be degraded in vivo. Biodegradable polyalkyl-cyanoacrylate nanoparticles that meet these requirements are contemplated for use in the present disclosure. Such particles may be made as described in Couvreur et al., *J Pharm Sci* 69(2):199-202, 1980; Couvreur et al., *Crit Rev Ther Drug Carrier Syst.* 5(1)1-20, 1988; zur Muhlen et al., *Eur J Pharm Biopharm,* 45(2):149-155, 1998; Zambaux et al., *J Control Release* 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res,* 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

Methods of Use. In particular embodiments, a composition including a physiologically active component described herein is administered to a subject to result in selective expression of a protein or nucleotide sequence that rescues voltage-gated sodium channel function within inhibitory neurons in the subject. In particular embodiments, rescuing voltage-gated sodium channel function includes converting a subject's interneurons lacking a sufficient quantity and/or activity of Nav1.1 sodium channels, into interneurons that express a sufficient quantity of exogenous voltage-gated sodium channels and activity, in order to recover neuronal function and to prevent epileptiform circuit activity.

In particular embodiments, rescued voltage-gated sodium channel function is evidenced by one or more of an increase in sodium channel current in and/or the increased excitability of an inhibitory neuron genetically-modified by the physiologically active component. In particular embodiments, rescued voltage-gated sodium channel function is evidenced by one or more of an increase in sodium channel conductance in and/or the sodium channel influx in response to voltage depolarization of an inhibitory neuron genetically-modified by the physiologically active component. An increase can be at least a 10% increase, at least a 20% increase, at least a 30% increase, at least a 40% increase, at least a 50% increase, at least a 60% increase, at least a 70% increase, at least an 80% increase or at least a 90% increase. The output of inhibitory neurons can be measured using an electrophysiological method, such as a multi-electrode array or a patch-clamp.

In particular embodiments, the inhibitory neuron is an inhibitory interneuron, a GABAergic neuron, a GABAergic interneuron, a pan-GABAergic neuron, or an inhibitory neuron in the hippocampus or cortex.

In particular embodiments, rescued voltage-gated sodium channel function is evidenced by increased sodium current-dependent fast spiking in forebrain interneurons, for example, using a mouse model. In particular embodiments, rescued voltage-gated sodium channel function is evidenced by delayed or prevented temperature-induced seizing in a mouse model as described herein.

Particular embodiments include identifying a subject with reduced Nav1.1 sodium channel function in inhibitory neurons. Such subjects can be identified based on a diagnosis of a disorder associated with Nav1.1 sodium channel dysfunction. Such disorders include epilepsy, an SCN1A-related seizure disorder, simple febrile seizures (FS), GEFS+, DS, intractable childhood epilepsy with generalized tonic-clonic seizures (ICE-GTC), intractable infantile partial seizures, myoclonic-astatic epilepsy, Lennox-Gastaut syndrome (LGS), and infantile spasms. Intractable seizures (also referred to as "uncontrolled" or "refractory" seizures) are seizures that cannot be controlled to a satisfactory degree based on sound medical judgment with conventional treatments.

Regarding DS particularly, 80% of DS patients test positive for an SCN1A gene mutation, but the absence of an SCN1A mutation does not exclude a DS diagnosis. DS is associated with mutations in SCN1A (such as partial or total deletion mutations, truncating mutations and/or missense mutations e.g. in the voltage or pore regions S4 to S6), SCN1B (encoding the sodium channel β1 subunit), SCN2A, SCN3A, SCN9A, GABRG2 (encoding the γ2 subunit of GABA receptor), GABRD (encoding the delta subunit of GABA receptor) and/or PCDH19 genes.

In particular embodiments, a subject in need of a treatment described herein may not experience diagnosable seizures, but exhibits subclinical electrical discharges, which refers to a high rate of seizure-like activity when their brain waves are measured with an electroencephalogram. Epileptic syndromes associated with these seizure-like discharges include Landau-Kleffner Syndrome, and Continuous Spike-wave Activity during Slow-wave Sleep.

In particular embodiments, patients may have an intellectual developmental disability (IDD) such as an Autism Spectrum Disorders (ASD). In particular embodiments, the patient of the disclosed method has epilepsy and an IDD or ASD disorder. Common IDD and ASD that are comorbid with seizures and epilepsy include fragile X syndrome (FXS), Rett syndrome (RTT), Angelman syndrome, Prader- Willi syndrome, Velocardiofacial syndrome, Smith-Lemli-Opitz syndrome, neuroligin mutations and "interneuronopathies" resulting from aristaless-related homeobox, X-linked (ARX) and Neuropilin 2 (NRP2) gene mutations.

The methods described herein may be particularly useful for treating children and infants, and for treating disorders that onset during infancy or childhood. In particular embodiments, the patient of the disclosed method is a newborn, a baby, a toddler, a preschooler, a school-age child, a tween, or a teenager. In particular embodiments, the patient is 18 years old or younger, 12 years old or younger, 10 years old or younger, 8 years old or younger, 6 years old or younger, 4 years old or younger, 2 years old or younger, 1 year old or younger. In particular embodiments, the patient is an adult that is over eighteen years old.

In particular embodiments, the methods reduce or prevent seizures, or symptoms thereof in a patient in need thereof. In particular embodiments, the methods provided may reduce or prevent one or more different types of seizures. Ideally, the methods of the disclosure result in a total prevention of seizures. However, the disclosure also encompasses methods in which the instances of seizures are decreased by at least 10%, at least 20%, at least 30%, at least 40%, at least 50%, at least 60%, at least 70%, at least 80% or at least 90%.

Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In particular embodiments, methods described herein may reduce the frequency of seizures, reduce the severity of seizures, change the type of seizures (e.g., from a more severe type to a less severe type), or a combination thereof in a patient after treatment compared to the absence of treatment (e.g., before treatment), or compared to treatment with an alternative conventional treatment.

Administration of compositions can be by any appropriate route. For example, in particular embodiments, administration may include administration to a cell or tissue slice for research purposes related to Nav1.1 sodium channel dysfunction.

In particular embodiments, administration is to a subject and can be intravenous, retro-orbital, intraocular, intravitreal, parenteral, subcutaneous, intracerebro-ventricular, intramuscular, intrathecal, intraspinal, oral, intraperitoneal, nasal, or direct to a targeted site administration. Delivery can be accomplished by a needle or a cannula or by any other technique of expelling fluidic materials. The methods of administration may also include those modalities as described in U.S. Pat. Nos. 5,543,158; 5,641,515 and 5,399,363.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from $10^5$ to $10^{10}$ copies of an expression construct of the disclosure. In particular embodiments, a patient receiving intravenous, intraspinal, retro-orbital, intracerebroventricular, or intrathecal administration can be infused with from $10^6$ to $10^{22}$ copies of the expression construct.

Therapeutically effective amounts include those that provide effective amounts and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to a disorder associated with Nav1.1 sodium channel dysfunction.

A "therapeutic treatment" includes a treatment administered to a subject who displays symptoms or signs of a disorder associated with Nav1.1 sodium channel dysfunction and is administered to the subject for the purpose of diminishing or eliminating those signs or symptoms of the disorder. The therapeutic treatment can reduce, control, or eliminate the presence or activity of the disorder, the cause of the disorder, and/or reduce control or eliminate side effects of the disorder.

In particular embodiments, the administration of therapeutically-effective amounts of the disclosed compositions may be achieved by a single administration, such as for example, a single injection of sufficient numbers of expression constructs to provide therapeutic benefit to the subject receiving the administration. Alternatively, in some circumstances, it may be desirable to provide multiple, or successive administrations of the compositions, either over a relatively short, or a relatively prolonged period of time.

For example, the number of expression constructs administered to a subject may be $10^7$, $10^8$, $10^9$, $10^{10}$, $10^{11}$, $10^{12}$, $10^{13}$, or even higher, expression constructs/ml given either as a single dose, or divided into two or more administrations as may be required to achieve a desired physiological outcome. In particular embodiments, it may be desirable to administer two or more different expression constructs, either alone, or in combination with one or more other therapeutic drugs to achieve the desired effects of a particular therapy regimen.

Particular dosing and timing of administration for a particular subject can be chosen by a treating physician, researcher, or veterinarian. In other words, the amount of compositions and/or expression constructs and time of administration will be within the purview of the skilled artisan having benefit of the present teachings.

In particular embodiments, treatments for Nav1.1 sodium channel disorders can be combined with another treatment. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, vagus nerve stimulation, corticetomy, and multiple subpial transections.

Common antiepileptic and anticonvulsive active compounds that may be used in combination with compositions described herein include acetazolamide, cannabidiol, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

Kits and Commercial Packages. Kits and commercial packages contain an expression construct described herein. The expression product can be isolated. In particular embodiments, the components of an expression product can be isolated from each other. In particular embodiments, the expression product can be within a vector, within a viral vector, within a cell, within a tissues slice or sample, and/or within a transgenic animal. In particular embodiments, an animal is transgenic following administration of a composition including the expression construct. In particular embodiments, a transgenic animal includes a genetic modification that renders the animal appropriate for use in an animal model of DS. For example, the transgenic animal such as a mouse can be $Scn1a^{+/-}$. Detailed methods for producing transgenic animals are described in U.S. Pat. No. 4,736,866. Transgenic animals may be of any nonhuman mammalian or avian species, but preferably include mice or nonhuman primates (NHPs). Sheep, horses, cattle, pigs, goats, dogs, cats, rabbits, chickens, and other rodents such as guinea pigs, hamsters, gerbils, rats, and ferrets are also included.

Embodiments of a kit or commercial package will also contain instructions regarding use of the included components, for example, in the research and/or treatment of disorders associated with Nav1.1 sodium channel dysfunction, such as epilepsy and/or DS. Such kits may further include one or more reagents, restriction enzymes, peptides, therapeutics, pharmaceutical compounds, or means for delivery of the compositions such as syringes, injectables, and the like.

The Exemplary Embodiments and Example below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. An expression construct (e.g, isolated polynucleotide) including (i) a concatemerized enhancer of SEQ ID: NO: 2 or SEQ ID NO: 6, (ii) a promoter; and (iii) a coding sequence encoding a protein or nucleic acid that rescues voltage-gated sodium channel function in a cell or subject in need thereof.
2. An expression construct of embodiment 1, wherein the concatemer includes a 3× concatemer of SEQ ID: NO: 2 or SEQ ID NO: 6.
3. An expression construct of embodiment 1, wherein the concatemer includes SEQ ID: NO: 2 and SEQ ID NO: 6 arranged in tandem.
4. An expression construct of embodiment 3, wherein the concatemer includes SEQ ID NO: 2-SEQ ID NO: 6-SEQ ID NO: 2; SEQ ID NO: 6-SEQ ID NO: 2-SEQ ID NO: 6; SEQ ID NO: 6-SEQ ID NO: 6-SEQ ID NO: 2; SEQ ID NO: 2-SEQ ID NO: 2-SEQ ID NO: 6; SEQ ID NO: 6-SEQ ID NO: 2-SEQ ID NO: 2; or SEQ ID NO: 2-SEQ ID NO: 6-SEQ ID NO: 6.
5. An expression construct (e.g, isolated polynucleotide) including (i) SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8, (ii) a promoter; and (iii) a coding sequence encoding a protein or nucleic acid that rescues voltage-gated sodium channel function in a cell or subject in need thereof.
6. An expression construct of any of embodiments 1-5, wherein the coding sequence includes or encodes NavSheP-D60N, NavBp, NavMs, 3×HA-NavSheP-D60N, 3×HA-NavBp, 3×HA-NavMs, or His-NavMs.
7. An expression construct of any of embodiments 1-6, wherein the coding sequence includes or encodes human SCN1A, mouse Scn1a, human SCN1A-3×HA, and/or mouse Scn1a-3×ha.
8. An expression construct of any of embodiments 1-7, wherein the coding sequence includes or encodes an artificial transcription factor that increases expression of endogenous SCN1A wherein the artificial transcription factor includes a targeted DNA-binding domain linked to a transcription-activating domain.
9. An expression construct of any of embodiments 1-8, wherein the coding sequence includes or encodes antisense RNA molecules that increase splicing or prevent microRNA negative regulation.
10. An expression construct of any of embodiments 1-9, wherein the coding sequence includes or encodes a nucleotide sequence that upregulates SCN1A expression (e.g., SEQ ID NOs: 66-163).
11. An expression construct of any of embodiments 1-10, wherein the coding sequence includes or encodes and/or one or more segments of SCN1A that assemble into full length SCN 1A after expression.
12. An expression construct of embodiment 11 including the SCN1A coding sequence of SEQ ID NO: 58, SEQ ID NO: 59, SEQ ID NO: 60, and SEQ ID NO: 61.
13. An expression construct of embodiment 11 wherein the SCN1A segments include SEQ ID NO: 62, SEQ ID NO: 63, SEQ ID NO: 64, and SEQ ID NO: 65.
14. An expression construct any of embodiments 1-13, wherein the promoter includes minBglobin or minCMV.
15. An expression construct of any of embodiments 1-14, wherein the expression construct is within an adeno-associated viral (AAV) vector.
16. An expression construct of any of embodiments 1-15, wherein the expression construct includes a coding sequence for a reporter protein.
17. An expression construct of embodiment 16, wherein the reporter protein includes a fluorescent reporter protein.
18. An expression construct of any of embodiments 1-17, wherein the expression construct includes or encodes a skipping element.
19. An expression construct of embodiment 18, wherein the skipping element includes a 2A peptide or an internal ribosome entry site (IRES).
20. An expression construct of embodiment 19, wherein the 2A peptide includes T2A, P2A, E2A, and/or F2A.
21. An expression construct of any of embodiments 1-20, wherein the construct includes the elements of CN1367, CN1244, CN1389, CN1390, CN1180, CN1203, CN1498, CN1499, CN1500, CN2001, CN2002, CN2003, CN1504 and CN1512, CN2004 and CN2005, CN2006 and CN2007, CN2008 and CN2009, or CN2026, CN2027, CN2028 and CN2029.

22. An expression construct of any of embodiments 1-21, wherein the construct includes SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, and/or SEQ ID NO: 52.
23. An expression construct of any of embodiments 1-22, wherein the construct includes SEQ ID NO: 45 and SEQ ID NO: 46, SEQ ID NO: 47 and SEQ ID NO: 48, SEQ ID NO: 49 and SEQ ID NO: 50, SEQ ID NO: 51, and SEQ ID NO: 52 or CN2026, CN2027, CN2028 and CN2029.
24. An expression construct of any of embodiments 15-23, wherein the AAV vector is associated with a capsid that crosses the blood brain barrier.
25. An expression construct of embodiment 24, wherein the capsid includes PHP.Eb.
26. An expression construct of embodiment 24 or 25, wherein the capsid includes SEQ ID NO: 53.
27. An expression construct of any of embodiments 24-26, wherein the capsid includes an AAV9 capsid with a SEQ ID NO: 54 or SEQ ID NO: 55 insert.
28. An expression construct of any of embodiments 24-27, wherein the capsid includes an AAV2 capsid with a SEQ ID NO: 56 insert.
29. A composition including the expression construct of any of embodiments 1-28.
30. A cell including the expression construct of any of embodiments 1-28.
31. A non-human animal including the expression construct of any of embodiments 1-28.
32. A kit including the expression construct of any of embodiments 1-28.
33. A method of rescuing voltage-gated sodium channel function in a defective cell in need thereof including administering a therapeutically effective amount of a composition of embodiment 29 to the cell.
34. A method of rescuing voltage-gated sodium channel function in a subject in need thereof including administering a therapeutically effective amount of a composition of embodiment 29 to the subject.
35. A method of embodiment 34, wherein the subject is need thereof due to a diagnosis of epilepsy, an SCN1A-related seizure disorder, simple febrile seizures (FS), generalized epilepsy with febrile seizures plus (GEFS+), Dravet Syndrome (DS), intractable childhood epilepsy with generalized tonic-clonic seizures (ICE-GTC), intractable infantile partial seizures, myoclonic-astatic epilepsy, Lennox-Gastaut syndrome (LGS), or infantile spasms.
36. A method of embodiment 34 or 35, wherein the subject is a pediatric patient.
37. A method of any of embodiments 34-36, wherein the subject is less than 4 years old.
38. A method of embodiment 34, 35, or 37, wherein the subject is a transgenic Scn1a$^{+/-}$ mouse undergoing a temperature-induced febrile seizure test.
39. A method of any of embodiments 34-38, wherein the composition is administered intravenously.
40. A method of any of embodiments 34-39, wherein the composition is administered intrathecally into cerebrospinal fluid, via the lateral ventricles or cisterna magna or lumbar space or cannula into the foramen magnum.
41. An expression construct (e.g, isolated polynucleotide) including:
   (a) a non-naturally occurring enhancer sequence; and
   (b) a nucleic acid encoding a protein or nucleotide sequence that rescues voltage-gated sodium channel function;

wherein the enhancer sequence:
   (i) consists of the sequence of SEQ ID NO: 3;
   (ii) includes two or more copies of SEQ ID NO: 2 or SEQ ID NO: 6 arranged in tandem (e.g, SEQ ID NO: 2-SEQ ID NO: 6-SEQ ID NO: 2; SEQ ID NO: 6-SEQ ID NO: 2-SEQ ID NO: 6; SEQ ID NO: 6-SEQ ID NO: 6-SEQ ID NO: 2; SEQ ID NO: 2-SEQ ID NO: 2-SEQ ID NO: 6; SEQ ID NO: 6-SEQ ID NO: 2-SEQ ID NO: 2; or SEQ ID NO: 2-SEQ ID NO: 6-SEQ ID NO: 6; SEQ ID NO: 6-SEQ ID NO: 6-SEQ ID NO: 6);
   (iii) includes a sequence having at least 90% sequence identity with SEQ ID NO: 3 and maintaining interneuron-specific enhancer function; or
   (iv) a sequence the complementary strand of which is capable of hybridizing to the sequence of (i), (ii), or (iii); and wherein the enhancer promotes the transcription of the nucleic acid selectively within inhibitory neurons following administration to a sample or subject.
42. An expression construct of embodiment 41, wherein nucleic acid includes or encodes NavSheP-D60N, NavBp, NavMs, 3×HA-NavSheP-D60N, 3×HA-NavBp, 3×HA-NavMs, or His-NavMs.
43. An expression construct of embodiment 41 or 42, wherein the nucleic acid includes or encodes human SCN1A, mouse Scn1a, human SCN1A-3×HA, and/or mouse Scn1a-3×ha.
44. An expression construct of any of embodiments 41-43, wherein the nucleic acid includes or encodes an artificial transcription factor that increases expression of endogenous SCN1A wherein the artificial transcription factor includes a targeted DNA-binding domain linked to a transcription-activating domain.
45. An expression construct of any of embodiments 41-44, wherein the nucleic acid includes or encodes antisense RNA molecules that increase splicing or prevent microRNA negative regulation.
46. An expression construct of any of embodiments 41-45, wherein the nucleic acid includes or encodes a nucleotide sequence that upregulates SCN1A expression (e.g., SEQ ID NOs: 66-163).
47. An expression construct of any of embodiments 41-46, wherein the nucleic acid includes or encodes and/or one or more segments of SCN1A that assemble into full length SCN1A after expression.
48. An expression construct of embodiment 47 including nucleic acid including the SCN1A coding sequence of SEQ ID NO: 58, SEQ ID NO: 59, SEQ ID NO: 60, and SEQ ID NO: 61.
49. An expression construct of embodiment 47 wherein the SCN1A segments include SEQ ID NO: 62, SEQ ID NO: 63, SEQ ID NO: 64, and SEQ ID NO: 65.
50. An expression construct of any of embodiment 41-49, including a promoter including minBglobin or minCMV.
51. An expression construct of any of embodiments 41-50, wherein the expression construct is within an adeno-associated viral (AAV) vector.

52. An expression construct of any of embodiments 41-51, wherein the expression construct includes a nucleic acid encoding a reporter protein.
53. An expression construct of embodiment 52, wherein the reporter protein includes a fluorescent reporter protein.
54. An expression construct of any of embodiments 41-53, wherein the expression construct includes or encodes a skipping element.
55. An expression construct of embodiment 54, wherein the skipping element includes a 2A peptide or an internal ribosome entry site (IRES).
56. An expression construct of embodiment 55, wherein the 2A peptide includes T2A, P2A, E2A, and/or F2A.
57. An expression construct of any of embodiments 41-56, wherein the construct includes the elements of CN1367, CN1244, CN1389, CN1390, CN1180, CN1203, CN1498, CN1499, CN1500, CN2001, CN2002, CN2003, CN1504 and CN1512, CN2004 and CN2005, CN2006 and CN2007, or CN2008 and CN2009.
58. An expression construct of any of embodiments 41-57, wherein the construct includes SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, and/or SEQ ID NO: 52.
59. An expression construct of any of embodiments 41-58, wherein the construct includes SEQ ID NO: 45 and SEQ ID NO: 46, SEQ ID NO: 47 and SEQ ID NO: 48, SEQ ID NO: 49 and SEQ ID NO: 50, or SEQ ID NO: 51, and SEQ ID NO: 52
60. An expression construct of any of embodiments 51-59, wherein the AAV vector is associated with a capsid that crosses the blood brain barrier.
61. An expression construct of embodiment 60, wherein the capsid includes PHP.Eb.
62. An expression construct of embodiment 60 or 61, wherein the capsid includes SEQ ID NO: 53.
63. An expression construct of any of embodiments 60-62, wherein the capsid includes AAV9 capsid with a SEQ ID NO: 54 or SEQ ID NO: 55 insert.
64. An expression construct of any of embodiments 60-63, wherein the capsid includes AAV2 capsid with a SEQ ID NO: 56 insert.
65. A composition including the expression construct of any of embodiments 41-64.
66. A cell including the expression construct of any of embodiments 41-64.
67. A non-human animal including the expression construct of any of embodiments 41-64.
68. A kit including the expression construct of any of embodiments 41-64.
69. A method of rescuing voltage-gated sodium channel function in a defective cell in need thereof including administering a therapeutically effective amount of a composition of embodiment 65 to the cell.
70. A method of rescuing voltage-gated sodium channel function in a subject in need thereof including administering a therapeutically effective amount of a composition of embodiment 65 to the subject.
71. A method of embodiment 70, wherein the subject is need thereof due to a diagnosis of epilepsy, an SCN1A-related seizure disorder, simple febrile seizures (FS), generalized epilepsy with febrile seizures plus (GEFS+), Dravet Syndrome (DS), intractable childhood epilepsy with generalized tonic-clonic seizures (ICE-GTC), intractable infantile partial seizures, myoclonic-astatic epilepsy, Lennox-Gastaut syndrome (LGS), or infantile spasms.
72. A method of embodiment 70 or 71, wherein the subject is a pediatric patient.
73. A method of any of any of embodiments 70-72, wherein the subject is less than 4 years old.
74. A method of any of embodiments 70, 71, or 73, wherein the subject is a transgenic Scn1a$^{+/-}$ mouse undergoing a temperature-induced febrile seizure test.
75. A method of any of embodiments 70-74, wherein the composition is administered intravenously.
76. A method of any of embodiments 70-75, wherein the composition is administered intrathecally into cerebrospinal fluid, via the lateral ventricles or cisterna magna or lumbar space or cannula into the foramen magnum.
77. A vector system including two AAV vectors wherein the first vector encodes the N-terminal portion of a protein that rescues voltage-gated sodium channel activity in a cell in need thereof, and the second vector encodes the C-terminal portion of the protein, wherein the portion of the gene encoded by the two vectors overlaps to provide a region of homology for homologous recombination to produce the full-length Nav1.1 protein, and wherein the first vector includes a promoter and an enhancer that consists of SEQ ID NO: 3 but does not include a termination signal or a polyA signal and the second vector includes a termination signal and a polyA signal but does not include a promoter or an enhancer.
78. A vector system of embodiment 77, wherein the protein includes human SCN1A.
79. A vector system of embodiment 77 or 78, wherein the region of homology is 75-1000 base pairs.
80. A vector system of embodiment 77 or 78, wherein the region of homology is 550-650 base pairs.
81. A vector system of any of embodiments 77-80, wherein the vectors selectively express the protein in inhibitory neurons.
82. A vector system of any of embodiments 77-81, wherein the region of homology further includes an intron element with a splice donor site on the first vector and a splice acceptor site on the second vector, so that trans-splicing across the homologous region drives more efficient full-length protein reconstitution following recombination.
83. A vector system of any of embodiments 77-82, wherein the vector system includes the elements of CN1504, CN1512, CN2004, CN2005, CN2006, CN2007, CN2008, and/or CN2009.
84. A vector system of any of embodiments 77-83, wherein the vector system includes the elements of CN1504 and CN1512, CN2004 and CN2005, CN2006 and CN2007, or CN2008 and CN2009.
85. A vector system of any of embodiments 77-84, wherein the vector system includes SEQ ID NO: 45 and SEQ ID NO: 46, SEQ ID NO: 47 and SEQ ID NO: 48, SEQ ID NO: 49 and SEQ ID NO: 50, or SEQ ID NO: 51, and SEQ ID NO: 52.
86. A viral vector including SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, or SEQ ID NO: 52.

87. An expression construct including SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8 and a coding sequence encoding an artificial transcription factor including a specific DNA-binding domain linked to a general transcription-activating domain wherein the artificial transcription factor increases the expression of the endogenous functional copy of SCN1A (or other SCN_A family gene).

88. An expression construct including SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8 and a coding sequence encoding an artificial transcription factor including a specific DNA-binding domain linked to a general transcription-activating domain wherein the artificial transcription factor increases the expression of the endogenous functional copy of SCN1A (or other SCN_A family gene).

89. An expression construct including SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8 and a coding sequence encoding antisense RNA molecules that increase splicing and/or prevent microRNA negative regulation of SCN1A expression.

90. A set of expression constructs including SEQ ID NO: 1, SEQ ID NO: 2, SEQ ID NO: 3, SEQ ID NO: 4, SEQ ID NO: 5, SEQ ID NO: 6, SEQ ID NO: 7, and/or SEQ ID NO: 8 wherein the set of expression constructs delivers hSCN1A protein as two or four subunit ORFs delivered by two or four separate vectors.

91. An isolated polynucleotide including an enhancer including the sequence of SEQ ID NO: 3, and further including a heterologous inducible promoter and a gene encoding a protein or nucleic acid sequence that rescues Nav1.1 channel function selectively in inhibitory neurons, wherein the enhancer and the heterologous inducible promoter are operably linked to the gene.

92. A vector including the isolated polynucleotide of embodiment 91.

93. A vector of embodiment 92, wherein the vector is a viral vector.

94. A vector of embodiment 93, wherein the viral vector is an AAV viral vector.

95. A human or non-human cell including the isolated polynucleotide of embodiment 91.

96. A set of vectors for selectively driving expression of a protein or nucleic acid sequence that rescues Nav1.1 channel function in inhibitory neurons including the vector of any of embodiment 92-94, and a second vector including an enhancer selected from SEQ ID NOS: 1, 2, 4, 5, 6, 7 or 8.

97. A method for selectively driving expression of a protein or nucleic acid sequence that rescues Nav1.1 channel function in inhibitory neurons including (1) providing the vector of any of embodiments 92-94, (2) using the vector to generate a transgenic mouse, and (3) detecting rescued Nav1.1 channel function in the transgenic mouse.

98. A method of embodiment 97, wherein the rescued Nav1.1 channel function is within inhibitory neurons.

99. A set of coding sequences including the coding sequences of the hSCN1A_Fragments within SEQ ID NO: 58, SEQ ID NO: 59, SEQ ID NO: 60, and SEQ ID NO: 61.

100. A set of vectors including CN2026, CN2027, CN2028, and CN2029.

Example 1. In relation to FIG. 1A, living human temporal cortex brain tissue was excised during neurosurgery to remove an epileptic focus. This tissue was dissected and sliced to 350-micron thick tissue slices, which were cultured on semipermeable membranes with semisynthetic culture medium as described by Ting et al. (*Scientific Reports* 8(1):8407, 2018). On the first day of culture, slices were infected with purified virus CN 1180/DJ (which labels inhibitory neurons) by applying purified virus directly to the brain slice. At 7 days post infection, the electrophysiology of SYFP2$^+$ (visible in the green channel) infected cells was assessed by patch-clamp recordings. The recorded cells were backfilled with Alexa 594 dye (visible in the red channel) to perform post-hoc visualization of their cell bodies and morphologies.

Figure 1B:
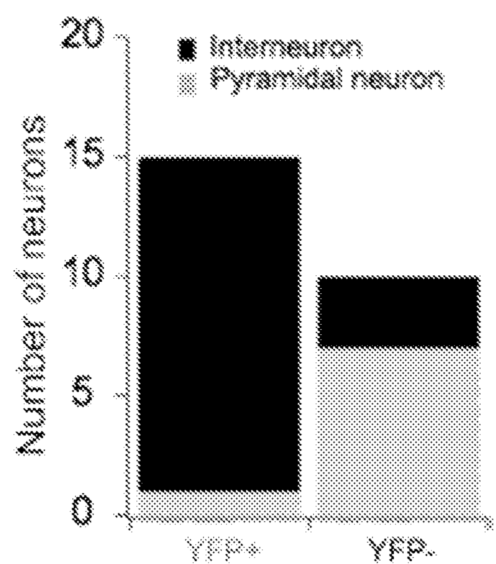
Figure 1C:
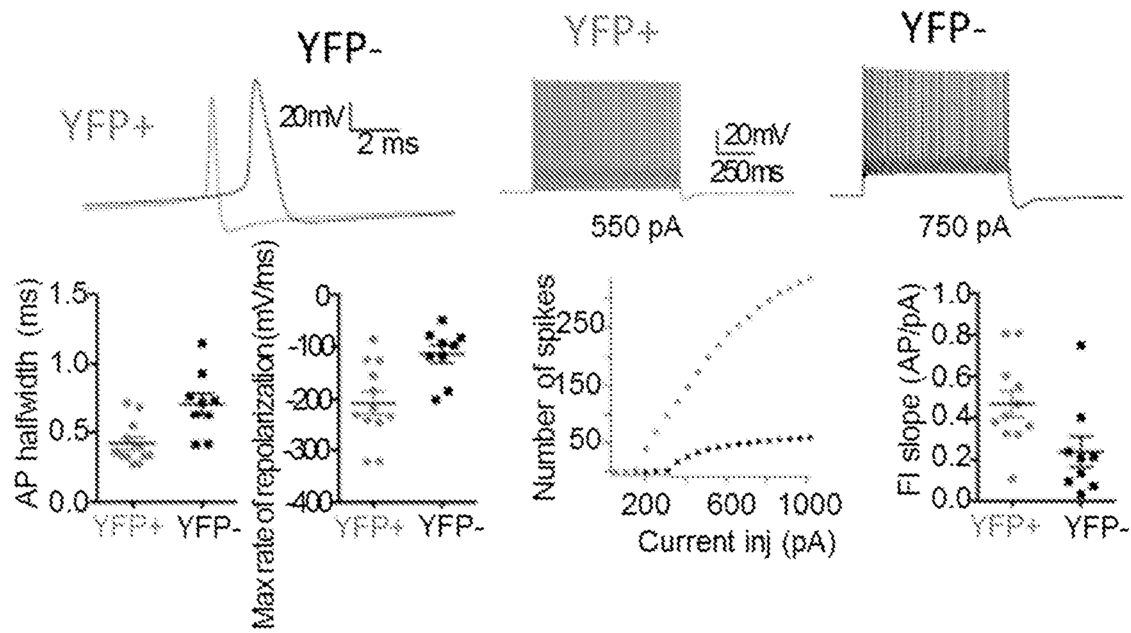

In relation to FIG. 1B, patch-clamp recordings were performed on multiple SYFP2$^+$ and SYFP2$^-$ cells. Their backfilled morphologies were tabulated as being pyramidal (indicative of excitatory neurons) or non-pyramidal (indicative of inhibitory neurons). This analysis indicated that SYFP2$^+$ cells are largely of inhibitory neuron character.

Figure 10:
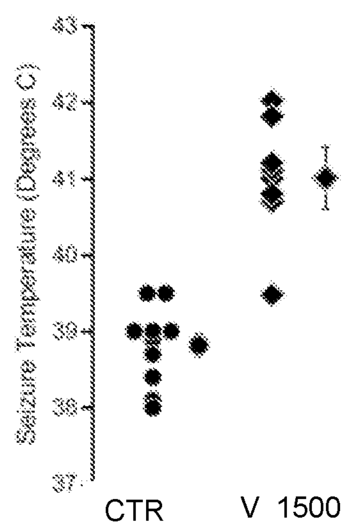
FIG. 10. CN1500 rAAV vector substantially reverses febrile seizures in $Scn1a^{+/-}$ mice. Febrile seizure assay shown as internal temperature where a seizure is first detected. (Top) Circles show $Scn1a^{+/-}$ mice untransduced with AAVs, while the diamonds represent animal that were transduced with CN1500. The large dot and error bars represent the average +/− SEM for each group of animals. (Bottom) Trends of the same data are shown as the percentage of mice in each group that remain seizure free at different temperatures using a Kaplan-Meier curve.
Figure 10:
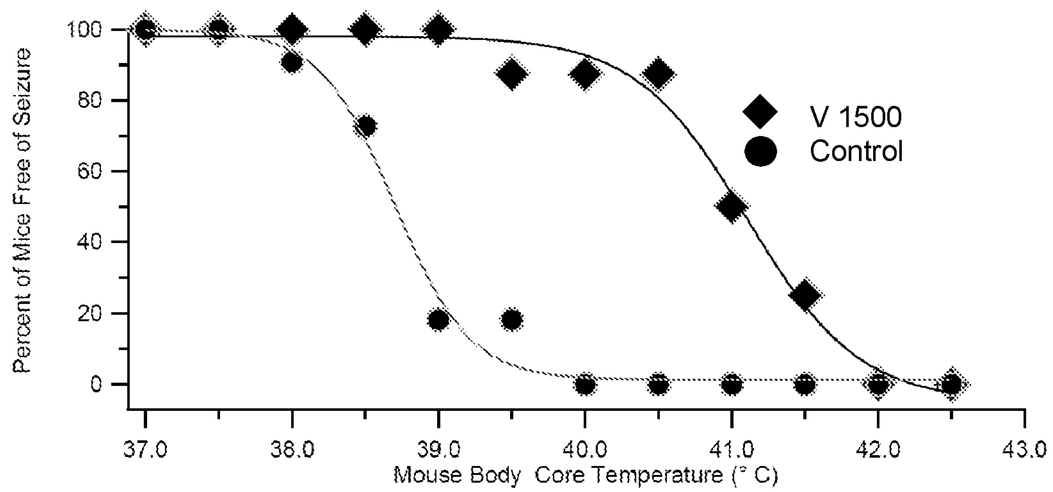

In relation to FIG. 10, the electrophysiological character of multiple SYFP2$^+$ and SYFP2$^-$ cells was analyzed. These analyses indicated that, compared to SYFP2$^-$ cells, the SYFP2$^+$ cells had shorter action potential (AP) half-widths, had greater firing rates, had faster rates of depolarization, and had faster rates of AP firing in response to injected current (FI slope). These metrics all suggest that SYFP2$^+$ cells are fast-spiking interneurons.

Figure 1D:
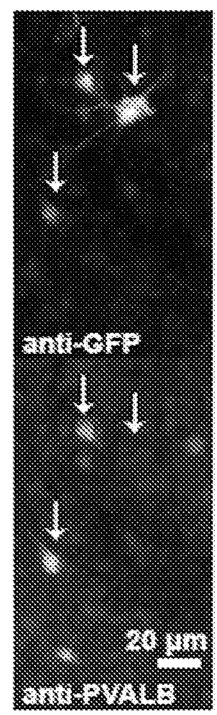
Figure 2:
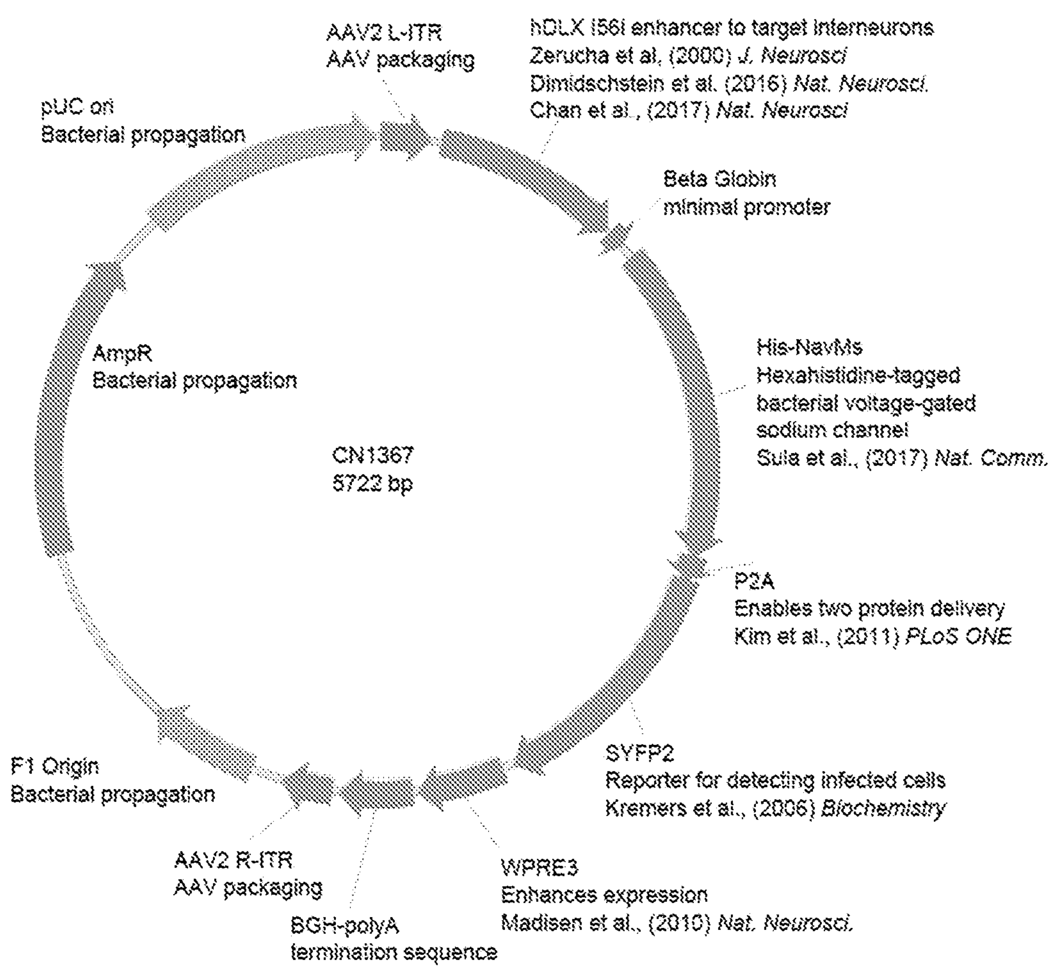
FIG. 2 depicts an exemplary vector for targeted expression of a protein in inhibitory interneurons: CN1367-rAAV2-hI56i-minBglobin-His-NavMs-P2A-SYFP2-WPRE3-BGHpA. Key: hI56i—full-length human DLX I56i enhancer (SEQ ID NO: 1); minBglobin—minimal beta globin promoter; His-NavMs—Hexahistidine-tagged voltage-gated sodium channel from *Magnetococcus marinus*; P2A—self-cleaving peptide; SYFP2—super yellow fluorescent protein 2; WPRE3—woodchuck hepatitis virus posttranscriptional regulatory element 3 (SEQ ID NO: 19); BGHpA—bovine growth hormone polyA sequence.

In relation to FIG. 1D, after performing patch-clamp electrophysiology tissue was fixed and immunostained with anti-GFP and anti-Parvalbumin antibodies. This analysis indicated that many GFP$^+$ cells are Parvalbumin$^+$, which suggests that these cells have molecular identities consistent with fast-spiking interneurons.

Figure 3:
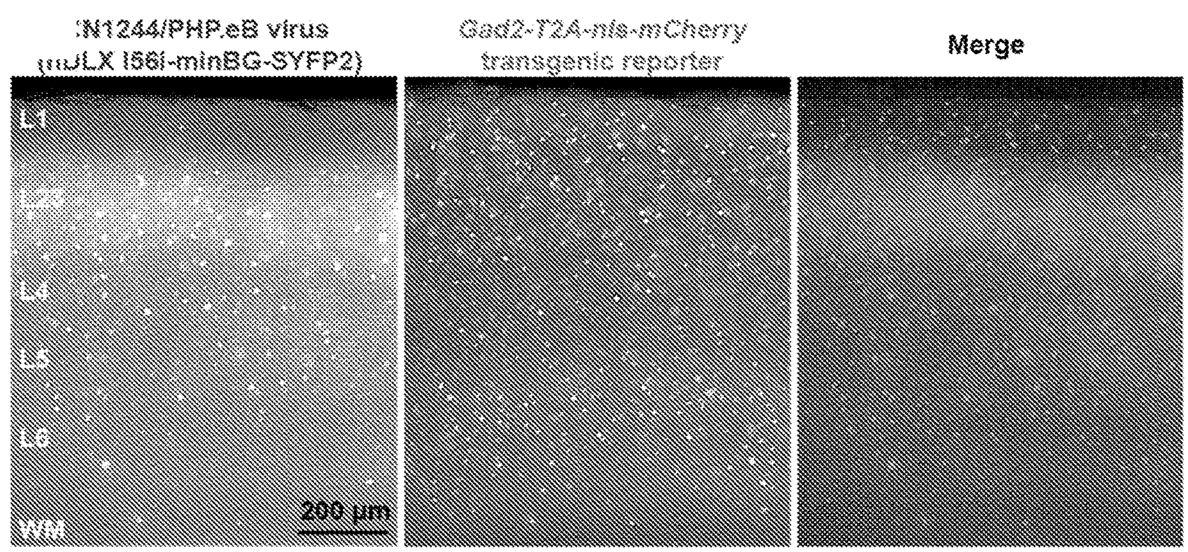
FIG. 3. Virus CN1244/PHP.eB. $10^{11}$ genome copies delivered intravenously (IV). PHP.eB encodes for a capsid originating from AAV9 that allows efficient AAV transit across the mouse blood brain barrier, which enables delivery of AAV vectors in a brain-wide fashion. This capsid differs from AAV9 such that amino acids starting at residue 586: SAQA are changed to SDGTLAVPFKA. The Gad2-T2A-nls-mCherry reporter marks nearly all inhibitory neurons in the mouse brain (here shown V1 visual cortex), and the delivered CN1244/PHP.eB virus drives specific SYFP2 reporter activity in forebrain inhibitory neurons.

In relation to FIG. 3, a Gad2-T2A-nls-mCherry (Peron et al., *Neuron* 86:783-799, 2015) mouse was injected retro-orbitally with 1E11 genome copies of the virus CN1244/PHP.eB. After 3 weeks the brain was harvested, sliced into 350-micron thick slices, and then imaged for SYFP2 and mCherry expression to visualize virus-expressing cells and all interneurons, respectively.

In relation to FIGS. 4A, 4B, adult wild type mice were retro-orbitally injected with 1E+11 genome copies of the indicated viruses. Animals were maintained for 3-4 weeks, then euthanized, with brains extracted and sliced, followed by live tissue epifluorescence imaging of native fluorescence. Exposure times were matched to allow direct comparison of transgene expression levels. The first three panels are a 500 msec exposure for each of the indicated constructs; the fourth panel is a shorter (50 msec) exposure image of CN1390.

In relation to FIG. 5, cortical/hippocampal brain slice cultures were prepared from P5-10 Gad2-IRES-Cre heterozygous;Ai75 heterozygous animals. These animals have Cre-mediated activation of a nuclear-tagged tdTomato transgene in Gad2-expressing cells, resulting in bright nuclear red fluorescence in inhibitory neurons. One hour after culturing, CN 1390 viral suspension was pipetted onto the slice surface to transduce brain cell types. At 10 DIV/10 DPI, native fluorescence was imaged in green and red channels on a Nikon inverted microscope.

In relation to FIGS. 6A-6E, human ex vivo neocortical brain slice cultures were prepared from live neurosurgical specimens (Ting et al., *Scientific Reports* 8(1):8407, 2018).

One hour after culturing, CN1390 viral suspension was pipetted onto the slice surface to transduce brain cell types. At 1, 3, and 6 DIV/DPI, native SYFP2 fluorescence was imaged using matched exposure times on aa Nikon microscope. FIGS. 6A-6D illustrate rapid viral-genetic labeling of human neocortical interneurons for targeted patch clamp recording and analysis. At various times in culture, slices were taken for terminal patch clamp recording analysis to establish the firing properties of labeled neurons. Functional analysis of human neocortical interneuron firing patterns and electrical properties by patch clamp recording was feasible as early as 40 hours post-infection with CN1390 eB virus.

Referring to FIG. 9, the top vector includes the enhancer of SEQ ID NO: 3 and promoter (minCMV) elements to drive expression in all inhibitory neurons (including both Pvalb+ and Pvalb− inhibitory neurons). The driven transgene includes a SYFP2 linked by a P2A tag to the N-terminal region of human SCN1A, which includes 604 bp homology to the C-terminal region included on the bottom vector. The bottom vector also includes a C-terminal 3×HA tag and 3'UTR regulatory sequences (WPRE3 and polyA sites).

Both AAV viral vectors were packaged into PHP.eB capsid and delivered both intravenously to a single C57Bl/6 mouse. After 21 days the mouse brain was harvested, fixed, and processed for immunofluorescence with anti-GFP (targeting SYFP2), anti-HA, and anti-Pvalb antibodies to detect transgene-expressing cells and their overlap with Pvalb+ inhibitory neurons (which are cells having particular importance in DS symptomology). Many inhibitory neurons were labeled with the N-terminal SYFP2+ tag at high level, including both Pvalb+ and Pvalb− inhibitory neurons. Some of these SYFP2+ cells also express HA which indicates fully intact SCN1A protein product being expressed in these GFP+HA+ cells (arrows). The vertical arrows indicate Pvalb+ interneurons expressing human SCN1A and the horizontal arrows indicate Pvalb− interneurons expressing human SCN1A. These SCN1A-expressing cells are found throughout the forebrain (both neocortex and hippocampus [here dentate gyrus]), which includes the brain region known to be important for most epilepsies and known to be dysfunctional in DS.

Example 2. Dravet syndrome (DS) is a drug-resistant and life-threatening form of epilepsy. It typically begins in the first year of life, with fever- or temperature-induced seizures that evolve into generalized clonic, tonic-clonic, and unilateral seizures. These seizures are often resistant to current anti-epileptic drugs, the first-line therapies for this syndrome; complete seizure control is typically not achieved. As the disease progresses, most affected children also suffer from comorbid conditions including developmental delays, intellectual disabilities, impaired motor control and coordination, autistic behaviors, sleep disturbances, and many die prematurely.

Heterozygous loss-of-function mutations in SCN1A, the gene that encodes the pore-forming subunit of the voltage-gated sodium channel Nav1.1 are the most common cause of DS and occur in nearly 1/16,000 newborns.

A mouse model, generated by knock-out of Scn1a, replicates the several key phenotypic features of this epilepsy including infantile (P21)-epilepsy onset, high susceptibility to thermal seizures, ataxia, spontaneous seizures, sleep impairments, autistic behaviors, and premature death. Seizures and several comorbidities arise from impaired interneuron function in these mice.

This mouse model was used to investigate the efficacy of a new viral vector for DS. The virus was delivered by retro-orbital injection using an insulin syringe and its ability to suppress seizure was evaluated using the thermal seizure test. In this test, the mouse body core temperature is elevated slowly, using a temperature controller and a heat lamp, until a seizure occurs, or 42.5° C. is attained. The temperature of seizure onset in treated and control mice are compared to determine the efficacy of the intervention. In additional tests, the efficacy of treatment on spontaneous seizure and premature mortality are assessed using video and electroencephalographic monitoring.

The viral vector is a new AAV viral vector named CN1500. This viral vector is a recombinant AAV that expresses the transgene SYFP2-P2A-NavSheP-D60N to rescue the loss of the voltage-gated sodium channel Nav1.1. NavSheP-D60N is a modified voltage-gated sodium channel of bacterial origin that has been modified to improve the kinetics and expression in mammalian cells. The transgene expression level is elevated by the addition of a WPRE3 element, and transcription is terminated with the bovine growth hormone poly adenylation sequence. Expression of the transgene is high and limited to inhibitory cells in forebrain structures including the cortex and the hippocampus, via the 3×hi56iCore synthetic enhancer (SEQ ID NO: 3) directly 5' of a CMV minimal promoter. Furthermore, the therapeutic transgene NavSheP-D60N is labeled by an HA epitope tag to verify correct protein localization.

To test the efficacy of the therapeutic AAV viral vector, CN1500 package using the PHP.eB serotype was used. A cohort of postnatal day 35 $Scn1a^{+/-}$ mice were either injected with $2\times10^{11}$ vg per animal or were left un-injected. The AAV was introduced intravenously using the retro-orbital delivery route. Two weeks after viral administration, animals from the treatment and control groups were assessed for their susceptibility to febrile seizures. As indicated previously, febrile seizures were measured by steadily raising the mouse's temperature under a heat lamp 0.5 Celsius every two minutes and measuring the internal temperature of the mouse with a rectal probe. The temperature where the mouse experienced a seizure is recorded.

The new therapeutic vector CN1500 was both highly expressed in mouse cortical and hippocampal GABAergic cells, but also raised the average temperature where $Scn1a^{+/-}$ mice experienced febrile seizures from 38.7° C. to 41° C. These data show that CN1500 can substantially rescue the loss of Scn1a.

Example 2 references include: Catterall et al. (2010) The Journal of physiology 588:1849-1859; Cheah et al. (2012) Proceedings of the National Academy of Sciences of the United States of America 109:14646-14651; Kalume (2013) Respir Physiol Neurobiol. 189(2):324-8; Kalume et al., (2007) J Neurosci 27:11065-11074; Kalume et al., (2013) The Journal of clinical investigation 123:1798-1808; Oakley et al., (2009) Proceedings of the National Academy of Sciences of the United States of America 106:3994-3999.

DESCRIPTION OF SEQUENCES

Nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate.

SEQ ID NO: 1: nucleic acid sequence of the human (h)DLX I56i enhancer;

SEQ ID NO: 2: nucleic acid sequence of the hI56i core enhancer;

SEQ ID NO: 3: nucleic acid sequence of the 3×hI56iCore enhancer;
SEQ ID NO: 4: nucleic acid sequence of the murine DLX I56i enhancer;
SEQ ID NO: 5: nucleic acid sequence of the zebrafish DLX I56i enhancer;
SEQ ID NO: 6: nucleic acid sequence of the zebrafish I56i core;
SEQ ID NO: 7: nucleic acid sequence of the zebrafish 3×I56i core;
SEQ ID NO: 8: hDLX 112b enhancer;
SEQ ID NO: 9: NavSheP-D60N, codon optimized, with N-terminal 3× HA tag;
SEQ ID NO: 10: NavSheP endogenous sequence;
SEQ ID NO: 11: NavBp, endogenous sequence;
SEQ ID NO: 12: NavBp, codon optimized, with N-terminal 3× HA tag;
SEQ ID NO: 13: NavMs, endogenous sequence;
SEQ ID NO: 14: NavMs, codon optimized, with N-terminal 3× HA tag and linker;
SEQ ID NO: 15: NavMs, codon optimized, with N-terminal His tag and linker;
SEQ ID NO: 16: Human SCN1A;
SEQ ID NO: 17: SYFP2;
SEQ ID NO: 18: P2A Encoding Sequence;
SEQ ID NO: 19: WPRE3;
SEQ ID NO: 20: BGHpA;
SEQ ID NO: 21: N-terminal 3×HA tag (Protein);
SEQ ID NO: 22: N-terminal 3×HA tag (DNA);
SEQ ID NO: 23: hSCN1A N-term of two-part expression system;
SEQ ID NO: 24: hSCN1A C-term of two-part expression system with c-terminal 3×HA sequence;
SEQ ID NO: 25: 604 bp homology region of hSCN1A N term and C term that can be used in two-part expression system;
SEQ ID NO: 26: P2A Translation from CN1498;
SEQ ID NO: 27: T2A;
SEQ ID NO: 28: E2A;
SEQ ID NO: 29: F2A;
SEQ ID NO: 30: MinBglobin;
SEQ ID NO: 31: minCMV;
SEQ ID NO: 32: AAV9 PHP.eB capsid replacement sequence;
SEQ ID NO: 33: CN1367—portion between L-ITR and R-ITR: positions 142-2984;
SEQ ID NO: 34: CN1500—portion between L-ITR and R-ITR: positions 142-2976;
SEQ ID NO: 35: CN1498—portion between L-ITR and R-ITR: positions 142-2943;
SEQ ID NO: 36: CN1499—portion between L-ITR and R-ITR: positions 142-2946;
SEQ ID NO: 37: CN1244—portion between L-ITR and R-ITR: positions 142-2042;
SEQ ID NO: 38: CN1389—portion between L-ITR and R-ITR positions 142-1897;
SEQ ID NO: 39: CN1390—portion between L-ITR and R-ITR positions 142-1660;
SEQ ID NO: 40: CN1203—portion between L-ITR and R-ITR positions 183-2052;
SEQ ID NO: 41: CN1180—portion between L-ITR and R-ITR positions 183-1891;
SEQ ID NO: 42: CN2001—portion between L-ITR and R-ITR positions 142-2023;
SEQ ID NO: 43: CN2002—portion between L-ITR and R-ITR positions 142-1993;
SEQ ID NO: 44: CN2003—portion between L-ITR and R-ITR positions 142-2056;
SEQ ID NO: 45: CN 1504—portion between L-ITR and R-ITR positions 142-4489;
SEQ ID NO: 46: CN1512—portion between L-ITR and R-ITR positions 142-4165;
SEQ ID NO: 47: CN2004—portion between L-ITR and R-ITR positions 142-3792;
SEQ ID NO: 48: CN2005—portion between L-ITR and R-ITR positions 142-4160;
SEQ ID NO: 49: CN2006—portion between L-ITR and R-ITR positions 142-4790;
SEQ ID NO: 50: CN2007—portion between L-ITR and R-ITR positions 142-4671;
SEQ ID NO: 51: CN2008—portion between L-ITR and R-ITR positions 142-3995;
SEQ ID NO: 52: CN2009—portion between L-ITR and R-ITR positions 142-4525;
SEQ ID NO: 53: epitope isolated during in vivo screening of a random AAV display peptide library;
SEQ ID NO: 54: 7-mer sequence of AAV-PHP.S;
SEQ ID NO: 55: 7-mer sequence of AAV-PHP.B;
SEQ ID NO: 56: 7-mer sequence of AAV-PPS;
SEQ ID NO: 57: AAV9 VP1 capsid protein sequence (UniProt Accession number Q6JC40);
SEQ ID NO: 58: CN2026-rAAV-3×hI56i(core)-minBG-hSCN1A_Fragment1-WPRE3-BGHpA;
SEQ ID NO: 59: CN2027-rAAV-3×hI56i(core)-minBG-hSCN1A_Fragment2-WPRE3-BGHpA;
SEQ ID NO: 60: CN2028-rAAV-3×hI56i(core)-minBG-hSCN1A_Fragment3-WPRE3-BGHpA;
SEQ ID NO: 61: CN2029-rAAV-3×hI56i(core)-minBG-hSCN1A_Fragment4-WPRE3-BGHpA;
SEQ ID NO: 62: >hSCN1A_Fragment1_ProteinSequence;
SEQ ID NO: 63: hSCN1A_Fragment2_ProteinSequence;
SEQ ID NO: 64: hSCN1A_Fragment3_ProteinSequence;
SEQ ID NO: 65: hSCN1A_Fragment4_ProteinSequence;
SEQ ID NOs. 66-163: Nucleotide sequences that result in upregulation of SCNA1.

Variants of the sequences disclosed and referenced herein are also included. Guidance in determining which amino acid residues can be substituted, inserted, or deleted without abolishing biological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W. H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

In particular embodiments references to gene editing systems, such as CRISPR and Cas-9 (also known as Csnl and Csxl2) above should be interpreted to include additional options and developments, as is understood by one of ordinary skill in the art. For example, any gene editing system capable of precise genomic recognition and binding can be used. When nucleases are used for targeted genome binding without associated cutting and editing, the nucleases can lack cutting functionality.

In relation to the use of Cas-9, numerous other options for Cas proteins are available and appropriate for use. Cas-9 itself can refer to one or more catalytic domains of a Cas9 protein derived from bacteria such as Corynebacter, Sutterella, Legionella, Treponema, Filif actor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, and Campylobacter. In some embodiments, the Cas9 is a fusion protein, e.g. the two catalytic domains are derived from different bacterial species. Additional exemplary Cas nucleases that can be used to bind DNA include Casl, CaslB, Cas2, Cas3, Cas4, Cas5, Cas6, Cas7, Cas8, Cas10, Cpfl, C2c3, C2c2 and C2clCsyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Cpfl, Csbl, Csb2, Csb3, Csxl7, Csxl4, CsxlO, Csxl6, CsaX, Csx3, Csxl, Csxl5, Csfl, Csf2, Csf3, and Csf4.

The Cpf1 nuclease particularly can provide added flexibility in target site selection by means of a short, three base pair recognition sequence (TTN), known as the protospacer-adjacent motif or PAM. Particular embodiments can utilize engineered Cpf1s. For example, US 2018/0030425 describes engineered Cpf1 nucleases from Lachnospiraceae bacterium ND2006 and *Acidaminococcus* sp. BV3L6 with altered and improved target specificity.

Other Cpf1 variants include Cpf1 homologs and orthologs of the Cpf1 polypeptides disclosed in Zetsche et al. (2015) Cell 163: 759-771 as well as the Cpf1 polypeptides disclosed in U.S. 2016/0208243. Other engineered Cpf1 variants are known to those of ordinary skill in the art and included within the scope of the current disclosure (see, e.g., WO/2017/184768).

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Zinc finger nucleases (ZFNs) are synthesized by fusing a zinc finger DNA-binding domain to a DNA cleavage domain. Particular embodiments described herein can utilize zinc fingers to bind specific DNA sequences. The DNA-binding domain includes three to six zinc finger proteins which are similar to those found in transcription factors. The DNA cleavage domain includes the catalytic domain of, for example, Fokl endonuclease. The Fokl domain functions as a dimer requiring two constructs with unique DNA binding domains for sites on either side of the target site cleavage sequence. The Fokl cleavage domain cleaves within a five or six base pair spacer sequence separating the two inverted half-sites.

For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; and U.S. Application Publication Nos. 2003/0232410 and 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs have been engineered to bind a target genetic sequence and cut DNA at the location of the target sequence. The TALEs of TALENs are DNA binding proteins secreted by Xanthomonas bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant Fokl endonucleases. For additional information regarding TALENs, see U.S. Pat. Nos. 8,440,431; 8,440,432; 8,450,471; 8,586,363; and 8,697,853; as well as Joung and Sander, Nat Rev Mol Cell Biot, 2013, 14(I):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Exemplary meganucleases include I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TIiI, I-Ppol, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PbolP, I-PculP, I-PcuAI, I-PcuVI, I-PgrIP, I-PobIP, I-Port, I-PorIIP, I-PbpIP, I-SpBetaIP, I-ScaI, I-SexIP, 1-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, 1-ZbiIP, PI-MtuI, PI-MtuHIP PI-MtuHIIP, PI-PfuI, PI-PfuII, PI-PkoI, PI-PkoII, PI-Rma438121P, PI-SpBetaIP, PI-SceI, PI-TfuI, PI-TfuII, PI-ThyI, PI-TIiI, and PI-THII.

Particular embodiments described herein can utilize gene editing systems to insert expression constructs within targeted genomic safe harbors. Methods for identifying genomic safe harbor sites are described in Sadelain et al., Nature Reviews (2012); 12:51-58; and Papapetrou et al., *Nat Biotechnol.* (2011) January; 29(1):73-8.

In particular embodiments, expression constructs refer to isolated polynucleotide sequences that include no elements, portions, or nucleotides that are not described in relation to the construct.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a significantly significant reduction in the ability of a vector to reverse febrile seizures in Scn1a+/− mice according to the protocol of Example 2 and FIG. 10.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An expression construct comprising (i) an enhancer having the sequence as set forth in SEQ ID NO: 3; (ii) a promoter having the sequence as set forth in SEQ ID NO: 30 or SEQ ID NO: 31; and (iii) a coding sequence encoding a protein that rescues voltage-gated sodium channel function.

2. The expression construct of claim 1, wherein the coding sequence comprises a sequence as set forth in SEQ ID NO: 10, SEQ ID NO: 10 with a D60N mutation, SEQ ID NO: 11, SEQ ID NO: 13, SEQ ID NO: 9, SEQ ID NO: 12, SEQ ID NO: 14, SEQ ID NO: 15, SEQ ID NO: 16, or SEQ ID NO: 24.

3. An expression construct comprising (i) an enhancer having 3, 4, 5, 6, 7, 8, or 9 copies of the sequence consisting of the sequence as set forth in SEQ ID NO: 2; (ii) a promoter; and (iii) a coding sequence encoding a protein that rescues voltage-gated sodium channel function.

4. The expression construct of claim 3, wherein the coding sequence comprises a sequence as set forth in SEQ ID NO: 10, SEQ ID NO: 10 with a D60N mutation, SEQ ID NO: 11, SEQ ID NO: 13, SEQ ID NO: 9, SEQ ID NO: 12, SEQ ID NO: 14, SEQ ID NO: 15, SEQ ID NO: 16, or SEQ ID NO: 24.

5. The expression construct of claim 3, wherein the expression construct further comprises a coding sequence for a reporter protein and a skipping element.

6. The expression construct of claim 3, wherein the expression construct is within an adeno-associated viral (AAV) vector.

7. The expression construct of claim 3, wherein the expression construct has the sequence as set forth in SEQ ID NO: 39, SEQ ID NO: 35, SEQ ID NO: 36, SEQ ID NO: 34, SEQ ID NO: 42, SEQ ID NO: 43, SEQ ID NO: 44, SEQ ID NO: 45, SEQ ID NO: 47, SEQ ID NO: 49, or SEQ ID NO: 51.

8. The expression construct of claim 3, wherein the expression construct is associated with a capsid that crosses the blood brain barrier.

9. The expression construct of claim 8, wherein the capsid comprises PHP.Eb.

10. The expression construct of claim 8, wherein the capsid comprises the sequence as set forth in SEQ ID NO: 53.

11. The expression construct of claim 8, wherein the capsid comprises an AAV9 capsid with an insert having the sequence as set forth in SEQ ID NO: 54 or SEQ ID NO: 55.

12. The expression construct of claim 8, wherein the capsid comprises an AAV2 capsid with an insert having the sequence as set forth in SEQ ID NO: 56.

13. A method for treating Dravet Syndrome in a subject in need thereof wherein the method comprises administering a therapeutically effective amount of an expression construct comprising:

(i) an enhancer having the sequence as set forth in SEQ ID NO: 3;

(ii) a promoter; and (iii) a coding sequence that encodes a protein that rescues voltage-gated sodium channel function, thereby treating Dravet Syndrome in the subject in need thereof.

14. The method of claim 13, wherein the promoter has the sequence as set forth in SEQ ID NO: 30 or SEQ ID NO: 31.

15. The method of claim 13, wherein the coding sequence has the sequence as set forth in SEQ ID NO: 10, SEQ ID NO: 10 with a D60N mutation, SEQ ID NO: 11, SEQ ID NO: 13, SEQ ID NO: 9, SEQ ID NO: 12, SEQ ID NO: 14, SEQ ID NO: 15, SEQ ID NO: 16, or SEQ ID NO: 24.

16. The method of claim 13, wherein the administering is intravenous and the expression construct is associated with a capsid that crosses the blood brain barrier.

17. The method of claim 16, wherein the capsid comprises PHP.Eb.

18. The method of claim 16, wherein the capsid comprises the sequence as set forth in SEQ ID NO: 53.

19. The method of claim 16, wherein the capsid comprises an AAV9 capsid with an insert having the sequence as set forth in SEQ ID NO: 54 or SEQ ID NO: 55.

20. The method of claim 16, wherein the capsid comprises an AAV2 capsid with an insert having the sequence as set forth in SEQ ID NO: 56.

* * * * *

UNITED STATES PATENT AND TRADEMARK OFFICE

CERTIFICATE OF CORRECTION

PATENT NO. : 12,121,563 B2
APPLICATION NO. : 17/044232
DATED : October 22, 2024
INVENTOR(S) : John K. Mich et al.

It is certified that error appears in the above-identified patent and that said Letters Patent is hereby corrected as shown below:

On the Title Page

In (71), Applicant, change “SEATTLE CHILDREN’S HOSPITAL” to “SEATTLE CHILDREN’S HOSPITAL D/B/A SEATTLE CHILDREN’S RESEARCH INSTITUTE”

Signed and Sealed this
Twenty-fifth Day of March, 2025

Coke Morgan Stewart
*Acting Director of the United States Patent and Trademark Office*

```
SEQUENCE LISTING


<160> NUMBER OF SEQ ID NOS: 163

<210> SEQ ID NO 1
<211> LENGTH: 528
<212> TYPE: DNA
<213> ORGANISM: artificial sequence
<220> FEATURE:
<223> OTHER INFORMATION: hDLX I56i enhancer

<400> SEQUENCE: 1

tatgcactca cagtggtttg gcatgcatct ggtgaatttt ttttaacgaa aaattagtgt     60

tggtttcgat gtatggtagc attctcccta acgtaatttg aataattcag caaagcccca    120

ctaccagctg tacttctgca gcctcttcca ttcttttcag cattataatt ttggttaatt    180

ttcaatttta ggtcctacgt ctctgcaatt tgtgtatgaa taacagaata atttccctct    240

tttgtttcgc ctttcctgtt cctgaatcta aataaagatg gctttttagt attaaaagtg    300

gaagaaaatt acaggtaatt atctttgacg gtaaaaacgc tgtaatcagc gggctacatg    360

aaaaattact ctaattatgg ctgcatttaa gagaatggaa aaaaaccttc ttgtggataa    420

aaaccttaaa ttgtccccaa tgtctgcttc aaattggatg gcactgcagc tggaggcttt    480

gttcagaatt gatcctgggg agctacgaac ccaaagtttc acagtagg                 528


<210> SEQ ID NO 2
<211> LENGTH: 131
<212> TYPE: DNA
<213> ORGANISM: artificial sequence
<220> FEATURE:
<223> OTHER INFORMATION: Core of the hDLX I56i enhancer

<400> SEQUENCE: 2

ctaaataaag atggcttttt agtattaaaa gtggaagaaa attacaggta attatctttg     60

acggtaaaaa cgctgtaatc agcgggctac atgaaaaatt actctaatta tggctgcatt    120

taagagaatg g                                                         131


<210> SEQ ID NO 3
<211> LENGTH: 393
<212> TYPE: DNA
<213> ORGANISM: artificial sequence
<220> FEATURE:
<223> OTHER INFORMATION: 3xhI56iCore, Triply Concatamerized Core of the
      hDLX I56i enhancer

<400> SEQUENCE: 3

ctaaataaag atggcttttt agtattaaaa gtggaagaaa attacaggta attatctttg     60

acggtaaaaa cgctgtaatc agcgggctac atgaaaaatt actctaatta tggctgcatt    120
```

```
taagagaatg gctaaataaa gatggctttt tagtattaaa agtggaagaa aattacaggt    180

aattatcttt gacggtaaaa acgctgtaat cagcgggcta catgaaaaat tactctaatt    240

atggctgcat ttaagagaat ggctaaataa agatggcttt ttagtattaa aagtggaaga    300

aaattacagg taattatctt tgacggtaaa aacgctgtaa tcagcgggct acatgaaaaa    360

ttactctaat tatggctgca tttaagagaa tgg                                  393


<210> SEQ ID NO 4
<211> LENGTH: 527
<212> TYPE: DNA
<213> ORGANISM: mus musculus

<400> SEQUENCE: 4

tatacactca cagtggtttg gcatatattt ggtgaaattt tttaaggaaa aattagtgtt     60

ggtttcgata tatggtagct ttttctctaa cataatttga ataattcagc aaagccctac    120

taccagctgt acttctgcag cctcttccat tctttccagc attataattt tggttaattt    180

tcaattttag gtcctacgtc tctgcaattt gtgtatgaat aacagaataa tttccctctt    240

ttgtttcgcc tttcctgttc ctgaatctaa ataaagatgg ctttttagta ttaaaagtgg    300

aagaaaatta caggtaatta tctttgacgg taaaaacgct gtaatcagcg ggctacatga    360

aaaattactc taattatggc tgcatttaag agaatggaaa aaaaccttct tgtggataaa    420

aaccttaaat tgtccccaat gtctgcttca aattggatgg cactgcagct ggaggctttg    480

ttcagaattg atcctgggga gctacgaacc caaagtttca cagtagg                   527


<210> SEQ ID NO 5
<211> LENGTH: 281
<212> TYPE: DNA
<213> ORGANISM: zebrafish

<400> SEQUENCE: 5

acattgtaat tttagataat atcccaagcg ttcactctcc tcggcaattt gtacatgaat     60

aaccgaataa tttcatcttt tgtttcgtct ttgccacttc aaatccaaat aaagatgcct    120

tttagtatta aaagtggtag aaaattacag gtaattatct ttgacggtaa aaacgctgta    180

atcagcgggc tacatcaaaa attaccctaa ttatgtctgc atttatgaga atggaaaaaa    240

accctctctt ggataaaacc cataaattgt cccaaatatc t                         281


<210> SEQ ID NO 6
<211> LENGTH: 130
<212> TYPE: DNA
<213> ORGANISM: zebrafish

<400> SEQUENCE: 6

ccaaataaag atgcctttta gtattaaaag tggtagaaaa ttacaggtaa ttatctttga     60

cggtaaaaac gctgtaatca gcgggctaca tcaaaaatta ccctaattat gtctgcattt    120

atgagaatgg                                                            130


<210> SEQ ID NO 7
<211> LENGTH: 390
<212> TYPE: DNA
<213> ORGANISM: zebrafish

<400> SEQUENCE: 7

ccaaataaag atgcctttta gtattaaaag tggtagaaaa ttacaggtaa ttatctttga     60

cggtaaaaac gctgtaatca gcgggctaca tcaaaaatta ccctaattat gtctgcattt    120
```

```
atgagaatgg ccaaataaag atgcctttta gtattaaaag tggtagaaaa ttacaggtaa    180

ttatctttga cggtaaaaac gctgtaatca gcgggctaca tcaaaaatta ccctaattat    240

gtctgcattt atgagaatgg ccaaataaag atgcctttta gtattaaaag tggtagaaaa    300

ttacaggtaa ttatctttga cggtaaaaac gctgtaatca gcgggctaca tcaaaaatta    360

ccctaattat gtctgcattt atgagaatgg                                     390
```

<210> SEQ ID NO 8
<211> LENGTH: 376
<212> TYPE: DNA
<213> ORGANISM: artificial sequence
<220> FEATURE:
<223> OTHER INFORMATION: hDLX I12b enhancer

<400> SEQUENCE: 8

```
cagctgcaaa cccaagaggg tcagcatcat ttcactgtat tctcttcttg attacaagcc     60

gggcccatca aacacaacat aattacagta atttcaggtt tatttattct aatgcagttt    120

ccccatctct ctggtaatta tgagcaattt tttcgcccag ggaatctttt tgcattaaca    180

aaagagataa cgcactgaaa gccaaatttg ctgtgcattg agaaaaggaa aaaaaaaaat    240

caaataggtg cgagctgcca tctctgcaat tctctggtac cggagccggc aaattgcttg    300

caggtgtatg gagcaagctt gtcaatggcc aggcctccaa attagcaaat gcacagcagc    360

aaagtaatga agacag                                                    376
```

<210> SEQ ID NO 9
<211> LENGTH: 984
<212> TYPE: DNA
<213> ORGANISM: artificial sequence
<220> FEATURE:
<223> OTHER INFORMATION: NavSheP-D60N, codon optimized, with N-terminal
      3x HA tag

<400> SEQUENCE: 9

```
atggtttacc cgtatgatgt cccggattac gctggcagct acccatacga tgtacccgac     60

tatgccggca gttatcccta cgacgtccct gactacgcat ctacgtccct tttgaatgcg    120

cctaccggcc ttcaagctag agtcattaat ctcgtcgaac aaaactggtt tggacacttt    180

atactgactc tcatactcat taatgctgtg cagcttggaa tggaaactag cgccagcctc    240

atggcacaat atggcgcgct gcttatgtcc ttgaataagg tccttctctc tgtgttcgtg    300

gtcgaactgc tgctccggat ttatgcgtat cggggcaagt tttttaagga cccgtggaat    360

gtgtttgact tcactgttat tgttattgct ctgattcctg catctggccc attggctgtc    420

ctccgctccc tccgagttct ccgcgtcttg agggttctga cgattgtccc cagcatgaaa    480

agagtagtgt cagcactgct tgggagcttg cccgggttgg cctccattgc aaccgtgctt    540

ctgttgatct attacgtttt cgctgtgatc gccactaaaa ttttcgggga tgcttttccg    600

gaatggttcg ggacgatagc ggactccttc tatacccttt ttcaaattat gaccttggaa    660

agttggtcta tggggatctc taggccagtg atggaggtgt acccttacgc ttgggtattc    720

tttgtgccct ttattcttgt tgctactttt accatgctta accttttcat cgccatcata    780

gtgaatacta tgcagacatt ctctgacgag gaacatgctc tggagcgaga gcaagataaa    840

cagatcttgg aacaggagca gagacaaatg cacgaggaac tgaaggccat tcgactcgag    900

cttcagcaac tccaaaccct tttgcgaaat gcggctgggg actcctccaa tgtctccaca    960

aagggcaata tcggctcaga ctaa                                           984
```

```
<210> SEQ ID NO 10
<211> LENGTH: 888
<212> TYPE: DNA
<213> ORGANISM: artificial sequence
<220> FEATURE:
<223> OTHER INFORMATION: NavSheP endogenous sequence

<400> SEQUENCE: 10

atgagtacat ctttacttaa cgcgccaacg ggtttgcagg cacgagtgat taacttggtt     60

gagcaaaact ggtttggtca ttttattttg acattgattt taatcaacgc ggtgcagtta    120

ggtatggaga cctcagccag cctgatggcg caatacggtg ctttgttgat gagtcttgat    180

aaggtgctgc tgagtgtatt tgtggtggag ttattgctgc ggatttatgc ctacaggggg    240

aaattttta aagacccttg gaacgtgttc gattttaccg tgatagtgat agcactgatc    300

cctgcatctg ggccattggc tgtcctgcgt tcgctcaggg tattgcgggt gctgagagtg    360

ttaacaattg tgccatcaat gaaacgggtg gtgtctgcgc tgttgggatc acttcctgga    420

ttggcatcga tcgccacagt attactgctg atttattatg tgtttgcggt gatcgctacc    480

aaaatttttg gcgatgcatt ccctgaatgg tttggcacta ttgctgactc attttatacc    540

ctatttcaaa taatgacgct tgaaagctgg tctatgggaa tttcgcggcc agtgatggaa    600

gtctaccctt atgcttgggt atttttcgta ccatttattc tggtagcgac tttcacaatg    660

ctaaatttgt ttattgcgat tatcgtcaat accatgcaaa ccttcagcga cgaagagcat    720

gcattagagc gtgagcaaga caaacaaatc ttagagcagg aacaaagaca aatgcacgag    780

gagttgaaag ccatcagact cgagctacaa caattacaaa ccttgctgcg caatgctgct    840

ggtgattctt ctaatgtgtc gacaaaggga aacattggtt ctgactaa                 888

<210> SEQ ID NO 11
<211> LENGTH: 855
<212> TYPE: DNA
<213> ORGANISM: artificial sequence
<220> FEATURE:
<223> OTHER INFORMATION: NavBp, endogenous sequence

<400> SEQUENCE: 11

atggaaaaca atccagccga acaacaagtt ccaccattag tagccttagc tcagcgtatc     60

gtctttcata aggcctttac cccaactatt attaccttga ttatcattaa tgccattatt    120

gtaggccttg aaacatatcc tactgtttat caaggttata atgattggtt ctacgcagca    180

gatttagcct tactttggat ttttacaatt gagattacac tgcgttttat cgcagcgaga    240

ccgactaaat cttttttaa aagcagctgg aactggtttg atttattaat cgttcttgcc    300

ggtcatgtct ttgccggtgc tcattttgta acggttcttc gtatcctgcg cgttcttcgc    360

gtattacgtg ccatttctgt cattccttct ctgcgtcgtt tagtcgatgc tttgctgatg    420

accatcccgg ctttaggaaa cattatgatc ctgatgggaa ttattttcta tattttcgct    480

gtgattggaa cgatgttatt tgcttctgta gcacctgagt actttggtaa cttacagctt    540

tctttattaa cattattcca agttgttaca cttgaatctt gggcaagcgg tgtcatgagg    600

ccgatttttg cagaggtttg gtggtcttgg atttattttg tcatctttat tttagtaggg    660

acatttattg tctttaactt atttatcggt gttatcgtta ataacgttga aaaagcaaac    720

gaagaagaac tcaaatcaga attagatgat aaagaggcag atacaaaaga agagcttgct    780

tctctgcgta atgaagtagc agagatgaaa gacctcatta aacaaatgca taaacagcaa    840
```

acaaaaaaag ggtaa 855

<210> SEQ ID NO 12
<211> LENGTH: 951
<212> TYPE: DNA
<213> ORGANISM: artificial sequence
<220> FEATURE:
<223> OTHER INFORMATION: NavBp, codon optimized, with N-terminal 3x HA tag

<400> SEQUENCE: 12
atggtttacc cgtatgatgt cccggattac gctggcagct acccatacga tgtacccgac 60
tatgccggca gttatcccta cgacgtccct gactacgcag aaaacaaccc agccgaacag 120
caagtcccac ccctcgtggc gctcgcccaa cgcatagtat ttcacaaggc gtttacgccg 180
acgataatca ccctcatcat tattaatgcg atcattgtgg gactcgagac atacccaacg 240
gtttaccagg gttacaatga ttggttctat gctgccgacc ttgctttgtt gtggatattc 300
actattgaaa tcacgctccg attcatcgcc gcccgaccga cgaagagttt cttcaagtct 360
agctggaact ggtttgatct gcttatcgta ttggcgggcc acgtcttcgc tggcgcccat 420
tttgttacgg tgcttaggat cctccgcgtc ctgagggtcc tcagagctat ctcagtcata 480
cccagtctcc ggcggctggt tgacgcactt ttgatgacaa tcccagcact cggtaacatc 540
atgatactga tggggattat tttttacata ttcgcggtta tcgggacgat gctctttgca 600
tcagtagcgc cagaatactt tggcaatttg cagctgtctc tgcttacact gttccaagtg 660
gttacgctgg aaagttgggc tagtggggtt atgcgaccta tttttgccga agtctggtgg 720
tcttggatct attttgtaat ctttattctc gtgggaactt tcatagtatt taacctttttc 780 attggcgtca tcgtgaacaa tgtggaaaaa gctaacgaag aggaactgaa aagcgaactg 840
gatgataaag aggctgatac aaaagaagaa ctggcatcat tgcgaaacga ggtggcagaa 900
atgaaggatc tcataaaaca gatgcataaa cagcaaacaa aaaagggtta a 951

<210> SEQ ID NO 13
<211> LENGTH: 825
<212> TYPE: DNA
<213> ORGANISM: artificial sequence
<220> FEATURE:
<223> OTHER INFORMATION: NavMs, endogenous sequence

<400> SEQUENCE: 13
atgtcacgca aaataagaga tttaatcgaa tccaaacgct ttcaaaacgt catcaccgcc 60
attattgtgc tcaatggcgc tgtgctgggt ctgctgaccg atacaaccct atcggcctcc 120
agccaaaacc tgctggagcg tgtggatcaa ctttgtctga ctatctttat tgttgaaata 180
tccctgaaaa tatacgccta tggcgtgcga ggctttttcc gcagcggctg gaatctgttt 240
gattttgtga ttgtggccat cgcgcttatg cccgcccagg gtagcctatc ggtgctgcga 300
accttccgta tattccgcgt catgcggctc gtatcggtca taccaaccat gcgaagagtg 360
gtgcaaggca tgctcttggc actgcccggc gtgggatcgg tagcggcact gttgacggtg 420
gtcttctata ttgcggctgt catggccacc aatctctacg gggcaacctt ccctgaatgg 480
tttggtgatc ttagcaagag cctgtacaca ctatttcagg tgatgacctt agagtcatgg 540
tctatgggca ttgtgcgtcc agtgatgaac gttcatccca acgcatgggt ttttttcatc 600
cccttcatca tgctcaccac ctttaccgtg ctcaacctgt ttattggcat tattgtagat 660
gccatggcca tcaccaagga acaggaggaa gaggccaaaa ccggccacca ccaagagcct 720

```
attagccaaa cattgctcca tctgggagat cgcctagata ggatcgaaaa gcagcttgcg    780

caaaacaacg agctcttaca acgacaacag ccgcaaaaaa aatag                    825


<210> SEQ ID NO 14
<211> LENGTH: 954
<212> TYPE: DNA
<213> ORGANISM: artificial sequence
<220> FEATURE:
<223> OTHER INFORMATION: NavMs, codon optimized, with N-terminal 3x HA
      tag and linker

<400> SEQUENCE: 14

atggtttatc cgtatgatgt tcctgactat gcaggatcct atccttatga tgttcccgat     60

tacgctggtt cttaccctta cgatgttccc gattatgcca gttctggatt ggtgccacga    120

ggcagccaca tgagccggaa gatcagagat cttatcgaat ctaagagatt tcagaatgtt    180

attaccgcga taatcgtact caacggggcg gtgctcggtc tcctcaccga taccacattg    240

agcgcttcta gccagaacct gctcgaaagg gttgaccaac tgtgcctgac aatttttatc    300

gtggaaatta gcttgaaaat ttacgcctac ggcgttcgcg gtttttttccg gagcggttgg    360

aatcttttttg acttcgttat cgttgccatc gcgctcatgc ccgcacaggg ttctttgtct    420

gtgttgagga cattccgaat atttcgcgtg atgcgcttgg tatccgtgat ccctacgatg    480

cgccgcgtcg tacaaggaat gttgctggct ctccccggcg tcgggagcgt tgctgccctc    540

cttaccgtgg tattttacat agcggcggtt atggctacta atctttacgg agctaccttc    600

ccggagtggt tcggggattt gtccaagagc ctctatacat tgtttcaagt tatgaccctg    660

gagtcctggt ctatgggcat tgtccggccc gtaatgaacg tacacccaaa tgcgtgggtg    720

tttttcattc cattcatcat gctgactacc tttaccgtgc tgaacttgtt cattgggatt    780

atcgtggatg cgatggccat cactaaggag caagaagaag aggctaaaac tggccaccac    840

caagagccaa tttctcaaac cctcttgcat ctcggggacc gactggaccg cattgagaag    900

caactcgcgc agaacaatga gctgttgcag cgacagcaac ctcaaaaaaa ataa          954


<210> SEQ ID NO 15
<211> LENGTH: 885
<212> TYPE: DNA
<213> ORGANISM: artificial sequence
<220> FEATURE:
<223> OTHER INFORMATION: NavMs, codon optimized, with N-terminal His tag
      and linker

<400> SEQUENCE: 15

atgggcagca gccatcatca tcatcatcac agcagcggcc tggtgccgcg cggcagccat     60

atgtcacgca aaatccgcga tttaatcgaa tccaaacgct ttcaaaacgt catcaccgcc    120

attattgtgc tcaatggcgc tgtgctgggt ctgctgaccg atacaaccct gtcggcctcc    180

agccaaaacc tgctggagcg tgtggatcaa ctttgtctga ctatctttat tgttgaaatc    240

tccctgaaaa tctacgccta tggcgtgcgc ggctttttcc gcagcggctg gaatctgttt    300

gattttgtga ttgtggccat cgcgcttatg ccggcccagg gtagcctgtc ggtgctgcgt    360

accttccgta tcttccgcgt catgcgcctc gtatcggtca tcccaaccat gcgccgtgtg    420

gtgcaaggca tgctcttggc actgccgggc gtgggctcgg tagcggcact gttgacggtg    480

gtcttctata ttgcggctgt catggccacc aatctctacg ggcaaccttt ccctgaatgg    540

tttggtgatc ttagcaagag cctgtacaca ctgtttcagg tgatgacctt agagtcatgg    600

tctatgggca ttgtgcgtcc agtgatgaac gttcatccga acgcatgggt ttttttcatc    660
```

```
ccgttcatca tgctcaccac ctttaccgtg ctcaacctgt ttattggcat tattgtagat    720

gcaatggcaa tcaccaagga acaggaggaa gaggccaaaa ccggtcacca tcaagaacct    780

atttctcaaa ctcttcttca tcttggtgat cgtcttgatc gtattgaaaa acaacttgct    840

caaaataatg aacttcttca acgtcaacaa cctcaaaaaa aataa                    885
```

<210> SEQ ID NO 16
<211> LENGTH: 6027
<212> TYPE: DNA
<213> ORGANISM: homo sapiens

<400> SEQUENCE: 16

```
atggagcaaa cagtgcttgt accaccagga cctgacagct tcaacttctt caccagagaa     60

tctcttgcgg ctattgaaag acgcattgca gaagaaaagg caaagaatcc caaaccagac    120

aaaaaagatg acgacgaaaa tggcccaaag ccaaatagtg acttggaagc tggaaagaac    180

cttccattta tttatggaga cattcctcca gagatggtgt cagagcccct ggaggacctg    240

gacccctact atatcaataa gaaaactttt atagtattga ataaagggaa ggccatcttc    300

cggttcagtg ccacctctgc cctgtacatt ttaactccct tcaatcctct taggaaaata    360

gctattaaga ttttggtaca ttcattattc agcatgctaa ttatgtgcac tattttgaca    420

aactgtgtgt ttatgacaat gagtaaccct cctgattgga caaagaatgt agaatacacc    480

ttcacaggaa tatatacttt tgaatcactt ataaaaatta ttgcaagggg attctgttta    540

gaagatttta ctttccttcg ggatccatgg aactggctcg atttcactgt cattacattt    600

gcgtacgtca cagagtttgt ggacctgggc aatgtctcgg cattgagaac attcagagtt    660

ctccgagcat tgaagacgat ttcagtcatt ccaggcctga aaccattgt gggagccctg    720

atccagtctg tgaagaagct ctcagatgta atgatcctga ctgtgttctg tctgagcgta    780

tttgctctaa ttgggctgca gctgttcatg ggcaacctga ggaataaatg tatacaatgg    840

cctcccacca atgcttcctt ggaggaacat agtatagaaa agaatataac tgtgaattat    900

aatggtacac ttataaatga aactgtcttt gagtttgact ggaagtcata tattcaagat    960

tcaagatatc attatttcct ggagggtttt ttagatgcac tactatgtgg aaatagctct   1020

gatgcaggcc aatgtccaga gggatatatg tgtgtgaaag ctggtagaaa tcccaattat   1080

ggctacacaa gctttgatac cttcagttgg gctttttgt ccttgtttcg actaatgact   1140

caggacttct gggaaaatct ttatcaactg acattacgtg ctgctgggaa aacgtacatg   1200

atattttttg tattggtcat tttcttgggc tcattctacc taataaattt gatcctggct   1260

gtggtggcca tggcctacga ggaacagaat caggccacct tggaagaagc agaacagaaa   1320

gaggccgaat ttcagcagat gattgaacag cttaaaaagc aacaggaggc agctcagcag   1380

gcagcaacgg caactgcctc agaacattcc agagagccca gtgcagcagg caggctctca   1440

gacagctcat ctgaagcctc taagttgagt tccaagagtg ctaaggaaag aagaaatcgg   1500

aggaagaaaa gaaaacagaa agagcagtct ggtggggaag agaaagatga ggatgaattc   1560

caaaaatctg aatctgagga cagcatcagg aggaaaggtt ttcgcttctc cattgaaggg   1620

aaccgattga catatgaaaa gaggtactcc tccccacacc agtctttgtt gagcatccgt   1680

ggctccctat tttcaccaag gcgaaatagc agaacaagcc ttttcagctt tagagggcga   1740

gcaaaggatg tgggatctga gaacgacttc gcagatgatg agcacagcac ctttgaggat   1800

aacgagagcc gtagagattc cttgtttgtg ccccgacgac acggagagag acgcaacagc   1860
```

-continued

```
aacctgagtc agaccagtag gtcatcccgg atgctggcag tgtttccagc gaatgggaag   1920
atgcacagca ctgtggattg caatggtgtg gtttccttgg ttggtggacc ttcagttcct   1980
acatcgcctg ttggacagct tctgccagag gtgataatag ataagccagc tactgatgac   2040
aatggaacaa ccactgaaac tgaaatgaga aagagaaggt caagttcttt ccacgtttcc   2100
atggactttc tagaagatcc ttcccaaagg caacgagcaa tgagtatagc cagcattcta   2160
acaaatacag tagaagaact tgaagaatcc aggcagaaat gcccaccctg ttggtataaa   2220
ttttccaaca tattcttaat ctgggactgt tctccatatt ggttaaaagt gaaacatgtt   2280
gtcaacctgg ttgtgatgga cccatttgtt gacctggcca tcaccatctg tattgtctta   2340
aatactcttt tcatggccat ggagcactat ccaatgacgg accatttcaa taatgtgctt   2400
acagtaggaa acttggtttt cactgggatc tttacagcag aaatgtttct gaaaattatt   2460
gccatggatc cttactatta tttccaagaa ggctggaata tctttgacgg ttttattgtg   2520
acgcttagcc tggtagaact tggactcgcc aatgtggaag gattatctgt tctccgttca   2580
tttcgattgc tgcgagtttt caagttggca aaatcttggc caacgttaaa tatgctaata   2640
aagatcatcg gcaattccgt gggggctctg ggaaatttaa ccctcgtctt ggccatcatc   2700
gtcttcattt ttgccgtggt cggcatgcag ctctttggta aaagctacaa agattgtgtc   2760
tgcaagatcg ccagtgattg tcaactccca cgctggcaca tgaatgactt cttccactcc   2820
ttcctgattg tgttccgcgt gctgtgtggg gagtggatag agaccatgtg ggactgtatg   2880
gaggttgctg gtcaagccat gtgccttact gtcttcatga tggtcatggt gattggaaac   2940
ctagtggtcc tgaatctctt tctggccttg cttctgagct catttagtgc agacaacctt   3000
gcagccactg atgatgataa tgaaatgaat aatctccaaa ttgctgtgga taggatgcac   3060
aaaggagtag cttatgtgaa aagaaaaata tatgaattta ttcaacagtc cttcattagg   3120
aaacaaaaga ttttagatga aattaaacca cttgatgatc taaacaacaa gaaagacagt   3180
tgtatgtcca atcatacagc agaaattggg aaagatcttg actatcttaa agatgtaaat   3240
ggaactacaa gtggtatagg aactggcagc agtgttgaat acattattga tgaaagtgat   3300
tacatgtcat tcataaacaa ccccagtctt actgtgactg taccaattgc tgtaggagaa   3360
tctgactttg aaaatttaaa cacggaagac tttagtagtg aatcggatct ggaagaaagc   3420
aaagagaaac tgaatgaaag cagtagctca tcagaaggta gcactgtgga catcggcgca   3480
cctgtagaag aacagcccgt agtggaacct gaagaaactc ttgaaccaga agcttgtttc   3540
actgaaggct gtgtacaaag attcaagtgt tgtcaaatca atgtggaaga aggcagagga   3600
aaacaatggt ggaacctgag aaggacgtgt ttccgaatag ttgaacataa ctggtttgag   3660
accttcattg ttttcatgat tctccttagt agtggtgctc tggcatttga agatatatat   3720
attgatcagc gaaagacgat taagacgatg ttggaatatg ctgacaaggt tttcacttac   3780
attttcattc tggaaatgct tctaaaatgg gtggcatatg gctatcaaac atatttcacc   3840
aatgcctggt gttggctgga cttcttaatt gttgatgttt cattggtcag tttaacagca   3900
aatgccttgg gttactcaga acttggagcc atcaaatctc tcaggacact aagagctctg   3960
agacctctaa gagccttatc tcgatttgaa gggatgaggg tggttgtgaa tgccctttta   4020
ggagcaattc catccatcat gaatgtgctt ctggtttgtc ttatattctg gctaattttc   4080
agcatcatgg gcgtaaattt gtttgctggc aaattctacc actgtattaa caccacaact   4140
ggtgacaggt ttgacatcga agacgtgaat aatcatactg attgcctaaa actaatagaa   4200
agaaatgaga ctgctcgatg gaaaaatgtg aaagtaaact ttgataatgt aggatttggg   4260
```

```
tatctctctt tgcttcaagt tgccacattc aaaggatgga tggatataat gtatgcagca   4320

gttgattcca gaaatgtgga actccagcct aagtatgaag aaagtctgta catgtatctt   4380

tactttgtta ttttcatcat ctttgggtcc ttcttcacct tgaacctgtt tattggtgtc   4440

atcatagata atttcaacca gcagaaaaag aagtttggag gtcaagacat ctttatgaca   4500

gaagaacaga agaaatacta taatgcaatg aaaaaattag gatcgaaaaa accgcaaaag   4560

cctatacctc gaccaggaaa caaatttcaa ggaatggtct ttgacttcgt aaccagacaa   4620

gtttttgaca taagcatcat gattctcatc tgtcttaaca tggtcacaat gatggtggaa   4680

acagatgacc agagtgaata tgtgactacc attttgtcac gcatcaatct ggtgttcatt   4740

gtgctattta ctggagagtg tgtactgaaa ctcatctctc tacgccatta ttattttacc   4800

attggatgga atatttttga ttttgtggtt gtcattctct ccattgtagg tatgtttctt   4860

gccgagctga tagaaaagta tttcgtgtcc cctaccctgt tccgagtgat ccgtcttgct   4920

aggattggcc gaatcctacg tctgatcaaa ggagcaaagg ggatccgcac gctgctcttt   4980

gctttgatga tgtcccttcc tgcgttgttt aacatcggcc tcctactctt cctagtcatg   5040

ttcatctacg ccatctttgg gatgtccaac tttgcctatg ttaagaggga agttgggatc   5100

gatgacatgt tcaactttga gacctttggc aacagcatga tctgcctatt ccaaattaca   5160

acctctgctg gctgggatgg attgctagca cccattctca acagtaagcc acccgactgt   5220

gaccctaata aagttaaccc tggaagctca gttaagggag actgtgggaa cccatctgtt   5280

ggaattttct tttttgtcag ttacatcatc atatccttcc tggttgtggt gaacatgtac   5340

atcgcggtca tcctggagaa cttcagtgtt gctactgaag aaagtgcaga gcctctgagt   5400

gaggatgact ttgagatgtt ctatgaggtt tgggagaagt ttgatcccga tgcaactcag   5460

ttcatggaat ttgaaaaatt atctcagttt gcagctgcgc ttgaaccgcc tctcaatctg   5520

ccacaaccaa acaaactcca gctcattgcc atggatttgc ccatggtgag tggtgaccgg   5580

atccactgtc ttgatatctt atttgctttt acaaagcggg ttctaggaga gagtggagag   5640

atggatgctc tacgaataca gatggaagag cgattcatgg cttccaatcc ttccaaggtc   5700

tcctatcagc caatcactac tactttaaaa cgaaaacaag aggaagtatc tgctgtcatt   5760

attcagcgtg cttacagacg ccacctttta aagcgaactg taaaacaagc ttcctttacg   5820

tacaataaaa acaaaatcaa aggtggggct aatcttctta taaaagaaga catgataatt   5880

gacagaataa atgaaaactc tattacagaa aaaactgatc tgaccatgtc cactgcagct   5940

tgtccacctt cctatgaccg ggtgacaaag ccaattgtgg aaaaacatga gcaagaaggc   6000

aaagatgaaa aagccaaagg gaaataa                                        6027
```

```
<210> SEQ ID NO 17
<211> LENGTH: 720
<212> TYPE: DNA
<213> ORGANISM: artificial sequence
<220> FEATURE:
<223> OTHER INFORMATION: SYFP2

<400> SEQUENCE: 17

atggtcagca agggcgagga gctgttcacc ggggtggtgc ccatcctggt cgagctggac     60

ggcgacgtca atggccacaa gttcagcgtg tccggcgagg gcgagggcga tgccacctac    120

ggcaagctga ccctgaagct gatctgcacc accggcaagc tgcccgtgcc ctggcccacc    180

ctcgtgacca ccctgggcta cggcgtgcag tgcttcgccc gctaccccga ccacatgaag    240
```

```
cagcacgact tcttcaagtc cgccatgccc gaaggctacg tccaggagcg caccatcttc    300

ttcaaagacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca ccgccgacaa gcagaagaac    480

ggcatcaagg ccaacttcaa gatccgccac aacatcgagg acggcggcgt gcagctcgcc    540

gaccactacc agcagaacac ccccatcggc gacggccccg tgctgctgcc cgacaaccac    600

tacctgagct accagtccaa gctgagcaaa gaccccaacg agaagcgcga tcacatggtc    660

ctgctggagt tcgtgaccgc cgccgggatc actctcggca tggacgagct gtacaaataa    720


<210> SEQ ID NO 18
<211> LENGTH: 78
<212> TYPE: DNA
<213> ORGANISM: artificial sequence
<220> FEATURE:
<223> OTHER INFORMATION: P2A Encoding Sequence

<400> SEQUENCE: 18

ggcagcggcg ccaccaactt cagcctgctg aagcaggccg gcgacgtgga ggagaacccc     60

ggccccggag ctagcgga                                                   78


<210> SEQ ID NO 19
<211> LENGTH: 246
<212> TYPE: DNA
<213> ORGANISM: artificial sequence
<220> FEATURE:
<223> OTHER INFORMATION: WPRE3

<400> SEQUENCE: 19

ataatcaacc tctggattac aaaatttgtg aaagattgac tggtattctt aactatgttg     60

ctccttttac gctatgtgga tacgctgctt taatgccttt gtatcatgct attgcttccc    120

gtatggcttt cattttctcc tccttgtata aatcctggtt agttcttgcc acggcggaac    180

tcatcgccgc ctgccttgcc cgctgctgga caggggctcg gctgttgggc actgacaatt    240

ccgtgg                                                               246


<210> SEQ ID NO 20
<211> LENGTH: 204
<212> TYPE: DNA
<213> ORGANISM: artificial sequence
<220> FEATURE:
<223> OTHER INFORMATION: BGHpA

<400> SEQUENCE: 20

cgactgtgcc ttctagttgc cagccatctg ttgtttgccc ctcccccgtg ccttccttga     60

ccctggaagg tgccactccc actgtccttt cctaataaaa tgaggaaatt gcatcgcatt    120

gtctgagtag gtgtcattct attctggggg gtggggtggg gcaggacagc aagggggagg    180

attgggaaga caatagcagg catg                                           204


<210> SEQ ID NO 21
<211> LENGTH: 33
<212> TYPE: PRT
<213> ORGANISM: artificial sequence
<220> FEATURE:
<223> OTHER INFORMATION: N-terminal 3XHA tag (Protein)

<400> SEQUENCE: 21

Met Val Tyr Pro Tyr Asp Val Pro Asp Tyr Ala Gly Ser Tyr Pro Tyr
```

```
1               5                   10                  15

Asp Val Pro Asp Tyr Ala Gly Ser Tyr Pro Tyr Asp Val Pro Asp Tyr
            20                  25                  30

Ala


<210> SEQ ID NO 22
<211> LENGTH: 99
<212> TYPE: DNA
<213> ORGANISM: artificial sequence
<220> FEATURE:
<223> OTHER INFORMATION: N-terminal 3XHA tag

<400> SEQUENCE: 22

atggtttacc cgtatgatgt cccggattac gctggcagct acccatacga tgtacccgac     60

tatgccggca gttatcccta cgacgtccct gactacgca                            99


<210> SEQ ID NO 23
<211> LENGTH: 3133
<212> TYPE: DNA
<213> ORGANISM: artificial sequence
<220> FEATURE:
<223> OTHER INFORMATION: hSCN1A N-term of two-part expression system

<400> SEQUENCE: 23

atggagcaaa cagtgcttgt accaccagga cctgacagct tcaacttctt caccagagaa     60

tctcttgcgg ctattgaaag acgcattgca gaagaaaagg caaagaatcc caaaccagac    120

aaaaaagatg acgacgaaaa tggcccaaag ccaaatagtg acttggaagc tggaaagaac    180

cttccattta tttatggaga cattcctcca gagatggtgt cagagcccct ggaggacctg    240

gacccctact atatcaataa gaaaactttt atagtattga ataaagggaa ggccatcttc    300

cggttcagtg ccacctctgc cctgtacatt ttaactccct tcaatcctct taggaaaata    360

gctattaaga ttttggtaca ttcattattc agcatgctaa ttatgtgcac tattttgaca    420

aactgtgtgt ttatgacaat gagtaaccct cctgattgga caaagaatgt agaatacacc    480

ttcacaggaa tatatacttt tgaatcactt ataaaaatta ttgcaagggg attctgttta    540

gaagatttta ctttccttcg ggatccatgg aactggctcg atttcactgt cattacattt    600

gcgtacgtca cagagtttgt ggacctgggc aatgtctcgg cattgagaac attcagagtt    660

ctccgagcat tgaagacgat ttcagtcatt ccaggcctga aaaccattgt gggagccctg    720

atccagtctg tgaagaagct ctcagatgta atgatcctga ctgtgttctg tctgagcgta    780

tttgctctaa ttgggctgca gctgttcatg ggcaacctga ggaataaatg tatacaatgg    840

cctcccacca atgcttcctt ggaggaacat agtatagaaa agaatataac tgtgaattat    900

aatggtacac ttataaatga aactgtcttt gagtttgact ggaagtcata tattcaagat    960

tcaagatatc attatttcct ggagggtttt ttagatgcac tactatgtgg aaatagctct   1020

gatgcaggcc aatgtccaga gggatatatg tgtgtgaaag ctggtagaaa tcccaattat   1080

ggctacacaa gctttgatac cttcagttgg gctttttgt ccttgtttcg actaatgact    1140

caggacttct gggaaaatct ttatcaactg acattacgtg ctgctgggaa aacgtacatg   1200

atattttttg tattggtcat tttcttgggc tcattctacc taataaattt gatcctggct   1260

gtggtggcca tggcctacga ggaacagaat caggccacct tggaagaagc agaacagaaa   1320

gaggccgaat ttcagcagat gattgaacag cttaaaaagc aacaggaggc agctcagcag   1380

gcagcaacgg caactgcctc agaacattcc agagagccca gtgcagcagg caggctctca   1440
```

-continued

```
gacagctcat ctgaagcctc taagttgagt tccaagagtg ctaaggaaag aagaaatcgg   1500

aggaagaaaa gaaaacagaa agagcagtct ggtggggaag agaaagatga ggatgaattc   1560

caaaaatctg aatctgagga cagcatcagg aggaaaggtt ttcgcttctc cattgaaggg   1620

aaccgattga catatgaaaa gaggtactcc tccccacacc agtctttgtt gagcatccgt   1680

ggctccctat tttcaccaag gcgaaatagc agaacaagcc ttttcagctt tagagggcga   1740

gcaaaggatg tgggatctga gaacgacttc gcagatgatg agcacagcac ctttgaggat   1800

aacgagagcc gtagagattc cttgtttgtg ccccgacgac acggagagag acgcaacagc   1860

aacctgagtc agaccagtag gtcatcccgg atgctggcag tgtttccagc gaatgggaag   1920

atgcacagca ctgtggattg caatggtgtg gtttccttgg ttggtggacc ttcagttcct   1980

acatcgcctg ttggacagct tctgccagag gtgataatag ataagccagc tactgatgac   2040

aatggaacaa ccactgaaac tgaaatgaga aagagaaggt caagttcttt ccacgtttcc   2100

atggactttc tagaagatcc ttcccaaagg caacgagcaa tgagtatagc cagcattcta   2160

acaaatacag tagaagaact tgaagaatcc aggcagaaat gcccaccctg ttggtataaa   2220

ttttccaaca tattcttaat ctgggactgt tctccatatt ggttaaaagt gaaacatgtt   2280

gtcaacctgg ttgtgatgga cccatttgtt gacctggcca tcaccatctg tattgtctta   2340

aatactcttt tcatggccat ggagcactat ccaatgacgg accatttcaa taatgtgctt   2400

acagtaggaa acttggtttt cactgggatc tttacagcag aaatgtttct gaaaattatt   2460

gccatggatc cttactatta tttccaagaa ggctggaata tctttgacgg ttttattgtg   2520

acgcttagcc tggtagaact tggactcgcc aatgtggaag gattatctgt tctccgttca   2580

tttcgattgc tgcgagtttt caagttggca aaatcttggc caacgttaaa tatgctaata   2640

aagatcatcg gcaattccgt gggggctctg ggaaatttaa ccctcgtctt ggccatcatc   2700

gtcttcattt ttgccgtggt cggcatgcag ctctttggta aaagctacaa agattgtgtc   2760

tgcaagatcg ccagtgattg tcaactccca cgctggcaca tgaatgactt cttccactcc   2820

ttcctgattg tgttccgcgt gctgtgtggg gagtggatag agaccatgtg ggactgtatg   2880

gaggttgctg gtcaagccat gtgccttact gtcttcatga tggtcatggt gattggaaac   2940

ctagtggtcc tgaatctctt tctggccttg cttctgagct catttagtgc agacaacctt   3000

gcagccactg atgatgataa tgaaatgaat aatctccaaa ttgctgtgga taggatgcac   3060

aaaggagtag cttatgtgaa aagaaaaata tatgaattta ttcaacagtc cttcattagg   3120

aaacaaaaga ttt                                                      3133
```

```
<210> SEQ ID NO 24
<211> LENGTH: 3639
<212> TYPE: DNA
<213> ORGANISM: artificial sequence
<220> FEATURE:
<223> OTHER INFORMATION: hSCN1A C-term of two-part expression system
      with c-terminal 3XHA sequence

<400> SEQUENCE: 24

ctggtagaac ttggactcgc caatgtggaa ggattatctg ttctccgttc atttcgattg     60

ctgcgagttt tcaagttggc aaaatcttgg ccaacgttaa atatgctaat aaagatcatc    120

ggcaattccg tgggggctct gggaaattta accctcgtct tggccatcat cgtcttcatt    180

tttgccgtgg tcggcatgca gctctttggt aaaagctaca aagattgtgt ctgcaagatc    240

gccagtgatt gtcaactccc acgctggcac atgaatgact tcttccactc cttcctgatt    300
```

-continued gtgttccgcg tgctgtgtgg ggagtggata gagaccatgt gggactgtat ggaggttgct 360
ggtcaagcca tgtgccttac tgtcttcatg atggtcatgg tgattggaaa cctagtggtc 420
ctgaatctct ttctggcctt gcttctgagc tcatttagtg cagacaacct tgcagccact 480
gatgatgata atgaaatgaa taatctccaa attgctgtgg ataggatgca caaaggagta 540
gcttatgtga aaagaaaaat atatgaattt attcaacagt ccttcattag gaaacaaaag 600
attttagatg aaattaaacc acttgatgat ctaaacaaca agaaagacag ttgtatgtcc 660
aatcatacag cagaaattgg gaaagatctt gactatctta aagatgtaaa tggaactaca 720
agtggtatag gaactggcag cagtgttgaa tacattattg atgaaagtga ttacatgtca 780
ttcataaaca accccagtct tactgtgact gtaccaattg ctgtaggaga atctgacttt 840
gaaaatttaa acacggaaga ctttagtagt gaatcggatc tggaagaaag caaagagaaa 900
ctgaatgaaa gcagtagctc atcagaaggt agcactgtgg acatcggcgc acctgtagaa 960
gaacagcccg tagtggaacc tgaagaaact cttgaaccag aagcttgttt cactgaaggc 1020
tgtgtacaaa gattcaagtg ttgtcaaatc aatgtggaag aaggcagagg aaaacaatgg 1080
tggaacctga gaaggacgtg tttccgaata gttgaacata actggtttga gaccttcatt 1140
gttttcatga ttctccttag tagtggtgct ctggcatttg aagatatata tattgatcag 1200
cgaaagacga ttaagacgat gttggaatat gctgacaagg ttttcactta cattttcatt 1260
ctggaaatgc ttctaaaatg ggtggcatat ggctatcaaa catatttcac caatgcctgg 1320
tgttggctgg acttcttaat tgttgatgtt tcattggtca gtttaacagc aaatgccttg 1380
ggttactcag aacttggagc catcaaatct ctcaggacac taagagctct gagacctcta 1440
agagccttat ctcgatttga agggatgagg gtggttgtga atgccctttt aggagcaatt 1500
ccatccatca tgaatgtgct tctggtttgt cttatattct ggctaatttt cagcatcatg 1560
ggcgtaaatt tgtttgctgg caaattctac cactgtatta acaccacaac tggtgacagg 1620
tttgacatcg aagacgtgaa taatcatact gattgcctaa aactaataga aagaaatgag 1680
actgctcgat ggaaaaatgt gaaagtaaac tttgataatg taggatttgg gtatctctct 1740
ttgcttcaag ttgccacatt caaaggatgg atggatataa tgtatgcagc agttgattcc 1800
agaaatgtgg aactccagcc taagtatgaa gaaagtctgt acatgtatct ttactttgtt 1860
attttcatca tctttgggtc cttcttcacc ttgaacctgt ttattggtgt catcatagat 1920
aatttcaacc agcagaaaaa gaagtttgga ggtcaagaca tctttatgac agaagaacag 1980
aagaaatact ataatgcaat gaaaaaatta ggatcgaaaa aaccgcaaaa gcctatacct 2040
cgaccaggaa acaaatttca aggaatggtc tttgacttcg taaccagaca agtttttgac 2100
ataagcatca tgattctcat ctgtcttaac atggtcacaa tgatggtgga aacagatgac 2160
cagagtgaat atgtgactac cattttgtca cgcatcaatc tggtgttcat tgtgctattt 2220
actggagagt gtgtactgaa actcatctct ctacgccatt attattttac cattggatgg 2280
aatatttttg attttgtggt tgtcattctc tccattgtag gtatgtttct tgccgagctg 2340
atagaaaagt atttcgtgtc ccctaccctg ttccgagtga tccgtcttgc taggattggc 2400
cgaatcctac gtctgatcaa aggagcaaag gggatccgca cgctgctctt tgctttgatg 2460
atgtcccttc ctgcgttgtt taacatcggc ctcctactct tcctagtcat gttcatctac 2520
gccatctttg ggatgtccaa ctttgcctat gttaagaggg aagttgggat cgatgacatg 2580
ttcaactttg agacctttgg caacagcatg atctgcctat tccaaattac aacctctgct 2640
ggctgggatg gattgctagc acccattctc aacagtaagc cacccgactg tgaccctaat 2700

```
aaagttaacc ctggaagctc agttaaggga gactgtggga acccatctgt tggaattttc   2760

ttttttgtca gttacatcat catatccttc ctggttgtgg tgaacatgta catcgcggtc   2820

atcctggaga acttcagtgt tgctactgaa gaaagtgcag agcctctgag tgaggatgac   2880

tttgagatgt tctatgaggt ttgggagaag tttgatcccg atgcaactca gttcatggaa   2940

tttgaaaaat tatctcagtt tgcagctgcg cttgaaccgc ctctcaatct gccacaacca   3000

aacaaactcc agctcattgc catggatttg cccatggtga gtggtgaccg gatccactgt   3060

cttgatatct tatttgcttt tacaaagcgg gttctaggag agagtggaga gatggatgct   3120

ctacgaatac agatggaaga gcgattcatg gcttccaatc cttccaaggt ctcctatcag   3180

ccaatcacta ctactttaaa acgaaaacaa gaggaagtat ctgctgtcat tattcagcgt   3240

gcttacagac gccacctttt aaagcgaact gtaaaacaag cttcctttac gtacaataaa   3300

aacaaaatca aaggtggggc taatcttctt ataaaagaag acatgataat tgacagaata   3360

aatgaaaact ctattacaga aaaaactgat ctgaccatgt ccactgcagc ttgtccacct   3420

tcctatgacc gggtgacaaa gccaattgtg gaaaaacatg agcaagaagg caaagatgaa   3480

aaagccaaag ggaaaggagg tggtggttca ggtgggggcg gctcagagta cccctatgat   3540

gtccctgatt atgcggcgga ataccctat gacgtgccgg actacgcggc tgaatatccg   3600

tatgacgttc ccgattatgc ggctaagctc gaataatga                          3639
```

<210> SEQ ID NO 25
<211> LENGTH: 604
<212> TYPE: DNA
<213> ORGANISM: artificial sequence
<220> FEATURE:
<223> OTHER INFORMATION: 604 bp homology region of hSCN1A N term and C term that can be used in two-part expression system

<400> SEQUENCE: 25

```
ctggtagaac ttggactcgc caatgtggaa ggattatctg ttctccgttc atttcgattg     60

ctgcgagttt tcaagttggc aaaatcttgg ccaacgttaa atatgctaat aaagatcatc    120

ggcaattccg tgggggctct gggaaattta accctcgtct tggccatcat cgtcttcatt    180

tttgccgtgg tcggcatgca gctctttggt aaaagctaca aagattgtgt ctgcaagatc    240

gccagtgatt gtcaactccc acgctggcac atgaatgact tcttccactc cttcctgatt    300

gtgttccgcg tgctgtgtgg ggagtggata gagaccatgt gggactgtat ggaggttgct    360

ggtcaagcca tgtgccttac tgtcttcatg atggtcatgg tgattggaaa cctagtggtc    420

ctgaatctct ttctggcctt gcttctgagc tcatttagtg cagacaacct tgcagccact    480

gatgatgata atgaaatgaa taatctccaa attgctgtgg ataggatgca caaaggagta    540

gcttatgtga aaagaaaaat atatgaattt attcaacagt ccttcattag gaaacaaaag    600

attt                                                                 604
```

<210> SEQ ID NO 26
<211> LENGTH: 26
<212> TYPE: PRT
<213> ORGANISM: artificial sequence
<220> FEATURE:
<223> OTHER INFORMATION: P2A Translation from CN1498

<400> SEQUENCE: 26

```
Gly Ser Gly Ala Thr Asn Phe Ser Leu Leu Lys Gln Ala Gly Asp Val
1               5                   10                  15
```

```
Glu Glu Asn Pro Gly Pro Gly Ala Ser Gly
            20                  25


<210> SEQ ID NO 27
<211> LENGTH: 21
<212> TYPE: PRT
<213> ORGANISM: artificial sequence
<220> FEATURE:
<223> OTHER INFORMATION: T2A

<400> SEQUENCE: 27

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 28
<211> LENGTH: 24
<212> TYPE: PRT
<213> ORGANISM: artificial sequence
<220> FEATURE:
<223> OTHER INFORMATION: E2A

<400> SEQUENCE: 28

Gly Ser Gly Gln Cys Thr Asn Tyr Ala Leu Leu Lys Leu Ala Gly Asp
1               5                   10                  15

Val Glu Ser Asn Pro Gly Pro Pro
            20


<210> SEQ ID NO 29
<211> LENGTH: 25
<212> TYPE: PRT
<213> ORGANISM: artificial sequence
<220> FEATURE:
<223> OTHER INFORMATION: F2A

<400> SEQUENCE: 29

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 30
<211> LENGTH: 53
<212> TYPE: DNA
<213> ORGANISM: artificial sequence
<220> FEATURE:
<223> OTHER INFORMATION: MinBglobin

<400> SEQUENCE: 30

gggctgggca taaaagtcag ggcagagcca tctattgctt acatttgctt ctg            53


<210> SEQ ID NO 31
<211> LENGTH: 68
<212> TYPE: DNA
<213> ORGANISM: artificial sequence
<220> FEATURE:
<223> OTHER INFORMATION: minCMV

<400> SEQUENCE: 31

gaggtaggcg tgtacggtgg gaggcctata taagcagagc tcgtttagtg aaccgtcaga     60

tcgcctgg                                                              68


<210> SEQ ID NO 32
```

<211> LENGTH: 11
<212> TYPE: PRT
<213> ORGANISM: artificial sequence
<220> FEATURE:
<223> OTHER INFORMATION: PHP.eB capsid: Corresponds to the AAV9 VP1 capsid sequence with a modification that starts at amino acid residue 586 where S AQ A are changed to S DGTLAVPFK A.

<400> SEQUENCE: 32

```
Ser Asp Gly Thr Leu Ala Val Pro Phe Lys Ala
1               5                   10
```

<210> SEQ ID NO 33
<211> LENGTH: 2843
<212> TYPE: DNA
<213> ORGANISM: artificial sequence
<220> FEATURE:
<223> OTHER INFORMATION: CN1367 - The portion between L-ITR and R-ITR: positions 142-2984

<400> SEQUENCE: 33

```
gcggccgcac gcgtataggt accgagctct atgcactcac agtggtttgg catgcatctg      60
gtgaattttt tttaacgaaa aattagtgtt ggtttcgatg tatggtagca ttctccctaa     120
cgtaatttga ataattcagc aaagccccac taccagctgt acttctgcag cctcttccat     180
tcttttcagc attataattt tggttaattt tcaattttag gtcctacgtc tctgcaattt     240
gtgtatgaat aacagaataa tttccctctt ttgtttcgcc tttcctgttc ctgaatctaa     300
ataaagatgg ctttttagta ttaaaagtgg aagaaaatta caggtaatta tctttgacgg     360
taaaaacgct gtaatcagcg ggctacatga aaaattactc taattatggc tgcatttaag     420
agaatggaaa aaaaccttct tgtggataaa aaccttaaat tgtccccaat gtctgcttca     480
aattggatgg cactgcagct ggaggctttg ttcagaattg atcctgggga gctacgaacc     540
caaagtttca cagtagggag ctcgggctgg gcataaaagt cagggcagag ccatctattg     600
cttacatttg cttctgggat ccagatcttt cgaagctagc gctaccggtc gccaccatgg     660
gcagcagcca tcatcatcat catcacagca gcggcctggt gccgcgcggc agccatatgt     720
cacgcaaaat ccgcgattta atcgaatcca aacgctttca aaacgtcatc accgccatta     780
ttgtgctcaa tggcgctgtg ctgggtctgc tgaccgatac aaccctgtcg gcctccagcc     840
aaaacctgct ggagcgtgtg gatcaacttt gtctgactat ctttattgtt gaaatctccc     900
tgaaaatcta cgcctatggc gtgcgcggct tttccgcag cggctggaat ctgtttgatt      960
ttgtgattgt ggccatcgcg cttatgccgg cccagggtag cctgtcggtg ctgcgtacct    1020
tccgtatctt ccgcgtcatg cgcctcgtat cggtcatccc aaccatgcgc cgtgtggtgc    1080
aaggcatgct cttggcactg ccgggcgtgg gctcggtagc ggcactgttg acggtggtct    1140
tctatattgc ggctgtcatg gccaccaatc tctacggggc aaccttccct gaatggtttg    1200
gtgatcttag caagagcctg tacacactgt ttcaggtgat gaccttagag tcatggtcta    1260
tgggcattgt gcgtccagtg atgaacgttc atccgaacgc atgggttttt ttcatcccgt    1320
tcatcatgct caccaccttt accgtgctca acctgtttat tggcattatt gtagatgcaa    1380
tggcaatcac caaggaacag gaggaagagg ccaaaaccgg tcaccatcaa gaacctattt    1440
ctcaaactct tcttcatctt ggtgatcgtc ttgatcgtat tgaaaaacaa cttgctcaaa    1500
ataatgaact tcttcaacgt caacaacctc aaaaaaaagg cagcggcgcc accaacttca    1560
gcctgctgaa gcaggccggc gacgtggagg agaaccccgg ccccatggtg agcaagggcg    1620
aggagctgtt caccggggtg gtgcccatcc tggtcgagct ggacggcgac gtaaacggcc    1680
```

acaagttcag cgtgtccggc gagggcgagg gcgatgccac ctacggcaag ctgaccctga 1740
agctgatctg caccaccggc aagctgcccg tgccctggcc caccctcgtg accaccctgg 1800
gctacggcgt gcagtgcttc gcccgctacc ccgaccacat gaagcagcac gacttcttca 1860
agtccgccat gcccgaaggc tacgtccagg agcgcaccat cttcttcaag gacgacggca 1920
actacaagac ccgcgccgag gtgaagttcg agggcgacac cctggtgaac cgcatcgagc 1980
tgaagggcat cgacttcaag gaggacggca acatcctggg gcacaagctg gagtacaact 2040
acaacagcca caacgtctat atcaccgccg acaagcagaa gaacggcatc aaggccaact 2100
tcaagatccg ccacaacatc gaggacggcg gcgtgcagct cgccgaccac taccagcaga 2160
acacccccat cggcgacggc cccgtgctgc tgcccgacaa ccactacctg agctaccagt 2220
ccaagctgag caaagacccc aacgagaagc gcgatcacat ggtcctgctg gagttcgtga 2280
ccgccgccgg gatcactctc ggcatggacg agctgtacaa gtaagtcgac ggcgcgccgc 2340
ggccgcgaat tcgatatcat aatcaacctc tggattacaa aatttgtgaa agattgactg 2400
gtattcttaa ctatgttgct ccttttacgc tatgtggata cgctgcttta atgcctttgt 2460
atcatgctat tgcttcccgt atggctttca ttttctcctc cttgtataaa tcctggttag 2520
ttcttgccac ggcggaactc atcgccgcct gccttgcccg ctgctggaca ggggctcggc 2580
tgttgggcac tgacaattcc gtggctcgag agatcttcga ctgtgccttc tagttgccag 2640
ccatctgttg tttgcccctc ccccgtgcct tccttgaccc tggaaggtgc cactcccact 2700
gtcctttcct aataaaatga ggaaattgca tcgcattgtc tgagtaggtg tcattctatt 2760
ctggggggtg gggtggggca ggacagcaag ggggaggatt gggaagacaa tagcaggcat 2820
gcacgtgcgg accgagcggc cgc 2843

<210> SEQ ID NO 34
<211> LENGTH: 2835
<212> TYPE: DNA
<213> ORGANISM: artificial sequence
<220> FEATURE:
<223> OTHER INFORMATION: CN1500 - The portion between L-ITR and R-ITR: positions 142-2976

<400> SEQUENCE: 34
gcggccgcac gcgtggtacc ctaaataaag atggcttttt agtattaaaa gtggaagaaa 60
attacaggta attatctttg acggtaaaaa cgctgtaatc agcgggctac atgaaaaatt 120
actctaatta tggctgcatt taagagaatg gctaaataaa gatggctttt tagtattaaa 180
agtggaagaa aattacaggt aattatcttt gacggtaaaa acgctgtaat cagcgggcta 240
catgaaaaat tactctaatt atggctgcat ttaagagaat ggctaaataa agatggcttt 300
ttagtattaa aagtggaaga aaattacagg taattatctt tgacggtaaa aacgctgtaa 360
tcagcgggct acatgaaaaa ttactctaat tatggctgca tttaagagaa tggagctcgg 420
gctggtcgac acaattggag gtaggcgtgt acggtgggag gcctatataa gcagagctcg 480
tttagtgaac cgtcagatcg cctggaggat ccttcgaaaa gcttgctacc ggtcgccacc 540
atggtcagca agggcgagga gctgttcacc ggggtggtgc ccatcctggt cgagctggac 600
ggcgacgtca atggccacaa gttcagcgtg tccggcgagg gcgagggcga tgccacctac 660
ggcaagctga ccctgaagct gatctgcacc accggcaagc tgcccgtgcc ctggcccacc 720
ctcgtgacca ccctgggcta cggcgtgcag tgcttcgccc gctaccccga ccacatgaag 780
cagcacgact tcttcaagtc cgccatgccc gaaggctacg tccaggagcg caccatcttc 840

```
ttcaaagacg acggcaacta caagacccgc gccgaggtga agttcgaggg cgacaccctg    900

gtgaaccgca tcgagctgaa gggcatcgac ttcaaggagg acggcaacat cctggggcac    960

aagctggagt acaactacaa cagccacaac gtctatatca ccgccgacaa gcagaagaac   1020

ggcatcaagg ccaacttcaa gatccgccac aacatcgagg acggcggcgt gcagctcgcc   1080

gaccactacc agcagaacac ccccatcggc gacggccccg tgctgctgcc cgacaaccac   1140

tacctgagct accagtccaa gctgagcaaa gaccccaacg agaagcgcga tcacatggtc   1200

ctgctggagt tcgtgaccgc cgccgggatc actctcggca tggacgagct gtacaaaggc   1260

agcggcgcca ccaacttcag cctgctgaag caggccggcg acgtggagga gaaccccggc   1320

cccggagcta gcggaatggt ttacccgtat gatgtcccgg attacgctgg cagctaccca   1380

tacgatgtac ccgactatgc cggcagttat ccctacgacg tccctgacta cgcatctacg   1440

tcccttttga atgcgcctac cggccttcaa gctagagtca ttaatctcgt cgaacaaaac   1500

tggtttggac actttatact gactctcata ctcattaatg ctgtgcagct tggaatggaa   1560

actagcgcca gcctcatggc acaatatggc gcgctgctta tgtccttgaa taaggtcctt   1620

ctctctgtgt tcgtggtcga actgctgctc cggatttatg cgtatcgggg caagtttttt   1680

aaggacccgt ggaatgtgtt tgacttcact gttattgtta ttgctctgat tcctgcatct   1740

ggcccattgg ctgtcctccg ctccctccga gttctccgcg tcttgagggt tctgacgatt   1800

gtccccagca tgaaaagagt agtgtcagca ctgcttggga gcttgcccgg gttggcctcc   1860

attgcaaccg tgcttctgtt gatctattac gttttcgctg tgatcgccac taaaattttc   1920

ggggatgctt ttccggaatg gttcgggacg atagcggact ccttctatac cctttttcaa   1980

attatgacct tggaaagttg gtctatgggg atctctaggc cagtgatgga ggtgtaccct   2040

tacgcttggg tattctttgt gccctttatt cttgttgcta cttttaccat gcttaacctt   2100

ttcatcgcca tcatagtgaa tactatgcag acattctctg acgaggaaca tgctctggag   2160

cgagagcaag ataaacagat cttggaacag gagcagagac aaatgcacga ggaactgaag   2220

gccattcgac tcgagcttca gcaactccaa acccttttgc gaaatgcggc tggggactcc   2280

tccaatgtct ccacaaaggg caatatcggc tcagactaat gaccgcggcc gcgaattcga   2340

tatcataatc aacctctgga ttacaaaatt tgtgaaagat tgactggtat tcttaactat   2400

gttgctcctt ttacgctatg tggatacgct gctttaatgc ctttgtatca tgctattgct   2460

tcccgtatgg ctttcatttt ctcctccttg tataaatcct ggttagttct tgccacggcg   2520

gaactcatcg ccgcctgcct tgcccgctgc tggacagggg ctcggctgtt gggcactgac   2580

aattccgtgg ctcgagagat cttcgactgt gccttctagt tgccagccat ctgttgtttg   2640

cccctccccc gtgccttcct tgaccctgga aggtgccact cccactgtcc tttcctaata   2700

aaatgaggaa attgcatcgc attgtctgag taggtgtcat tctattctgg ggggtggggt   2760

ggggcaggac agcaaggggg aggattggga agacaatagc aggcatgaga tctcacgtgc   2820

ggaccgagcg gccgc                                                    2835
```

<210> SEQ ID NO 35
<211> LENGTH: 5681
<212> TYPE: DNA
<213> ORGANISM: artificial sequence
<220> FEATURE:
<223> OTHER INFORMATION: CN1498 - The portion between L-ITR and R-ITR: positions 142-2943

<400> SEQUENCE: 35

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggtac cctaaataaa gatggctttt    180
tagtattaaa agtggaagaa aattacaggt aattatcttt gacggtaaaa acgctgtaat    240
cagcgggcta catgaaaaat tactctaatt atggctgcat ttaagagaat ggctaaataa    300
agatggcttt ttagtattaa aagtggaaga aaattacagg taattatctt tgacggtaaa    360
aacgctgtaa tcagcgggct acatgaaaaa ttactctaat tatggctgca tttaagagaa    420
tggctaaata aagatggctt tttagtatta aaagtggaag aaaattacag gtaattatct    480
ttgacggtaa aaacgctgta atcagcgggc tacatgaaaa attactctaa ttatggctgc    540
atttaagaga atggagctcg ggctggtcga cacaattgga ggtaggcgtg tacggtggga    600
ggcctatata agcagagctc gtttagtgaa ccgtcagatc gcctggagga tccttcgaaa    660
agcttgctac cggtcgccac catggtcagc aagggcgagg agctgttcac cggggtggtg    720
cccatcctgg tcgagctgga cggcgacgtc aatggccaca agttcagcgt gtccggcgag    780
ggcgagggcg atgccaccta cggcaagctg accctgaagc tgatctgcac caccggcaag    840
ctgcccgtgc cctggcccac cctcgtgacc accctgggct acggcgtgca gtgcttcgcc    900
cgctaccccg accacatgaa gcagcacgac ttcttcaagt ccgccatgcc cgaaggctac    960
gtccaggagc gcaccatctt cttcaaagac gacggcaact acaagacccg cgccgaggtg   1020
aagttcgagg gcgacaccct ggtgaaccgc atcgagctga agggcatcga cttcaaggag   1080
gacggcaaca tcctggggca caagctggag tacaactaca acagccacaa cgtctatatc   1140
accgccgaca agcagaagaa cggcatcaag gccaacttca agatccgcca caacatcgag   1200
gacggcggcg tgcagctcgc cgaccactac cagcagaaca cccccatcgg cgacggcccc   1260
gtgctgctgc ccgacaacca ctacctgagc taccagtcca agctgagcaa agaccccaac   1320
gagaagcgcg atcacatggt cctgctggag ttcgtgaccg ccgccgggat cactctcggc   1380
atggacgagc tgtacaaagg cagcggcgcc accaacttca gcctgctgaa gcaggccggc   1440
gacgtggagg agaaccccgg ccccggagct agcggaatgg tttacccgta tgatgtcccg   1500
gattacgctg gcagctaccc atacgatgta cccgactatg ccggcagtta tccctacgac   1560
gtccctgact acgcagaaaa caacccagcc gaacagcaag tcccacccct cgtggcgctc   1620
gcccaacgca tagtatttca caaggcgttt acgccgacga taatcaccct catcattatt   1680
aatgcgatca ttgtgggact cgagacatac ccaacggttt accagggtta caatgattgg   1740
ttctatgctg ccgaccttgc tttgttgtgg atattcacta ttgaaatcac gctccgattc   1800
atcgccgccc gaccgacgaa gagtttcttc aagtctagct ggaactggtt tgatctgctt   1860
atcgtattgg cgggccacgt cttcgctggc gcccattttg ttacggtgct taggatcctc   1920
cgcgtcctga gggtcctcag agctatctca gtcataccca gtctccggcg gctggttgac   1980
gcacttttga tgacaatccc agcactcggt aacatcatga tactgatggg gattattttt   2040
tacatattcg cggttatcgg gacgatgctc tttgcatcag tagcgccaga atactttggc   2100
aatttgcagc tgtctctgct tacactgttc caagtggtta cgctggaaag ttgggctagt   2160
ggggttatgc gacctatttt tgccgaagtc tggtggtctt ggatctattt tgtaatcttt   2220
attctcgtgg gaactttcat agtatttaac cttttcattg gcgtcatcgt gaacaatgtg   2280
gaaaaagcta acgaagagga actgaaaagc gaactggatg ataaagaggc tgatacaaaa   2340
```

```
gaagaactgg catcattgcg aaacgaggtg gcagaaatga aggatctcat aaaacagatg   2400
cataaacagc aaacaaaaaa gggttaatga ccgcggccgc gaattcgata tcataatcaa   2460
cctctggatt acaaaatttg tgaaagattg actggtattc ttaactatgt tgctcctttt   2520
acgctatgtg gatacgctgc tttaatgcct ttgtatcatg ctattgcttc ccgtatggct   2580
ttcattttct cctccttgta taaatcctgg ttagttcttg ccacggcgga actcatcgcc   2640
gcctgccttg cccgctgctg gacaggggct cggctgttgg gcactgacaa ttccgtggct   2700
cgagagatct tcgactgtgc cttctagttg ccagccatct gttgtttgcc cctcccccgt   2760
gccttccttg accctggaag gtgccactcc cactgtcctt tcctaataaa atgaggaaat   2820
tgcatcgcat tgtctgagta ggtgtcattc tattctgggg ggtggggtgg ggcaggacag   2880
caagggggag gattgggaag acaatagcag gcatgagatc tcacgtgcgg accgagcggc   2940
cgcaggaacc cctagtgatg gagttggcca ctccctctct gcgcgctcgc tcgctcactg   3000
aggccgggcg accaaaggtc gcccgacgcc cgggctttgc ccgggcggcc tcagtgagcg   3060
agcgagcgcg cagctgcctg caggggcgcc tgatgcggta ttttctcctt acgcatctgt   3120
gcggtatttc acaccgcata cgtcaaagca accatagtac gcgccctgta gcggcgcatt   3180
aagcgcggcg ggtgtggtgg ttacgcgcag cgtgaccgct acacttgcca gcgccctagc   3240
gcccgctcct ttcgctttct tcccttcctt tctcgccacg ttcgccggct ttccccgtca   3300
agctctaaat cgggggctcc ctttagggtt ccgatttagt gctttacggc acctcgaccc   3360
caaaaaactt gatttgggtg atggttcacg tagtgggcca tcgccctgat agacggtttt   3420
tcgccctttg acgttggagt ccacgttctt taatagtgga ctcttgttcc aaactggaac   3480
aacactcaac cctatctcgg gctattcttt tgatttataa gggattttgc cgatttcggc   3540
ctattggtta aaaaatgagc tgatttaaca aaaatttaac gcgaatttta acaaaatatt   3600
aacgtttaca attttatggt gcactctcag tacaatctgc tctgatgccg catagttaag   3660
ccagccccga cacccgccaa cacccgctga cgcgccctga cgggcttgtc tgctcccggc   3720
atccgcttac agacaagctg tgaccgtctc cgggagctgc atgtgtcaga ggttttcacc   3780
gtcatcaccg aaacgcgcga gacgaaaggg cctcgtgata cgcctatttt tataggttaa   3840
tgtcatgata ataatggttt cttagacgtc aggtggcact tttcggggaa atgtgcgcgg   3900
aacccctatt tgtttatttt tctaaataca ttcaaatatg tatccgctca tgagacaata   3960
accctgataa atgcttcaat aatattgaaa aaggaagagt atgagtattc aacatttccg   4020
tgtcgccctt attccctttt ttgcggcatt ttgccttcct gtttttgctc acccagaaac   4080
gctggtgaaa gtaaaagatg ctgaagatca gttgggtgca cgagtgggtt acatcgaact   4140
ggatctcaac agcggtaaga tccttgagag ttttcgcccc gaagaacgtt ttccaatgat   4200
gagcactttt aaagttctgc tatgtggcgc ggtattatcc cgtattgacg ccgggcaaga   4260
gcaactcggt cgccgcatac actattctca gaatgacttg gttgagtact caccagtcac   4320
agaaaagcat cttacggatg gcatgacagt aagagaatta tgcagtgctg ccataaccat   4380
gagtgataac actgcggcca acttacttct gacaacgatc ggaggaccga aggagctaac   4440
cgcttttttg cacaacatgg gggatcatgt aactcgcctt gatcgttggg aaccggagct   4500
gaatgaagcc ataccaaacg acgagcgtga caccacgatg cctgtagcaa tggcaacaac   4560
gttgcgcaaa ctattaactg gcgaactact tactctagct tcccggcaac aattaataga   4620
ctggatggag gcggataaag ttgcaggacc acttctgcgc tcggcccttc cggctggctg   4680
gtttattgct gataaatctg gagccggtga gcgtgggtct cgcggtatca ttgcagcact   4740
```

```
ggggccagat ggtaagccct cccgtatcgt agttatctac acgacgggga gtcaggcaac   4800

tatggatgaa cgaaatagac agatcgctga gataggtgcc tcactgatta agcattggta   4860

actgtcagac caagtttact catatatact ttagattgat ttaaaacttc atttttaatt   4920

taaaaggatc taggtgaaga tcctttttga taatctcatg accaaaatcc cttaacgtga   4980

gttttcgttc cactgagcgt cagaccccgt agaaaagatc aaaggatctt cttgagatcc   5040

tttttttctg cgcgtaatct gctgcttgca aacaaaaaaa ccaccgctac cagcggtggt   5100

ttgtttgccg gatcaagagc taccaactct ttttccgaag gtaactggct tcagcagagc   5160

gcagatacca aatactgtcc ttctagtgta gccgtagtta ggccaccact tcaagaactc   5220

tgtagcaccg cctacatacc tcgctctgct aatcctgtta ccagtggctg ctgccagtgg   5280

cgataagtcg tgtcttaccg ggttggactc aagacgatag ttaccggata aggcgcagcg   5340

gtcgggctga acggggggtt cgtgcacaca gcccagcttg gagcgaacga cctacaccga   5400

actgagatac ctacagcgtg agctatgaga aagcgccacg cttcccgaag ggagaaaggc   5460

ggacaggtat ccggtaagcg gcagggtcgg aacaggagag cgcacgaggg agcttccagg   5520

gggaaacgcc tggtatcttt atagtcctgt cgggtttcgc cacctctgac ttgagcgtcg   5580

atttttgtga tgctcgtcag gggggcggag cctatggaaa aacgccagca acgcggcctt   5640

tttacggttc ctggcctttt gctggccttt tgctcacatg t                       5681
```

```
<210> SEQ ID NO 36
<211> LENGTH: 5684
<212> TYPE: DNA
<213> ORGANISM: artificial sequence
<220> FEATURE:
<223> OTHER INFORMATION: CN1499 - The portion between L-ITR and R-ITR:
      positions 142-2946

<400> SEQUENCE: 36
```

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctggtcga cacaattgga ggtaggcgtg tacggtggga    600

ggcctatata agcagagctc gtttagtgaa ccgtcagatc gcctggagga tccttcgaaa    660

agcttgctac cggtcgccac catggtcagc aagggcgagg agctgttcac cggggtggtg    720

cccatcctgg tcgagctgga cggcgacgtc aatggccaca agttcagcgt gtccggcgag    780

ggcgagggcg atgccaccta cggcaagctg accctgaagc tgatctgcac caccggcaag    840

ctgcccgtgc cctggcccac cctcgtgacc accctgggct acggcgtgca gtgcttcgcc    900

cgctaccccg accacatgaa gcagcacgac ttcttcaagt ccgccatgcc cgaaggctac    960

gtccaggagc gcaccatctt cttcaaagac gacggcaact acaagacccg cgccgaggtg   1020

aagttcgagg gcgacaccct ggtgaaccgc atcgagctga agggcatcga cttcaaggag   1080
```

```
gacggcaaca tcctggggca caagctggag tacaactaca acagccacaa cgtctatatc   1140
accgccgaca agcagaagaa cggcatcaag gccaacttca agatccgcca caacatcgag   1200
gacggcggcg tgcagctcgc cgaccactac cagcagaaca cccccatcgg cgacggcccc   1260
gtgctgctgc ccgacaacca ctacctgagc taccagtcca agctgagcaa agaccccaac   1320
gagaagcgcg atcacatggt cctgctggag ttcgtgaccg ccgccgggat cactctcggc   1380
atggacgagc tgtacaaagg cagcggcgcc accaacttca gcctgctgaa gcaggccggc   1440
gacgtggagg agaaccccgg ccccggagct agcggaatgg tttatccgta tgatgttcct   1500
gactatgcag gatcctatcc ttatgatgtt cccgattacg ctggttctta cccttacgat   1560
gttcccgatt atgccagttc tggattggtg ccacgaggca gccacatgag ccggaagatc   1620
agagatctta tcgaatctaa gagatttcag aatgttatta ccgcgataat cgtactcaac   1680
ggggcggtgc tcggtctcct caccgatacc acattgagcg cttctagcca gaacctgctc   1740
gaaagggttg accaactgtg cctgacaatt tttatcgtgg aaattagctt gaaaatttac   1800
gcctacggcg ttcgcggttt tttccggagc ggttggaatc tttttgactt cgttatcgtt   1860
gccatcgcgc tcatgcccgc acagggttct ttgtctgtgt tgaggacatt ccgaatattt   1920
cgcgtgatgc gcttggtatc cgtgatccct acgatgcgcc gcgtcgtaca aggaatgttg   1980
ctggctctcc ccggcgtcgg gagcgttgct gccctcctta ccgtggtatt ttacatagcg   2040
gcggttatgg ctactaatct ttacggagct accttcccgg agtggttcgg ggatttgtcc   2100
aagagcctct atacattgtt tcaagttatg accctggagt cctggtctat gggcattgtc   2160
cggcccgtaa tgaacgtaca cccaaatgcg tgggtgtttt tcattccatt catcatgctg   2220
actaccttta ccgtgctgaa cttgttcatt gggattatcg tggatgcgat ggccatcact   2280
aaggagcaag aagaagaggc taaaactggc caccaccaag agccaatttc tcaaaccctc   2340
ttgcatctcg gggaccgact ggaccgcatt gagaagcaac tcgcgcagaa caatgagctg   2400
ttgcagcgac agcaacctca aaaaaaataa tgaccgcggc cgcgaattcg atatcataat   2460
caacctctgg attacaaaat ttgtgaaaga ttgactggta ttcttaacta tgttgctcct   2520
tttacgctat gtggatacgc tgctttaatg cctttgtatc atgctattgc ttcccgtatg   2580
gctttcattt tctcctcctt gtataaatcc tggttagttc ttgccacggc ggaactcatc   2640
gccgcctgcc ttgcccgctg ctggacaggg gctcggctgt tgggcactga caattccgtg   2700
gctcgagaga tcttcgactg tgccttctag ttgccagcca tctgttgttt gcccctcccc   2760
cgtgccttcc ttgaccctgg aaggtgccac tcccactgtc ctttcctaat aaaatgagga   2820
aattgcatcg cattgtctga gtaggtgtca ttctattctg gggggtgggg tggggcagga   2880
cagcaagggg gaggattggg aagacaatag caggcatgag atctcacgtg cggaccgagc   2940
ggccgcagga acccctagtg atggagttgg ccactccctc tctgcgcgct cgctcgctca   3000
ctgaggccgg gcgaccaaag gtcgcccgac gcccgggctt tgcccgggcg gcctcagtga   3060
gcgagcgagc gcgcagctgc ctgcaggggc gcctgatgcg gtattttctc cttacgcatc   3120
tgtgcggtat ttcacaccgc atacgtcaaa gcaaccatag tacgcgccct gtagcggcgc   3180
attaagcgcg gcgggtgtgg tggttacgcg cagcgtgacc gctacacttg ccagcgccct   3240
agcgcccgct cctttcgctt tcttcccttc ctttctcgcc acgttcgccg gctttccccg   3300
tcaagctcta aatcgggggc tccctttagg gttccgattt agtgctttac ggcacctcga   3360
ccccaaaaaa cttgatttgg gtgatggttc acgtagtggg ccatcgccct gatagacggt   3420
```

```
ttttcgccct ttgacgttgg agtccacgtt ctttaatagt ggactcttgt tccaaactgg   3480
aacaacactc aaccctatct cgggctattc ttttgattta taagggattt tgccgatttc   3540
ggcctattgg ttaaaaaatg agctgattta acaaaaattt aacgcgaatt ttaacaaaat   3600
attaacgttt acaattttat ggtgcactct cagtacaatc tgctctgatg ccgcatagtt   3660
aagccagccc cgacacccgc caacacccgc tgacgcgccc tgacgggctt gtctgctccc   3720
ggcatccgct tacagacaag ctgtgaccgt ctccgggagc tgcatgtgtc agaggttttc   3780
accgtcatca ccgaaacgcg cgagacgaaa gggcctcgtg atacgcctat ttttataggt   3840
taatgtcatg ataataatgg tttcttagac gtcaggtggc acttttcggg gaaatgtgcg   3900
cggaacccct atttgtttat ttttctaaat acattcaaat atgtatccgc tcatgagaca   3960
ataaccctga taaatgcttc aataatattg aaaaaggaag agtatgagta ttcaacattt   4020
ccgtgtcgcc cttattccct tttttgcggc attttgcctt cctgtttttg ctcacccaga   4080
aacgctggtg aaagtaaaag atgctgaaga tcagttgggt gcacgagtgg gttacatcga   4140
actggatctc aacagcggta agatccttga gagttttcgc cccgaagaac gttttccaat   4200
gatgagcact tttaaagttc tgctatgtgg cgcggtatta tcccgtattg acgccgggca   4260
agagcaactc ggtcgccgca tacactattc tcagaatgac ttggttgagt actcaccagt   4320
cacagaaaag catcttacgg atggcatgac agtaagagaa ttatgcagtg ctgccataac   4380
catgagtgat aacactgcgg ccaacttact tctgacaacg atcggaggac cgaaggagct   4440
aaccgctttt ttgcacaaca tgggggatca tgtaactcgc cttgatcgtt gggaaccgga   4500
gctgaatgaa gccataccaa acgacgagcg tgacaccacg atgcctgtag caatggcaac   4560
aacgttgcgc aaactattaa ctggcgaact acttactcta gcttcccggc aacaattaat   4620
agactggatg gaggcggata aagttgcagg accacttctg cgctcggccc ttccggctgg   4680
ctggtttatt gctgataaat ctggagccgg tgagcgtggg tctcgcggta tcattgcagc   4740
actggggcca gatggtaagc cctcccgtat cgtagttatc tacacgacgg ggagtcaggc   4800
aactatggat gaacgaaata gacagatcgc tgagataggt gcctcactga ttaagcattg   4860
gtaactgtca gaccaagttt actcatatat actttagatt gatttaaaac ttcattttta   4920
atttaaaagg atctaggtga agatcctttt tgataatctc atgaccaaaa tcccttaacg   4980
tgagttttcg ttccactgag cgtcagaccc cgtagaaaag atcaaaggat cttcttgaga   5040
tccttttttt ctgcgcgtaa tctgctgctt gcaaacaaaa aaaccaccgc taccagcggt   5100
ggtttgtttg ccggatcaag agctaccaac tctttttccg aaggtaactg gcttcagcag   5160
agcgcagata ccaaatactg tccttctagt gtagccgtag ttaggccacc acttcaagaa   5220
ctctgtagca ccgcctacat acctcgctct gctaatcctg ttaccagtgg ctgctgccag   5280
tggcgataag tcgtgtctta ccgggttgga ctcaagacga tagttaccgg ataaggcgca   5340
gcggtcgggc tgaacggggg gttcgtgcac acagcccagc ttggagcgaa cgacctacac   5400
cgaactgaga tacctacagc gtgagctatg agaaagcgcc acgcttcccg aagggagaaa   5460
ggcggacagg tatccggtaa gcggcagggt cggaacagga gagcgcacga gggagcttcc   5520
agggggaaac gcctggtatc tttatagtcc tgtcgggttt cgccacctct gacttgagcg   5580
tcgatttttg tgatgctcgt caggggggcg gagcctatgg aaaaacgcca gcaacgcggc   5640
ctttttacgg ttcctggcct tttgctggcc ttttgctcac atgt                    5684
```

<210> SEQ ID NO 37
<211> LENGTH: 4780

```
<212> TYPE: DNA
<213> ORGANISM: artificial sequence
<220> FEATURE:
<223> OTHER INFORMATION: CN1244 - The portion between L-ITR and R-ITR:
      positions 142-2042

<400> SEQUENCE: 37

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtatagg taccgagctc tatgcactca    180

cagtggtttg gcatgcatct ggtgaatttt ttttaacgaa aaattagtgt tggtttcgat    240

gtatggtagc attctcccta acgtaatttg aataattcag caaagcccca ctaccagctg    300

tacttctgca gcctcttcca ttcttttcag cattataatt ttggttaatt ttcaatttta    360

ggtcctacgt ctctgcaatt tgtgtatgaa taacagaata atttccctct tttgtttcgc    420

ctttcctgtt cctgaatcta aataaagatg gctttttagt attaaaagtg gaagaaaatt    480

acaggtaatt atctttgacg gtaaaaacgc tgtaatcagc gggctacatg aaaaattact    540

ctaattatgg ctgcatttaa gagaatggaa aaaaaccttc ttgtggataa aaaccttaaa    600

ttgtccccaa tgtctgcttc aaattggatg gcactgcagc tggaggcttt gttcagaatt    660

gatcctgggg agctacgaac ccaaagtttc acagtaggga gctcgggctg ggcataaaag    720

tcagggcaga gccatctatt gcttacattt gcttctggga tccagatctt tcgaagctag    780

cgctaccggt cgccaccatg gtgagcaagg gcgaggagct gttcaccggg gtggtgccca    840

tcctggtcga gctggacggc gacgtaaacg gccacaagtt cagcgtgtcc ggcgagggcg    900

agggcgatgc cacctacggc aagctgaccc tgaagctgat ctgcaccacc ggcaagctgc    960

ccgtgccctg gcccaccctc gtgaccaccc tgggctacgg cgtgcagtgc ttcgcccgct   1020

accccgacca catgaagcag cacgacttct tcaagtccgc catgcccgaa ggctacgtcc   1080

aggagcgcac catcttcttc aaggacgacg gcaactacaa gacccgcgcc gaggtgaagt   1140

tcgagggcga caccctggtg aaccgcatcg agctgaaggg catcgacttc aaggaggacg   1200

gcaacatcct ggggcacaag ctggagtaca actacaacag ccacaacgtc tatatcaccg   1260

ccgacaagca gaagaacggc atcaaggcca acttcaagat ccgccacaac atcgaggacg   1320

gcggcgtgca gctcgccgac cactaccagc agaacacccc catcggcgac ggccccgtgc   1380

tgctgcccga caaccactac ctgagctacc agtccaagct gagcaaagac cccaacgaga   1440

agcgcgatca catggtcctg ctggagttcg tgaccgccgc cgggatcact ctcggcatgg   1500

acgagctgta caagtaagtc gacggcgcgc cgcggccgcg aattcgatat cataatcaac   1560

ctctggatta caaaatttgt gaaagattga ctggtattct taactatgtt gctcctttta   1620

cgctatgtgg atacgctgct ttaatgcctt tgtatcatgc tattgcttcc cgtatggctt   1680

tcattttctc ctccttgtat aaatcctggt tagttcttgc cacggcggaa ctcatcgccg   1740

cctgccttgc ccgctgctgg acaggggctc ggctgttggg cactgacaat tccgtggctc   1800

gagagatctt cgactgtgcc ttctagttgc cagccatctg ttgtttgccc ctcccccgtg   1860

ccttccttga ccctggaagg tgccactccc actgtccttt cctaataaaa tgaggaaatt   1920

gcatcgcatt gtctgagtag gtgtcattct attctggggg gtggggtggg gcaggacagc   1980

aagggggagg attgggaaga caatagcagg catgagatct cacgtgcgga ccgagcggcc   2040

gcaggaaccc ctagtgatgg agttggccac tccctctctg cgcgctcgct cgctcactga   2100

ggccgggcga ccaaaggtcg cccgacgccc gggctttgcc cgggcggcct cagtgagcga   2160
```

```
gcgagcgcgc agctgcctgc aggggcgcct gatgcggtat tttctcctta cgcatctgtg   2220
cggtatttca caccgcatac gtcaaagcaa ccatagtacg cgccctgtag cggcgcatta   2280
agcgcggcgg gtgtggtggt tacgcgcagc gtgaccgcta cacttgccag cgccctagcg   2340
cccgctcctt tcgctttctt cccttccttt ctcgccacgt tcgccggctt tccccgtcaa   2400
gctctaaatc gggggctccc tttagggttc cgatttagtg ctttacggca cctcgacccc   2460
aaaaaacttg atttgggtga tggttcacgt agtgggccat cgccctgata gacggttttt   2520
cgccctttga cgttggagtc cacgttcttt aatagtggac tcttgttcca aactggaaca   2580
acactcaacc ctatctcggg ctattctttt gatttataag ggattttgcc gatttcggcc   2640
tattggttaa aaaatgagct gatttaacaa aaatttaacg cgaattttaa caaaatatta   2700
acgtttacaa ttttatggtg cactctcagt acaatctgct ctgatgccgc atagttaagc   2760
cagccccgac acccgccaac acccgctgac gcgccctgac gggcttgtct gctcccggca   2820
tccgcttaca gacaagctgt gaccgtctcc gggagctgca tgtgtcagag gttttcaccg   2880
tcatcaccga aacgcgcgag acgaaagggc ctcgtgatac gcctattttt ataggttaat   2940
gtcatgataa taatggtttc ttagacgtca ggtggcactt ttcggggaaa tgtgcgcgga   3000
acccctattt gtttattttt ctaaatacat tcaaatatgt atccgctcat gagacaataa   3060
ccctgataaa tgcttcaata atattgaaaa aggaagagta tgagtattca acatttccgt   3120
gtcgccctta ttcccttttt tgcggcattt tgccttcctg tttttgctca cccagaaacg   3180
ctggtgaaag taaaagatgc tgaagatcag ttgggtgcac gagtgggtta catcgaactg   3240
gatctcaaca gcggtaagat ccttgagagt tttcgccccg aagaacgttt tccaatgatg   3300
agcactttta aagttctgct atgtggcgcg gtattatccc gtattgacgc cgggcaagag   3360
caactcggtc gccgcataca ctattctcag aatgacttgg ttgagtactc accagtcaca   3420
gaaaagcatc ttacggatgg catgacagta agagaattat gcagtgctgc cataaccatg   3480
agtgataaca ctgcggccaa cttacttctg acaacgatcg gaggaccgaa ggagctaacc   3540
gcttttttgc acaacatggg ggatcatgta actcgccttg atcgttggga accggagctg   3600
aatgaagcca taccaaacga cgagcgtgac accacgatgc ctgtagcaat ggcaacaacg   3660
ttgcgcaaac tattaactgg cgaactactt actctagctt cccggcaaca attaatagac   3720
tggatggagg cggataaagt tgcaggacca cttctgcgct cggcccttcc ggctggctgg   3780
tttattgctg ataaatctgg agccggtgag cgtgggtctc gcggtatcat tgcagcactg   3840
gggccagatg gtaagccctc ccgtatcgta gttatctaca cgacggggag tcaggcaact   3900
atggatgaac gaaatagaca gatcgctgag ataggtgcct cactgattaa gcattggtaa   3960
ctgtcagacc aagtttactc atatatactt tagattgatt taaaacttca tttttaattt   4020
aaaaggatct aggtgaagat cctttttgat aatctcatga ccaaaatccc ttaacgtgag   4080
ttttcgttcc actgagcgtc agaccccgta gaaaagatca aaggatcttc ttgagatcct   4140
ttttttctgc gcgtaatctg ctgcttgcaa acaaaaaaac caccgctacc agcggtggtt   4200
tgtttgccgg atcaagagct accaactctt tttccgaagg taactggctt cagcagagcg   4260
cagataccaa atactgtcct tctagtgtag ccgtagttag gccaccactt caagaactct   4320
gtagcaccgc ctacatacct cgctctgcta atcctgttac cagtggctgc tgccagtggc   4380
gataagtcgt gtcttaccgg gttggactca agacgatagt taccggataa ggcgcagcgg   4440
tcgggctgaa cggggggttc gtgcacacag cccagcttgg agcgaacgac ctacaccgaa   4500
```

```
ctgagatacc tacagcgtga gctatgagaa agcgccacgc ttcccgaagg gagaaaggcg   4560

gacaggtatc cggtaagcgg cagggtcgga acaggagagc gcacgaggga gcttccaggg   4620

ggaaacgcct ggtatcttta tagtcctgtc gggtttcgcc acctctgact tgagcgtcga   4680

tttttgtgat gctcgtcagg ggggcggagc ctatggaaaa acgccagcaa cgcggccttt   4740

ttacggttcc tggccttttg ctggcctttt gctcacatgt                          4780
```

<210> SEQ ID NO 38
<211> LENGTH: 4398
<212> TYPE: DNA
<213> ORGANISM: artificial sequence
<220> FEATURE:
<223> OTHER INFORMATION: CN1389 - The portion between L-ITR and R-ITR corresponds to positions 142-1897

<400> SEQUENCE: 38

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgttcgcc tttcctgttc ctgaatctaa    180

ataaagatgg ctttttagta ttaaaagtgg aagaaaatta caggtaatta tctttgacgg    240

taaaaacgct gtaatcagcg ggctacatga aaaattactc taattatggc tgcatttaag    300

agaatggacc tgcagggagc tcgggctggg cataaaagtc agggcagagc catctattgc    360

ttacatttgc ttctgggatc cagatctttc gaagctagcg ctaccggtcg ccaccatggt    420

gagcaagggc gaggagctgt tcaccggggt ggtgcccatc ctggtcgagc tggacggcga    480

cgtaaacggc cacaagttca gcgtgtccgg cgagggcgag ggcgatgcca cctacggcaa    540

gctgaccctg aagctgatct gcaccaccgg caagctgccc gtgccctggc ccaccctcgt    600

gaccaccctg ggctacggcg tgcagtgctt cgcccgctac cccgaccaca tgaagcagca    660

cgacttcttc aagtccgcca tgcccgaagg ctacgtccag gagcgcacca tcttcttcaa    720

ggacgacggc aactacaaga cccgcgccga ggtgaagttc gagggcgaca ccctggtgaa    780

ccgcatcgag ctgaagggca tcgacttcaa ggaggacggc aacatcctgg ggcacaagct    840

ggagtacaac tacaacagcc acaacgtcta tatcaccgcc gacaagcaga agaacggcat    900

caaggccaac ttcaagatcc gccacaacat cgaggacggc ggcgtgcagc tcgccgacca    960

ctaccagcag aacaccccca tcggcgacgg ccccgtgctg ctgcccgaca accactacct   1020

gagctaccag tccaagctga gcaaagaccc caacgagaag cgcgatcaca tggtcctgct   1080

ggagttcgtg accgccgccg ggatcactct cggcatggac gagctgtaca agtaagtcga   1140

cggcgcgccg cggccgcgaa ttcgatatca taatcaacct ctggattaca aaatttgtga   1200

aagattgact ggtattctta actatgttgc tccttttacg ctatgtggat acgctgcttt   1260

aatgcctttg tatcatgcta ttgcttcccg tatggctttc attttctcct ccttgtataa   1320

atcctggtta gttcttgcca cggcggaact catcgccgcc tgccttgccc gctgctggac   1380

aggggctcgg ctgttgggca ctgacaattc cgtggctcga gagatcttcg actgtgcctt   1440

ctagttgcca gccatctgtt gtttgcccct cccccgtgcc ttccttgacc ctggaaggtg   1500

ccactcccac tgtcctttcc taataaaatg aggaaattgc atcgcattgt ctgagtaggt   1560

gtcattctat tctggggggt ggggtggggc aggacagcaa gggggaggat tgggaagaca   1620

atagcaggca tgagatctca cgtgcggacc gagcggccgc aggaacccct agtgatggag   1680

ttggccactc cctctctgcg cgctcgctcg ctcactgagg ccgggcgacc aaaggtcgcc   1740
```

```
cgacgcccgg gctttgcccg ggcggcctca gtgagcgagc gagcgcgcag ctgcctgcag   1800
gggcgcctga tgcggtattt tctccttacg catctgtgcg gtatttcaca ccgcatacgt   1860
caaagcaacc atagtacgcg ccctgtagcg gcgcattaag cgcggcgggt gtggtggtta   1920
cgcgcagcgt gaccgctaca cttgccagcg ccctagcgcc cgctcctttc gctttcttcc   1980
cttcctttct cgccacgttc gccggctttc cccgtcaagc tctaaatcgg gggctccctt   2040
tagggttccg atttagtgct ttacggcacc tcgaccccaa aaaacttgat ttgggtgatg   2100
gttcacgtag tgggccatcg ccctgataga cggtttttcg ccctttgacg ttggagtcca   2160
cgttctttaa tagtggactc ttgttccaaa ctggaacaac actcaaccct atctcgggct   2220
attcttttga tttataaggg attttgccga tttcggccta ttggttaaaa aatgagctga   2280
tttaacaaaa atttaacgcg aattttaaca aaatattaac gtttacaatt ttatggtgca   2340
ctctcagtac aatctgctct gatgccgcat agttaagcca gccccgacac ccgccaacac   2400
ccgctgacgc gccctgacgg gcttgtctgc tcccggcatc cgcttacaga caagctgtga   2460
ccgtctccgg gagctgcatg tgtcagaggt tttcaccgtc atcaccgaaa cgcgcgagac   2520
gaaagggcct cgtgatacgc ctatttttat aggttaatgt catgataata atggtttctt   2580
agacgtcagg tggcactttt cggggaaatg tgcgcggaac ccctatttgt ttatttttct   2640
aaatacattc aaatatgtat ccgctcatga gacaataacc ctgataaatg cttcaataat   2700
attgaaaaag gaagagtatg agtattcaac atttccgtgt cgcccttatt cccttttttg   2760
cggcattttg ccttcctgtt tttgctcacc cagaaacgct ggtgaaagta aaagatgctg   2820
aagatcagtt gggtgcacga gtgggttaca tcgaactgga tctcaacagc ggtaagatcc   2880
ttgagagttt tcgccccgaa gaacgttttc caatgatgag cacttttaaa gttctgctat   2940
gtggcgcggt attatcccgt attgacgccg ggcaagagca actcggtcgc cgcatacact   3000
attctcagaa tgacttggtt gagtactcac cagtcacaga aaagcatctt acggatggca   3060
tgacagtaag agaattatgc agtgctgcca taaccatgag tgataacact gcggccaact   3120
tacttctgac aacgatcgga ggaccgaagg agctaaccgc ttttttgcac aacatggggg   3180
atcatgtaac tcgccttgat cgttgggaac cggagctgaa tgaagccata ccaaacgacg   3240
agcgtgacac cacgatgcct gtagcaatgg caacaacgtt gcgcaaacta ttaactggcg   3300
aactacttac tctagcttcc cggcaacaat taatagactg gatggaggcg gataaagttg   3360
caggaccact tctgcgctcg gcccttccgg ctggctggtt tattgctgat aaatctggag   3420
ccggtgagcg tgggtctcgc ggtatcattg cagcactggg gccagatggt aagccctccc   3480
gtatcgtagt tatctacacg acggggagtc aggcaactat ggatgaacga aatagacaga   3540
tcgctgagat aggtgcctca ctgattaagc attggtaact gtcagaccaa gtttactcat   3600
atatacttta gattgattta aaacttcatt tttaatttaa aaggatctag gtgaagatcc   3660
tttttgataa tctcatgacc aaaatccctt aacgtgagtt ttcgttccac tgagcgtcag   3720
accccgtaga aaagatcaaa ggatcttctt gagatccttt ttttctgcgc gtaatctgct   3780
gcttgcaaac aaaaaaacca ccgctaccag cggtggtttg tttgccggat caagagctac   3840
caactctttt tccgaaggta actggcttca gcagagcgca gataccaaat actgtccttc   3900
tagtgtagcc gtagttaggc caccacttca agaactctgt agcaccgcct acatacctcg   3960
ctctgctaat cctgttacca gtggctgctg ccagtggcga taagtcgtgt cttaccgggt   4020
tggactcaag acgatagtta ccggataagg cgcagcggtc gggctgaacg gggggttcgt   4080
gcacacagcc cagcttggag cgaacgacct acaccgaact gagataccta cagcgtgagc   4140
```

```
tatgagaaag cgccacgctt cccgaaggga gaaaggcgga caggtatccg gtaagcggca   4200

gggtcggaac aggagagcgc acgagggagc ttccaggggg aaacgcctgg tatctttata   4260

gtcctgtcgg gtttcgccac ctctgacttg agcgtcgatt tttgtgatgc tcgtcagggg   4320

ggcggagcct atggaaaaac gccagcaacg cggccttttt acggttcctg gccttttgct   4380

ggccttttgc tcacatgt                                                 4398


<210> SEQ ID NO 39
<211> LENGTH: 4635
<212> TYPE: DNA
<213> ORGANISM: artificial sequence
<220> FEATURE:
<223> OTHER INFORMATION: CN1390 - The portion between L-ITR and R-ITR
      corresponds to positions 142-1660

<400> SEQUENCE: 39

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctgggcat aaaagtcagg gcagagccat ctattgctta    600

catttgcttc tgggatccag atctttcgaa gctagcgcta ccggtcgcca ccatggtgag    660

caagggcgag gagctgttca ccggggtggt gcccatcctg gtcgagctgg acggcgacgt    720

aaacggccac aagttcagcg tgtccggcga gggcgagggc gatgccacct acggcaagct    780

gaccctgaag ctgatctgca ccaccggcaa gctgcccgtg ccctggccca ccctcgtgac    840

caccctgggc tacggcgtgc agtgcttcgc ccgctacccc gaccacatga agcagcacga    900

cttcttcaag tccgccatgc ccgaaggcta cgtccaggag cgcaccatct tcttcaagga    960

cgacggcaac tacaagaccc gcgccgaggt gaagttcgag ggcgacaccc tggtgaaccg   1020

catcgagctg aagggcatcg acttcaagga ggacggcaac atcctggggc acaagctgga   1080

gtacaactac aacagccaca acgtctatat caccgccgac aagcagaaga acggcatcaa   1140

ggccaacttc aagatccgcc acaacatcga ggacggcggc gtgcagctcg ccgaccacta   1200

ccagcagaac acccccatcg gcgacggccc cgtgctgctg cccgacaacc actacctgag   1260

ctaccagtcc aagctgagca aagaccccaa cgagaagcgc gatcacatgg tcctgctgga   1320

gttcgtgacc gccgccggga tcactctcgg catggacgag ctgtacaagt aagtcgacgg   1380

cgcgccgcgg ccgcgaattc gatatcataa tcaacctctg gattacaaaa tttgtgaaag   1440

attgactggt attcttaact atgttgctcc ttttacgcta tgtggatacg ctgctttaat   1500

gcctttgtat catgctattg cttcccgtat ggctttcatt ttctcctcct tgtataaatc   1560

ctggttagtt cttgccacgg cggaactcat cgccgcctgc cttgcccgct gctggacagg   1620

ggctcggctg ttgggcactg acaattccgt ggctcgagag atcttcgact gtgccttcta   1680

gttgccagcc atctgttgtt tgcccctccc ccgtgccttc cttgaccctg gaaggtgcca   1740
```

```
ctcccactgt cctttcctaa taaaatgagg aaattgcatc gcattgtctg agtaggtgtc   1800
attctattct ggggggtggg gtggggcagg acagcaaggg ggaggattgg gaagacaata   1860
gcaggcatga gatctcacgt gcggaccgag cggccgcagg aacccctagt gatggagttg   1920
gccactccct ctctgcgcgc tcgctcgctc actgaggccg ggcgaccaaa ggtcgcccga   1980
cgcccgggct ttgcccgggc ggcctcagtg agcgagcgag cgcgcagctg cctgcagggg   2040
cgcctgatgc ggtattttct ccttacgcat ctgtgcggta tttcacaccg catacgtcaa   2100
agcaaccata gtacgcgccc tgtagcggcg cattaagcgc ggcgggtgtg gtggttacgc   2160
gcagcgtgac cgctacactt gccagcgccc tagcgcccgc tcctttcgct ttcttccctt   2220
cctttctcgc cacgttcgcc ggctttcccc gtcaagctct aaatcggggg ctccctttag   2280
ggttccgatt tagtgcttta cggcacctcg accccaaaaa acttgatttg ggtgatggtt   2340
cacgtagtgg gccatcgccc tgatagacgg tttttcgccc tttgacgttg gagtccacgt   2400
tctttaatag tggactcttg ttccaaactg gaacaacact caaccctatc tcgggctatt   2460
cttttgattt ataagggatt ttgccgattt cggcctattg gttaaaaaat gagctgattt   2520
aacaaaaatt taacgcgaat tttaacaaaa tattaacgtt tacaatttta tggtgcactc   2580
tcagtacaat ctgctctgat gccgcatagt taagccagcc ccgacacccg ccaacacccg   2640
ctgacgcgcc ctgacgggct tgtctgctcc cggcatccgc ttacagacaa gctgtgaccg   2700
tctccgggag ctgcatgtgt cagaggtttt caccgtcatc accgaaacgc gcgagacgaa   2760
agggcctcgt gatacgccta tttttatagg ttaatgtcat gataataatg gtttcttaga   2820
cgtcaggtgg cacttttcgg ggaaatgtgc gcggaacccc tatttgttta tttttctaaa   2880
tacattcaaa tatgtatccg ctcatgagac aataaccctg ataaatgctt caataatatt   2940
gaaaaaggaa gagtatgagt attcaacatt tccgtgtcgc ccttattccc ttttttgcgg   3000
cattttgcct tcctgttttt gctcacccag aaacgctggt gaaagtaaaa gatgctgaag   3060
atcagttggg tgcacgagtg ggttacatcg aactggatct caacagcggt aagatccttg   3120
agagttttcg ccccgaagaa cgttttccaa tgatgagcac ttttaaagtt ctgctatgtg   3180
gcgcggtatt atcccgtatt gacgccgggc aagagcaact cggtcgccgc atacactatt   3240
ctcagaatga cttggttgag tactcaccag tcacagaaaa gcatcttacg gatggcatga   3300
cagtaagaga attatgcagt gctgccataa ccatgagtga taacactgcg gccaacttac   3360
ttctgacaac gatcggagga ccgaaggagc taaccgcttt tttgcacaac atgggggatc   3420
atgtaactcg ccttgatcgt tgggaaccgg agctgaatga agccatacca aacgacgagc   3480
gtgacaccac gatgcctgta gcaatggcaa caacgttgcg caaactatta actggcgaac   3540
tacttactct agcttcccgg caacaattaa tagactggat ggaggcggat aaagttgcag   3600
gaccacttct gcgctcggcc cttccggctg gctggtttat tgctgataaa tctggagccg   3660
gtgagcgtgg gtctcgcggt atcattgcag cactggggcc agatggtaag ccctcccgta   3720
tcgtagttat ctacacgacg gggagtcagg caactatgga tgaacgaaat agacagatcg   3780
ctgagatagg tgcctcactg attaagcatt ggtaactgtc agaccaagtt tactcatata   3840
tactttagat tgatttaaaa cttcattttt aatttaaaag gatctaggtg aagatccttt   3900
ttgataatct catgaccaaa atcccttaac gtgagttttc gttccactga gcgtcagacc   3960
ccgtagaaaa gatcaaagga tcttcttgag atcctttttt tctgcgcgta atctgctgct   4020
tgcaaacaaa aaaaccaccg ctaccagcgg tggtttgttt gccggatcaa gagctaccaa   4080
```

```
ctctttttcc gaaggtaact ggcttcagca gagcgcagat accaaatact gtccttctag   4140

tgtagccgta gttaggccac cacttcaaga actctgtagc accgcctaca tacctcgctc   4200

tgctaatcct gttaccagtg gctgctgcca gtggcgataa gtcgtgtctt accgggttgg   4260

actcaagacg atagttaccg gataaggcgc agcggtcggg ctgaacgggg ggttcgtgca   4320

cacagcccag cttggagcga acgacctaca ccgaactgag atacctacag cgtgagctat   4380

gagaaagcgc cacgcttccc gaagggagaa aggcggacag gtatccggta agcggcaggg   4440

tcggaacagg agagcgcacg agggagcttc caggggggaaa cgcctggtat ctttatagtc   4500

ctgtcgggtt tcgccacctc tgacttgagc gtcgattttt gtgatgctcg tcaggggggc   4560

ggagcctatg gaaaaacgcc agcaacgcgg cctttttacg gttcctggcc ttttgctggc   4620

cttttgctca catgt                                                    4635
```

<210> SEQ ID NO 40
<211> LENGTH: 4841
<212> TYPE: DNA
<213> ORGANISM: artificial sequence
<220> FEATURE:
<223> OTHER INFORMATION: CN1203 - The portion between L-ITR and R-ITR corresponds to positions 183-2052

<400> SEQUENCE: 40

```
aaagcttccc gggggggatct gggccactcc ctctctgcgc gctcgctcgc tcactgaggc     60

cgggcgacca aaggtcgccc gacgcccggg ctttgcccgg gcggcctcag tgagcgagcg    120

agcgcgcaga gagggagtgg ccaactccat cactaggggt tcctggaggg gtggagtcgt    180

gacctaggac gcgtataggt accgagctct atgcactcac agtggtttgg catgcatctg    240

gtgaattttt tttaacgaaa aattagtgtt ggtttcgatg tatggtagca ttctccctaa    300

cgtaatttga ataattcagc aaagccccac taccagctgt acttctgcag cctcttccat    360

tcttttcagc attataattt tggttaattt tcaattttag gtcctacgtc tctgcaattt    420

gtgtatgaat aacagaataa tttccctctt ttgtttcgcc tttcctgttc ctgaatctaa    480

ataaagatgg ctttttagta ttaaaagtgg aagaaaatta caggtaatta tctttgacgg    540

taaaaacgct gtaatcagcg ggctacatga aaaattactc taattatggc tgcatttaag    600

agaatggaaa aaaaccttct tgtggataaa aaccttaaat tgtccccaat gtctgcttca    660

aattggatgg cactgcagct ggaggctttg ttcagaattg atcctgggga gctacgaacc    720

caaagtttca cagtagggag ctcgggctgg gcataaaagt cagggcagag ccatctattg    780

cttacatttg cttctgggat ccagatcttt cgaagctagc gctaccggtc gccaccatgg    840

tgagcaaggg cgaggagctg ttcaccgggg tggtgcccat cctggtcgag ctggacggcg    900

acgtaaacgg ccacaagttc agcgtgtccg gcgagggcga gggcgatgcc acctacggca    960

agctgaccct gaagctgatc tgcaccaccg gcaagctgcc cgtgccctgg cccaccctcg   1020

tgaccaccct gggctacggc gtgcagtgct tcgcccgcta ccccgaccac atgaagcagc   1080

acgacttctt caagtccgcc atgcccgaag gctacgtcca ggagcgcacc atcttcttca   1140

aggacgacgg caactacaag acccgcgccg aggtgaagtt cgagggcgac accctggtga   1200

accgcatcga gctgaagggc atcgacttca aggaggacgg caacatcctg gggcacaagc   1260

tggagtacaa ctacaacagc cacaacgtct atatcaccgc cgacaagcag aagaacggca   1320

tcaaggccaa cttcaagatc cgccacaaca tcgaggacgg cggcgtgcag ctcgccgacc   1380

actaccagca gaacaccccc atcggcgacg gccccgtgct gctgcccgac aaccactacc   1440
```

-continued

```
tgagctacca gtccaagctg agcaaagacc ccaacgagaa gcgcgatcac atggtcctgc   1500
tggagttcgt gaccgccgcc gggatcactc tcggcatgga cgagctgtac aagtaagtcg   1560
acggcgcgcc gcggccgcga attcgatatc ataatcaacc tctggattac aaaatttgtg   1620
aaagattgac tggtattctt aactatgttg ctccttttac gctatgtgga tacgctgctt   1680
taatgccttt gtatcatgct attgcttccc gtatggcttt cattttctcc tccttgtata   1740
aatcctggtt agttcttgcc acggcggaac tcatcgccgc ctgccttgcc cgctgctgga   1800
caggggctcg gctgttgggc actgacaatt ccgtggctcg agcgactgtg ccttctagtt   1860
gccagccatc tgttgtttgc ccctcccccg tgccttcctt gaccctggaa ggtgccactc   1920
ccactgtcct ttcctaataa aatgaggaaa ttgcatcgca ttgtctgagt aggtgtcatt   1980
ctattctggg gggtggggtg gggcaggaca gcaaggggga ggattgggaa gacaatagca   2040
ggcatgacta gtccactccc tctctgcgcg ctcgctcgct cactgaggcc gggcgaccaa   2100
aggtcgcccg acgcccgggc tttgcccggg cggcctcagt gagcgagcga gcgcgcagag   2160
agggacagat ccgggcccgc atgcgtcgac aattcactgg ccgtcgtttt acaacgtcgt   2220
gactgggaaa accctggcgt tacccaactt aatcgccttg cagcacatcc ccctttcgcc   2280
agctggcgta atagcgaaga ggcccgcacc gatcgccctt cccaacagtt gcgcagcctg   2340
aatggcgaat ggcgcctgat gcggtatttt ctccttacgc atctgtgcgg tatttcacac   2400
cgcatatggt gcactctcag tacaatctgc tctgatgccg catagttaag ccagccccga   2460
cacccgccaa cacccgctga cgcgccctga cgggcttgtc tgctcccggc atccgcttac   2520
agacaagctg tgaccgtctc cgggagctgc atgtgtcaga ggttttcacc gtcatcaccg   2580
aaacgcgcga gacgaaaggg cctcgtgata cgcctatttt tataggttaa tgtcatgata   2640
ataatggttt cttagacgtc aggtggcact tttcggggaa atgtgcgcgg aacccctatt   2700
tgtttatttt tctaaataca ttcaaatatg tatccgctca tgagacaata accctgataa   2760
atgcttcaat aatattgaaa aaggaagagt atgagtattc aacatttccg tgtcgccctt   2820
attccctttt ttgcggcatt ttgccttcct gtttttgctc acccagaaac gctggtgaaa   2880
gtaaaagatg ctgaagatca gttgggtgca cgagtgggtt acatcgaact ggatctcaac   2940
agcggtaaga tccttgagag ttttcgcccc gaagaacgtt ttccaatgat gagcactttt   3000
aaagttctgc tatgtggcgc ggtattatcc cgtattgacg ccgggcaaga gcaactcggt   3060
cgccgcatac actattctca gaatgacttg gttgagtact caccagtcac agaaaagcat   3120
cttacggatg gcatgacagt aagagaatta tgcagtgctg ccataaccat gagtgataac   3180
actgcggcca acttacttct gacaacgatc ggaggaccga aggagctaac cgcttttttg   3240
cacaacatgg gggatcatgt aactcgcctt gatcgttggg aaccggagct gaatgaagcc   3300
ataccaaacg acgagcgtga caccacgatg cctgtagcaa tggcaacaac gttgcgcaaa   3360
ctattaactg gcgaactact tactctagct tcccggcaac aattaataga ctggatggag   3420
gcggataaag ttgcaggacc acttctgcgc tcggcccttc cggctggctg gtttattgct   3480
gataaatctg gagccggtga gcgtgggtct cgcggtatca ttgcagcact ggggccagat   3540
ggtaagccct cccgtatcgt agttatctac acgacgggga gtcaggcaac tatggatgaa   3600
cgaaatagac agatcgctga gataggtgcc tcactgatta agcattggta actgtcagac   3660
caagtttact catatatact ttagattgat ttaaaacttc atttttaatt taaaaggatc   3720
taggtgaaga tcctttttga taatctcatg accaaaatcc cttaacgtga gttttcgttc   3780
cactgagcgt cagaccccgt agaaaagatc aaaggatctt cttgagatcc tttttttctg   3840
```

```
cgcgtaatct gctgcttgca aacaaaaaaa ccaccgctac cagcggtggt ttgtttgccg   3900

gatcaagagc taccaactct ttttccgaag gtaactggct tcagcagagc gcagatacca   3960

aatactgttc ttctagtgta gccgtagtta ggccaccact tcaagaactc tgtagcaccg   4020

cctacatacc tcgctctgct aatcctgtta ccagtggctg ctgccagtgg cgataagtcg   4080

tgtcttaccg ggttggactc aagacgatag ttaccggata aggcgcagcg gtcgggctga   4140

acggggggtt cgtgcacaca gcccagcttg gagcgaacga cctacaccga actgagatac   4200

ctacagcgtg agctatgaga aagcgccacg cttcccgaag ggagaaaggc ggacaggtat   4260

ccggtaagcg gcagggtcgg aacaggagag cgcacgaggg agcttccagg gggaaacgcc   4320

tggtatcttt atagtcctgt cgggtttcgc cacctctgac ttgagcgtcg atttttgtga   4380

tgctcgtcag gggggcggag cctatggaaa aacgccagca acgcggcctt tttacggttc   4440

ctggcctttt gctggccttt tgctcacatg ttctttcctg cgttatcccc tgattctgtg   4500

gataaccgta ttaccgcctt tgagtgagct gataccgctc gccgcagccg aacgaccgag   4560

cgcagcgagt cagtgagcga ggaagcggaa gagcgcccaa tacgcaaacc gcctctcccc   4620

gcgcgttggc cgattcatta atgcagctgg cacgacaggt ttcccgactg gaaagcgggc   4680

agtgagcgca acgcaattaa tgtgagttag ctcactcatt aggcacccca ggctttacac   4740

tttatgcttc cggctcgtat gttgtgtgga attgtgagcg gataacaatt tcacacagga   4800

aacagctatg accatgatta cgccaagctc tcgagatcta g                       4841
```

```
<210> SEQ ID NO 41
<211> LENGTH: 4680
<212> TYPE: DNA
<213> ORGANISM: artificial sequence
<220> FEATURE:
<223> OTHER INFORMATION: CN1180 - The portion between L-ITR and R-ITR
      corresponds to positions 183-1891

<400> SEQUENCE: 41
```

```
aaagcttccc ggggggatct gggccactcc ctctctgcgc gctcgctcgc tcactgaggc     60

cgggcgacca aaggtcgccc gacgcccggg ctttgcccgg gcggcctcag tgagcgagcg    120

agcgcgcaga gagggagtgg ccaactccat cactaggggt tcctggaggg gtggagtcgt    180

gacctaggac gcgtcagctg caaacccaag agggtcagca tcatttcact gtattctctt    240

cttgattaca agccgggccc atcaaacaca acataattac agtaatttca ggtttattta    300

ttctaatgca gtttccccat ctctctggta attatgagca attttttcgc ccagggaatc    360

tttttgcatt aacaaaagag ataacgcact gaaagccaaa tttgctgtgc attgagaaaa    420

ggaaaaaaaa aaatcaaata ggtgcgagct gccatctctg caattctctg gtaccggagc    480

cggcaaattg cttgcaggtg tatggagcaa gcttgtcaat ggccaggcct ccaaattagc    540

aaatgcacag cagcaaagta atgaagacag gagctcgggc tgggcataaa agtcagggca    600

gagccatcta ttgcttacat ttgcttctgg gatccagatc tttcgaagct agcgctaccg    660

gtcgccacca tggtgagcaa gggcgaggag ctgttcaccg gggtggtgcc catcctggtc    720

gagctggacg gcgacgtaaa cggccacaag ttcagcgtgt ccggcgaggg cgagggcgat    780

gccacctacg gcaagctgac cctgaagctg atctgcacca ccggcaagct gcccgtgccc    840

tggcccaccc tcgtgaccac cctgggctac ggcgtgcagt gcttcgcccg ctaccccgac    900

cacatgaagc agcacgactt cttcaagtcc gccatgcccg aaggctacgt ccaggagcgc    960

accatcttct tcaaggacga cggcaactac aagacccgcg ccgaggtgaa gttcgagggc   1020
```

```
gacaccctgg tgaaccgcat cgagctgaag ggcatcgact tcaaggagga cggcaacatc   1080

ctggggcaca agctggagta caactacaac agccacaacg tctatatcac cgccgacaag   1140

cagaagaacg gcatcaaggc caacttcaag atccgccaca acatcgagga cggcggcgtg   1200

cagctcgccg accactacca gcagaacacc cccatcggcg acggccccgt gctgctgccc   1260

gacaaccact acctgagcta ccagtccaag ctgagcaaag accccaacga gaagcgcgat   1320

cacatggtcc tgctggagtt cgtgaccgcc gccgggatca ctctcggcat ggacgagctg   1380

tacaagtaag tcgacggcgc gccgcggccg cgaattcgat atcataatca acctctggat   1440

tacaaaattt gtgaaagatt gactggtatt cttaactatg ttgctccttt tacgctatgt   1500

ggatacgctg ctttaatgcc tttgtatcat gctattgctt cccgtatggc tttcattttc   1560

tcctccttgt ataaatcctg gttagttctt gccacggcgg aactcatcgc cgcctgcctt   1620

gcccgctgct ggacaggggc tcggctgttg ggcactgaca attccgtggc tcgagcgact   1680

gtgccttcta gttgccagcc atctgttgtt tgcccctccc ccgtgccttc cttgaccctg   1740

gaaggtgcca ctcccactgt cctttcctaa taaaatgagg aaattgcatc gcattgtctg   1800

agtaggtgtc attctattct ggggggtggg gtggggcagg acagcaaggg ggaggattgg   1860

gaagacaata gcaggcatga ctagtgcatg cccactccct ctctgcgcgc tcgctcgctc   1920

actgaggccg ggcgaccaaa ggtcgcccga cgcccgggct ttgcccgggc ggcctcagtg   1980

agcgagcgag cgcgcagaga gggacagatc cgggcccgca tgcgtcgaca attcactggc   2040

cgtcgtttta caacgtcgtg actgggaaaa ccctggcgtt acccaactta atcgccttgc   2100

agcacatccc cctttcgcca gctggcgtaa tagcgaagag gcccgcaccg atcgcccttc   2160

ccaacagttg cgcagcctga atggcgaatg gcgcctgatg cggtattttc tccttacgca   2220

tctgtgcggt atttcacacc gcatatggtg cactctcagt acaatctgct ctgatgccgc   2280

atagttaagc cagccccgac acccgccaac acccgctgac gcgccctgac gggcttgtct   2340

gctcccggca tccgcttaca gacaagctgt gaccgtctcc gggagctgca tgtgtcagag   2400

gttttcaccg tcatcaccga aacgcgcgag acgaaagggc ctcgtgatac gcctattttt   2460

ataggttaat gtcatgataa taatggtttc ttagacgtca ggtggcactt ttcggggaaa   2520

tgtgcgcgga acccctattt gtttattttt ctaaatacat tcaaatatgt atccgctcat   2580

gagacaataa ccctgataaa tgcttcaata atattgaaaa aggaagagta tgagtattca   2640

acatttccgt gtcgccctta ttcccttttt tgcggcattt tgccttcctg tttttgctca   2700

cccagaaacg ctggtgaaag taaaagatgc tgaagatcag ttgggtgcac gagtgggtta   2760

catcgaactg gatctcaaca gcggtaagat ccttgagagt tttcgccccg aagaacgttt   2820

tccaatgatg agcactttta aagttctgct atgtggcgcg gtattatccc gtattgacgc   2880

cgggcaagag caactcggtc gccgcataca ctattctcag aatgacttgg ttgagtactc   2940

accagtcaca gaaaagcatc ttacggatgg catgacagta agagaattat gcagtgctgc   3000

cataaccatg agtgataaca ctgcggccaa cttacttctg acaacgatcg gaggaccgaa   3060

ggagctaacc gcttttttgc acaacatggg ggatcatgta actcgccttg atcgttggga   3120

accggagctg aatgaagcca taccaaacga cgagcgtgac accacgatgc ctgtagcaat   3180

ggcaacaacg ttgcgcaaac tattaactgg cgaactactt actctagctt cccggcaaca   3240

attaatagac tggatggagg cggataaagt tgcaggacca cttctgcgct cggcccttcc   3300

ggctggctgg tttattgctg ataaatctgg agccggtgag cgtgggtctc gcggtatcat   3360
```

-continued

```
tgcagcactg gggccagatg gtaagccctc ccgtatcgta gttatctaca cgacggggag   3420

tcaggcaact atggatgaac gaaatagaca gatcgctgag ataggtgcct cactgattaa   3480

gcattggtaa ctgtcagacc aagtttactc atatatactt tagattgatt taaaacttca   3540

tttttaattt aaaaggatct aggtgaagat cctttttgat aatctcatga ccaaaatccc   3600

ttaacgtgag ttttcgttcc actgagcgtc agaccccgta gaaaagatca aaggatcttc   3660

ttgagatcct ttttttctgc gcgtaatctg ctgcttgcaa acaaaaaaac caccgctacc   3720

agcggtggtt tgtttgccgg atcaagagct accaactctt tttccgaagg taactggctt   3780

cagcagagcg cagataccaa atactgttct tctagtgtag ccgtagttag gccaccactt   3840

caagaactct gtagcaccgc ctacatacct cgctctgcta atcctgttac cagtggctgc   3900

tgccagtggc gataagtcgt gtcttaccgg gttggactca agacgatagt taccggataa   3960

ggcgcagcgg tcgggctgaa cggggggttc gtgcacacag cccagcttgg agcgaacgac   4020

ctacaccgaa ctgagatacc tacagcgtga gctatgagaa agcgccacgc ttcccgaagg   4080

gagaaaggcg gacaggtatc cggtaagcgg cagggtcgga acaggagagc gcacgaggga   4140

gcttccaggg ggaaacgcct ggtatcttta tagtcctgtc gggtttcgcc acctctgact   4200

tgagcgtcga tttttgtgat gctcgtcagg ggggcggagc ctatggaaaa acgccagcaa   4260

cgcggccttt ttacggttcc tggccttttg ctggcctttt gctcacatgt tctttcctgc   4320

gttatcccct gattctgtgg ataaccgtat taccgccttt gagtgagctg ataccgctcg   4380

ccgcagccga acgaccgagc gcagcgagtc agtgagcgag gaagcggaag agcgcccaat   4440

acgcaaaccg cctctccccg cgcgttggcc gattcattaa tgcagctggc acgacaggtt   4500

tcccgactgg aaagcgggca gtgagcgcaa cgcaattaat gtgagttagc tcactcatta   4560

ggcaccccag gctttacact ttatgcttcc ggctcgtatg ttgtgtggaa ttgtgagcgg   4620

ataacaattt cacacaggaa acagctatga ccatgattac gccaagctct cgagatctag   4680
```

```
<210> SEQ ID NO 42
<211> LENGTH: 4761
<212> TYPE: DNA
<213> ORGANISM: artificial sequence
<220> FEATURE:
<223> OTHER INFORMATION: CN2001 - The portion between L-ITR and R-ITR
      corresponds to positions 142-2023

<400> SEQUENCE: 42

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctgggcat aaaagtcagg gcagagccat ctattgctta    600

catttgcttc tgggatccag atctttcgaa gctagcgcta ccaccatgga aaacaaccca    660

gccgaacagc aagtcccacc cctcgtggcg ctcgcccaac gcatagtatt tcacaaggcg    720
```

-continued

```
tttacgccga cgataatcac cctcatcatt attaatgcga tcattgtggg actcgagaca    780
tacccaacgg tttaccaggg ttacaatgat tggttctatg ctgccgacct tgctttgttg    840
tggatattca ctattgaaat cacgctccga ttcatcgccg cccgaccgac gaagagtttc    900
ttcaagtcta gctggaactg gtttgatctg cttatcgtat tggcgggcca cgtcttcgct    960
ggcgcccatt ttgttacggt gcttaggatc ctccgcgtcc tgagggtcct cagagctatc   1020
tcagtcatac ccagtctccg gcggctggtt gacgcacttt tgatgacaat cccagcactc   1080
ggtaacatca tgatactgat ggggattatt ttttacatat tcgcggttat cgggacgatg   1140
ctctttgcat cagtagcgcc agaatacttt ggcaatttgc agctgtctct gcttacactg   1200
ttccaagtgg ttacgctgga aagttgggct agtggggtta tgcgacctat ttttgccgaa   1260
gtctggtggt cttggatcta ttttgtaatc tttattctcg tgggaacttt catagtattt   1320
aacctttca ttggcgtcat cgtgaacaat gtggaaaaag ctaacgaaga ggaactgaaa   1380
agcgaactgg atgataaaga ggctgataca aaagaagaac tggcatcatt gcgaaacgag   1440
gtggcagaaa tgaaggatct cataaaacag atgcataaac agcaaacaaa aaagggttaa   1500
tgacggcgcg ccgcggccgc gaattcgata tcataatcaa cctctggatt acaaaatttg   1560
tgaaagattg actggtattc ttaactatgt tgctcctttt acgctatgtg gatacgctgc   1620
tttaatgcct ttgtatcatg ctattgcttc ccgtatggct ttcattttct cctccttgta   1680
taaatcctgg ttagttcttg ccacggcgga actcatcgcc gcctgccttg cccgctgctg   1740
gacaggggct cggctgttgg gcactgacaa ttccgtggct cgagagatct tcgactgtgc   1800
cttctagttg ccagccatct gttgtttgcc cctcccccgt gccttccttg accctggaag   1860
gtgccactcc cactgtcctt tcctaataaa atgaggaaat tgcatcgcat tgtctgagta   1920
ggtgtcattc tattctgggg ggtggggtgg ggcaggacag caagggggag gattgggaag   1980
acaatagcag gcatgagatc tcacgtgcgg accgagcggc cgcaggaacc cctagtgatg   2040
gagttggcca ctccctctct gcgcgctcgc tcgctcactg aggccgggcg accaaaggtc   2100
gcccgacgcc cgggctttgc ccgggcggcc tcagtgagcg agcgagcgcg cagctgcctg   2160
caggggcgcc tgatgcggta ttttctcctt acgcatctgt gcggtatttc acaccgcata   2220
cgtcaaagca accatagtac gcgccctgta gcggcgcatt aagcgcggcg ggtgtggtgg   2280
ttacgcgcag cgtgaccgct acacttgcca gcgccctagc gcccgctcct ttcgctttct   2340
tcccttcctt tctcgccacg ttcgccggct ttccccgtca agctctaaat cgggggctcc   2400
ctttagggtt ccgatttagt gctttacggc acctcgaccc caaaaaactt gatttgggtg   2460
atggttcacg tagtgggcca tcgccctgat agacggtttt tcgccctttg acgttggagt   2520
ccacgttctt taatagtgga ctcttgttcc aaactggaac aacactcaac cctatctcgg   2580
gctattcttt tgatttataa gggattttgc cgatttcggc ctattggtta aaaaatgagc   2640
tgatttaaca aaaatttaac gcgaatttta acaaaatatt aacgtttaca attttatggt   2700
gcactctcag tacaatctgc tctgatgccg catagttaag ccagccccga cacccgccaa   2760
cacccgctga cgcgccctga cgggcttgtc tgctcccggc atccgcttac agacaagctg   2820
tgaccgtctc cgggagctgc atgtgtcaga ggttttcacc gtcatcaccg aaacgcgcga   2880
gacgaaaggg cctcgtgata cgcctatttt tataggttaa tgtcatgata ataatggttt   2940
cttagacgtc aggtggcact tttcggggaa atgtgcgcgg aacccctatt tgtttatttt   3000
tctaaataca ttcaaatatg tatccgctca tgagacaata accctgataa atgcttcaat   3060
aatattgaaa aaggaagagt atgagtattc aacatttccg tgtcgccctt attccctttt   3120
```

```
ttgcggcatt ttgccttcct gtttttgctc acccagaaac gctggtgaaa gtaaaagatg   3180
ctgaagatca gttgggtgca cgagtgggtt acatcgaact ggatctcaac agcggtaaga   3240
tccttgagag ttttcgcccc gaagaacgtt ttccaatgat gagcactttt aaagttctgc   3300
tatgtggcgc ggtattatcc cgtattgacg ccgggcaaga gcaactcggt cgccgcatac   3360
actattctca gaatgacttg gttgagtact caccagtcac agaaaagcat cttacggatg   3420
gcatgacagt aagagaatta tgcagtgctg ccataaccat gagtgataac actgcggcca   3480
acttacttct gacaacgatc ggaggaccga aggagctaac cgcttttttg cacaacatgg   3540
gggatcatgt aactcgcctt gatcgttggg aaccggagct gaatgaagcc ataccaaacg   3600
acgagcgtga caccacgatg cctgtagcaa tggcaacaac gttgcgcaaa ctattaactg   3660
gcgaactact tactctagct tcccggcaac aattaataga ctggatggag gcggataaag   3720
ttgcaggacc acttctgcgc tcggcccttc cggctggctg gtttattgct gataaatctg   3780
gagccggtga gcgtgggtct cgcggtatca ttgcagcact ggggccagat ggtaagccct   3840
cccgtatcgt agttatctac acgacgggga gtcaggcaac tatggatgaa cgaaatagac   3900
agatcgctga gataggtgcc tcactgatta agcattggta actgtcagac caagtttact   3960
catatatact ttagattgat ttaaaacttc atttttaatt taaaaggatc taggtgaaga   4020
tcctttttga taatctcatg accaaaatcc cttaacgtga gttttcgttc cactgagcgt   4080
cagaccccgt agaaaagatc aaaggatctt cttgagatcc tttttttctg cgcgtaatct   4140
gctgcttgca aacaaaaaaa ccaccgctac cagcggtggt ttgtttgccg gatcaagagc   4200
taccaactct ttttccgaag gtaactggct tcagcagagc gcagatacca aatactgtcc   4260
ttctagtgta gccgtagtta ggccaccact tcaagaactc tgtagcaccg cctacatacc   4320
tcgctctgct aatcctgtta ccagtggctg ctgccagtgg cgataagtcg tgtcttaccg   4380
ggttggactc aagacgatag ttaccggata aggcgcagcg gtcgggctga acggggggtt   4440
cgtgcacaca gcccagcttg gagcgaacga cctacaccga actgagatac ctacagcgtg   4500
agctatgaga aagcgccacg cttcccgaag ggagaaaggc ggacaggtat ccggtaagcg   4560
gcagggtcgg aacaggagag cgcacgaggg agcttccagg gggaaacgcc tggtatcttt   4620
atagtcctgt cgggtttcgc cacctctgac ttgagcgtcg atttttgtga tgctcgtcag   4680
gggggcggag cctatggaaa aacgccagca acgcggcctt tttacggttc ctggcctttt   4740
gctggccttt tgctcacatg t                                             4761
```

```
<210> SEQ ID NO 43
<211> LENGTH: 4732
<212> TYPE: DNA
<213> ORGANISM: artificial sequence
<220> FEATURE:
<223> OTHER INFORMATION: CN2002 - The portion between L-ITR and R-ITR
      corresponds to positions 142-1993

<400> SEQUENCE: 43
```

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggtac cctaaataaa gatggctttt    180
tagtattaaa agtggaagaa aattacaggt aattatcttt gacggtaaaa acgctgtaat    240
cagcgggcta catgaaaaat tactctaatt atggctgcat ttaagagaat ggctaaataa    300
agatggcttt ttagtattaa aagtggaaga aaattacagg taattatctt tgacggtaaa    360
```

```
aacgctgtaa tcagcgggct acatgaaaaa ttactctaat tatggctgca tttaagagaa    420
tggctaaata aagatggctt tttagtatta aaagtggaag aaaattacag gtaattatct    480
ttgacggtaa aaacgctgta atcagcgggc tacatgaaaa attactctaa ttatggctgc    540
atttaagaga atggagctcg ggctgggcat aaaagtcagg gcagagccat ctattgctta    600
catttgcttc tgggatccag atctttcgaa gctagcgcta ccaccatgag ccggaagatc    660
agagatctta tcgaatctaa gagatttcag aatgttatta ccgcgataat cgtactcaac    720
ggggcggtgc tcggtctcct caccgatacc acattgagcg cttctagcca gaacctgctc    780
gaaagggttg accaactgtg cctgacaatt tttatcgtgg aaattagctt gaaaatttac    840
gcctacggcg ttcgcggttt tttccggagc ggttggaatc tttttgactt cgttatcgtt    900
gccatcgcgc tcatgcccgc acagggttct ttgtctgtgt tgaggacatt ccgaatattt    960
cgcgtgatgc gcttggtatc cgtgatccct acgatgcgcc gcgtcgtaca aggaatgttg   1020
ctggctctcc ccggcgtcgg gagcgttgct gccctcctta ccgtggtatt ttacatagcg   1080
gcggttatgg ctactaatct ttacggagct accttcccgg agtggttcgg ggatttgtcc   1140
aagagcctct atacattgtt tcaagttatg accctggagt cctggtctat gggcattgtc   1200
cggcccgtaa tgaacgtaca cccaaatgcg tgggtgtttt tcattccatt catcatgctg   1260
actaccttta ccgtgctgaa cttgttcatt gggattatcg tggatgcgat ggccatcact   1320
aaggagcaag aagaagaggc taaaactggc caccaccaag agccaatttc tcaaaccctc   1380
ttgcatctcg gggaccgact ggaccgcatt gagaagcaac tcgcgcagaa caatgagctg   1440
ttgcagcgac agcaacctca aaaaaaataa tgacggcgcg ccgcggccgc gaattcgata   1500
tcataatcaa cctctggatt acaaaatttg tgaaagattg actggtattc ttaactatgt   1560
tgctcctttt acgctatgtg gatacgctgc tttaatgcct ttgtatcatg ctattgcttc   1620
ccgtatggct ttcattttct cctccttgta taaatcctgg ttagttcttg ccacggcgga   1680
actcatcgcc gcctgccttg cccgctgctg gacaggggct cggctgttgg gcactgacaa   1740
ttccgtggct cgagagatct tcgactgtgc cttctagttg ccagccatct gttgtttgcc   1800
cctcccccgt gccttccttg accctggaag gtgccactcc cactgtcctt tcctaataaa   1860
atgaggaaat tgcatcgcat tgtctgagta ggtgtcattc tattctgggg ggtggggtgg   1920
ggcaggacag caagggggag gattgggaag acaatagcag gcatgagatc tcacgtgcgg   1980
accgagcggc cgcaggaacc cctagtgatg gagttggcca ctccctctct gcgcgctcgc   2040
tcgctcactg aggccgggcg accaaaggtc gcccgacgcc cgggctttgc ccgggcggcc   2100
tcagtgagcg agcgagcgcg cagctgcctg caggggcgcc tgatgcggta ttttctcctt   2160
acgcatctgt gcggtatttc acaccgcata cgtcaaagca accatagtac gcgccctgta   2220
gcggcgcatt aagcgcggcg ggtgtggtgg ttacgcgcag cgtgaccgct acacttgcca   2280
gcgccctagc gcccgctcct ttcgctttct tcccttcctt tctcgccacg ttcgccggct   2340
ttccccgtca agctctaaat cgggggctcc ctttagggtt ccgatttagt gctttacggc   2400
acctcgaccc caaaaaactt gatttgggtg atggttcacg tagtgggcca tcgccctgat   2460
agacggtttt tcgccctttg acgttggagt ccacgttctt taatagtgga ctcttgttcc   2520
aaactggaac aacactcaac cctatctcgg gctattcttt tgatttataa gggattttgc   2580
cgatttcggc ctattggtta aaaaatgagc tgatttaaca aaaatttaac gcgaatttta   2640
acaaaatatt aacgtttaca attttatggt gcactctcag tacaatctgc tctgatgccg   2700
```

```
catagttaag ccagccccga cacccgccaa cacccgctga cgcgccctga cgggcttgtc   2760

tgctcccggc atccgcttac agacaagctg tgaccgtctc cgggagctgc atgtgtcaga   2820

ggttttcacc gtcatcaccg aaacgcgcga gacgaaaggg cctcgtgata cgcctatttt   2880

tataggttaa tgtcatgata ataatggttt cttagacgtc aggtggcact tttcggggaa   2940

atgtgcgcgg aacccctatt tgtttatttt tctaaataca ttcaaatatg tatccgctca   3000

tgagacaata accctgataa atgcttcaat aatattgaaa aaggaagagt atgagtattc   3060

aacatttccg tgtcgccctt attccctttt ttgcggcatt ttgccttcct gtttttgctc   3120

acccagaaac gctggtgaaa gtaaaagatg ctgaagatca gttgggtgca cgagtgggtt   3180

acatcgaact ggatctcaac agcggtaaga tccttgagag ttttcgcccc gaagaacgtt   3240

ttccaatgat gagcactttt aaagttctgc tatgtggcgc ggtattatcc cgtattgacg   3300

ccgggcaaga gcaactcggt cgccgcatac actattctca gaatgacttg gttgagtact   3360

caccagtcac agaaaagcat cttacggatg gcatgacagt aagagaatta tgcagtgctg   3420

ccataaccat gagtgataac actgcggcca acttacttct gacaacgatc ggaggaccga   3480

aggagctaac cgcttttttg cacaacatgg gggatcatgt aactcgcctt gatcgttggg   3540

aaccggagct gaatgaagcc ataccaaacg acgagcgtga caccacgatg cctgtagcaa   3600

tggcaacaac gttgcgcaaa ctattaactg gcgaactact tactctagct tcccggcaac   3660

aattaataga ctggatggag gcggataaag ttgcaggacc acttctgcgc tcggcccttc   3720

cggctggctg gtttattgct gataaatctg gagccggtga gcgtgggtct cgcggtatca   3780

ttgcagcact ggggccagat ggtaagccct cccgtatcgt agttatctac acgacgggga   3840

gtcaggcaac tatggatgaa cgaaatagac agatcgctga gataggtgcc tcactgatta   3900

agcattggta actgtcagac caagtttact catatatact ttagattgat ttaaaacttc   3960

atttttaatt taaaaggatc taggtgaaga tcctttttga taatctcatg accaaaatcc   4020

cttaacgtga gttttcgttc cactgagcgt cagaccccgt agaaaagatc aaaggatctt   4080

cttgagatcc tttttttctg cgcgtaatct gctgcttgca aacaaaaaaa ccaccgctac   4140

cagcggtggt ttgtttgccg gatcaagagc taccaactct ttttccgaag gtaactggct   4200

tcagcagagc gcagatacca aatactgtcc ttctagtgta gccgtagtta ggccaccact   4260

tcaagaactc tgtagcaccg cctacatacc tcgctctgct aatcctgtta ccagtggctg   4320

ctgccagtgg cgataagtcg tgtcttaccg ggttggactc aagacgatag ttaccggata   4380

aggcgcagcg gtcgggctga acggggggtt cgtgcacaca gcccagcttg gagcgaacga   4440

cctacaccga actgagatac ctacagcgtg agctatgaga aagcgccacg cttcccgaag   4500

ggagaaaggc ggacaggtat ccggtaagcg gcagggtcgg aacaggagag cgcacgaggg   4560

agcttccagg gggaaacgcc tggtatcttt atagtcctgt cgggtttcgc cacctctgac   4620

ttgagcgtcg atttttgtga tgctcgtcag gggggcggag cctatggaaa aacgccagca   4680

acgcggcctt tttacggttc ctggcctttt gctggccttt tgctcacatg ts           4732
```

<210> SEQ ID NO 44
<211> LENGTH: 4794
<212> TYPE: DNA
<213> ORGANISM: artificial sequence
<220> FEATURE:
<223> OTHER INFORMATION: CN2003 - The portion between L-ITR and R-ITR corresponds to positions 142-2056

<400> SEQUENCE: 44

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggtac cctaaataaa gatggctttt    180
tagtattaaa agtggaagaa aattacaggt aattatcttt gacggtaaaa acgctgtaat    240
cagcgggcta catgaaaaat tactctaatt atggctgcat ttaagagaat ggctaaataa    300
agatggcttt ttagtattaa aagtggaaga aaattacagg taattatctt tgacggtaaa    360
aacgctgtaa tcagcgggct acatgaaaaa ttactctaat tatggctgca tttaagagaa    420
tggctaaata aagatggctt tttagtatta aaagtggaag aaaattacag gtaattatct    480
ttgacggtaa aaacgctgta atcagcgggc tacatgaaaa attactctaa ttatggctgc    540
atttaagaga atggagctcg ggctgggcat aaaagtcagg gcagagccat ctattgctta    600
catttgcttc tgggatccag atctttcgaa gctagcgcta ccaccatgtc tacgtccctt    660
ttgaatgcgc ctaccggcct tcaagctaga gtcattaatc tcgtcgaaca aaactggttt    720
ggacacttta tactgactct catactcatt aatgctgtgc agcttggaat ggaaactagc    780
gccagcctca tggcacaata tggcgcgctg cttatgtcct tgaataaggt ccttctctct    840
gtgttcgtgg tcgaactgct gctccggatt tatgcgtatc ggggcaagtt ttttaaggac    900
ccgtggaatg tgtttgactt cactgttatt gttattgctc tgattcctgc atctggccca    960
ttggctgtcc tccgctccct ccgagttctc cgcgtcttga gggttctgac gattgtcccc   1020
agcatgaaaa gagtagtgtc agcactgctt gggagcttgc ccgggttggc ctccattgca   1080
accgtgcttc tgttgatcta ttacgttttc gctgtgatcg ccactaaaat tttcggggat   1140
gcttttccgg aatggttcgg gacgatagcg gactccttct ataccctttt tcaaattatg   1200
accttggaaa gttggtctat ggggatctct aggccagtga tggaggtgta cccttacgct   1260
tgggtattct ttgtgccctt tattcttgtt gctactttta ccatgcttaa ccttttcatc   1320
gccatcatag tgaatactat gcagacattc tctgacgagg aacatgctct ggagcgagag   1380
caagataaac agatcttgga acaggagcag agacaaatgc acgaggaact gaaggccatt   1440
cgactcgagc ttcagcaact ccaaaccctt ttgcgaaatg cggctgggga ctcctccaat   1500
gtctccacaa agggcaatat cggctcagac taatgacggc gcgccgcggc cgcgaattcg   1560
atatcataat caacctctgg attacaaaat ttgtgaaaga ttgactggta ttcttaacta   1620
tgttgctcct tttacgctat gtggatacgc tgctttaatg cctttgtatc atgctattgc   1680
ttcccgtatg gctttcattt tctcctcctt gtataaatcc tggttagttc ttgccacggc   1740
ggaactcatc gccgcctgcc ttgcccgctg ctggacaggg gctcggctgt tgggcactga   1800
caattccgtg gctcgagaga tcttcgactg tgccttctag ttgccagcca tctgttgttt   1860
gcccctcccc cgtgccttcc ttgaccctgg aaggtgccac tcccactgtc ctttcctaat   1920
aaaatgagga aattgcatcg cattgtctga gtaggtgtca ttctattctg gggggtgggg   1980
tggggcagga cagcaagggg gaggattggg aagacaatag caggcatgag atctcacgtg   2040
cggaccgagc ggccgcagga acccctagtg atggagttgg ccactccctc tctgcgcgct   2100
cgctcgctca ctgaggccgg gcgaccaaag gtcgcccgac gcccgggctt tgcccgggcg   2160
gcctcagtga gcgagcgagc gcgcagctgc ctgcaggggc gcctgatgcg gtattttctc   2220
cttacgcatc tgtgcggtat ttcacaccgc atacgtcaaa gcaaccatag tacgcgccct   2280
gtagcggcgc attaagcgcg gcgggtgtgg tggttacgcg cagcgtgacc gctacacttg   2340
ccagcgccct agcgcccgct cctttcgctt tcttcccttc ctttctcgcc acgttcgccg   2400
```

```
gctttccccg tcaagctcta aatcgggggc tccctttagg gttccgattt agtgctttac   2460

ggcacctcga ccccaaaaaa cttgatttgg gtgatggttc acgtagtggg ccatcgccct   2520

gatagacggt ttttcgccct ttgacgttgg agtccacgtt ctttaatagt ggactcttgt   2580

tccaaactgg aacaacactc aaccctatct cgggctattc ttttgattta taagggattt   2640

tgccgatttc ggcctattgg ttaaaaaatg agctgattta acaaaaattt aacgcgaatt   2700

ttaacaaaat attaacgttt acaattttat ggtgcactct cagtacaatc tgctctgatg   2760

ccgcatagtt aagccagccc cgacacccgc caacacccgc tgacgcgccc tgacgggctt   2820

gtctgctccc ggcatccgct tacagacaag ctgtgaccgt ctccgggagc tgcatgtgtc   2880

agaggttttc accgtcatca ccgaaacgcg cgagacgaaa gggcctcgtg atacgcctat   2940

ttttataggt taatgtcatg ataataatgg tttcttagac gtcaggtggc acttttcggg   3000

gaaatgtgcg cggaacccct atttgtttat ttttctaaat acattcaaat atgtatccgc   3060

tcatgagaca ataaccctga taaatgcttc aataatattg aaaaaggaag agtatgagta   3120

ttcaacattt ccgtgtcgcc cttattccct tttttgcggc attttgcctt cctgtttttg   3180

ctcacccaga aacgctggtg aaagtaaaag atgctgaaga tcagttgggt gcacgagtgg   3240

gttacatcga actggatctc aacagcggta agatccttga gagttttcgc cccgaagaac   3300

gttttccaat gatgagcact tttaaagttc tgctatgtgg cgcggtatta tcccgtattg   3360

acgccgggca agagcaactc ggtcgccgca tacactattc tcagaatgac ttggttgagt   3420

actcaccagt cacagaaaag catcttacgg atggcatgac agtaagagaa ttatgcagtg   3480

ctgccataac catgagtgat aacactgcgg ccaacttact tctgacaacg atcggaggac   3540

cgaaggagct aaccgctttt ttgcacaaca tgggggatca tgtaactcgc cttgatcgtt   3600

gggaaccgga gctgaatgaa gccataccaa acgacgagcg tgacaccacg atgcctgtag   3660

caatggcaac aacgttgcgc aaactattaa ctggcgaact acttactcta gcttcccggc   3720

aacaattaat agactggatg gaggcggata aagttgcagg accacttctg cgctcggccc   3780

ttccggctgg ctggtttatt gctgataaat ctggagccgg tgagcgtggg tctcgcggta   3840

tcattgcagc actggggcca gatggtaagc cctcccgtat cgtagttatc tacacgacgg   3900

ggagtcaggc aactatggat gaacgaaata gacagatcgc tgagataggt gcctcactga   3960

ttaagcattg gtaactgtca gaccaagttt actcatatat actttagatt gatttaaaac   4020

ttcattttta atttaaaagg atctaggtga agatcctttt tgataatctc atgaccaaaa   4080

tcccttaacg tgagttttcg ttccactgag cgtcagaccc cgtagaaaag atcaaaggat   4140

cttcttgaga tccttttttt ctgcgcgtaa tctgctgctt gcaaacaaaa aaaccaccgc   4200

taccagcggt ggtttgtttg ccggatcaag agctaccaac tctttttccg aaggtaactg   4260

gcttcagcag agcgcagata ccaaatactg tccttctagt gtagccgtag ttaggccacc   4320

acttcaagaa ctctgtagca ccgcctacat acctcgctct gctaatcctg ttaccagtgg   4380

ctgctgccag tggcgataag tcgtgtctta ccgggttgga ctcaagacga tagttaccgg   4440

ataaggcgca gcggtcgggc tgaacggggg gttcgtgcac acagcccagc ttggagcgaa   4500

cgacctacac cgaactgaga tacctacagc gtgagctatg agaaagcgcc acgcttcccg   4560

aagggagaaa ggcggacagg tatccggtaa gcggcagggt cggaacagga gagcgcacga   4620

gggagcttcc agggggaaac gcctggtatc tttatagtcc tgtcgggttt cgccacctct   4680

gacttgagcg tcgatttttg tgatgctcgt caggggggcg gagcctatgg aaaaacgcca   4740
```

gcaacgcggc ctttttacgg ttcctggcct tttgctggcc ttttgctcac atgt 4794

<210> SEQ ID NO 45
<211> LENGTH: 7368
<212> TYPE: DNA
<213> ORGANISM: artificial sequence
<220> FEATURE:
<223> OTHER INFORMATION: CN1504 - The portion between L-ITR and R-ITR corresponds to positions 142-4489

<400> SEQUENCE: 45
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtggtac cctaaataaa gatggctttt 180
tagtattaaa agtggaagaa aattacaggt aattatcttt gacggtaaaa acgctgtaat 240
cagcgggcta catgaaaaat tactctaatt atggctgcat ttaagagaat ggctaaataa 300
agatggcttt ttagtattaa aagtggaaga aaattacagg taattatctt tgacggtaaa 360
aacgctgtaa tcagcgggct acatgaaaaa ttactctaat tatggctgca tttaagagaa 420
tggctaaata aagatggctt tttagtatta aaagtggaag aaaattacag gtaattatct 480
ttgacggtaa aaacgctgta atcagcgggc tacatgaaaa attactctaa ttatggctgc 540
atttaagaga atggagctcg ggctggtcga cacaattgga ggtaggcgtg tacggtggga 600
ggcctatata agcagagctc gtttagtgaa ccgtcagatc gcctggagga tccttcgaaa 660
agcttgctac cggtgccacc atggtcagca agggcgagga gctgttcacc ggggtggtgc 720
ccatcctggt cgagctggac ggcgacgtca atggccacaa gttcagcgtg tccggcgagg 780
gcgagggcga tgccacctac ggcaagctga ccctgaagct gatctgcacc accggcaagc 840
tgcccgtgcc ctggcccacc ctcgtgacca ccctgggcta cggcgtgcag tgcttcgccc 900
gctaccccga ccacatgaag cagcacgact tcttcaagtc cgccatgccc gaaggctacg 960
tccaggagcg caccatcttc ttcaaagacg acggcaacta caagacccgc gccgaggtga 1020
agttcgaggg cgacaccctg gtgaaccgca tcgagctgaa gggcatcgac ttcaaggagg 1080
acggcaacat cctggggcac aagctggagt acaactacaa cagccacaac gtctatatca 1140
ccgccgacaa gcagaagaac ggcatcaagg ccaacttcaa gatccgccac aacatcgagg 1200
acggcggcgt gcagctcgcc gaccactacc agcagaacac ccccatcggc gacggccccg 1260
tgctgctgcc cgacaaccac tacctgagct accagtccaa gctgagcaaa gaccccaacg 1320
agaagcgcga tcacatggtc ctgctggagt tcgtgaccgc cgccgggatc actctcggca 1380
tggacgagct gtacaaaggc agcggcgcca ccaacttcag cctgctgaag caggccggcg 1440
acgtggagga gaaccccggc cccggaacta gtggtatgga gcaaacagtg cttgtaccac 1500
caggacctga cagcttcaac ttcttcacca gagaatctct tgcggctatt gaaagacgca 1560
ttgcagaaga aaaggcaaag aatcccaaac cagacaaaaa agatgacgac gaaaatggcc 1620
caaagccaaa tagtgacttg gaagctggaa agaaccttcc atttatttat ggagacattc 1680
ctccagagat ggtgtcagag cccctggagg acctggaccc ctactatatc aataagaaaa 1740
cttttatagt attgaataaa gggaaggcca tcttccggtt cagtgccacc tctgccctgt 1800
acattttaac tcccttcaat cctcttagga aaatagctat taagattttg gtacattcat 1860
tattcagcat gctaattatg tgcactattt tgacaaactg tgtgtttatg acaatgagta 1920
accctcctga ttggacaaag aatgtagaat acaccttcac aggaatatat acttttgaat 1980

-continued

```
cacttataaa aattattgca aggggattct gtttagaaga ttttactttc cttcgggatc   2040
catggaactg gctcgatttc actgtcatta catttgcgta cgtcacagag tttgtggacc   2100
tgggcaatgt ctcggcattg agaacattca gagttctccg agcattgaag acgatttcag   2160
tcattccagg cctgaaaacc attgtgggag ccctgatcca gtctgtgaag aagctctcag   2220
atgtaatgat cctgactgtg ttctgtctga gcgtatttgc tctaattggg ctgcagctgt   2280
tcatgggcaa cctgaggaat aaatgtatac aatggcctcc caccaatgct tccttggagg   2340
aacatagtat agaaaagaat ataactgtga attataatgg tacacttata aatgaaactg   2400
tctttgagtt tgactggaag tcatatattc aagattcaag atatcattat ttcctggagg   2460
gtttttttaga tgcactacta tgtggaaata gctctgatgc aggccaatgt ccagagggat   2520
atatgtgtgt gaaagctggt agaaatccca attatggcta cacaagcttt gataccttca   2580
gttgggcttt tttgtccttg tttcgactaa tgactcagga cttctgggaa aatctttatc   2640
aactgacatt acgtgctgct gggaaaacgt acatgatatt ttttgtattg gtcattttct   2700
tgggctcatt ctacctaata aatttgatcc tggctgtggt ggccatggcc tacgaggaac   2760
agaatcaggc caccttggaa gaagcagaac agaaagaggc cgaatttcag cagatgattg   2820
aacagcttaa aaagcaacag gaggcagctc agcaggcagc aacggcaact gcctcagaac   2880
attccagaga gcccagtgca gcaggcaggc tctcagacag ctcatctgaa gcctctaagt   2940
tgagttccaa gagtgctaag gaaagaagaa atcggaggaa gaaaagaaaa cagaaagagc   3000
agtctggtgg ggaagagaaa gatgaggatg aattccaaaa atctgaatct gaggacagca   3060
tcaggaggaa aggttttcgc ttctccattg aagggaaccg attgacatat gaaaagaggt   3120
actcctcccc acaccagtct ttgttgagca tccgtggctc cctattttca ccaaggcgaa   3180
atagcagaac aagccttttc agctttagag ggcgagcaaa ggatgtggga tctgagaacg   3240
acttcgcaga tgatgagcac agcacctttg aggataacga gagccgtaga gattccttgt   3300
ttgtgccccg acgacacgga gagagacgca acagcaacct gagtcagacc agtaggtcat   3360
cccggatgct ggcagtgttt ccagcgaatg ggaagatgca cagcactgtg gattgcaatg   3420
gtgtggtttc cttggttggt ggaccttcag ttcctacatc gcctgttgga cagcttctgc   3480
cagaggtgat aatagataag ccagctactg atgacaatgg aacaaccact gaaactgaaa   3540
tgagaaagag aaggtcaagt tctttccacg tttccatgga ctttctagaa gatccttccc   3600
aaaggcaacg agcaatgagt atagccagca ttctaacaaa tacagtagaa gaacttgaag   3660
aatccaggca gaaatgccca ccctgttggt ataaattttc caacatattc ttaatctggg   3720
actgttctcc atattggtta aaagtgaaac atgttgtcaa cctggttgtg atggacccat   3780
ttgttgacct ggccatcacc atctgtattg tcttaaatac tcttttcatg gccatggagc   3840
actatccaat gacggaccat ttcaataatg tgcttacagt aggaaacttg gttttcactg   3900
ggatctttac agcagaaatg tttctgaaaa ttattgccat ggatccttac tattatttcc   3960
aagaaggctg gaatatcttt gacggtttta ttgtgacgct tagcctggta gaacttggac   4020
tcgccaatgt ggaaggatta tctgttctcc gttcatttcg attgctgcga gttttcaagt   4080
tggcaaaatc ttggccaacg ttaaatatgc taataaagat catcggcaat tccgtggggg   4140
ctctgggaaa tttaaccctc gtcttggcca tcatcgtctt catttttgcc gtggtcggca   4200
tgcagctctt tggtaaaagc tacaaagatt gtgtctgcaa gatcgccagt gattgtcaac   4260
tcccacgctg gcacatgaat gacttcttcc actccttcct gattgtgttc cgcgtgctgt   4320
gtggggagtg gatagagacc atgtgggact gtatggaggt tgctggtcaa gccatgtgcc   4380
```

```
ttactgtctt catgatggtc atggtgattg gaaacctagt ggtcctgaat ctctttctgg   4440
ccttgcttct gagctcattt agtgcagaca accttgcagc cactgatgat gataatgaaa   4500
tgaataatct ccaaattgct gtggatagga tgcacaaagg agtagcttat gtgaaaagaa   4560
aaatatatga atttattcaa cagtccttca ttaggaaaca aaagatctca cgtgcggacc   4620
gagcggccgc aggaacccct agtgatggag ttggccactc cctctctgcg cgctcgctcg   4680
ctcactgagg ccgggcgacc aaaggtcgcc cgacgcccgg gctttgcccg ggcggcctca   4740
gtgagcgagc gagcgcgcag ctgcctgcag gggcgcctga tgcggtattt tctccttacg   4800
catctgtgcg gtatttcaca ccgcatacgt caaagcaacc atagtacgcg ccctgtagcg   4860
gcgcattaag cgcggcgggt gtggtggtta cgcgcagcgt gaccgctaca cttgccagcg   4920
ccctagcgcc cgctcctttc gctttcttcc cttcctttct cgccacgttc gccggctttc   4980
cccgtcaagc tctaaatcgg gggctccctt tagggttccg atttagtgct ttacggcacc   5040
tcgaccccaa aaaacttgat ttgggtgatg gttcacgtag tgggccatcg ccctgataga   5100
cggtttttcg ccctttgacg ttggagtcca cgttctttaa tagtggactc ttgttccaaa   5160
ctggaacaac actcaaccct atctcgggct attcttttga tttataaggg attttgccga   5220
tttcggccta ttggttaaaa aatgagctga tttaacaaaa atttaacgcg aattttaaca   5280
aaatattaac gtttacaatt ttatggtgca ctctcagtac aatctgctct gatgccgcat   5340
agttaagcca gccccgacac ccgccaacac ccgctgacgc gccctgacgg gcttgtctgc   5400
tcccggcatc cgcttacaga caagctgtga ccgtctccgg gagctgcatg tgtcagaggt   5460
tttcaccgtc atcaccgaaa cgcgcgagac gaaagggcct cgtgatacgc ctatttttat   5520
aggttaatgt catgataata atggtttctt agacgtcagg tggcactttt cggggaaatg   5580
tgcgcggaac ccctatttgt ttatttttct aaatacattc aaatatgtat ccgctcatga   5640
gacaataacc ctgataaatg cttcaataat attgaaaaag gaagagtatg agtattcaac   5700
atttccgtgt cgcccttatt cccttttttg cggcattttg ccttcctgtt tttgctcacc   5760
cagaaacgct ggtgaaagta aaagatgctg aagatcagtt gggtgcacga gtgggttaca   5820
tcgaactgga tctcaacagc ggtaagatcc ttgagagttt tcgccccgaa gaacgttttc   5880
caatgatgag cacttttaaa gttctgctat gtggcgcggt attatcccgt attgacgccg   5940
ggcaagagca actcggtcgc cgcatacact attctcagaa tgacttggtt gagtactcac   6000
cagtcacaga aaagcatctt acggatggca tgacagtaag agaattatgc agtgctgcca   6060
taaccatgag tgataacact gcggccaact tacttctgac aacgatcgga ggaccgaagg   6120
agctaaccgc ttttttgcac aacatggggg atcatgtaac tcgccttgat cgttgggaac   6180
cggagctgaa tgaagccata ccaaacgacg agcgtgacac cacgatgcct gtagcaatgg   6240
caacaacgtt gcgcaaacta ttaactggcg aactacttac tctagcttcc cggcaacaat   6300
taatagactg gatggaggcg gataaagttg caggaccact tctgcgctcg gcccttccgg   6360
ctggctggtt tattgctgat aaatctggag ccggtgagcg tgggtctcgc ggtatcattg   6420
cagcactggg gccagatggt aagccctccc gtatcgtagt tatctacacg acggggagtc   6480
aggcaactat ggatgaacga aatagacaga tcgctgagat aggtgcctca ctgattaagc   6540
attggtaact gtcagaccaa gtttactcat atatacttta gattgattta aaacttcatt   6600
tttaatttaa aaggatctag gtgaagatcc tttttgataa tctcatgacc aaaatccctt   6660
aacgtgagtt ttcgttccac tgagcgtcag accccgtaga aaagatcaaa ggatcttctt   6720
```

```
gagatccttt ttttctgcgc gtaatctgct gcttgcaaac aaaaaaacca ccgctaccag   6780

cggtggtttg tttgccggat caagagctac caactctttt tccgaaggta actggcttca   6840

gcagagcgca gataccaaat actgtccttc tagtgtagcc gtagttaggc caccacttca   6900

agaactctgt agcaccgcct acatacctcg ctctgctaat cctgttacca gtggctgctg   6960

ccagtggcga taagtcgtgt cttaccgggt tggactcaag acgatagtta ccggataagg   7020

cgcagcggtc gggctgaacg gggggttcgt gcacacagcc cagcttggag cgaacgacct   7080

acaccgaact gagataccta cagcgtgagc tatgagaaag cgccacgctt cccgaaggga   7140

gaaaggcgga caggtatccg gtaagcggca gggtcggaac aggagagcgc acgagggagc   7200

ttccaggggg aaacgcctgg tatctttata gtcctgtcgg gtttcgccac ctctgacttg   7260

agcgtcgatt tttgtgatgc tcgtcagggg ggcggagcct atggaaaaac gccagcaacg   7320

cggccttttt acggttcctg gccttttgct ggccttttgc tcacatgt                7368
```

<210> SEQ ID NO 46
<211> LENGTH: 7044
<212> TYPE: DNA
<213> ORGANISM: artificial sequence
<220> FEATURE:
<223> OTHER INFORMATION: CN1512 - The portion between L-ITR and R-ITR corresponds to positions 142-4165

<400> SEQUENCE: 46

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtatagg taccctggta gaacttggac    180

tcgccaatgt ggaaggatta tctgttctcc gttcatttcg attgctgcga gttttcaagt    240

tggcaaaatc ttggccaacg ttaaatatgc taataaagat catcggcaat tccgtggggg    300

ctctgggaaa tttaaccctc gtcttggcca tcatcgtctt catttttgcc gtggtcggca    360

tgcagctctt tggtaaaagc tacaaagatt gtgtctgcaa gatcgccagt gattgtcaac    420

tcccacgctg gcacatgaat gacttcttcc actccttcct gattgtgttc cgcgtgctgt    480

gtggggagtg gatagagacc atgtgggact gtatggaggt tgctggtcaa gccatgtgcc    540

ttactgtctt catgatggtc atggtgattg gaaacctagt ggtcctgaat ctctttctgg    600

ccttgcttct gagctcattt agtgcagaca accttgcagc cactgatgat gataatgaaa    660

tgaataatct ccaaattgct gtggatagga tgcacaaagg agtagcttat gtgaaaagaa    720

aaatatatga atttattcaa cagtccttca ttaggaaaca aaagatttta gatgaaatta    780

aaccacttga tgatctaaac aacaagaaag acagttgtat gtccaatcat acagcagaaa    840

ttgggaaaga tcttgactat cttaaagatg taaatggaac tacaagtggt ataggaactg    900

gcagcagtgt tgaatacatt attgatgaaa gtgattacat gtcattcata aacaacccca    960

gtcttactgt gactgtacca attgctgtag gagaatctga ctttgaaaat ttaaacacgg   1020

aagactttag tagtgaatcg gatctggaag aaagcaaaga gaaactgaat gaaagcagta   1080

gctcatcaga aggtagcact gtggacatcg gcgcacctgt agaagaacag cccgtagtgg   1140

aacctgaaga aactcttgaa ccagaagctt gtttcactga aggctgtgta caaagattca   1200

agtgttgtca aatcaatgtg gaagaaggca gaggaaaaca atggtggaac ctgagaagga   1260

cgtgtttccg aatagttgaa cataactggt ttgagacctt cattgttttc atgattctcc   1320

ttagtagtgg tgctctggca tttgaagata tatatattga tcagcgaaag acgattaaga   1380
```

-continued

```
cgatgttgga atatgctgac aaggttttca cttacatttt cattctggaa atgcttctaa   1440
aatgggtggc atatggctat caaacatatt tcaccaatgc ctggtgttgg ctggacttct   1500
taattgttga tgtttcattg gtcagtttaa cagcaaatgc cttgggttac tcagaacttg   1560
gagccatcaa atctctcagg acactaagag ctctgagacc tctaagagcc ttatctcgat   1620
ttgaagggat gagggtggtt gtgaatgccc ttttaggagc aattccatcc atcatgaatg   1680
tgcttctggt ttgtcttata ttctggctaa ttttcagcat catgggcgta aatttgtttg   1740
ctggcaaatt ctaccactgt attaacacca caactggtga caggtttgac atcgaagacg   1800
tgaataatca tactgattgc ctaaaactaa tagaaagaaa tgagactgct cgatggaaaa   1860
atgtgaaagt aaactttgat aatgtaggat ttgggtatct ctctttgctt caagttgcca   1920
cattcaaagg atggatggat ataatgtatg cagcagttga ttccagaaat gtggaactcc   1980
agcctaagta tgaagaaagt ctgtacatgt atctttactt tgttattttc atcatctttg   2040
ggtccttctt caccttgaac ctgtttattg gtgtcatcat agataatttc aaccagcaga   2100
aaaagaagtt tggaggtcaa gacatcttta tgacagaaga acagaagaaa tactataatg   2160
caatgaaaaa attaggatcg aaaaaaccgc aaaagcctat acctcgacca ggaaacaaat   2220
ttcaaggaat ggtctttgac ttcgtaacca gacaagtttt tgacataagc atcatgattc   2280
tcatctgtct taacatggtc acaatgatgg tggaaacaga tgaccagagt gaatatgtga   2340
ctaccatttt gtcacgcatc aatctggtgt tcattgtgct atttactgga gagtgtgtac   2400
tgaaactcat ctctctacgc cattattatt ttaccattgg atggaatatt tttgattttg   2460
tggttgtcat tctctccatt gtaggtatgt ttcttgccga gctgatagaa aagtatttcg   2520
tgtcccctac cctgttccga gtgatccgtc ttgctaggat tggccgaatc ctacgtctga   2580
tcaaaggagc aaaggggatc cgcacgctgc tctttgcttt gatgatgtcc cttcctgcgt   2640
tgtttaacat cggcctccta ctcttcctag tcatgttcat ctacgccatc tttgggatgt   2700
ccaactttgc ctatgttaag agggaagttg ggatcgatga catgttcaac tttgagacct   2760
ttggcaacag catgatctgc ctattccaaa ttacaacctc tgctggctgg gatggattgc   2820
tagcacccat tctcaacagt aagccacccg actgtgaccc taataaagtt aaccctggaa   2880
gctcagttaa gggagactgt gggaacccat ctgttggaat tttctttttt gtcagttaca   2940
tcatcatatc cttcctggtt gtggtgaaca tgtacatcgc ggtcatcctg gagaacttca   3000
gtgttgctac tgaagaaagt gcagagcctc tgagtgagga tgactttgag atgttctatg   3060
aggtttggga gaagtttgat cccgatgcaa ctcagttcat ggaatttgaa aaattatctc   3120
agtttgcagc tgcgcttgaa ccgcctctca atctgccaca accaaacaaa ctccagctca   3180
ttgccatgga tttgcccatg gtgagtggtg accggatcca ctgtcttgat atcttatttg   3240
cttttacaaa gcgggttcta ggagagagtg gagagatgga tgctctacga atacagatgg   3300
aagagcgatt catggcttcc aatccttcca aggtctccta tcagccaatc actactactt   3360
taaaacgaaa acaagaggaa gtatctgctg tcattattca gcgtgcttac agacgccacc   3420
ttttaaagcg aactgtaaaa caagcttcct ttacgtacaa taaaaacaaa atcaaaggtg   3480
gggctaatct tcttataaaa gaagacatga taattgacag aataaatgaa aactctatta   3540
cagaaaaaac tgatctgacc atgtccactg cagcttgtcc accttcctat gaccgggtga   3600
caaagccaat tgtggaaaaa catgagcaag aaggcaaaga tgaaaaagcc aaagggaaag   3660
gaggtggtgg ttcaggtggg ggcggctcag agtaccccta tgatgtccct gattatgcgg   3720
cggaataccc ctatgacgtg ccggactacg cggctgaata tccgtatgac gttcccgatt   3780
```

```
atgcggctaa gctcgaataa tgatgagaat tcatcataat caacctctgg attacaaaat   3840
ttgtgaaaga ttgactggta ttcttaacta tgttgctcct tttacgctat gtggatacgc   3900
tgctttaatg cctttgtatc atgctattgc ttcccgtatg gctttcattt tctcctcctt   3960
gtataaatcc tggttagttc ttgccacggc ggaactcatc gccgcctgcc ttgcccgctg   4020
ctggacaggg gctcggctgt tgggcactga caattccgtg gctcgagaga tcttcgactg   4080
tgccttctag ttgccagcca tctgttgttt gcccctcccc cgtgccttcc ttgaccctgg   4140
aaggtgccac tcccactgtc ctttcctaat aaaatgagga aattgcatcg cattgtctga   4200
gtaggtgtca ttctattctg gggggtgggg tggggcagga cagcaagggg gaggattggg   4260
aagacaatag caggcatgag atctcacgtg cggaccgagc ggccgcagga acccctagtg   4320
atggagttgg ccactccctc tctgcgcgct cgctcgctca ctgaggccgg gcgaccaaag   4380
gtcgcccgac gcccgggctt tgcccgggcg gcctcagtga gcgagcgagc gcgcagctgc   4440
ctgcaggggc gcctgatgcg gtattttctc cttacgcatc tgtgcggtat ttcacaccgc   4500
atacgtcaaa gcaaccatag tacgcgccct gtagcggcgc attaagcgcg gcgggtgtgg   4560
tggttacgcg cagcgtgacc gctacacttg ccagcgccct agcgcccgct cctttcgctt   4620
tcttcccttc ctttctcgcc acgttcgccg gctttccccg tcaagctcta aatcgggggc   4680
tccctttagg gttccgattt agtgctttac ggcacctcga ccccaaaaaa cttgatttgg   4740
gtgatggttc acgtagtggg ccatcgccct gatagacggt ttttcgccct ttgacgttgg   4800
agtccacgtt ctttaatagt ggactcttgt tccaaactgg aacaacactc aaccctatct   4860
cgggctattc ttttgattta taagggattt tgccgatttc ggcctattgg ttaaaaaatg   4920
agctgattta acaaaaattt aacgcgaatt ttaacaaaat attaacgttt acaattttat   4980
ggtgcactct cagtacaatc tgctctgatg ccgcatagtt aagccagccc cgacacccgc   5040
caacacccgc tgacgcgccc tgacgggctt gtctgctccc ggcatccgct tacagacaag   5100
ctgtgaccgt ctccgggagc tgcatgtgtc agaggttttc accgtcatca ccgaaacgcg   5160
cgagacgaaa gggcctcgtg atacgcctat ttttataggt taatgtcatg ataataatgg   5220
tttcttagac gtcaggtggc acttttcggg gaaatgtgcg cggaacccct atttgtttat   5280
ttttctaaat acattcaaat atgtatccgc tcatgagaca ataaccctga taaatgcttc   5340
aataatattg aaaaaggaag agtatgagta ttcaacattt ccgtgtcgcc cttattccct   5400
tttttgcggc attttgcctt cctgtttttg ctcacccaga aacgctggtg aaagtaaaag   5460
atgctgaaga tcagttgggt gcacgagtgg gttacatcga actggatctc aacagcggta   5520
agatccttga gagttttcgc cccgaagaac gttttccaat gatgagcact tttaaagttc   5580
tgctatgtgg cgcggtatta tcccgtattg acgccgggca agagcaactc ggtcgccgca   5640
tacactattc tcagaatgac ttggttgagt actcaccagt cacagaaaag catcttacgg   5700
atggcatgac agtaagagaa ttatgcagtg ctgccataac catgagtgat aacactgcgg   5760
ccaacttact tctgacaacg atcggaggac cgaaggagct aaccgctttt ttgcacaaca   5820
tgggggatca tgtaactcgc cttgatcgtt gggaaccgga gctgaatgaa gccataccaa   5880
acgacgagcg tgacaccacg atgcctgtag caatggcaac aacgttgcgc aaactattaa   5940
ctggcgaact acttactcta gcttcccggc aacaattaat agactggatg gaggcggata   6000
aagttgcagg accacttctg cgctcggccc ttccggctgg ctggtttatt gctgataaat   6060
ctggagccgg tgagcgtggg tctcgcggta tcattgcagc actggggcca gatggtaagc   6120
```

```
cctcccgtat cgtagttatc tacacgacgg ggagtcaggc aactatggat gaacgaaata   6180

gacagatcgc tgagataggt gcctcactga ttaagcattg gtaactgtca gaccaagttt   6240

actcatatat actttagatt gatttaaaac ttcattttta atttaaaagg atctaggtga   6300

agatcctttt tgataatctc atgaccaaaa tcccttaacg tgagttttcg ttccactgag   6360

cgtcagaccc cgtagaaaag atcaaaggat cttcttgaga tccttttttt ctgcgcgtaa   6420

tctgctgctt gcaaacaaaa aaaccaccgc taccagcggt ggtttgtttg ccggatcaag   6480

agctaccaac tctttttccg aaggtaactg gcttcagcag agcgcagata ccaaatactg   6540

tccttctagt gtagccgtag ttaggccacc acttcaagaa ctctgtagca ccgcctacat   6600

acctcgctct gctaatcctg ttaccagtgg ctgctgccag tggcgataag tcgtgtctta   6660

ccgggttgga ctcaagacga tagttaccgg ataaggcgca gcggtcgggc tgaacggggg   6720

gttcgtgcac acagcccagc ttggagcgaa cgacctacac cgaactgaga tacctacagc   6780

gtgagctatg agaaagcgcc acgcttcccg aagggagaaa ggcggacagg tatccggtaa   6840

gcggcagggt cggaacagga gagcgcacga gggagcttcc agggggaaac gcctggtatc   6900

tttatagtcc tgtcgggttt cgccacctct gacttgagcg tcgatttttg tgatgctcgt   6960

caggggggcg gagcctatgg aaaaacgcca gcaacgcggc ctttttacgg ttcctggcct   7020

tttgctggcc ttttgctcac atgt                                          7044
```

```
<210> SEQ ID NO 47
<211> LENGTH: 6530
<212> TYPE: DNA
<213> ORGANISM: artificial sequence
<220> FEATURE:
<223> OTHER INFORMATION: CN2004 - The portion between L-ITR and R-ITR
      corresponds to positions 142-3792

<400> SEQUENCE: 47

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctgggcat aaaagtcagg gcagagccat ctattgctta    600

catttgcttc tgggatccag atctttcgaa gctagcgcta atggagcaaa cagtgcttgt    660

accaccagga cctgacagct tcaacttctt caccagagaa tctcttgcgg ctattgaaag    720

acgcattgca gaagaaaagg caaagaatcc caaaccagac aaaaaagatg acgacgaaaa    780

tggcccaaag ccaaatagtg acttggaagc tggaaagaac cttccattta tttatggaga    840

cattcctcca gagatggtgt cagagcccct ggaggacctg gacccctact atatcaataa    900

gaaaactttt atagtattga ataaagggaa ggccatcttc cggttcagtg ccacctctgc    960

cctgtacatt ttaactccct tcaatcctct taggaaaata gctattaaga ttttggtaca   1020

ttcattattc agcatgctaa ttatgtgcac tattttgaca aactgtgtgt ttatgacaat   1080
```

-continued

```
gagtaaccct cctgattgga caaagaatgt agaatacacc ttcacaggaa tatatacttt   1140
tgaatcactt ataaaaatta ttgcaagggg attctgttta gaagatttta ctttccttcg   1200
ggatccatgg aactggctcg atttcactgt cattacattt gcgtacgtca cagagtttgt   1260
ggacctgggc aatgtctcgg cattgagaac attcagagtt ctccgagcat tgaagacgat   1320
ttcagtcatt ccaggcctga aaccattgt gggagccctg atccagtctg tgaagaagct    1380
ctcagatgta atgatcctga ctgtgttctg tctgagcgta tttgctctaa ttgggctgca   1440
gctgttcatg ggcaacctga ggaataaatg tatacaatgg cctcccacca atgcttcctt   1500
ggaggaacat agtatagaaa agaatataac tgtgaattat aatggtacac ttataaatga   1560
aactgtcttt gagtttgact ggaagtcata tattcaagat tcaagatatc attatttcct   1620
ggagggtttt ttagatgcac tactatgtgg aaatagctct gatgcaggcc aatgtccaga   1680
gggatatatg tgtgtgaaag ctggtagaaa tcccaattat ggctacacaa gctttgatac   1740
cttcagttgg gctttttttgt ccttgtttcg actaatgact caggacttct gggaaaatct   1800
ttatcaactg acattacgtg ctgctgggaa aacgtacatg atattttttg tattggtcat   1860
tttcttgggc tcattctacc taataaattt gatcctggct gtggtggcca tggcctacga   1920
ggaacagaat caggccacct tggaagaagc agaacagaaa gaggccgaat ttcagcagat   1980
gattgaacag cttaaaaagc aacaggaggc agctcagcag gcagcaacgg caactgcctc   2040
agaacattcc agagagccca gtgcagcagg caggctctca gacagctcat ctgaagcctc   2100
taagttgagt tccaagagtg ctaaggaaag aagaaatcgg aggaagaaaa gaaaacagaa   2160
agagcagtct ggtggggaag agaaagatga ggatgaattc caaaaatctg aatctgagga   2220
cagcatcagg aggaaaggtt ttcgcttctc cattgaaggg aaccgattga catatgaaaa   2280
gaggtactcc tccccacacc agtctttgtt gagcatccgt ggctccctat tttcaccaag   2340
gcgaaatagc agaacaagcc ttttcagctt tagagggcga gcaaaggatg tgggatctga   2400
gaacgacttc gcagatgatg agcacagcac ctttgaggat aacgagagcc gtagagattc   2460
cttgtttgtg ccccgacgac acggagagag acgcaacagc aacctgagtc agaccagtag   2520
gtcatcccgg atgctggcag tgtttccagc gaatgggaag atgcacagca ctgtggattg   2580
caatggtgtg gtttccttgg ttggtggacc ttcagttcct acatcgcctg ttggacagct   2640
tctgccagag gtgataatag ataagccagc tactgatgac aatggaacaa ccactgaaac   2700
tgaaatgaga aagagaaggt caagttcttt ccacgtttcc atggactttc tagaagatcc   2760
ttcccaaagg caacgagcaa tgagtatagc cagcattcta acaaatacag tagaagaact   2820
tgaagaatcc aggcagaaat gcccaccctg ttggtataaa ttttccaaca tattcttaat   2880
ctgggactgt tctccatatt ggttaaaagt gaaacatgtt gtcaacctgg ttgtgatgga   2940
cccatttgtt gacctggcca tcaccatctg tattgtctta aatactcttt tcatggccat   3000
ggagcactat ccaatgacgg accatttcaa taatgtgctt acagtaggaa acttggtttt   3060
cactgggatc tttacagcag aaatgtttct gaaaattatt gccatggatc cttactatta   3120
tttccaagaa ggctggaata tctttgacgg ttttattgtg acgcttagcc tggtagaact   3180
tggactcgcc aatgtggaag gattatctgt tctccgttca tttcgattgc tgcgagtttt   3240
caagttggca aaatcttggc caacgttaaa tatgctaata aagatcatcg gcaattccgt   3300
gggggctctg ggaaatttaa ccctcgtctt ggccatcatc gtcttcattt ttgccgtggt   3360
cggcatgcag ctctttggta aaagctacaa agattgtgtc tgcaagatcg ccagtgattg   3420
tcaactccca cgctggcaca tgaatgactt cttccactcc ttcctgattg tgttccgcgt   3480
```

```
gctgtgtggg gagtggatag agaccatgtg ggactgtatg gaggttgctg gtcaagccat   3540
gtgccttact gtcttcatga tggtcatggt gattggaaac ctagtggtcc tgaatctctt   3600
tctggccttg cttctgagct catttagtgc agacaacctt gcagccactg atgatgataa   3660
tgaaatgaat aatctccaaa ttgctgtgga taggatgcac aaaggagtag cttatgtgaa   3720
aagaaaaata tatgaattta ttcaacagtc cttcattagg aaacaaaaga tctgtgcgga   3780
ccgagcggcc gcaggaaccc ctagtgatgg agttggccac tccctctctg cgcgctcgct   3840
cgctcactga ggccgggcga ccaaaggtcg cccgacgccc gggctttgcc cgggcggcct   3900
cagtgagcga gcgagcgcgc agctgcctgc aggggcgcct gatgcggtat tttctcctta   3960
cgcatctgtg cggtatttca caccgcatac gtcaaagcaa ccatagtacg cgccctgtag   4020
cggcgcatta agcgcggcgg gtgtggtggt tacgcgcagc gtgaccgcta cacttgccag   4080
cgccctagcg cccgctcctt tcgctttctt cccttccttt ctcgccacgt tcgccggctt   4140
tccccgtcaa gctctaaatc gggggctccc tttagggttc cgatttagtg ctttacggca   4200
cctcgacccc aaaaaacttg atttgggtga tggttcacgt agtgggccat cgccctgata   4260
gacggttttt cgccctttga cgttggagtc cacgttcttt aatagtggac tcttgttcca   4320
aactggaaca acactcaacc ctatctcggg ctattctttt gatttataag ggattttgcc   4380
gatttcggcc tattggttaa aaaatgagct gatttaacaa aaatttaacg cgaattttaa   4440
caaaatatta acgtttacaa ttttatggtg cactctcagt acaatctgct ctgatgccgc   4500
atagttaagc cagccccgac acccgccaac acccgctgac gcgccctgac gggcttgtct   4560
gctcccggca tccgcttaca gacaagctgt gaccgtctcc gggagctgca tgtgtcagag   4620
gttttcaccg tcatcaccga aacgcgcgag acgaaagggc ctcgtgatac gcctattttt   4680
ataggttaat gtcatgataa taatggtttc ttagacgtca ggtggcactt ttcggggaaa   4740
tgtgcgcgga acccctattt gtttattttt ctaaatacat tcaaatatgt atccgctcat   4800
gagacaataa ccctgataaa tgcttcaata atattgaaaa aggaagagta tgagtattca   4860
acatttccgt gtcgccctta ttcccttttt tgcggcattt tgccttcctg tttttgctca   4920
cccagaaacg ctggtgaaag taaaagatgc tgaagatcag ttgggtgcac gagtgggtta   4980
catcgaactg gatctcaaca gcggtaagat ccttgagagt tttcgccccg aagaacgttt   5040
tccaatgatg agcactttta aagttctgct atgtggcgcg gtattatccc gtattgacgc   5100
cgggcaagag caactcggtc gccgcataca ctattctcag aatgacttgg ttgagtactc   5160
accagtcaca gaaaagcatc ttacggatgg catgacagta agagaattat gcagtgctgc   5220
cataaccatg agtgataaca ctgcggccaa cttacttctg acaacgatcg gaggaccgaa   5280
ggagctaacc gcttttttgc acaacatggg ggatcatgta actcgccttg atcgttggga   5340
accggagctg aatgaagcca taccaaacga cgagcgtgac accacgatgc ctgtagcaat   5400
ggcaacaacg ttgcgcaaac tattaactgg cgaactactt actctagctt cccggcaaca   5460
attaatagac tggatggagg cggataaagt tgcaggacca cttctgcgct cggcccttcc   5520
ggctggctgg tttattgctg ataaatctgg agccggtgag cgtgggtctc gcggtatcat   5580
tgcagcactg gggccagatg gtaagccctc ccgtatcgta gttatctaca cgacggggag   5640
tcaggcaact atggatgaac gaaatagaca gatcgctgag ataggtgcct cactgattaa   5700
gcattggtaa ctgtcagacc aagtttactc atatatactt tagattgatt taaaacttca   5760
tttttaattt aaaaggatct aggtgaagat cctttttgat aatctcatga ccaaaatccc   5820
```

```
ttaacgtgag ttttcgttcc actgagcgtc agaccccgta gaaaagatca aaggatcttc   5880

ttgagatcct ttttttctgc gcgtaatctg ctgcttgcaa acaaaaaaac caccgctacc   5940

agcggtggtt tgtttgccgg atcaagagct accaactctt tttccgaagg taactggctt   6000

cagcagagcg cagataccaa atactgtcct tctagtgtag ccgtagttag gccaccactt   6060

caagaactct gtagcaccgc ctacatacct cgctctgcta atcctgttac cagtggctgc   6120

tgccagtggc gataagtcgt gtcttaccgg gttggactca agacgatagt taccggataa   6180

ggcgcagcgg tcgggctgaa cggggggttc gtgcacacag cccagcttgg agcgaacgac   6240

ctacaccgaa ctgagatacc tacagcgtga gctatgagaa agcgccacgc ttcccgaagg   6300

gagaaaggcg gacaggtatc cggtaagcgg cagggtcgga acaggagagc gcacgaggga   6360

gcttccaggg ggaaacgcct ggtatcttta tagtcctgtc gggtttcgcc acctctgact   6420

tgagcgtcga tttttgtgat gctcgtcagg ggggcggagc ctatggaaaa acgccagcaa   6480

cgcggccttt ttacggttcc tggccttttg ctggcctttt gctcacatgt              6530
```

<210> SEQ ID NO 48
<211> LENGTH: 6898
<212> TYPE: DNA
<213> ORGANISM: artificial sequence
<220> FEATURE:
<223> OTHER INFORMATION: CN2005 - The portion between L-ITR and R-ITR corresponds to positions 142-4160

<400> SEQUENCE: 48

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtatagg taccctggta gaacttggac    180

tcgccaatgt ggaaggatta tctgttctcc gttcatttcg attgctgcga gttttcaagt    240

tggcaaaatc ttggccaacg ttaaatatgc taataaagat catcggcaat tccgtggggg    300

ctctgggaaa tttaaccctc gtcttggcca tcatcgtctt catttttgcc gtggtcggca    360

tgcagctctt tggtaaaagc tacaaagatt gtgtctgcaa gatcgccagt gattgtcaac    420

tcccacgctg gcacatgaat gacttcttcc actccttcct gattgtgttc cgcgtgctgt    480

gtggggagtg gatagagacc atgtgggact gtatggaggt tgctggtcaa gccatgtgcc    540

ttactgtctt catgatggtc atggtgattg gaaacctagt ggtcctgaat ctctttctgg    600

ccttgcttct gagctcattt agtgcagaca accttgcagc cactgatgat gataatgaaa    660

tgaataatct ccaaattgct gtggatagga tgcacaaagg agtagcttat gtgaaaagaa    720

aaatatatga atttattcaa cagtccttca ttaggaaaca aaagatttta gatgaaatta    780

aaccacttga tgatctaaac aacaagaaag acagttgtat gtccaatcat acagcagaaa    840

ttgggaaaga tcttgactat cttaaagatg taaatggaac tacaagtggt ataggaactg    900

gcagcagtgt tgaatacatt attgatgaaa gtgattacat gtcattcata aacaacccca    960

gtcttactgt gactgtacca attgctgtag gagaatctga ctttgaaaat ttaaacacgg   1020

aagactttag tagtgaatcg gatctggaag aaagcaaaga gaaactgaat gaaagcagta   1080

gctcatcaga aggtagcact gtggacatcg gcgcacctgt agaagaacag cccgtagtgg   1140

aacctgaaga aactcttgaa ccagaagctt gtttcactga aggctgtgta caaagattca   1200

agtgttgtca aatcaatgtg gaagaaggca gaggaaaaca atggtggaac ctgagaagga   1260

cgtgtttccg aatagttgaa cataactggt ttgagacctt cattgttttc atgattctcc   1320
```

```
ttagtagtgg tgctctggca tttgaagata tatatattga tcagcgaaag acgattaaga   1380
cgatgttgga atatgctgac aaggttttca cttacatttt cattctggaa atgcttctaa   1440
aatgggtggc atatggctat caaacatatt tcaccaatgc ctggtgttgg ctggacttct   1500
taattgttga tgtttcattg gtcagtttaa cagcaaatgc cttgggttac tcagaacttg   1560
gagccatcaa atctctcagg acactaagag ctctgagacc tctaagagcc ttatctcgat   1620
ttgaagggat gagggtggtt gtgaatgccc ttttaggagc aattccatcc atcatgaatg   1680
tgcttctggt ttgtcttata ttctggctaa ttttcagcat catgggcgta aatttgtttg   1740
ctggcaaatt ctaccactgt attaacacca caactggtga caggtttgac atcgaagacg   1800
tgaataatca tactgattgc ctaaaactaa tagaaagaaa tgagactgct cgatggaaaa   1860
atgtgaaagt aaactttgat aatgtaggat ttgggtatct ctctttgctt caagttgcca   1920
cattcaaagg atggatggat ataatgtatg cagcagttga ttccagaaat gtggaactcc   1980
agcctaagta tgaagaaagt ctgtacatgt atctttactt tgttattttc atcatctttg   2040
ggtccttctt caccttgaac ctgtttattg gtgtcatcat agataatttc aaccagcaga   2100
aaaagaagtt tggaggtcaa gacatcttta tgacagaaga acagaagaaa tactataatg   2160
caatgaaaaa attaggatcg aaaaaaccgc aaaagcctat acctcgacca ggaaacaaat   2220
ttcaaggaat ggtctttgac ttcgtaacca gacaagtttt tgacataagc atcatgattc   2280
tcatctgtct taacatggtc acaatgatgg tggaaacaga tgaccagagt gaatatgtga   2340
ctaccatttt gtcacgcatc aatctggtgt tcattgtgct atttactgga gagtgtgtac   2400
tgaaactcat ctctctacgc cattattatt ttaccattgg atggaatatt tttgattttg   2460
tggttgtcat tctctccatt gtaggtatgt ttcttgccga gctgatagaa aagtatttcg   2520
tgtcccctac cctgttccga gtgatccgtc ttgctaggat tggccgaatc ctacgtctga   2580
tcaaaggagc aaaggggatc cgcacgctgc tctttgcttt gatgatgtcc cttcctgcgt   2640
tgtttaacat cggcctccta ctcttcctag tcatgttcat ctacgccatc tttgggatgt   2700
ccaactttgc ctatgttaag agggaagttg ggatcgatga catgttcaac tttgagacct   2760
ttggcaacag catgatctgc ctattccaaa ttacaacctc tgctggctgg gatggattgc   2820
tagcacccat tctcaacagt aagccacccg actgtgaccc taataaagtt aaccctggaa   2880
gctcagttaa gggagactgt gggaacccat ctgttggaat tttctttttt gtcagttaca   2940
tcatcatatc cttcctggtt gtggtgaaca tgtacatcgc ggtcatcctg gagaacttca   3000
gtgttgctac tgaagaaagt gcagagcctc tgagtgagga tgactttgag atgttctatg   3060
aggtttggga gaagtttgat cccgatgcaa ctcagttcat ggaatttgaa aaattatctc   3120
agtttgcagc tgcgcttgaa ccgcctctca atctgccaca accaaacaaa ctccagctca   3180
ttgccatgga tttgcccatg gtgagtggtg accggatcca ctgtcttgat atcttatttg   3240
cttttacaaa gcgggttcta ggagagagtg gagagatgga tgctctacga atacagatgg   3300
aagagcgatt catggcttcc aatccttcca aggtctccta tcagccaatc actactactt   3360
taaaacgaaa acaagaggaa gtatctgctg tcattattca gcgtgcttac agacgccacc   3420
ttttaaagcg aactgtaaaa caagcttcct ttacgtacaa taaaaacaaa atcaaaggtg   3480
gggctaatct tcttataaaa gaagacatga taattgacag aataaatgaa aactctatta   3540
cagaaaaaac tgatctgacc atgtccactg cagcttgtcc accttcctat gaccgggtga   3600
caaagccaat tgtggaaaaa catgagcaag aaggcaaaga tgaaaaagcc aaagggaaat   3660
aatgacatca taatcaacct ctggattaca aaatttgtga aagattgact ggtattctta   3720
```

```
actatgttgc tccttttacg ctatgtggat acgctgcttt aatgcctttg tatcatgcta   3780
ttgcttcccg tatggctttc attttctcct ccttgtataa atcctggtta gttcttgcca   3840
cggcggaact catcgccgcc tgccttgccc gctgctggac aggggctcgg ctgttgggca   3900
ctgacaattc cgtggctcga gagatcttcg actgtgcctt ctagttgcca gccatctgtt   3960
gtttgcccct cccccgtgcc ttccttgacc ctggaaggtg ccactcccac tgtcctttcc   4020
taataaaatg aggaaattgc atcgcattgt ctgagtaggt gtcattctat tctggggggt   4080
ggggtggggc aggacagcaa gggggaggat tgggaagaca atagcaggca tgagatctca   4140
cgtgcggacc gagcggccgc aggaacccct agtgatggag ttggccactc cctctctgcg   4200
cgctcgctcg ctcactgagg ccgggcgacc aaaggtcgcc cgacgcccgg gctttgcccg   4260
ggcggcctca gtgagcgagc gagcgcgcag ctgcctgcag gggcgcctga tgcggtattt   4320
tctccttacg catctgtgcg gtatttcaca ccgcatacgt caaagcaacc atagtacgcg   4380
ccctgtagcg gcgcattaag cgcggcgggt gtggtggtta cgcgcagcgt gaccgctaca   4440
cttgccagcg ccctagcgcc cgctcctttc gctttcttcc cttcctttct cgccacgttc   4500
gccggctttc cccgtcaagc tctaaatcgg gggctccctt tagggttccg atttagtgct   4560
ttacggcacc tcgaccccaa aaaacttgat ttgggtgatg gttcacgtag tgggccatcg   4620
ccctgataga cggtttttcg ccctttgacg ttggagtcca cgttctttaa tagtggactc   4680
ttgttccaaa ctggaacaac actcaaccct atctcgggct attcttttga tttataaggg   4740
attttgccga tttcggccta ttggttaaaa aatgagctga tttaacaaaa atttaacgcg   4800
aattttaaca aaatattaac gtttacaatt ttatggtgca ctctcagtac aatctgctct   4860
gatgccgcat agttaagcca gccccgacac ccgccaacac ccgctgacgc gccctgacgg   4920
gcttgtctgc tcccggcatc cgcttacaga caagctgtga ccgtctccgg gagctgcatg   4980
tgtcagaggt tttcaccgtc atcaccgaaa cgcgcgagac gaaagggcct cgtgatacgc   5040
ctatttttat aggttaatgt catgataata atggtttctt agacgtcagg tggcactttt   5100
cggggaaatg tgcgcggaac ccctatttgt ttatttttct aaatacattc aaatatgtat   5160
ccgctcatga gacaataacc ctgataaatg cttcaataat attgaaaaag gaagagtatg   5220
agtattcaac atttccgtgt cgcccttatt cccttttttg cggcattttg ccttcctgtt   5280
tttgctcacc cagaaacgct ggtgaaagta aaagatgctg aagatcagtt gggtgcacga   5340
gtgggttaca tcgaactgga tctcaacagc ggtaagatcc ttgagagttt tcgccccgaa   5400
gaacgttttc caatgatgag cacttttaaa gttctgctat gtggcgcggt attatcccgt   5460
attgacgccg ggcaagagca actcggtcgc cgcatacact attctcagaa tgacttggtt   5520
gagtactcac cagtcacaga aaagcatctt acggatggca tgacagtaag agaattatgc   5580
agtgctgcca taaccatgag tgataacact gcggccaact tacttctgac aacgatcgga   5640
ggaccgaagg agctaaccgc ttttttgcac aacatggggg atcatgtaac tcgccttgat   5700
cgttgggaac cggagctgaa tgaagccata ccaaacgacg agcgtgacac cacgatgcct   5760
gtagcaatgg caacaacgtt gcgcaaacta ttaactggcg aactacttac tctagcttcc   5820
cggcaacaat taatagactg gatggaggcg gataaagttg caggaccact tctgcgctcg   5880
gcccttccgg ctggctggtt tattgctgat aaatctggag ccggtgagcg tgggtctcgc   5940
ggtatcattg cagcactggg gccagatggt aagccctccc gtatcgtagt tatctacacg   6000
acggggagtc aggcaactat ggatgaacga aatagacaga tcgctgagat aggtgcctca   6060
```

```
ctgattaagc attggtaact gtcagaccaa gtttactcat atatacttta gattgattta   6120

aaacttcatt tttaatttaa aaggatctag gtgaagatcc tttttgataa tctcatgacc   6180

aaaatccctt aacgtgagtt ttcgttccac tgagcgtcag accccgtaga aaagatcaaa   6240

ggatcttctt gagatccttt ttttctgcgc gtaatctgct gcttgcaaac aaaaaaacca   6300

ccgctaccag cggtggtttg tttgccggat caagagctac caactctttt tccgaaggta   6360

actggcttca gcagagcgca gataccaaat actgtccttc tagtgtagcc gtagttaggc   6420

caccacttca agaactctgt agcaccgcct acatacctcg ctctgctaat cctgttacca   6480

gtggctgctg ccagtggcga taagtcgtgt cttaccgggt tggactcaag acgatagtta   6540

ccggataagg cgcagcggtc gggctgaacg gggggttcgt gcacacagcc cagcttggag   6600

cgaacgacct acaccgaact gagataccta cagcgtgagc tatgagaaag cgccacgctt   6660

cccgaaggga gaaaggcgga caggtatccg gtaagcggca gggtcggaac aggagagcgc   6720

acgagggagc ttccaggggg aaacgcctgg tatctttata gtcctgtcgg gtttcgccac   6780

ctctgacttg agcgtcgatt tttgtgatgc tcgtcagggg ggcggagcct atggaaaaac   6840

gccagcaacg cggccttttt acggttcctg gccttttgct ggccttttgc tcacatgt     6898
```

<210> SEQ ID NO 49
<211> LENGTH: 7528
<212> TYPE: DNA
<213> ORGANISM: artificial sequence
<220> FEATURE:
<223> OTHER INFORMATION: CN2006 - The portion between L-ITR and R-ITR corresponds to positions 142-4790

<400> SEQUENCE: 49

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctggtcga cacaattgga ggtaggcgtg tacggtggga    600

ggcctatata agcagagctc gtttagtgaa ccgtcagatc gcctggagga tccttcgaaa    660

agcttgctac cggtgccacc atggtcagca agggcgagga gctgttcacc ggggtggtgc    720

ccatcctggt cgagctggac ggcgacgtca atggccacaa gttcagcgtg tccggcgagg    780

gcgagggcga tgccacctac ggcaagctga ccctgaagct gatctgcacc accggcaagc    840

tgcccgtgcc ctggcccacc ctcgtgacca ccctgggcta cggcgtgcag tgcttcgccc    900

gctaccccga ccacatgaag cagcacgact tcttcaagtc cgccatgccc gaaggctacg    960

tccaggagcg caccatcttc ttcaaagacg acggcaacta caagacccgc gccgaggtga   1020

agttcgaggg cgacaccctg gtgaaccgca tcgagctgaa gggcatcgac ttcaaggagg   1080

acggcaacat cctggggcac aagctggagt acaactacaa cagccacaac gtctatatca   1140

ccgccgacaa gcagaagaac ggcatcaagg ccaacttcaa gatccgccac aacatcgagg   1200
```

-continued

```
acggcggcgt gcagctcgcc gaccactacc agcagaacac ccccatcggc gacggccccg   1260
tgctgctgcc cgacaaccac tacctgagct accagtccaa gctgagcaaa gaccccaacg   1320
agaagcgcga tcacatggtc ctgctggagt tcgtgaccgc cgccgggatc actctcggca   1380
tggacgagct gtacaaaggc agcggcgcca ccaacttcag cctgctgaag caggccggcg   1440
acgtggagga gaaccccggc cccggaacta gtggtatgga gcaaacagtg cttgtaccac   1500
caggacctga cagcttcaac ttcttcacca gagaatctct tgcggctatt gaaagacgca   1560
ttgcagaaga aaaggcaaag aatcccaaac cagacaaaaa agatgacgac gaaaatggcc   1620
caaagccaaa tagtgacttg gaagctggaa agaaccttcc atttatttat ggagacattc   1680
ctccagagat ggtgtcagag cccctggagg acctggaccc ctactatatc aataagaaaa   1740
cttttatagt attgaataaa gggaaggcca tcttccggtt cagtgccacc tctgccctgt   1800
acattttaac tcccttcaat cctcttagga aaatagctat taagattttg gtacattcat   1860
tattcagcat gctaattatg tgcactattt tgacaaactg tgtgtttatg acaatgagta   1920
accctcctga ttggacaaag aatgtagaat acaccttcac aggaatatat acttttgaat   1980
cacttataaa aattattgca aggggattct gtttagaaga ttttactttc cttcgggatc   2040
catggaactg gctcgatttc actgtcatta catttgcgta cgtcacagag tttgtggacc   2100
tgggcaatgt ctcggcattg agaacattca gagttctccg agcattgaag acgatttcag   2160
tcattccagg cctgaaaacc attgtgggag ccctgatcca gtctgtgaag aagctctcag   2220
atgtaatgat cctgactgtg ttctgtctga gcgtatttgc tctaattggg ctgcagctgt   2280
tcatgggcaa cctgaggaat aaatgtatac aatggcctcc caccaatgct tccttggagg   2340
aacatagtat agaaaagaat ataactgtga attataatgg tacacttata aatgaaactg   2400
tctttgagtt tgactggaag tcatatattc aagattcaag atatcattat ttcctggagg   2460
gtttttttaga tgcactacta tgtggaaata gctctgatgc aggccaatgt ccagagggat   2520
atatgtgtgt gaaagctggt agaaatccca attatggcta cacaagcttt gataccttca   2580
gttgggcttt tttgtccttg tttcgactaa tgactcagga cttctgggaa aatctttatc   2640
aactgacatt acgtgctgct gggaaaacgt acatgatatt ttttgtattg gtcattttct   2700
tgggctcatt ctacctaata aatttgatcc tggctgtggt ggccatggcc tacgaggaac   2760
agaatcaggc caccttggaa gaagcagaac agaaagaggc cgaatttcag cagatgattg   2820
aacagcttaa aaagcaacag gaggcagctc agcaggcagc aacggcaact gcctcagaac   2880
attccagaga gcccagtgca gcaggcaggc tctcagacag ctcatctgaa gcctctaagt   2940
tgagttccaa gagtgctaag gaaagaagaa atcggaggaa gaaaagaaaa cagaaagagc   3000
agtctggtgg ggaagagaaa gatgaggatg aattccaaaa atctgaatct gaggacagca   3060
tcaggaggaa aggttttcgc ttctccattg aagggaaccg attgacatat gaaaagaggt   3120
actcctcccc acaccagtct ttgttgagca tccgtggctc cctattttca ccaaggcgaa   3180
atagcagaac aagccttttc agctttagag ggcgagcaaa ggatgtggga tctgagaacg   3240
acttcgcaga tgatgagcac agcacctttg aggataacga gagccgtaga gattccttgt   3300
ttgtgccccg acgacacgga gagagacgca acagcaacct gagtcagacc agtaggtcat   3360
cccggatgct ggcagtgttt ccagcgaatg ggaagatgca cagcactgtg gattgcaatg   3420
gtgtggtttc cttggttggt ggaccttcag ttcctacatc gcctgttgga cagcttctgc   3480
cagaggtgat aatagataag ccagctactg atgacaatgg aacaaccact gaaactgaaa   3540
tgagaaagag aaggtcaagt tctttccacg tttccatgga ctttctagaa gatccttccc   3600
```

```
aaaggcaacg agcaatgagt atagccagca ttctaacaaa tacagtagaa gaacttgaag   3660
aatccaggca gaaatgccca ccctgttggt ataaattttc caacatattc ttaatctggg   3720
actgttctcc atattggtta aaagtgaaac atgttgtcaa cctggttgtg atggacccat   3780
ttgttgacct ggccatcacc atctgtattg tcttaaatac tcttttcatg gccatggagc   3840
actatccaat gacggaccat ttcaataatg tgcttacagt aggaaacttg gttttcactg   3900
ggatctttac agcagaaatg tttctgaaaa ttattgccat ggatccttac tattatttcc   3960
aagaaggctg gaatatcttt gacggtttta ttgtgacgct tagcctggta gaacttggac   4020
tcgccaatgt ggaaggatta tctgttctcc gttcatttcg attgctgcga gttttcaagt   4080
tggcaaaatc ttggccaacg ttaaatatgc taataaagat catcggcaat tccgtggggg   4140
ctctgggaaa tttaaccctc gtcttggcca tcatcgtctt catttttgcc gtggtcgtga   4200
gtttggggac ccttgattgt tctttctttt tcgctattgt aaaattcatg ttatatggag   4260
ggggcaaagt tttcagggtg ttgtttagaa tgggaagatg tcccttgtat caccatggac   4320
cctcatgata attttgtttc tttcactttc tactctgttg acaaccattg tctcctctta   4380
ttttcttttc attttctgta actttttcgt taaactttag cttgcatttg taacgaattt   4440
ttaaattcac ttttgtttat ttgtcagatt gtaagtactt tctctaatca cttttttttc   4500
aaggcaatca gggtatatta tattgtactt cagcacagtt ttagagaaca attgttataa   4560
ttaaatgata aggtagaata tttctgcata taaattctgg ctggcgtgga aatattctta   4620
ttggtagaaa caactacacc ctggtcatca tcctgccttt ctctttatgg ttacaatgat   4680
atacactgtt tgagatgagg ataaaatact ctgagtccaa accgggcccc tctgctaacc   4740
atgttcatgc cttcttctct ttcctactca cgtgcggacc gagcggccgc aggaacccct   4800
agtgatggag ttggccactc cctctctgcg cgctcgctcg ctcactgagg ccgggcgacc   4860
aaaggtcgcc cgacgcccgg gctttgcccg ggcggcctca gtgagcgagc gagcgcgcag   4920
ctgcctgcag gggcgcctga tgcggtattt tctccttacg catctgtgcg gtatttcaca   4980
ccgcatacgt caaagcaacc atagtacgcg ccctgtagcg gcgcattaag cgcggcgggt   5040
gtggtggtta cgcgcagcgt gaccgctaca cttgccagcg ccctagcgcc cgctcctttc   5100
gctttcttcc cttcctttct cgccacgttc gccggctttc cccgtcaagc tctaaatcgg   5160
gggctccctt tagggttccg atttagtgct ttacggcacc tcgaccccaa aaaacttgat   5220
ttgggtgatg gttcacgtag tgggccatcg ccctgataga cggtttttcg ccctttgacg   5280
ttggagtcca cgttctttaa tagtggactc ttgttccaaa ctggaacaac actcaaccct   5340
atctcgggct attcttttga tttataaggg attttgccga tttcggccta ttggttaaaa   5400
aatgagctga tttaacaaaa atttaacgcg aattttaaca aaatattaac gtttacaatt   5460
ttatggtgca ctctcagtac aatctgctct gatgccgcat agttaagcca gccccgacac   5520
ccgccaacac ccgctgacgc gccctgacgg gcttgtctgc tcccggcatc cgcttacaga   5580
caagctgtga ccgtctccgg gagctgcatg tgtcagaggt tttcaccgtc atcaccgaaa   5640
cgcgcgagac gaaagggcct cgtgatacgc ctatttttat aggttaatgt catgataata   5700
atggtttctt agacgtcagg tggcactttt cggggaaatg tgcgcggaac ccctatttgt   5760
ttatttttct aaatacattc aaatatgtat ccgctcatga gacaataacc ctgataaatg   5820
cttcaataat attgaaaaag gaagagtatg agtattcaac atttccgtgt cgcccttatt   5880
ccctttttttg cggcattttg ccttcctgtt tttgctcacc cagaaacgct ggtgaaagta   5940
```

```
aaagatgctg aagatcagtt gggtgcacga gtgggttaca tcgaactgga tctcaacagc   6000

ggtaagatcc ttgagagttt tcgccccgaa gaacgttttc caatgatgag cacttttaaa   6060

gttctgctat gtggcgcggt attatcccgt attgacgccg ggcaagagca actcggtcgc   6120

cgcatacact attctcagaa tgacttggtt gagtactcac cagtcacaga aaagcatctt   6180

acggatggca tgacagtaag agaattatgc agtgctgcca taaccatgag tgataacact   6240

gcggccaact tacttctgac aacgatcgga ggaccgaagg agctaaccgc tttttttgcac   6300

aacatggggg atcatgtaac tcgccttgat cgttgggaac cggagctgaa tgaagccata   6360

ccaaacgacg agcgtgacac cacgatgcct gtagcaatgg caacaacgtt gcgcaaacta   6420

ttaactggcg aactacttac tctagcttcc cggcaacaat taatagactg gatggaggcg   6480

gataaagttg caggaccact tctgcgctcg gcccttccgg ctggctggtt tattgctgat   6540

aaatctggag ccggtgagcg tgggtctcgc ggtatcattg cagcactggg gccagatggt   6600

aagccctccc gtatcgtagt tatctacacg acggggagtc aggcaactat ggatgaacga   6660

aatagacaga tcgctgagat aggtgcctca ctgattaagc attggtaact gtcagaccaa   6720

gtttactcat atatacttta gattgattta aaacttcatt tttaatttaa aaggatctag   6780

gtgaagatcc tttttgataa tctcatgacc aaaatccctt aacgtgagtt ttcgttccac   6840

tgagcgtcag accccgtaga aaagatcaaa ggatcttctt gagatccttt ttttctgcgc   6900

gtaatctgct gcttgcaaac aaaaaaacca ccgctaccag cggtggtttg tttgccggat   6960

caagagctac caactctttt tccgaaggta actggcttca gcagagcgca gataccaaat   7020

actgtccttc tagtgtagcc gtagttaggc caccacttca agaactctgt agcaccgcct   7080

acatacctcg ctctgctaat cctgttacca gtggctgctg ccagtggcga taagtcgtgt   7140

cttaccgggt tggactcaag acgatagtta ccggataagg cgcagcggtc gggctgaacg   7200

gggggttcgt gcacacagcc cagcttggag cgaacgacct acaccgaact gagataccta   7260

cagcgtgagc tatgagaaag cgccacgctt cccgaaggga gaaaggcgga caggtatccg   7320

gtaagcggca gggtcggaac aggagagcgc acgagggagc ttccaggggg aaacgcctgg   7380

tatctttata gtcctgtcgg gtttcgccac ctctgacttg agcgtcgatt tttgtgatgc   7440

tcgtcagggg ggcggagcct atggaaaaac gccagcaacg cggccttttt acggttcctg   7500

gccttttgct ggccttttgc tcacatgt                                      7528
```

<210> SEQ ID NO 50
<211> LENGTH: 7409
<212> TYPE: DNA
<213> ORGANISM: artificial sequence
<220> FEATURE:
<223> OTHER INFORMATION: CN2007 - The portion between L-ITR and R-ITR corresponds to positions 142-4671

<400> SEQUENCE: 50

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca gagtttgggg acccttgatt gttctttctt    180

tttcgctatt gtaaaattca tgttatatgg agggggcaaa gttttcaggg tgttgtttag    240

aatgggaaga tgtcccttgt atcaccatgg accctcatga taattttgtt tctttcactt    300

tctactctgt tgacaaccat tgtctcctct tattttcttt tcattttctg taactttttc    360

gttaaacttt agcttgcatt tgtaacgaat ttttaaattc acttttgttt atttgtcaga    420
```

```
ttgtaagtac tttctctaat cacttttttt tcaaggcaat cagggtatat tatattgtac    480
ttcagcacag ttttagagaa caattgttat aattaaatga taaggtagaa tatttctgca    540
tataaattct ggctggcgtg gaaatattct tattggtaga aacaactaca ccctggtcat    600
catcctgcct ttctctttat ggttacaatg atatacactg tttgagatga ggataaaata    660
ctctgagtcc aaaccgggcc cctctgctaa ccatgttcat gccttcttct ctttcctaca    720
gggcatgcag ctctttggta aaagctacaa agattgtgtc tgcaagatcg ccagtgattg    780
tcaactccca cgctggcaca tgaatgactt cttccactcc ttcctgattg tgttccgcgt    840
gctgtgtggg gagtggatag agaccatgtg ggactgtatg gaggttgctg gtcaagccat    900
gtgccttact gtcttcatga tggtcatggt gattggaaac ctagtggtcc tgaatctctt    960
tctggccttg cttctgagct catttagtgc agacaacctt gcagccactg atgatgataa   1020
tgaaatgaat aatctccaaa ttgctgtgga taggatgcac aaaggagtag cttatgtgaa   1080
aagaaaaata tatgaattta ttcaacagtc cttcattagg aaacaaaaga ttttagatga   1140
aattaaacca cttgatgatc taaacaacaa gaaagacagt tgtatgtcca atcatacagc   1200
agaaattggg aaagatcttg actatcttaa agatgtaaat ggaactacaa gtggtatagg   1260
aactggcagc agtgttgaat acattattga tgaaagtgat tacatgtcat tcataaacaa   1320
ccccagtctt actgtgactg taccaattgc tgtaggagaa tctgactttg aaaatttaaa   1380
cacggaagac tttagtagtg aatcggatct ggaagaaagc aaagagaaac tgaatgaaag   1440
cagtagctca tcagaaggta gcactgtgga catcggcgca cctgtagaag aacagcccgt   1500
agtggaacct gaagaaactc ttgaaccaga agcttgtttc actgaaggct gtgtacaaag   1560
attcaagtgt tgtcaaatca atgtggaaga aggcagagga aaacaatggt ggaacctgag   1620
aaggacgtgt ttccgaatag ttgaacataa ctggtttgag accttcattg ttttcatgat   1680
tctccttagt agtggtgctc tggcatttga agatatatat attgatcagc gaaagacgat   1740
taagacgatg ttggaatatg ctgacaaggt tttcacttac attttcattc tggaaatgct   1800
tctaaaatgg gtggcatatg gctatcaaac atatttcacc aatgcctggt gttggctgga   1860
cttcttaatt gttgatgttt cattggtcag tttaacagca aatgccttgg gttactcaga   1920
acttggagcc atcaaatctc tcaggacact aagagctctg agacctctaa gagccttatc   1980
tcgatttgaa gggatgaggg tggttgtgaa tgccctttta ggagcaattc catccatcat   2040
gaatgtgctt ctggtttgtc ttatattctg gctaattttc agcatcatgg gcgtaaattt   2100
gtttgctggc aaattctacc actgtattaa caccacaact ggtgacaggt ttgacatcga   2160
agacgtgaat aatcatactg attgcctaaa actaatagaa agaaatgaga ctgctcgatg   2220
gaaaaatgtg aaagtaaact ttgataatgt aggatttggg tatctctctt tgcttcaagt   2280
tgccacattc aaaggatgga tggatataat gtatgcagca gttgattcca gaaatgtgga   2340
actccagcct aagtatgaag aaagtctgta catgtatctt tactttgtta ttttcatcat   2400
ctttgggtcc ttcttcacct tgaacctgtt tattggtgtc atcatagata atttcaacca   2460
gcagaaaaag aagtttggag gtcaagacat ctttatgaca gaagaacaga agaaatacta   2520
taatgcaatg aaaaaattag gatcgaaaaa accgcaaaag cctatacctc gaccaggaaa   2580
caaatttcaa ggaatggtct ttgacttcgt aaccagacaa gtttttgaca taagcatcat   2640
gattctcatc tgtcttaaca tggtcacaat gatggtggaa acagatgacc agagtgaata   2700
tgtgactacc attttgtcac gcatcaatct ggtgttcatt gtgctattta ctggagagtg   2760
tgtactgaaa ctcatctctc tacgccatta ttattttacc attggatgga atatttttga   2820
```

```
ttttgtggtt gtcattctct ccattgtagg tatgtttctt gccgagctga tagaaaagta   2880
tttcgtgtcc cctaccctgt tccgagtgat ccgtcttgct aggattggcc gaatcctacg   2940
tctgatcaaa ggagcaaagg ggatccgcac gctgctcttt gctttgatga tgtcccttcc   3000
tgcgttgttt aacatcggcc tcctactctt cctagtcatg ttcatctacg ccatctttgg   3060
gatgtccaac tttgcctatg ttaagaggga agttgggatc gatgacatgt tcaactttga   3120
gacctttggc aacagcatga tctgcctatt ccaaattaca acctctgctg gctgggatgg   3180
attgctagca cccattctca acagtaagcc acccgactgt gaccctaata aagttaaccc   3240
tggaagctca gttaagggag actgtgggaa cccatctgtt ggaattttct tttttgtcag   3300
ttacatcatc atatccttcc tggttgtggt gaacatgtac atcgcggtca tcctggagaa   3360
cttcagtgtt gctactgaag aaagtgcaga gcctctgagt gaggatgact ttgagatgtt   3420
ctatgaggtt tgggagaagt ttgatcccga tgcaactcag ttcatggaat ttgaaaaatt   3480
atctcagttt gcagctgcgc ttgaaccgcc tctcaatctg ccacaaccaa acaaactcca   3540
gctcattgcc atggatttgc ccatggtgag tggtgaccgg atccactgtc ttgatatctt   3600
atttgctttt acaaagcggg ttctaggaga gagtggagag atggatgctc tacgaataca   3660
gatggaagag cgattcatgg cttccaatcc ttccaaggtc tcctatcagc caatcactac   3720
tactttaaaa cgaaaacaag aggaagtatc tgctgtcatt attcagcgtg cttacagacg   3780
ccacctttta aagcgaactg taaaacaagc ttcctttacg tacaataaaa acaaaatcaa   3840
aggtggggct aatcttctta taaaagaaga catgataatt gacagaataa atgaaaactc   3900
tattacagaa aaaactgatc tgaccatgtc cactgcagct tgtccacctt cctatgaccg   3960
ggtgacaaag ccaattgtgg aaaaacatga gcaagaaggc aaagatgaaa aagccaaagg   4020
gaaaggaggt ggtggttcag gtgggggcgg ctcagagtac ccctatgatg tccctgatta   4080
tgcggcggaa taccccctatg acgtgccgga ctacgcggct gaatatccgt atgacgttcc   4140
cgattatgcg gctaagctcg aataatgatg agaattcatc ataatcaacc tctggattac   4200
aaaatttgtg aaagattgac tggtattctt aactatgttg ctccttttac gctatgtgga   4260
tacgctgctt taatgccttt gtatcatgct attgcttccc gtatggcttt cattttctcc   4320
tccttgtata aatcctggtt agttcttgcc acggcggaac tcatcgccgc ctgccttgcc   4380
cgctgctgga caggggctcg gctgttgggc actgacaatt ccgtggctcg agagatcttc   4440
gactgtgcct tctagttgcc agccatctgt tgtttgcccc tcccccgtgc cttccttgac   4500
cctggaaggt gccactccca ctgtcctttc ctaataaaat gaggaaattg catcgcattg   4560
tctgagtagg tgtcattcta ttctgggggg tggggtgggg caggacagca agggggagga   4620
ttgggaagac aatagcaggc atgagatctc acgtgcggac cgagcggccg caggaacccc   4680
tagtgatgga gttggccact ccctctctgc gcgctcgctc gctcactgag gccgggcgac   4740
caaaggtcgc ccgacgcccg ggctttgccc gggcggcctc agtgagcgag cgagcgcgca   4800
gctgcctgca ggggcgcctg atgcggtatt ttctccttac gcatctgtgc ggtatttcac   4860
accgcatacg tcaaagcaac catagtacgc gccctgtagc ggcgcattaa gcgcggcggg   4920
tgtggtggtt acgcgcagcg tgaccgctac acttgccagc gccctagcgc ccgctccttt   4980
cgctttcttc ccttcctttc tcgccacgtt cgccggcttt ccccgtcaag ctctaaatcg   5040
ggggctccct ttagggttcc gatttagtgc tttacggcac ctcgacccca aaaaacttga   5100
tttgggtgat ggttcacgta gtgggccatc gccctgatag acggtttttc gccctttgac   5160
```

```
gttggagtcc acgttcttta atagtggact cttgttccaa actggaacaa cactcaaccc   5220

tatctcgggc tattcttttg atttataagg gattttgccg atttcggcct attggttaaa   5280

aaatgagctg atttaacaaa aatttaacgc gaattttaac aaaatattaa cgtttacaat   5340

tttatggtgc actctcagta caatctgctc tgatgccgca tagttaagcc agccccgaca   5400

cccgccaaca cccgctgacg cgccctgacg ggcttgtctg ctcccggcat ccgcttacag   5460

acaagctgtg accgtctccg ggagctgcat gtgtcagagg ttttcaccgt catcaccgaa   5520

acgcgcgaga cgaaagggcc tcgtgatacg cctattttta taggttaatg tcatgataat   5580

aatggtttct tagacgtcag gtggcacttt tcggggaaat gtgcgcggaa cccctatttg   5640

tttatttttc taaatacatt caaatatgta tccgctcatg agacaataac cctgataaat   5700

gcttcaataa tattgaaaaa ggaagagtat gagtattcaa catttccgtg tcgcccttat   5760

tccctttttt gcggcatttt gccttcctgt ttttgctcac ccagaaacgc tggtgaaagt   5820

aaaagatgct gaagatcagt tgggtgcacg agtgggttac atcgaactgg atctcaacag   5880

cggtaagatc cttgagagtt ttcgccccga agaacgtttt ccaatgatga gcacttttaa   5940

agttctgcta tgtggcgcgg tattatcccg tattgacgcc gggcaagagc aactcggtcg   6000

ccgcatacac tattctcaga atgacttggt tgagtactca ccagtcacag aaaagcatct   6060

tacggatggc atgacagtaa gagaattatg cagtgctgcc ataaccatga gtgataacac   6120

tgcggccaac ttacttctga caacgatcgg aggaccgaag gagctaaccg cttttttgca   6180

caacatgggg gatcatgtaa ctcgccttga tcgttgggaa ccggagctga atgaagccat   6240

accaaacgac gagcgtgaca ccacgatgcc tgtagcaatg gcaacaacgt tgcgcaaact   6300

attaactggc gaactactta ctctagcttc ccggcaacaa ttaatagact ggatggaggc   6360

ggataaagtt gcaggaccac ttctgcgctc ggcccttccg gctggctggt ttattgctga   6420

taaatctgga gccggtgagc gtgggtctcg cggtatcatt gcagcactgg ggccagatgg   6480

taagccctcc cgtatcgtag ttatctacac gacggggagt caggcaacta tggatgaacg   6540

aaatagacag atcgctgaga taggtgcctc actgattaag cattggtaac tgtcagacca   6600

agtttactca tatatacttt agattgattt aaaacttcat ttttaattta aaaggatcta   6660

ggtgaagatc ctttttgata atctcatgac caaaatccct taacgtgagt tttcgttcca   6720

ctgagcgtca gaccccgtag aaaagatcaa aggatcttct tgagatcctt tttttctgcg   6780

cgtaatctgc tgcttgcaaa caaaaaaacc accgctacca gcggtggttt gtttgccgga   6840

tcaagagcta ccaactcttt ttccgaaggt aactggcttc agcagagcgc agataccaaa   6900

tactgtcctt ctagtgtagc cgtagttagg ccaccacttc aagaactctg tagcaccgcc   6960

tacatacctc gctctgctaa tcctgttacc agtggctgct gccagtggcg ataagtcgtg   7020

tcttaccggg ttggactcaa gacgatagtt accggataag gcgcagcggt cgggctgaac   7080

ggggggttcg tgcacacagc ccagcttgga gcgaacgacc tacaccgaac tgagatacct   7140

acagcgtgag ctatgagaaa gcgccacgct tcccgaaggg agaaaggcgg acaggtatcc   7200

ggtaagcggc agggtcggaa caggagagcg cacgagggag cttccagggg gaaacgcctg   7260

gtatctttat agtcctgtcg ggtttcgcca cctctgactt gagcgtcgat ttttgtgatg   7320

ctcgtcaggg gggcggagcc tatggaaaaa cgccagcaac gcggcctttt tacggttcct   7380

ggccttttgc tggccttttg ctcacatgt                                     7409
```

<210> SEQ ID NO 51
<211> LENGTH: 6733

<212> TYPE: DNA
<213> ORGANISM: artificial sequence
<220> FEATURE:
<223> OTHER INFORMATION: CN2008 - The portion between L-ITR and R-ITR corresponds to positions 142-3995

<400> SEQUENCE: 51

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggtac cctaaataaa gatggctttt    180
tagtattaaa agtggaagaa aattacaggt aattatcttt gacggtaaaa acgctgtaat    240
cagcgggcta catgaaaaat tactctaatt atggctgcat ttaagagaat ggctaaataa    300
agatggcttt ttagtattaa aagtggaaga aaattacagg taattatctt tgacggtaaa    360
aacgctgtaa tcagcgggct acatgaaaaa ttactctaat tatggctgca tttaagagaa    420
tggctaaata aagatggctt tttagtatta aaagtggaag aaaattacag gtaattatct    480
ttgacggtaa aaacgctgta atcagcgggc tacatgaaaa attactctaa ttatggctgc    540
atttaagaga atggagctcg ggctggtcga cacaattgga ggtaggcgtg tacggtggga    600
ggcctatata agcagagctc gtttagtgaa ccgtcagatc gcctggagga tccttcgaaa    660
agcttgctac cggtgccacc atggagcaaa cagtgcttgt accaccagga cctgacagct    720
tcaacttctt caccagagaa tctcttgcgg ctattgaaag acgcattgca gaagaaaagg    780
caaagaatcc caaaccagac aaaaaagatg acgacgaaaa tggcccaaag ccaaatagtg    840
acttggaagc tggaaagaac cttccattta tttatggaga cattcctcca gagatggtgt    900
cagagcccct ggaggacctg gacccctact atatcaataa gaaaactttt atagtattga    960
ataaagggaa ggccatcttc cggttcagtg ccacctctgc cctgtacatt ttaactccct   1020
tcaatcctct taggaaaata gctattaaga ttttggtaca ttcattattc agcatgctaa   1080
ttatgtgcac tattttgaca aactgtgtgt ttatgacaat gagtaaccct cctgattgga   1140
caaagaatgt agaatacacc ttcacaggaa tatatacttt tgaatcactt ataaaaatta   1200
ttgcaagggg attctgttta gaagatttta ctttccttcg ggatccatgg aactggctcg   1260
atttcactgt cattacattt gcgtacgtca cagagtttgt ggacctgggc aatgtctcgg   1320
cattgagaac attcagagtt ctccgagcat tgaagacgat ttcagtcatt ccaggcctga   1380
aaaccattgt gggagccctg atccagtctg tgaagaagct ctcagatgta atgatcctga   1440
ctgtgttctg tctgagcgta tttgctctaa ttgggctgca gctgttcatg ggcaacctga   1500
ggaataaatg tatacaatgg cctcccacca atgcttcctt ggaggaacat agtatagaaa   1560
agaatataac tgtgaattat aatggtacac ttataaatga aactgtcttt gagtttgact   1620
ggaagtcata tattcaagat tcaagatatc attatttcct ggagggtttt ttagatgcac   1680
tactatgtgg aaatagctct gatgcaggcc aatgtccaga gggatatatg tgtgtgaaag   1740
ctggtagaaa tcccaattat ggctacacaa gctttgatac cttcagttgg gctttttgt    1800
ccttgtttcg actaatgact caggacttct gggaaaatct ttatcaactg acattacgtg   1860
ctgctgggaa aacgtacatg atattttttg tattggtcat tttcttgggc tcattctacc   1920
taataaattt gatcctggct gtggtggcca tggcctacga ggaacagaat caggccacct   1980
tggaagaagc agaacagaaa gaggccgaat ttcagcagat gattgaacag cttaaaaagc   2040
aacaggaggc agctcagcag gcagcaacgg caactgcctc agaacattcc agagagccca   2100
gtgcagcagg caggctctca gacagctcat ctgaagcctc taagttgagt tccaagagtg   2160
```

```
ctaaggaaag aagaaatcgg aggaagaaaa gaaaacagaa agagcagtct ggtggggaag   2220
agaaagatga ggatgaattc caaaaatctg aatctgagga cagcatcagg aggaaaggtt   2280
ttcgcttctc cattgaaggg aaccgattga catatgaaaa gaggtactcc tccccacacc   2340
agtctttgtt gagcatccgt ggctccctat tttcaccaag gcgaaatagc agaacaagcc   2400
ttttcagctt tagagggcga gcaaaggatg tgggatctga gaacgacttc gcagatgatg   2460
agcacagcac ctttgaggat aacgagagcc gtagagattc cttgtttgtg ccccgacgac   2520
acggagagag acgcaacagc aacctgagtc agaccagtag gtcatcccgg atgctggcag   2580
tgtttccagc gaatgggaag atgcacagca ctgtggattg caatggtgtg gtttccttgg   2640
ttggtggacc ttcagttcct acatcgcctg ttggacagct tctgccagag gtgataatag   2700
ataagccagc tactgatgac aatggaacaa ccactgaaac tgaaatgaga aagagaaggt   2760
caagttcttt ccacgtttcc atggactttc tagaagatcc ttcccaaagg caacgagcaa   2820
tgagtatagc cagcattcta acaaatacag tagaagaact tgaagaatcc aggcagaaat   2880
gcccaccctg ttggtataaa ttttccaaca tattcttaat ctgggactgt tctccatatt   2940
ggttaaaagt gaaacatgtt gtcaacctgg ttgtgatgga cccatttgtt gacctggcca   3000
tcaccatctg tattgtctta aatactcttt tcatggccat ggagcactat ccaatgacgg   3060
accatttcaa taatgtgctt acagtaggaa acttggtttt cactgggatc tttacagcag   3120
aaatgtttct gaaaattatt gccatggatc cttactatta tttccaagaa ggctggaata   3180
tctttgacgg ttttattgtg acgcttagcc tggtagaact tggactcgcc aatgtggaag   3240
gattatctgt tctccgttca tttcgattgc tgcgagtttt caagttggca aaatcttggc   3300
caacgttaaa tatgctaata aagatcatcg gcaattccgt gggggctctg ggaaatttaa   3360
ccctcgtctt ggccatcatc gtcttcattt ttgccgtggt cgtgagtttg gggacccttg   3420
attgttcttt ctttttcgct attgtaaaat tcatgttata tggagggggc aaagttttca   3480
gggtgttgtt tagaatggga agatgtccct tgtatcacca tggaccctca tgataatttt   3540
gtttctttca ctttctactc tgttgacaac cattgtctcc tcttattttc ttttcatttt   3600
ctgtaacttt ttcgttaaac tttagcttgc atttgtaacg aatttttaaa ttcacttttg   3660
tttatttgtc agattgtaag tactttctct aatcactttt ttttcaaggc aatcagggta   3720
tattatattg tacttcagca cagttttaga gaacaattgt tataattaaa tgataaggta   3780
gaatatttct gcatataaat tctggctggc gtggaaatat tcttattggt agaaacaact   3840
acaccctggt catcatcctg cctttctctt tatggttaca atgatataca ctgtttgaga   3900
tgaggataaa atactctgag tccaaaccgg gcccctctgc taaccatgtt catgccttct   3960
tctctttcct actcacgtgc ggaccgagcg gccgcaggaa cccctagtga tggagttggc   4020
cactccctct ctgcgcgctc gctcgctcac tgaggccggg cgaccaaagg tcgcccgacg   4080
cccgggcttt gcccgggcgg cctcagtgag cgagcgagcg cgcagctgcc tgcaggggcg   4140
cctgatgcgg tattttctcc ttacgcatct gtgcggtatt tcacaccgca tacgtcaaag   4200
caaccatagt acgcgccctg tagcggcgca ttaagcgcgg cgggtgtggt ggttacgcgc   4260
agcgtgaccg ctacacttgc cagcgcccta gcgcccgctc ctttcgcttt cttcccttcc   4320
tttctcgcca cgttcgccgg ctttccccgt caagctctaa atcgggggct ccctttaggg   4380
ttccgattta gtgctttacg gcacctcgac cccaaaaaac ttgatttggg tgatggttca   4440
cgtagtgggc catcgccctg atagacggtt tttcgccctt tgacgttgga gtccacgttc   4500
```

```
tttaatagtg gactcttgtt ccaaactgga acaacactca accctatctc gggctattct   4560

tttgatttat aagggatttt gccgatttcg gcctattggt taaaaaatga gctgatttaa   4620

caaaaattta acgcgaattt taacaaaata ttaacgttta caattttatg gtgcactctc   4680

agtacaatct gctctgatgc cgcatagtta agccagcccc gacacccgcc aacacccgct   4740

gacgcgccct gacgggcttg tctgctcccg gcatccgctt acagacaagc tgtgaccgtc   4800

tccgggagct gcatgtgtca gaggttttca ccgtcatcac cgaaacgcgc gagacgaaag   4860

ggcctcgtga tacgcctatt tttataggtt aatgtcatga taataatggt ttcttagacg   4920

tcaggtggca cttttcgggg aaatgtgcgc ggaaccccta tttgtttatt tttctaaata   4980

cattcaaata tgtatccgct catgagacaa taaccctgat aaatgcttca ataatattga   5040

aaaaggaaga gtatgagtat tcaacatttc cgtgtcgccc ttattccctt ttttgcggca   5100

ttttgccttc ctgtttttgc tcacccagaa acgctggtga aagtaaaaga tgctgaagat   5160

cagttgggtg cacgagtggg ttacatcgaa ctggatctca acagcggtaa gatccttgag   5220

agttttcgcc ccgaagaacg ttttccaatg atgagcactt ttaaagttct gctatgtggc   5280

gcggtattat cccgtattga cgccgggcaa gagcaactcg gtcgccgcat acactattct   5340

cagaatgact tggttgagta ctcaccagtc acagaaaagc atcttacgga tggcatgaca   5400

gtaagagaat tatgcagtgc tgccataacc atgagtgata acactgcggc caacttactt   5460

ctgacaacga tcggaggacc gaaggagcta accgcttttt tgcacaacat gggggatcat   5520

gtaactcgcc ttgatcgttg ggaaccggag ctgaatgaag ccataccaaa cgacgagcgt   5580

gacaccacga tgcctgtagc aatggcaaca acgttgcgca aactattaac tggcgaacta   5640

cttactctag cttcccggca acaattaata gactggatgg aggcggataa agttgcagga   5700

ccacttctgc gctcggccct tccggctggc tggtttattg ctgataaatc tggagccggt   5760

gagcgtgggt ctcgcggtat cattgcagca ctggggccag atggtaagcc ctcccgtatc   5820

gtagttatct acacgacggg gagtcaggca actatggatg aacgaaatag acagatcgct   5880

gagataggtg cctcactgat taagcattgg taactgtcag accaagttta ctcatatata   5940

ctttagattg atttaaaact tcatttttaa tttaaaagga tctaggtgaa gatccttttt   6000

gataatctca tgaccaaaat cccttaacgt gagttttcgt tccactgagc gtcagacccc   6060

gtagaaaaga tcaaaggatc ttcttgagat cctttttttc tgcgcgtaat ctgctgcttg   6120

caaacaaaaa aaccaccgct accagcggtg gtttgtttgc cggatcaaga gctaccaact   6180

ctttttccga aggtaactgg cttcagcaga gcgcagatac caaatactgt ccttctagtg   6240

tagccgtagt taggccacca cttcaagaac tctgtagcac cgcctacata cctcgctctg   6300

ctaatcctgt taccagtggc tgctgccagt ggcgataagt cgtgtcttac cgggttggac   6360

tcaagacgat agttaccgga taaggcgcag cggtcgggct gaacgggggg ttcgtgcaca   6420

cagcccagct tggagcgaac gacctacacc gaactgagat acctacagcg tgagctatga   6480

gaaagcgcca cgcttcccga agggagaaag gcggacaggt atccggtaag cggcagggtc   6540

ggaacaggag agcgcacgag ggagcttcca gggggaaacg cctggtatct ttatagtcct   6600

gtcgggtttc gccacctctg acttgagcgt cgatttttgt gatgctcgtc aggggggcgg   6660

agcctatgga aaaacgccag caacgcggcc tttttacggt tcctggcctt ttgctggcct   6720

tttgctcaca tgt                                                      6733
```

<210> SEQ ID NO 52
<211> LENGTH: 7263

<212> TYPE: DNA
<213> ORGANISM: artificial sequence
<220> FEATURE:
<223> OTHER INFORMATION: CN2009 - The portion between L-ITR and R-ITR corresponds to positions 142-4525

<400> SEQUENCE: 52

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca gagtttgggg acccttgatt gttctttctt    180
tttcgctatt gtaaaattca tgttatatgg agggggcaaa gttttcaggg tgttgtttag    240
aatgggaaga tgtcccttgt atcaccatgg accctcatga taatttttgtt tctttcactt    300
tctactctgt tgacaaccat tgtctcctct tattttcttt tcattttctg taactttttc    360
gttaaacttt agcttgcatt tgtaacgaat ttttaaattc acttttgttt atttgtcaga    420
ttgtaagtac tttctctaat cacttttttt tcaaggcaat cagggtatat tatattgtac    480
ttcagcacag ttttagagaa caattgttat aattaaatga taaggtagaa tatttctgca    540
tataaattct ggctggcgtg gaaatattct tattggtaga aacaactaca ccctggtcat    600
catcctgcct ttctctttat ggttacaatg atatacactg tttgagatga ggataaaata    660
ctctgagtcc aaaccgggcc cctctgctaa ccatgttcat gccttcttct ctttcctaca    720
gggcatgcag ctctttggta aaagctacaa agattgtgtc tgcaagatcg ccagtgattg    780
tcaactccca cgctggcaca tgaatgactt cttccactcc ttcctgattg tgttccgcgt    840
gctgtgtggg gagtggatag agaccatgtg ggactgtatg gaggttgctg gtcaagccat    900
gtgccttact gtcttcatga tggtcatggt gattggaaac ctagtggtcc tgaatctctt    960
tctggccttg cttctgagct catttagtgc agacaacctt gcagccactg atgatgataa   1020
tgaaatgaat aatctccaaa ttgctgtgga taggatgcac aaaggagtag cttatgtgaa   1080
aagaaaaata tatgaattta ttcaacagtc cttcattagg aaacaaaaga ttttagatga   1140
aattaaacca cttgatgatc taaacaacaa gaaagacagt tgtatgtcca atcatacagc   1200
agaaattggg aaagatcttg actatcttaa agatgtaaat ggaactacaa gtggtatagg   1260
aactggcagc agtgttgaat acattattga tgaaagtgat tacatgtcat tcataaacaa   1320
ccccagtctt actgtgactg taccaattgc tgtaggagaa tctgactttg aaaatttaaa   1380
cacggaagac tttagtagtg aatcggatct ggaagaaagc aaagagaaac tgaatgaaag   1440
cagtagctca tcagaaggta gcactgtgga catcggcgca cctgtagaag aacagcccgt   1500
agtggaacct gaagaaactc ttgaaccaga agcttgtttc actgaaggct gtgtacaaag   1560
attcaagtgt tgtcaaatca atgtggaaga aggcagagga aaacaatggt ggaacctgag   1620
aaggacgtgt ttccgaatag ttgaacataa ctggtttgag accttcattg ttttcatgat   1680
tctccttagt agtggtgctc tggcatttga agatatatat attgatcagc gaaagacgat   1740
taagacgatg ttggaatatg ctgacaaggt tttcacttac attttcattc tggaaatgct   1800
tctaaaatgg gtggcatatg gctatcaaac atatttcacc aatgcctggt gttggctgga   1860
cttcttaatt gttgatgttt cattggtcag tttaacagca aatgccttgg gttactcaga   1920
acttggagcc atcaaatctc tcaggacact aagagctctg agacctctaa gagccttatc   1980
tcgatttgaa gggatgaggg tggttgtgaa tgccctttta ggagcaattc catccatcat   2040
gaatgtgctt ctggtttgtc ttatattctg gctaattttc agcatcatgg gcgtaaattt   2100
gtttgctggc aaattctacc actgtattaa caccacaact ggtgacaggt ttgacatcga   2160
```

```
agacgtgaat aatcatactg attgcctaaa actaatagaa agaaatgaga ctgctcgatg   2220
gaaaaatgtg aaagtaaact ttgataatgt aggatttggg tatctctctt tgcttcaagt   2280
tgccacattc aaaggatgga tggatataat gtatgcagca gttgattcca gaaatgtgga   2340
actccagcct aagtatgaag aaagtctgta catgtatctt tactttgtta ttttcatcat   2400
ctttgggtcc ttcttcacct tgaacctgtt tattggtgtc atcatagata atttcaacca   2460
gcagaaaaag aagtttggag gtcaagacat ctttatgaca gaagaacaga agaaatacta   2520
taatgcaatg aaaaaattag gatcgaaaaa accgcaaaag cctatacctc gaccaggaaa   2580
caaatttcaa ggaatggtct ttgacttcgt aaccagacaa gtttttgaca taagcatcat   2640
gattctcatc tgtcttaaca tggtcacaat gatggtggaa acagatgacc agagtgaata   2700
tgtgactacc attttgtcac gcatcaatct ggtgttcatt gtgctattta ctggagagtg   2760
tgtactgaaa ctcatctctc tacgccatta ttattttacc attggatgga atatttttga   2820
ttttgtggtt gtcattctct ccattgtagg tatgtttctt gccgagctga tagaaaagta   2880
tttcgtgtcc cctaccctgt tccgagtgat ccgtcttgct aggattggcc gaatcctacg   2940
tctgatcaaa ggagcaaagg ggatccgcac gctgctcttt gctttgatga tgtcccttcc   3000
tgcgttgttt aacatcggcc tcctactctt cctagtcatg ttcatctacg ccatctttgg   3060
gatgtccaac tttgcctatg ttaagaggga agttgggatc gatgacatgt tcaactttga   3120
gacctttggc aacagcatga tctgcctatt ccaaattaca acctctgctg gctgggatgg   3180
attgctagca cccattctca acagtaagcc acccgactgt gaccctaata aagttaaccc   3240
tggaagctca gttaagggag actgtgggaa cccatctgtt ggaattttct tttttgtcag   3300
ttacatcatc atatccttcc tggttgtggt gaacatgtac atcgcggtca tcctggagaa   3360
cttcagtgtt gctactgaag aaagtgcaga gcctctgagt gaggatgact ttgagatgtt   3420
ctatgaggtt tgggagaagt ttgatcccga tgcaactcag ttcatggaat ttgaaaaatt   3480
atctcagttt gcagctgcgc ttgaaccgcc tctcaatctg ccacaaccaa acaaactcca   3540
gctcattgcc atggatttgc ccatggtgag tggtgaccgg atccactgtc ttgatatctt   3600
atttgctttt acaaagcggg ttctaggaga gagtggagag atggatgctc tacgaataca   3660
gatggaagag cgattcatgg cttccaatcc ttccaaggtc tcctatcagc caatcactac   3720
tactttaaaa cgaaaacaag aggaagtatc tgctgtcatt attcagcgtg cttacagacg   3780
ccacctttta aagcgaactg taaaacaagc ttcctttacg tacaataaaa acaaaatcaa   3840
aggtggggct aatcttctta taaaagaaga catgataatt gacagaataa atgaaaactc   3900
tattacagaa aaaactgatc tgaccatgtc cactgcagct tgtccacctt cctatgaccg   3960
ggtgacaaag ccaattgtgg aaaaacatga gcaagaaggc aaagatgaaa aagccaaagg   4020
gaaataatga catcataatc aacctctgga ttacaaaatt tgtgaaagat tgactggtat   4080
tcttaactat gttgctcctt ttacgctatg tggatacgct gctttaatgc ctttgtatca   4140
tgctattgct tcccgtatgg ctttcatttt ctcctccttg tataaatcct ggttagttct   4200
tgccacggcg gaactcatcg ccgcctgcct tgcccgctgc tggacagggg ctcggctgtt   4260
gggcactgac aattccgtgg ctcgagagat cttcgactgt gccttctagt tgccagccat   4320
ctgttgtttg cccctccccc gtgccttcct tgaccctgga aggtgccact cccactgtcc   4380
tttcctaata aaatgaggaa attgcatcgc attgtctgag taggtgtcat tctattctgg   4440
ggggtggggt ggggcaggac agcaaggggg aggattggga agacaatagc aggcatgaga   4500
```

```
tctcacgtgc ggaccgagcg gccgcaggaa cccctagtga tggagttggc cactccctct   4560
ctgcgcgctc gctcgctcac tgaggccggg cgaccaaagg tcgcccgacg cccgggcttt   4620
gcccgggcgg cctcagtgag cgagcgagcg cgcagctgcc tgcaggggcg cctgatgcgg   4680
tattttctcc ttacgcatct gtgcggtatt tcacaccgca tacgtcaaag caaccatagt   4740
acgcgccctg tagcggcgca ttaagcgcgg cgggtgtggt ggttacgcgc agcgtgaccg   4800
ctacacttgc cagcgcccta gcgcccgctc ctttcgcttt cttcccttcc tttctcgcca   4860
cgttcgccgg ctttccccgt caagctctaa atcgggggct ccctttaggg ttccgattta   4920
gtgctttacg gcacctcgac cccaaaaaac ttgatttggg tgatggttca cgtagtgggc   4980
catcgccctg atagacggtt tttcgccctt tgacgttgga gtccacgttc tttaatagtg   5040
gactcttgtt ccaaactgga acaacactca accctatctc gggctattct tttgatttat   5100
aagggatttt gccgatttcg gcctattggt taaaaaatga gctgatttaa caaaaattta   5160
acgcgaattt taacaaaata ttaacgttta caattttatg gtgcactctc agtacaatct   5220
gctctgatgc cgcatagtta agccagcccc gacacccgcc aacacccgct gacgcgccct   5280
gacgggcttg tctgctcccg gcatccgctt acagacaagc tgtgaccgtc tccgggagct   5340
gcatgtgtca gaggttttca ccgtcatcac cgaaacgcgc gagacgaaag ggcctcgtga   5400
tacgcctatt tttataggtt aatgtcatga taataatggt ttcttagacg tcaggtggca   5460
cttttcgggg aaatgtgcgc ggaaccccta tttgtttatt tttctaaata cattcaaata   5520
tgtatccgct catgagacaa taaccctgat aaatgcttca ataatattga aaaaggaaga   5580
gtatgagtat tcaacatttc cgtgtcgccc ttattccctt ttttgcggca ttttgccttc   5640
ctgtttttgc tcacccagaa acgctggtga aagtaaaaga tgctgaagat cagttgggtg   5700
cacgagtggg ttacatcgaa ctggatctca acagcggtaa gatccttgag agttttcgcc   5760
ccgaagaacg ttttccaatg atgagcactt ttaaagttct gctatgtggc gcggtattat   5820
cccgtattga cgccgggcaa gagcaactcg gtcgccgcat acactattct cagaatgact   5880
tggttgagta ctcaccagtc acagaaaagc atcttacgga tggcatgaca gtaagagaat   5940
tatgcagtgc tgccataacc atgagtgata acactgcggc caacttactt ctgacaacga   6000
tcggaggacc gaaggagcta accgcttttt tgcacaacat gggggatcat gtaactcgcc   6060
ttgatcgttg ggaaccggag ctgaatgaag ccataccaaa cgacgagcgt gacaccacga   6120
tgcctgtagc aatggcaaca acgttgcgca aactattaac tggcgaacta cttactctag   6180
cttcccggca acaattaata gactggatgg aggcggataa agttgcagga ccacttctgc   6240
gctcggccct tccggctggc tggtttattg ctgataaatc tggagccggt gagcgtgggt   6300
ctcgcggtat cattgcagca ctggggccag atggtaagcc ctcccgtatc gtagttatct   6360
acacgacggg gagtcaggca actatggatg aacgaaatag acagatcgct gagataggtg   6420
cctcactgat taagcattgg taactgtcag accaagttta ctcatatata ctttagattg   6480
atttaaaact tcatttttaa tttaaaagga tctaggtgaa gatccttttt gataatctca   6540
tgaccaaaat cccttaacgt gagttttcgt tccactgagc gtcagacccc gtagaaaaga   6600
tcaaaggatc ttcttgagat cctttttttc tgcgcgtaat ctgctgcttg caaacaaaaa   6660
aaccaccgct accagcggtg gtttgtttgc cggatcaaga gctaccaact ctttttccga   6720
aggtaactgg cttcagcaga gcgcagatac caaatactgt ccttctagtg tagccgtagt   6780
taggccacca cttcaagaac tctgtagcac cgcctacata cctcgctctg ctaatcctgt   6840
taccagtggc tgctgccagt ggcgataagt cgtgtcttac cgggttggac tcaagacgat   6900
```

```
agttaccgga taaggcgcag cggtcgggct gaacgggggg ttcgtgcaca cagcccagct   6960

tggagcgaac gacctacacc gaactgagat acctacagcg tgagctatga gaaagcgcca   7020

cgcttcccga agggagaaag gcggacaggt atccggtaag cggcagggtc ggaacaggag   7080

agcgcacgag ggagcttcca gggggaaacg cctggtatct ttatagtcct gtcgggtttc   7140

gccacctctg acttgagcgt cgatttttgt gatgctcgtc aggggggcgg agcctatgga   7200

aaaacgccag caacgcggcc tttttacggt tcctggcctt ttgctggcct tttgctcaca   7260

tgt                                                                  7263
```

```
<210> SEQ ID NO 53
<211> LENGTH: 7
<212> TYPE: PRT
<213> ORGANISM: artificial sequence
<220> FEATURE:
<223> OTHER INFORMATION: AAV-BR1

<400> SEQUENCE: 53

Asn Arg Gly Thr Glu Trp Asp
1               5


<210> SEQ ID NO 54
<211> LENGTH: 7
<212> TYPE: PRT
<213> ORGANISM: artificial sequence
<220> FEATURE:
<223> OTHER INFORMATION: AAV-PHP.S

<400> SEQUENCE: 54

Gln Ala Val Arg Thr Ser Leu
1               5


<210> SEQ ID NO 55
<211> LENGTH: 7
<212> TYPE: PRT
<213> ORGANISM: artificial sequence
<220> FEATURE:
<223> OTHER INFORMATION: AAV-PHP.B

<400> SEQUENCE: 55

Thr Leu Ala Val Pro Phe Lys
1               5


<210> SEQ ID NO 56
<211> LENGTH: 7
<212> TYPE: PRT
<213> ORGANISM: artificial sequence
<220> FEATURE:
<223> OTHER INFORMATION: AAV-PPS

<400> SEQUENCE: 56

Asp Ser Pro Ala His Pro Ser
1               5


<210> SEQ ID NO 57
<211> LENGTH: 736
<212> TYPE: PRT
<213> ORGANISM: artificial sequence
<220> FEATURE:
<223> OTHER INFORMATION: Capsid protein VP1 from Adeno-associated virus
      9 (AVV9)

<400> SEQUENCE: 57

Met Ala Ala Asp Gly Tyr Leu Pro Asp Trp Leu Glu Asp Asn Leu Ser
```

-continued

```
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

```
Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 58
<211> LENGTH: 5799
<212> TYPE: DNA
<213> ORGANISM: Artificial Sequence
<220> FEATURE:
<223> OTHER INFORMATION: CN2027-rAAV-3xhI56i(core)-minBG-hSCN1A_Fragment2-WPRE3-BGHpA

<400> SEQUENCE: 58

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300
```

-continued

```
agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctgggcat aaaagtcagg gcagagccat ctattgctta    600

catttgcttc tgggatccag atctttcgaa gctagcgcta ccaccatgga gcaaacagtg    660

cttgtaccac caggacctga cagcttcaac ttcttcacca gagaatctct tgcggctatt    720

gaaagacgca ttgcagaaga aaaggcaaag aatcccaaac cagacaaaaa agatgacgac    780

gaaaatggcc caaagccaaa tagtgacttg gaagctggaa agaaccttcc atttatttat    840

ggagacattc ctccagagat ggtgtcagag cccctggagg acctggaccc ctactatatc    900

aataagaaaa cttttatagt attgaataaa gggaaggcca tcttccggtt cagtgccacc    960

tctgccctgt acattttaac tcccttcaat cctcttagga aaatagctat taagattttg   1020

gtacattcat tattcagcat gctaattatg tgcactattt tgacaaactg tgtgtttatg   1080

acaatgagta accctcctga ttggacaaag aatgtagaat acaccttcac aggaatatat   1140

acttttgaat cacttataaa aattattgca aggggattct gtttagaaga ttttactttc   1200

cttcgggatc catggaactg gctcgatttc actgtcatta catttgcgta cgtcacagag   1260

tttgtggacc tgggcaatgt ctcggcattg agaacattca gagttctccg agcattgaag   1320

acgatttcag tcattccagg cctgaaaacc attgtgggag ccctgatcca gtctgtgaag   1380

aagctctcag atgtaatgat cctgactgtg ttctgtctga gcgtatttgc tctaattggg   1440

ctgcagctgt tcatgggcaa cctgaggaat aaatgtatac aatggcctcc caccaatgct   1500

tccttggagg aacatagtat agaaaagaat ataactgtga attataatgg tacacttata   1560

aatgaaactg tctttgagtt tgactggaag tcatatattc aagattcaag atatcattat   1620

ttcctggagg gtttttaga tgcactacta tgtggaaata gctctgatgc aggccaatgt   1680

ccagagggat atatgtgtgt gaaagctggt agaaatccca attatggcta cacaagcttt   1740

gataccttca gttgggcttt tttgtccttg tttcgactaa tgactcagga cttctgggaa   1800

aatctttatc aactgacatt acgtgctgct gggaaaacgt acatgatatt ttttgtgttg   1860

gtcattttct tgggctcatt ctacctaata aatttgatcc tggctgtggt ggccatggcc   1920

tacgaggaac agaatcaggc caccttggaa gaagcagaac agaaagaggc cgaatttcag   1980

cagatgattg aacagcttaa aaagcaacag gaggcagctc agcaggcagc aacggcaact   2040

gcctcagaac attccagaga gcccagtgca gcaggcaggc tctcagacag ctcatctgaa   2100

gcctctaagt tgagttccaa gagtgctaag gaaagaagaa atcggaggaa gaaaagaaaa   2160

cagaaagagc agtctggtgg ggaagagaaa gatgaggatg aattccaaaa atctgaatct   2220

gaggacagca tcaggaggaa aggttttcgc ttctccattg aagggaaccg attgacatat   2280

gaaaagaggt actcctcccc acaccagtct ttgttgagca tccgtggctc cctattttca   2340

ccaaggcgaa atagcagaac aagccttttc agctttagag ggcgagcaaa ggatgtggga   2400

tctgagaacg acttcgcaga tgatgagcac agcacctttg aggataacga gagccgtaga   2460

gattccttgt ttgtgccccg acgacacgga gagagacgca acagcaacct gagtcagacc   2520

agtaggtcat cccggtgatg acggcgcgcc gcggccgcga attcgatatc ataatcaacc   2580

tctggattac aaaatttgtg aaagattgac tggtattctt aactatgttg ctccttttac   2640

gctatgtgga tacgctgctt taatgccttt gtatcatgct attgcttccc gtatggcttt   2700
```

```
cattttctcc tccttgtata aatcctggtt agttcttgcc acggcggaac tcatcgccgc   2760
ctgccttgcc cgctgctgga caggggctcg gctgttgggc actgacaatt ccgtggctcg   2820
agagatcttc gactgtgcct tctagttgcc agccatctgt tgtttgcccc tcccccgtgc   2880
cttccttgac cctggaaggt gccactccca ctgtcctttc ctaataaaat gaggaaattg   2940
catcgcattg tctgagtagg tgtcattcta ttctgggggg tggggtgggg caggacagca   3000
agggggagga ttgggaagac aatagcaggc atgagatctc acgtgcggac cgagcggccg   3060
caggaacccc tagtgatgga gttggccact ccctctctgc gcgctcgctc gctcactgag   3120
gccgggcgac caaaggtcgc ccgacgcccg ggctttgccc gggcggcctc agtgagcgag   3180
cgagcgcgca gctgcctgca ggggcgcctg atgcggtatt ttctccttac gcatctgtgc   3240
ggtatttcac accgcatacg tcaaagcaac catagtacgc gccctgtagc ggcgcattaa   3300
gcgcggcggg tgtggtggtt acgcgcagcg tgaccgctac acttgccagc gccctagcgc   3360
ccgctccttt cgctttcttc ccttcctttc tcgccacgtt cgccggcttt ccccgtcaag   3420
ctctaaatcg ggggctccct ttagggttcc gatttagtgc tttacggcac ctcgacccca   3480
aaaaacttga tttgggtgat ggttcacgta gtgggccatc gccctgatag acggtttttc   3540
gccctttgac gttggagtcc acgttcttta atagtggact cttgttccaa actggaacaa   3600
cactcaaccc tatctcgggc tattcttttg atttataagg gattttgccg atttcggcct   3660
attggttaaa aaatgagctg atttaacaaa aatttaacgc gaattttaac aaaatattaa   3720
cgtttacaat tttatggtgc actctcagta caatctgctc tgatgccgca tagttaagcc   3780
agccccgaca cccgccaaca cccgctgacg cgccctgacg ggcttgtctg ctcccggcat   3840
ccgcttacag acaagctgtg accgtctccg ggagctgcat gtgtcagagg ttttcaccgt   3900
catcaccgaa acgcgcgaga cgaaagggcc tcgtgatacg cctattttta taggttaatg   3960
tcatgataat aatggtttct tagacgtcag gtggcacttt tcggggaaat gtgcgcggaa   4020
cccctatttg tttatttttc taaatacatt caaatatgta tccgctcatg agacaataac   4080
cctgataaat gcttcaataa tattgaaaaa ggaagagtat gagtattcaa catttccgtg   4140
tcgcccttat tccctttttt gcggcatttt gccttcctgt ttttgctcac ccagaaacgc   4200
tggtgaaagt aaaagatgct gaagatcagt tgggtgcacg agtgggttac atcgaactgg   4260
atctcaacag cggtaagatc cttgagagtt ttcgccccga agaacgtttt ccaatgatga   4320
gcacttttaa agttctgcta tgtggcgcgg tattatcccg tattgacgcc gggcaagagc   4380
aactcggtcg ccgcatacac tattctcaga atgacttggt tgagtactca ccagtcacag   4440
aaaagcatct tacggatggc atgacagtaa gagaattatg cagtgctgcc ataaccatga   4500
gtgataacac tgcggccaac ttacttctga caacgatcgg aggaccgaag gagctaaccg   4560
cttttttgca caacatgggg gatcatgtaa ctcgccttga tcgttgggaa ccggagctga   4620
atgaagccat accaaacgac gagcgtgaca ccacgatgcc tgtagcaatg gcaacaacgt   4680
tgcgcaaact attaactggc gaactactta ctctagcttc ccggcaacaa ttaatagact   4740
ggatggaggc ggataaagtt gcaggaccac ttctgcgctc ggcccttccg gctggctggt   4800
ttattgctga taaatctgga gccggtgagc gtgggtctcg cggtatcatt gcagcactgg   4860
ggccagatgg taagccctcc cgtatcgtag ttatctacac gacggggagt caggcaacta   4920
tggatgaacg aaatagacag atcgctgaga taggtgcctc actgattaag cattggtaac   4980
tgtcagacca agtttactca tatatacttt agattgattt aaaacttcat ttttaattta   5040
```

```
aaaggatcta ggtgaagatc ctttttgata atctcatgac caaaatccct taacgtgagt   5100

tttcgttcca ctgagcgtca gaccccgtag aaaagatcaa aggatcttct tgagatcctt   5160

tttttctgcg cgtaatctgc tgcttgcaaa caaaaaaacc accgctacca gcggtggttt   5220

gtttgccgga tcaagagcta ccaactcttt ttccgaaggt aactggcttc agcagagcgc   5280

agataccaaa tactgtcctt ctagtgtagc cgtagttagg ccaccacttc aagaactctg   5340

tagcaccgcc tacatacctc gctctgctaa tcctgttacc agtggctgct gccagtggcg   5400

ataagtcgtg tcttaccggg ttggactcaa gacgatagtt accggataag gcgcagcggt   5460

cgggctgaac ggggggttcg tgcacacagc ccagcttgga gcgaacgacc tacaccgaac   5520

tgagatacct acagcgtgag ctatgagaaa gcgccacgct tcccgaaggg agaaaggcgg   5580

acaggtatcc ggtaagcggc agggtcggaa caggagagcg cacgagggag cttccagggg   5640

gaaacgcctg gtatctttat agtcctgtcg ggtttcgcca cctctgactt gagcgtcgat   5700

ttttgtgatg ctcgtcaggg gggcggagcc tatggaaaaa cgccagcaac gcggcctttt   5760

tacggttcct ggccttttgc tggccttttg ctcacatgt                         5799
```

```
<210> SEQ ID NO 59
<211> LENGTH: 5202
<212> TYPE: DNA
<213> ORGANISM: Artificial Sequence
<220> FEATURE:
<223> OTHER INFORMATION: CN2027-rAAV-3xhI56i(core)-minBG-
      hSCN1A_Fragment2-WPRE3-BGHpA

<400> SEQUENCE: 59
```

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480

ttgacggtaa aaacgctgta atcagcgggc tacatgaaaa attactctaa ttatggctgc    540

atttaagaga atggagctcg ggctgggcat aaaagtcagg gcagagccat ctattgctta    600

catttgcttc tgggatccag atctttcgaa gctagcgcta ccaccatgct ggcagtgttt    660

ccagcgaatg ggaagatgca cagcactgtg gattgcaatg gtgtggtttc cttggttggt    720

ggaccttcag ttcctacatc gcctgttgga cagcttctgc cagaggtgat aatagataag    780

ccagctactg atgacaatgg aacaaccact gaaactgaaa tgagaaagag aaggtcaagt    840

tctttccacg tttccatgga ctttctagaa gatccttccc aaaggcaacg agcaatgagt    900

atagccagca ttctaacaaa tacagtagaa gaacttgaag aatccaggca gaaatgccca    960

ccctgttggt ataaattttc caacatattc ttaatctggg actgttctcc atattggtta   1020

aaagtgaaac atgttgtcaa cctggtcgtg atggacccat ttgttgacct ggccatcacc   1080

atctgtattg tcttaaatac tcttttcatg gccatggagc actatccaat gacggaccat   1140

ttcaataatg tgcttacagt aggaaacttg gttttcactg ggatctttac agcagaaatg   1200

tttctgaaaa ttattgccat ggatccttac tattatttcc aagaaggctg gaatatcttt   1260
```

```
gacggtttta ttgtgacgct tagcctggta gaacttggac tcgccaatgt ggaaggatta   1320
tctgttctcc gttcatttcg attgctgcga gttttcaagt tggcaaaatc ttggccaacg   1380
ttaaatatgc taataaagat catcggcaat tccgtggggg ctctgggaaa tttaaccctc   1440
gtcttggcca tcatcgtctt catttttgcc gtggtcggca tgcagctctt tggtaaaagc   1500
tacaaagatt gtgtctgcaa gatcgccagt gattgtcaac tcccacgctg gcacatgaat   1560
gacttcttcc actccttcct gattgtgttc cgcgtgctgt gtggggagtg gatagagacc   1620
atgtgggact gtatggaggt tgctggtcaa gccatgtgcc ttactgtctt catgatggtc   1680
atggtgattg gaaacctagt ggtcctgaat ctctttctgg ccttgcttct gagctcattt   1740
agtgcagaca accttgcagc cactgatgat gataatgaaa tgaataatct ccaaattgct   1800
gtggatagga tgcacaaagg agtagcttat gtgaaaagaa aaatatatga atttattcaa   1860
cagtccttca ttaggaaaca aaagatttta gatgaaatta aaccacttga tgatctaaac   1920
aacaagaaag acagttgttg atgacggcgc gccgcggccg cgaattcgat atcataatca   1980
acctctggat tacaaaattt gtgaaagatt gactggtatt cttaactatg ttgctccttt   2040
tacgctatgt ggatacgctg ctttaatgcc tttgtatcat gctattgctt cccgtatggc   2100
tttcattttc tcctccttgt ataaatcctg gttagttctt gccacggcgg aactcatcgc   2160
cgcctgcctt gcccgctgct ggacaggggc tcggctgttg ggcactgaca attccgtggc   2220
tcgagagatc ttcgactgtg ccttctagtt gccagccatc tgttgtttgc ccctcccccg   2280
tgccttcctt gaccctggaa ggtgccactc ccactgtcct ttcctaataa aatgaggaaa   2340
ttgcatcgca ttgtctgagt aggtgtcatt ctattctggg gggtggggtg gggcaggaca   2400
gcaaggggga ggattgggaa gacaatagca ggcatgagat ctcacgtgcg gaccgagcgg   2460
ccgcaggaac ccctagtgat ggagttggcc actccctctc tgcgcgctcg ctcgctcact   2520
gaggccgggc gaccaaaggt cgcccgacgc ccgggctttg cccgggcggc ctcagtgagc   2580
gagcgagcgc gcagctgcct gcaggggcgc ctgatgcggt attttctcct tacgcatctg   2640
tgcggtattt cacaccgcat acgtcaaagc aaccatagta cgcgccctgt agcggcgcat   2700
taagcgcggc gggtgtggtg gttacgcgca gcgtgaccgc tacacttgcc agcgccctag   2760
cgcccgctcc tttcgctttc ttcccttcct ttctcgccac gttcgccggc tttccccgtc   2820
aagctctaaa tcgggggctc cctttagggt tccgatttag tgctttacgg cacctcgacc   2880
ccaaaaaact tgatttgggt gatggttcac gtagtgggcc atcgccctga tagacggttt   2940
ttcgcccttt gacgttggag tccacgttct ttaatagtgg actcttgttc caaactggaa   3000
caacactcaa ccctatctcg ggctattctt ttgatttata agggattttg ccgatttcgg   3060
cctattggtt aaaaaatgag ctgatttaac aaaaatttaa cgcgaatttt aacaaaatat   3120
taacgtttac aattttatgg tgcactctca gtacaatctg ctctgatgcc gcatagttaa   3180
gccagccccg acacccgcca acacccgctg acgcgccctg acgggcttgt ctgctcccgg   3240
catccgctta cagacaagct gtgaccgtct ccgggagctg catgtgtcag aggttttcac   3300
cgtcatcacc gaaacgcgcg agacgaaagg gcctcgtgat acgcctattt ttataggtta   3360
atgtcatgat aataatggtt tcttagacgt caggtggcac ttttcgggga aatgtgcgcg   3420
gaacccctat ttgtttattt ttctaaatac attcaaatat gtatccgctc atgagacaat   3480
aaccctgata aatgcttcaa taatattgaa aaaggaagag tatgagtatt caacatttcc   3540
gtgtcgccct tattcccttt tttgcggcat tttgccttcc tgtttttgct cacccagaaa   3600
cgctggtgaa agtaaaagat gctgaagatc agttgggtgc acgagtgggt tacatcgaac   3660
```

```
tggatctcaa cagcggtaag atccttgaga gttttcgccc cgaagaacgt tttccaatga   3720

tgagcacttt taaagttctg ctatgtggcg cggtattatc ccgtattgac gccgggcaag   3780

agcaactcgg tcgccgcata cactattctc agaatgactt ggttgagtac tcaccagtca   3840

cagaaaagca tcttacggat ggcatgacag taagagaatt atgcagtgct gccataacca   3900

tgagtgataa cactgcggcc aacttacttc tgacaacgat cggaggaccg aaggagctaa   3960

ccgctttttt gcacaacatg ggggatcatg taactcgcct tgatcgttgg gaaccggagc   4020

tgaatgaagc cataccaaac gacgagcgtg acaccacgat gcctgtagca atggcaacaa   4080

cgttgcgcaa actattaact ggcgaactac ttactctagc ttcccggcaa caattaatag   4140

actggatgga ggcggataaa gttgcaggac cacttctgcg ctcggccctt ccggctggct   4200

ggtttattgc tgataaatct ggagccggtg agcgtgggtc tcgcggtatc attgcagcac   4260

tggggccaga tggtaagccc tcccgtatcg tagttatcta cacgacgggg agtcaggcaa   4320

ctatggatga acgaaataga cagatcgctg agataggtgc ctcactgatt aagcattggt   4380

aactgtcaga ccaagtttac tcatatatac tttagattga tttaaaactt catttttaat   4440

ttaaaaggat ctaggtgaag atcctttttg ataatctcat gaccaaaatc ccttaacgtg   4500

agttttcgtt ccactgagcg tcagaccccg tagaaaagat caaaggatct tcttgagatc   4560

cttttttct gcgcgtaatc tgctgcttgc aaacaaaaaa accaccgcta ccagcggtgg   4620

tttgtttgcc ggatcaagag ctaccaactc tttttccgaa ggtaactggc ttcagcagag   4680

cgcagatacc aaatactgtc cttctagtgt agccgtagtt aggccaccac ttcaagaact   4740

ctgtagcacc gcctacatac ctcgctctgc taatcctgtt accagtggct gctgccagtg   4800

gcgataagtc gtgtcttacc gggttggact caagacgata gttaccggat aaggcgcagc   4860

ggtcgggctg aacggggggt tcgtgcacac agcccagctt ggagcgaacg acctacaccg   4920

aactgagata cctacagcgt gagctatgag aaagcgccac gcttcccgaa gggagaaagg   4980

cggacaggta tccggtaagc ggcagggtcg gaacaggaga gcgcacgagg gagcttccag   5040

ggggaaacgc ctggtatctt tatagtcctg tcgggtttcg ccacctctga cttgagcgtc   5100

gatttttgtg atgctcgtca ggggggcgga gcctatggaa aaacgccagc aacgcggcct   5160

ttttacggtt cctggccttt tgctggcctt ttgctcacat gt                        5202
```

```
<210> SEQ ID NO 60
<211> LENGTH: 5223
<212> TYPE: DNA
<213> ORGANISM: Artificial Sequence
<220> FEATURE:
<223> OTHER INFORMATION: CN2028-rAAV-3xhI56i(core)-minBG-
      hSCN1A_Fragment3-WPRE3-BGHpA

<400> SEQUENCE: 60

cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtggtac cctaaataaa gatggctttt    180

tagtattaaa agtggaagaa aattacaggt aattatcttt gacggtaaaa acgctgtaat    240

cagcgggcta catgaaaaat tactctaatt atggctgcat ttaagagaat ggctaaataa    300

agatggcttt ttagtattaa aagtggaaga aaattacagg taattatctt tgacggtaaa    360

aacgctgtaa tcagcgggct acatgaaaaa ttactctaat tatggctgca tttaagagaa    420

tggctaaata aagatggctt tttagtatta aaagtggaag aaaattacag gtaattatct    480
```

```
ttgacggtaa aaacgctgta atcagcgggc tacatgaaaa attactctaa ttatggctgc    540
atttaagaga atggagctcg ggctgggcat aaaagtcagg gcagagccat ctattgctta    600
catttgcttc tgggatccag atctttcgaa gctagcgcta ccaccatgtc caatcataca    660
acagaaattg ggaaagatct tgactatctt aaagatgtaa atggaactac aagtggtata    720
ggaactggca gcagtgttga aaaatacatt attgatgaaa gtgattacat gtcattcata    780
aacaacccca gtcttactgt gactgtacca attgctgtag gagaatctga ctttgaaaat    840
ttaaacacgg aagactttag tagtgaatcg gatctggaag aaagcaaaga gaaactgaat    900
gaaagcagta gctcatcaga aggtagcact gtggacatcg gcgcacctgt agaagaacag    960
cccgtagtgg aacctgaaga aactcttgaa ccagaagctt gtttcactga aggctgtgta   1020
caaagattca agtgttgtca aatcaatgtg gaagaaggca gaggaaaaca atggtggaac   1080
ctgagaagga cgtgtttccg aatagttgaa cataactggt ttgagacctt cattgttttc   1140
atgattctcc ttagtagtgg tgctctggca tttgaagata tatatattga tcagcgaaag   1200
acgattaaga cgatgttgga atatgctgac aaggttttca cttacatttt cattctggaa   1260
atgcttctaa aatgggtggc atatggctat caaacatatt tcaccaatgc ctggtgttgg   1320
ctggacttct taattgttga tgtttcattg gtcagtttaa cagcaaatgc cttgggttac   1380
tcagaacttg gagccatcaa atctctcagg acactaagag ctctgagacc tctaagagcc   1440
ttatctcgat ttgaagggat gagggtggtt gtgaatgccc ttttaggagc aattccatcc   1500
atcatgaatg tgcttctggt ttgtcttata ttctggctaa ttttcagcat catgggcgta   1560
aatttgtttg ctggcaaatt ctaccactgt attaacacca caactggtga caggtttgac   1620
atcgaagacg tgaataatca tactgattgc ctaaaactaa tagaaagaaa tgagactgct   1680
cgatggaaaa atgtgaaagt aaactttgat aatgtaggat ttgggtatct ctctttgctt   1740
caagttgcca cattcaaagg atggatggat ataatgtatg cagcagttga ttccagaaat   1800
gtggaactcc agcctaagta tgaagaaagt ctgtacatgt atctttactt tgttattttc   1860
atcatctttg ggtccttctt caccttgaac ctgtttattg gtgtcatcat agataatttc   1920
aaccagcaga aaaagaagtt tggaggtcaa gacatctttt gatgacggcg cgccgcggcc   1980
gcgaattcga tatcataatc aacctctgga ttacaaaatt tgtgaaagat tgactggtat   2040
tcttaactat gttgctcctt ttacgctatg tggatacgct gctttaatgc ctttgtatca   2100
tgctattgct tcccgtatgg ctttcatttt ctcctccttg tataaatcct ggttagttct   2160
tgccacggcg gaactcatcg ccgcctgcct tgcccgctgc tggacagggg ctcggctgtt   2220
gggcactgac aattccgtgg ctcgagagat cttcgactgt gccttctagt tgccagccat   2280
ctgttgtttg cccctccccc gtgccttcct tgaccctgga aggtgccact cccactgtcc   2340
tttcctaata aaatgaggaa attgcatcgc attgtctgag taggtgtcat tctattctgg   2400
ggggtggggt ggggcaggac agcaaggggg aggattggga agacaatagc aggcatgaga   2460
tctcacgtgc ggaccgagcg gccgcaggaa cccctagtga tggagttggc cactccctct   2520
ctgcgcgctc gctcgctcac tgaggccggg cgaccaaagg tcgcccgacg cccgggcttt   2580
gcccgggcgg cctcagtgag cgagcgagcg cgcagctgcc tgcaggggcg cctgatgcgg   2640
tattttctcc ttacgcatct gtgcggtatt tcacaccgca tacgtcaaag caaccatagt   2700
acgcgccctg tagcggcgca ttaagcgcgg cgggtgtggt ggttacgcgc agcgtgaccg   2760
ctacacttgc cagcgcccta gcgcccgctc ctttcgcttt cttcccttcc tttctcgcca   2820
```

```
cgttcgccgg ctttccccgt caagctctaa atcgggggct ccctttaggg ttccgattta   2880
gtgctttacg gcacctcgac cccaaaaaac ttgatttggg tgatggttca cgtagtgggc   2940
catcgccctg atagacggtt tttcgccctt tgacgttgga gtccacgttc tttaatagtg   3000
gactcttgtt ccaaactgga acaacactca accctatctc gggctattct tttgatttat   3060
aagggatttt gccgatttcg gcctattggt taaaaaatga gctgatttaa caaaaattta   3120
acgcgaattt taacaaaata ttaacgttta caattttatg gtgcactctc agtacaatct   3180
gctctgatgc cgcatagtta agccagcccc gacacccgcc aacacccgct gacgcgccct   3240
gacgggcttg tctgctcccg gcatccgctt acagacaagc tgtgaccgtc tccgggagct   3300
gcatgtgtca gaggttttca ccgtcatcac cgaaacgcgc gagacgaaag ggcctcgtga   3360
tacgcctatt tttataggtt aatgtcatga taataatggt ttcttagacg tcaggtggca   3420
cttttcgggg aaatgtgcgc ggaaccccta tttgtttatt tttctaaata cattcaaata   3480
tgtatccgct catgagacaa taaccctgat aaatgcttca ataatattga aaaaggaaga   3540
gtatgagtat tcaacatttc cgtgtcgccc ttattccctt ttttgcggca ttttgccttc   3600
ctgtttttgc tcacccagaa acgctggtga aagtaaaaga tgctgaagat cagttgggtg   3660
cacgagtggg ttacatcgaa ctggatctca acagcggtaa gatccttgag agttttcgcc   3720
ccgaagaacg ttttccaatg atgagcactt ttaaagttct gctatgtggc gcggtattat   3780
cccgtattga cgccgggcaa gagcaactcg gtcgccgcat acactattct cagaatgact   3840
tggttgagta ctcaccagtc acagaaaagc atcttacgga tggcatgaca gtaagagaat   3900
tatgcagtgc tgccataacc atgagtgata acactgcggc caacttactt ctgacaacga   3960
tcggaggacc gaaggagcta accgcttttt tgcacaacat gggggatcat gtaactcgcc   4020
ttgatcgttg ggaaccggag ctgaatgaag ccataccaaa cgacgagcgt gacaccacga   4080
tgcctgtagc aatggcaaca acgttgcgca aactattaac tggcgaacta cttactctag   4140
cttcccggca acaattaata gactggatgg aggcggataa agttgcagga ccacttctgc   4200
gctcggccct tccggctggc tggtttattg ctgataaatc tggagccggt gagcgtgggt   4260
ctcgcggtat cattgcagca ctggggccag atggtaagcc ctcccgtatc gtagttatct   4320
acacgacggg gagtcaggca actatggatg aacgaaatag acagatcgct gagataggtg   4380
cctcactgat taagcattgg taactgtcag accaagttta ctcatatata ctttagattg   4440
atttaaaact tcatttttaa tttaaaagga tctaggtgaa gatccttttt gataatctca   4500
tgaccaaaat cccttaacgt gagttttcgt tccactgagc gtcagacccc gtagaaaaga   4560
tcaaaggatc ttcttgagat cctttttttc tgcgcgtaat ctgctgcttg caaacaaaaa   4620
aaccaccgct accagcggtg gtttgtttgc cggatcaaga gctaccaact ctttttccga   4680
aggtaactgg cttcagcaga gcgcagatac caaatactgt ccttctagtg tagccgtagt   4740
taggccacca cttcaagaac tctgtagcac cgcctacata cctcgctctg ctaatcctgt   4800
taccagtggc tgctgccagt ggcgataagt cgtgtcttac cgggttggac tcaagacgat   4860
agttaccgga taaggcgcag cggtcgggct gaacgggggg ttcgtgcaca cagcccagct   4920
tggagcgaac gacctacacc gaactgagat acctacagcg tgagctatga gaaagcgcca   4980
cgcttcccga agggagaaag gcggacaggt atccggtaag cggcagggtc ggaacaggag   5040
agcgcacgag ggagcttcca gggggaaacg cctggtatct ttatagtcct gtcgggtttc   5100
gccacctctg acttgagcgt cgatttttgt gatgctcgtc aggggggcgg agcctatgga   5160
aaaacgccag caacgcggcc tttttacggt tcctggcctt ttgctggcct tttgctcaca   5220
```

tgt 5223

<210> SEQ ID NO 61
<211> LENGTH: 5439
<212> TYPE: DNA
<213> ORGANISM: Artificial Sequence
<220> FEATURE:
<223> OTHER INFORMATION: CN2029-rAAV-3xhI56i(core)-minBG-hSCN1A_Fragment4-WPRE3-BGHpA

<400> SEQUENCE: 61
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtggtac cctaaataaa gatggctttt 180
tagtattaaa agtggaagaa aattacaggt aattatcttt gacggtaaaa acgctgtaat 240
cagcgggcta catgaaaaat tactctaatt atggctgcat ttaagagaat ggctaaataa 300
agatggcttt ttagtattaa aagtggaaga aaattacagg taattatctt tgacggtaaa 360
aacgctgtaa tcagcgggct acatgaaaaa ttactctaat tatggctgca tttaagagaa 420
tggctaaata aagatggctt tttagtatta aaagtggaag aaaattacag gtaattatct 480
ttgacggtaa aaacgctgta atcagcgggc tacatgaaaa attactctaa ttatggctgc 540
atttaagaga atggagctcg ggctgggcat aaaagtcagg gcagagccat ctattgctta 600
catttgcttc tgggatccag atctttcgaa gctagcgcta ccaccatgac agaagaacag 660
aagaaatact ataatgcaat gaaaaaatta ggatcgaaaa aaccgcaaaa gcctatacct 720
cgaccaggaa acaaatttca aggaatggtc tttgacttcg taaccagaca agtttttgac 780
ataagcatca tgattctcat ctgtcttaac atggtcacaa tgatggtgga aacagatgac 840
cagagtgaat atgtgactac cattttgtca cgcatcaatc tggtgttcat tgtgctattt 900
actggagagt gtgtactgaa actcatctct ctacgccatt attattttac cattggatgg 960
aatatttttg attttgtggt tgtcattctc tccattgtag gtatgtttct tgccgagctg 1020
atagaaaagt atttcgtgtc ccctaccctg ttccgagtga tccgtcttgc taggattggc 1080
cgaatcctac gtctgatcaa aggagcaaag gggatccgca cgctgctctt tgctttgatg 1140
atgtcccttc ctgcgttgtt taacatcggc ctcctactct tcctagtcat gttcatctac 1200
gccatctttg ggatgtccaa ctttgcctat gttaagaggg aagttgggat cgatgacatg 1260
ttcaactttg agacctttgg caacagcatg atctgcctat tccaaattac aacctctgct 1320
ggctgggatg gattgctagc acccattctc aacagtaagc cacccgactg tgaccctaat 1380
aaagttaacc ctggaagctc agttaaggga gactgtggga acccatctgt tggaattttc 1440
ttttttgtca gttacatcat catatccttc ctggttgtgg tgaacatgta catcgcggtc 1500
atcctggaga acttcagtgt tgctactgaa gaaagtgcag agcctctgag tgaggatgac 1560
tttgagatgt tctatgaggt ttgggagaag tttgatcccg atgcaactca gttcatggaa 1620
tttgaaaaat tatctcagtt tgcagctgcg cttgaaccgc ctctcaatct gccacaacca 1680
aacaaactcc agctcattgc catggatttg cccatggtga gtggtgaccg gatccactgt 1740
cttgatatct tatttgcttt tacaaagcgg gttctaggag agagtggaga gatggatgct 1800
ctacgaatac agatggaaga gcgattcatg gcttccaatc cttccaaggt ctcctatcag 1860
ccaatcacta ctactttaaa acgaaaacaa gaggaagtat ctgctgtcat tattcagcgt 1920
gcttacagac gccacctttt aaagcgaact gtaaaacaag cttcctttac gtacaataaa 1980

```
aacaaaatca aaggtggggc taatcttctt ataaaagaag acatgataat tgacagaata   2040
aatgaaaact ctattacaga aaaaactgat ctgaccatgt ccactgcagc ttgtccacct   2100
tcctatgacc gggtgacaaa gccaattgtg gaaaaacatg agcaagaagg caaagatgaa   2160
aaagccaaag ggaaataatg acggcgcgcc gcggccgcga attcgatatc ataatcaacc   2220
tctggattac aaaatttgtg aaagattgac tggtattctt aactatgttg ctccttttac   2280
gctatgtgga tacgctgctt taatgccttt gtatcatgct attgcttccc gtatggcttt   2340
cattttctcc tccttgtata aatcctggtt agttcttgcc acggcggaac tcatcgccgc   2400
ctgccttgcc cgctgctgga caggggctcg gctgttgggc actgacaatt ccgtggctcg   2460
agagatcttc gactgtgcct tctagttgcc agccatctgt tgtttgcccc tcccccgtgc   2520
cttccttgac cctggaaggt gccactccca ctgtcctttc ctaataaaat gaggaaattg   2580
catcgcattg tctgagtagg tgtcattcta ttctgggggg tggggtgggg caggacagca   2640
agggggagga ttgggaagac aatagcaggc atgagatctc acgtgcggac cgagcggccg   2700
caggaacccc tagtgatgga gttggccact ccctctctgc gcgctcgctc gctcactgag   2760
gccgggcgac caaaggtcgc ccgacgcccg ggctttgccc gggcggcctc agtgagcgag   2820
cgagcgcgca gctgcctgca ggggcgcctg atgcggtatt ttctccttac gcatctgtgc   2880
ggtatttcac accgcatacg tcaaagcaac catagtacgc gccctgtagc ggcgcattaa   2940
gcgcggcggg tgtggtggtt acgcgcagcg tgaccgctac acttgccagc gccctagcgc   3000
ccgctccttt cgctttcttc ccttcctttc tcgccacgtt cgccggcttt ccccgtcaag   3060
ctctaaatcg ggggctccct ttagggttcc gatttagtgc tttacggcac ctcgacccca   3120
aaaaacttga tttgggtgat ggttcacgta gtgggccatc gccctgatag acggtttttc   3180
gccctttgac gttggagtcc acgttcttta atagtggact cttgttccaa actggaacaa   3240
cactcaaccc tatctcgggc tattcttttg atttataagg gattttgccg atttcggcct   3300
attggttaaa aaatgagctg atttaacaaa aatttaacgc gaattttaac aaaatattaa   3360
cgtttacaat tttatggtgc actctcagta caatctgctc tgatgccgca tagttaagcc   3420
agccccgaca cccgccaaca cccgctgacg cgccctgacg ggcttgtctg ctcccggcat   3480
ccgcttacag acaagctgtg accgtctccg ggagctgcat gtgtcagagg ttttcaccgt   3540
catcaccgaa acgcgcgaga cgaaagggcc tcgtgatacg cctattttta taggttaatg   3600
tcatgataat aatggtttct tagacgtcag gtggcacttt tcggggaaat gtgcgcggaa   3660
cccctatttg tttatttttc taaatacatt caaatatgta tccgctcatg agacaataac   3720
cctgataaat gcttcaataa tattgaaaaa ggaagagtat gagtattcaa catttccgtg   3780
tcgcccttat tccctttttt gcggcatttt gccttcctgt ttttgctcac ccagaaacgc   3840
tggtgaaagt aaaagatgct gaagatcagt tgggtgcacg agtgggttac atcgaactgg   3900
atctcaacag cggtaagatc cttgagagtt ttcgccccga agaacgtttt ccaatgatga   3960
gcacttttaa agttctgcta tgtggcgcgg tattatcccg tattgacgcc gggcaagagc   4020
aactcggtcg ccgcatacac tattctcaga atgacttggt tgagtactca ccagtcacag   4080
aaaagcatct tacggatggc atgacagtaa gagaattatg cagtgctgcc ataaccatga   4140
gtgataacac tgcggccaac ttacttctga caacgatcgg aggaccgaag gagctaaccg   4200
ctttttttgca caacatgggg gatcatgtaa ctcgccttga tcgttgggaa ccggagctga   4260
atgaagccat accaaacgac gagcgtgaca ccacgatgcc tgtagcaatg gcaacaacgt   4320
```

-continued

```
tgcgcaaact attaactggc gaactactta ctctagcttc ccggcaacaa ttaatagact   4380

ggatggaggc ggataaagtt gcaggaccac ttctgcgctc ggcccttccg gctggctggt   4440

ttattgctga taaatctgga gccggtgagc gtgggtctcg cggtatcatt gcagcactgg   4500

ggccagatgg taagccctcc cgtatcgtag ttatctacac gacggggagt caggcaacta   4560

tggatgaacg aaatagacag atcgctgaga taggtgcctc actgattaag cattggtaac   4620

tgtcagacca agtttactca tatatacttt agattgattt aaaacttcat ttttaattta   4680

aaaggatcta ggtgaagatc ctttttgata atctcatgac caaaatccct taacgtgagt   4740

tttcgttcca ctgagcgtca gaccccgtag aaaagatcaa aggatcttct tgagatcctt   4800

tttttctgcg cgtaatctgc tgcttgcaaa caaaaaaacc accgctacca gcggtggttt   4860

gtttgccgga tcaagagcta ccaactcttt ttccgaaggt aactggcttc agcagagcgc   4920

agataccaaa tactgtcctt ctagtgtagc cgtagttagg ccaccacttc aagaactctg   4980

tagcaccgcc tacatacctc gctctgctaa tcctgttacc agtggctgct gccagtggcg   5040

ataagtcgtg tcttaccggg ttggactcaa gacgatagtt accggataag gcgcagcggt   5100

cgggctgaac ggggggttcg tgcacacagc ccagcttgga gcgaacgacc tacaccgaac   5160

tgagatacct acagcgtgag ctatgagaaa gcgccacgct tcccgaaggg agaaaggcgg   5220

acaggtatcc ggtaagcggc agggtcggaa caggagagcg cacgagggag cttccagggg   5280

gaaacgcctg gtatctttat agtcctgtcg ggtttcgcca cctctgactt gagcgtcgat   5340

ttttgtgatg ctcgtcaggg gggcggagcc tatggaaaaa cgccagcaac gcggcctttt   5400

tacggttcct ggccttttgc tggccttttg ctcacatgt                          5439
```

<210> SEQ ID NO 62
<211> LENGTH: 630
<212> TYPE: PRT
<213> ORGANISM: Artificial Sequence
<220> FEATURE:
<223> OTHER INFORMATION: hSCN1A_Fragment1_Protein Sequence

<400> SEQUENCE: 62

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
```

```
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590
```

```
Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg
625                 630


<210> SEQ ID NO 63
<211> LENGTH: 431
<212> TYPE: PRT
<213> ORGANISM: Artificial Sequence
<220> FEATURE:
<223> OTHER INFORMATION: hSCN1A_Fragment2_Protein Sequence

<400> SEQUENCE: 63

Met Leu Ala Val Phe Pro Ala Asn Gly Lys Met His Ser Thr Val Asp
1               5                   10                  15

Cys Asn Gly Val Val Ser Leu Val Gly Gly Pro Ser Val Pro Thr Ser
            20                  25                  30

Pro Val Gly Gln Leu Leu Pro Glu Val Ile Ile Asp Lys Pro Ala Thr
        35                  40                  45

Asp Asp Asn Gly Thr Thr Thr Glu Thr Glu Met Arg Lys Arg Arg Ser
    50                  55                  60

Ser Ser Phe His Val Ser Met Asp Phe Leu Glu Asp Pro Ser Gln Arg
65                  70                  75                  80

Gln Arg Ala Met Ser Ile Ala Ser Ile Leu Thr Asn Thr Val Glu Glu
                85                  90                  95

Leu Glu Glu Ser Arg Gln Lys Cys Pro Pro Cys Trp Tyr Lys Phe Ser
            100                 105                 110

Asn Ile Phe Leu Ile Trp Asp Cys Ser Pro Tyr Trp Leu Lys Val Lys
        115                 120                 125

His Val Val Asn Leu Val Val Met Asp Pro Phe Val Asp Leu Ala Ile
    130                 135                 140

Thr Ile Cys Ile Val Leu Asn Thr Leu Phe Met Ala Met Glu His Tyr
145                 150                 155                 160

Pro Met Thr Asp His Phe Asn Asn Val Leu Thr Val Gly Asn Leu Val
                165                 170                 175

Phe Thr Gly Ile Phe Thr Ala Glu Met Phe Leu Lys Ile Ile Ala Met
            180                 185                 190

Asp Pro Tyr Tyr Tyr Phe Gln Glu Gly Trp Asn Ile Phe Asp Gly Phe
        195                 200                 205

Ile Val Thr Leu Ser Leu Val Glu Leu Gly Leu Ala Asn Val Glu Gly
    210                 215                 220

Leu Ser Val Leu Arg Ser Phe Arg Leu Leu Arg Val Phe Lys Leu Ala
225                 230                 235                 240

Lys Ser Trp Pro Thr Leu Asn Met Leu Ile Lys Ile Ile Gly Asn Ser
                245                 250                 255

Val Gly Ala Leu Gly Asn Leu Thr Leu Val Leu Ala Ile Ile Val Phe
            260                 265                 270

Ile Phe Ala Val Val Gly Met Gln Leu Phe Gly Lys Ser Tyr Lys Asp
        275                 280                 285

Cys Val Cys Lys Ile Ala Ser Asp Cys Gln Leu Pro Arg Trp His Met
    290                 295                 300

Asn Asp Phe Phe His Ser Phe Leu Ile Val Phe Arg Val Leu Cys Gly
305                 310                 315                 320
```

```
Glu Trp Ile Glu Thr Met Trp Asp Cys Met Glu Val Ala Gly Gln Ala
                325                 330                 335

Met Cys Leu Thr Val Phe Met Met Val Met Val Ile Gly Asn Leu Val
            340                 345                 350

Val Leu Asn Leu Phe Leu Ala Leu Leu Leu Ser Ser Phe Ser Ala Asp
        355                 360                 365

Asn Leu Ala Ala Thr Asp Asp Asp Asn Glu Met Asn Asn Leu Gln Ile
    370                 375                 380

Ala Val Asp Arg Met His Lys Gly Val Ala Tyr Val Lys Arg Lys Ile
385                 390                 395                 400

Tyr Glu Phe Ile Gln Gln Ser Phe Ile Arg Lys Gln Lys Ile Leu Asp
                405                 410                 415

Glu Ile Lys Pro Leu Asp Asp Leu Asn Asn Lys Lys Asp Ser Cys
            420                 425                 430
```

<210> SEQ ID NO 64
<211> LENGTH: 438
<212> TYPE: PRT
<213> ORGANISM: Artificial Sequence
<220> FEATURE:
<223> OTHER INFORMATION: hSCN1A_Fragment3_Protein Sequence

<400> SEQUENCE: 64

```
Met Ser Asn His Thr Thr Glu Ile Gly Lys Asp Leu Asp Tyr Leu Lys
1               5                   10                  15

Asp Val Asn Gly Thr Thr Ser Gly Ile Gly Thr Gly Ser Ser Val Glu
            20                  25                  30

Lys Tyr Ile Ile Asp Glu Ser Asp Tyr Met Ser Phe Ile Asn Asn Pro
        35                  40                  45

Ser Leu Thr Val Thr Val Pro Ile Ala Val Gly Glu Ser Asp Phe Glu
    50                  55                  60

Asn Leu Asn Thr Glu Asp Phe Ser Ser Glu Ser Asp Leu Glu Glu Ser
65                  70                  75                  80

Lys Glu Lys Leu Asn Glu Ser Ser Ser Ser Ser Glu Gly Ser Thr Val
                85                  90                  95

Asp Ile Gly Ala Pro Val Glu Glu Gln Pro Val Val Glu Pro Glu Glu
            100                 105                 110

Thr Leu Glu Pro Glu Ala Cys Phe Thr Glu Gly Cys Val Gln Arg Phe
        115                 120                 125

Lys Cys Cys Gln Ile Asn Val Glu Glu Gly Arg Gly Lys Gln Trp Trp
    130                 135                 140

Asn Leu Arg Arg Thr Cys Phe Arg Ile Val Glu His Asn Trp Phe Glu
145                 150                 155                 160

Thr Phe Ile Val Phe Met Ile Leu Leu Ser Ser Gly Ala Leu Ala Phe
                165                 170                 175

Glu Asp Ile Tyr Ile Asp Gln Arg Lys Thr Ile Lys Thr Met Leu Glu
            180                 185                 190

Tyr Ala Asp Lys Val Phe Thr Tyr Ile Phe Ile Leu Glu Met Leu Leu
        195                 200                 205

Lys Trp Val Ala Tyr Gly Tyr Gln Thr Tyr Phe Thr Asn Ala Trp Cys
    210                 215                 220

Trp Leu Asp Phe Leu Ile Val Asp Val Ser Leu Val Ser Leu Thr Ala
225                 230                 235                 240

Asn Ala Leu Gly Tyr Ser Glu Leu Gly Ala Ile Lys Ser Leu Arg Thr
                245                 250                 255
```

```
Leu Arg Ala Leu Arg Pro Leu Arg Ala Leu Ser Arg Phe Glu Gly Met
            260                 265                 270

Arg Val Val Val Asn Ala Leu Leu Gly Ala Ile Pro Ser Ile Met Asn
        275                 280                 285

Val Leu Leu Val Cys Leu Ile Phe Trp Leu Ile Phe Ser Ile Met Gly
    290                 295                 300

Val Asn Leu Phe Ala Gly Lys Phe Tyr His Cys Ile Asn Thr Thr Thr
305                 310                 315                 320

Gly Asp Arg Phe Asp Ile Glu Asp Val Asn Asn His Thr Asp Cys Leu
                325                 330                 335

Lys Leu Ile Glu Arg Asn Glu Thr Ala Arg Trp Lys Asn Val Lys Val
            340                 345                 350

Asn Phe Asp Asn Val Gly Phe Gly Tyr Leu Ser Leu Leu Gln Val Ala
        355                 360                 365

Thr Phe Lys Gly Trp Met Asp Ile Met Tyr Ala Ala Val Asp Ser Arg
    370                 375                 380

Asn Val Glu Leu Gln Pro Lys Tyr Glu Glu Ser Leu Tyr Met Tyr Leu
385                 390                 395                 400

Tyr Phe Val Ile Phe Ile Ile Phe Gly Ser Phe Phe Thr Leu Asn Leu
                405                 410                 415

Phe Ile Gly Val Ile Ile Asp Asn Phe Asn Gln Gln Lys Lys Lys Phe
            420                 425                 430

Gly Gly Gln Asp Ile Phe
        435
```

<210> SEQ ID NO 65
<211> LENGTH: 510
<212> TYPE: PRT
<213> ORGANISM: Artificial Sequence
<220> FEATURE:
<223> OTHER INFORMATION: hSCN1A_Fragment4_Protein Sequence

<400> SEQUENCE: 65

```
Met Thr Glu Glu Gln Lys Lys Tyr Tyr Asn Ala Met Lys Lys Leu Gly
1               5                   10                  15

Ser Lys Lys Pro Gln Lys Pro Ile Pro Arg Pro Gly Asn Lys Phe Gln
            20                  25                  30

Gly Met Val Phe Asp Phe Val Thr Arg Gln Val Phe Asp Ile Ser Ile
        35                  40                  45

Met Ile Leu Ile Cys Leu Asn Met Val Thr Met Met Val Glu Thr Asp
    50                  55                  60

Asp Gln Ser Glu Tyr Val Thr Thr Ile Leu Ser Arg Ile Asn Leu Val
65                  70                  75                  80

Phe Ile Val Leu Phe Thr Gly Glu Cys Val Leu Lys Leu Ile Ser Leu
                85                  90                  95

Arg His Tyr Tyr Phe Thr Ile Gly Trp Asn Ile Phe Asp Phe Val Val
            100                 105                 110

Val Ile Leu Ser Ile Val Gly Met Phe Leu Ala Glu Leu Ile Glu Lys
        115                 120                 125

Tyr Phe Val Ser Pro Thr Leu Phe Arg Val Ile Arg Leu Ala Arg Ile
    130                 135                 140

Gly Arg Ile Leu Arg Leu Ile Lys Gly Ala Lys Gly Ile Arg Thr Leu
145                 150                 155                 160

Leu Phe Ala Leu Met Met Ser Leu Pro Ala Leu Phe Asn Ile Gly Leu
                165                 170                 175
```

```
Leu Leu Phe Leu Val Met Phe Ile Tyr Ala Ile Phe Gly Met Ser Asn
            180                 185                 190

Phe Ala Tyr Val Lys Arg Glu Val Gly Ile Asp Asp Met Phe Asn Phe
        195                 200                 205

Glu Thr Phe Gly Asn Ser Met Ile Cys Leu Phe Gln Ile Thr Thr Ser
    210                 215                 220

Ala Gly Trp Asp Gly Leu Leu Ala Pro Ile Leu Asn Ser Lys Pro Pro
225                 230                 235                 240

Asp Cys Asp Pro Asn Lys Val Asn Pro Gly Ser Ser Val Lys Gly Asp
                245                 250                 255

Cys Gly Asn Pro Ser Val Gly Ile Phe Phe Phe Val Ser Tyr Ile Ile
            260                 265                 270

Ile Ser Phe Leu Val Val Val Asn Met Tyr Ile Ala Val Ile Leu Glu
        275                 280                 285

Asn Phe Ser Val Ala Thr Glu Glu Ser Ala Glu Pro Leu Ser Glu Asp
    290                 295                 300

Asp Phe Glu Met Phe Tyr Glu Val Trp Glu Lys Phe Asp Pro Asp Ala
305                 310                 315                 320

Thr Gln Phe Met Glu Phe Glu Lys Leu Ser Gln Phe Ala Ala Ala Leu
                325                 330                 335

Glu Pro Pro Leu Asn Leu Pro Gln Pro Asn Lys Leu Gln Leu Ile Ala
            340                 345                 350

Met Asp Leu Pro Met Val Ser Gly Asp Arg Ile His Cys Leu Asp Ile
        355                 360                 365

Leu Phe Ala Phe Thr Lys Arg Val Leu Gly Glu Ser Gly Glu Met Asp
    370                 375                 380

Ala Leu Arg Ile Gln Met Glu Glu Arg Phe Met Ala Ser Asn Pro Ser
385                 390                 395                 400

Lys Val Ser Tyr Gln Pro Ile Thr Thr Thr Leu Lys Arg Lys Gln Glu
                405                 410                 415

Glu Val Ser Ala Val Ile Ile Gln Arg Ala Tyr Arg Arg His Leu Leu
            420                 425                 430

Lys Arg Thr Val Lys Gln Ala Ser Phe Thr Tyr Asn Lys Asn Lys Ile
        435                 440                 445

Lys Gly Gly Ala Asn Leu Leu Ile Lys Glu Asp Met Ile Ile Asp Arg
    450                 455                 460

Ile Asn Glu Asn Ser Ile Thr Glu Lys Thr Asp Leu Thr Met Ser Thr
465                 470                 475                 480

Ala Ala Cys Pro Pro Ser Tyr Asp Arg Val Thr Lys Pro Ile Val Glu
                485                 490                 495

Lys His Glu Gln Glu Gly Lys Asp Glu Lys Ala Lys Gly Lys
            500                 505                 510
```

<210> SEQ ID NO 66
<211> LENGTH: 13
<212> TYPE: DNA
<213> ORGANISM: Artificial Sequence
<220> FEATURE:
<223> OTHER INFORMATION: synthetic oligonucleotide for upregulation of SCN1A expression

<400> SEQUENCE: 66
tcgactttga aaa 13

<210> SEQ ID NO 67

<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression

<400> SEQUENCE: 67
cctctccacg cgcagtacat t 21

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated base
<220> FEATURE:
<221> NAME/KEY: modified_base
<222> LOCATION: (1)..(20)
<223> OTHER INFORMATION: phosphorothioated bases

<400> SEQUENCE: 68
tcggtgtcca ctctggcagt 20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 69
tgcactgtgg gagcctgtct 20

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 70
gtagcactgt ggacatcggc 20

<210> SEQ ID NO 71
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 71
gtagaagaac agcccgtagt g 21

<210> SEQ ID NO 72
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 72
gtggtctctg cattctgtca 20

<210> SEQ ID NO 73
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 73
gtggtatagg aactggcagc a 21

<210> SEQ ID NO 74
<211> LENGTH: 19
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(18)
<223> OTHER INFORMATION: phosphorothioated bases

<400> SEQUENCE: 74
gtccaatcat acagcagaa 19

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 75
gtgactgtac caattgctgt 20

<210> SEQ ID NO 76
<211> LENGTH: 19
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(18)
<223> OTHER INFORMATION: phosphorothioated bases

<400> SEQUENCE: 76
acttcttcca ctccttcct 19

<210> SEQ ID NO 77
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 77
gatgtccctt cctgcgttgt 20

<210> SEQ ID NO 78
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 78
tgtggatgct gggtgtctct c 21

<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 79
tcccagtgac tcccgatgct 20

<210> SEQ ID NO 80
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 80
agtctcagtt gtcagtacct c 21

<210> SEQ ID NO 81
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 81
gttattgaat gccctggtgt 20

<210> SEQ ID NO 82
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 82
tcggatcatc agggttgtag t 21

<210> SEQ ID NO 83
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 83
gtggtatagg aactggcagc a 21

<210> SEQ ID NO 84
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 84
tctgctcttc cctacattgg 20

<210> SEQ ID NO 85
<211> LENGTH: 19
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(18)
<223> OTHER INFORMATION: phosphorothioated bases

<400> SEQUENCE: 85
gtaatctgct cttccctac 19

<210> SEQ ID NO 86
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 86
gggagaactt gagagcaaca g 21

<210> SEQ ID NO 87
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 87
gccagtcaca aattcagatc a 21

<210> SEQ ID NO 88
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 88
gtggcatagg gacgggcagc a 21

<210> SEQ ID NO 89
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 89
gtagcactgt ggacatcggc 20

<210> SEQ ID NO 90
<211> LENGTH: 21
<212> TYPE: DNA
<213> ORGANISM: Artificial Sequence
<220> FEATURE:

```
<223> OTHER INFORMATION: synthetic oligonucleotide for upregulation of
      SCN1A expression
<220> FEATURE:
<221> NAME/KEY: modified_base
<222> LOCATION: (1)..(20)
<223> OTHER INFORMATION: phosphorothioated bases

<400> SEQUENCE: 90

gtagaagaac agcccgtagt g                                              21


<210> SEQ ID NO 91
<211> LENGTH: 19
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(18)
<223> OTHER INFORMATION: phosphorothioated bases

<400> SEQUENCE: 91

gtccaatcat acagcagaa                                                 19


<210> SEQ ID NO 92
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(19)
<223> OTHER INFORMATION: phosphorothioated bases

<400> SEQUENCE: 92

gtgactgtac caattgctgt                                                20


<210> SEQ ID NO 93
<211> LENGTH: 19
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(18)
<223> OTHER INFORMATION: phosphorothioated bases

<400> SEQUENCE: 93

acttcttcca ctccttcct                                                 19


<210> SEQ ID NO 94
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(19)
<223> OTHER INFORMATION: phosphorothioated bases

<400> SEQUENCE: 94

gatgtccctt cctgcgttgt                                                20
```

<210> SEQ ID NO 95
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 95
tgtggatgct gggtgtctct c 21

<210> SEQ ID NO 96
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 96
tcccagtgac tcccgatgct 20

<210> SEQ ID NO 97
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 97
agtctcagtt gtcagtacct c 21

<210> SEQ ID NO 98
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 98
tcggatcatc agggttgtag t 21

<210> SEQ ID NO 99
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)

<223> OTHER INFORMATION: phosphorothioated bases

<400> SEQUENCE: 99
gtggtatagg aactggcagc a 21

<210> SEQ ID NO 100
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: phosphorothioated bases
<220> FEATURE:
<221> NAME/KEY: modified_base
<222> LOCATION: (6)..(6)
<223> OTHER INFORMATION: phosphorothioated base
<220> FEATURE:
<221> NAME/KEY: modified_base
<222> LOCATION: (11)..(11)
<223> OTHER INFORMATION: phosphorothioated base
<220> FEATURE:
<221> NAME/KEY: modified_base
<222> LOCATION: (15)..(15)
<223> OTHER INFORMATION: phosphorothioated base
<220> FEATURE:
<221> NAME/KEY: modified_base
<222> LOCATION: (20)..(20)
<223> OTHER INFORMATION: phosphorothioated base

<400> SEQUENCE: 100
gtggacagga tgcacaaagg a 21

<210> SEQ ID NO 101
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(19)
<223> OTHER INFORMATION: phosphorothioated bases

<400> SEQUENCE: 101
tggtatagga actggcagca 20

<210> SEQ ID NO 102
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(20)
<223> OTHER INFORMATION: phosphorothioated bases

<400> SEQUENCE: 102
gtggcatagg gacgggcagc a 21

<210> SEQ ID NO 103
<211> LENGTH: 19
<212> TYPE: DNA
<213> ORGANISM: Artificial Sequence
<220> FEATURE:

<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: phosphorothioated bases
<220> FEATURE:
<221> NAME/KEY: modified_base
<222> LOCATION: (16)..(18)
<223> OTHER INFORMATION: phosphorothioated bases

<400> SEQUENCE: 103
gtgactgtgc ccattgctg 19

<210> SEQ ID NO 104
<211> LENGTH: 19
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: phosphorothioated bases
<220> FEATURE:
<221> NAME/KEY: modified_base
<222> LOCATION: (7)..(7)
<223> OTHER INFORMATION: phosphorothioated bases
<220> FEATURE:
<221> NAME/KEY: modified_base
<222> LOCATION: (13)..(13)
<223> OTHER INFORMATION: phosphorothioated bases
<220> FEATURE:
<221> NAME/KEY: modified_base
<222> LOCATION: (16)..(18)
<223> OTHER INFORMATION: phosphorothioated bases

<400> SEQUENCE: 104
gccacttgat gatctaaac 19

<210> SEQ ID NO 105
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: phosphorothioated bases
<220> FEATURE:
<221> NAME/KEY: modified_base
<222> LOCATION: (6)..(6)
<223> OTHER INFORMATION: phosphorothioated bases
<220> FEATURE:
<221> NAME/KEY: modified_base
<222> LOCATION: (11)..(11)
<223> OTHER INFORMATION: phosphorothioated bases
<220> FEATURE:
<221> NAME/KEY: modified_base
<222> LOCATION: (15)..(15)
<223> OTHER INFORMATION: phosphorothioated bases
<220> FEATURE:
<221> NAME/KEY: modified_base
<222> LOCATION: (20)..(20)
<223> OTHER INFORMATION: phosphorothioated bases

<400> SEQUENCE: 105
gtggacagga tgcacaaagg a 21

<210> SEQ ID NO 106

```
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(19)
<223> OTHER INFORMATION: phosphorothioated bases

<400> SEQUENCE: 106

tggtatagga actggcagca                                                20


<210> SEQ ID NO 107
<211> LENGTH: 15
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: locked nucleic acid; phosphorothioated base
<220> FEATURE:
<221> NAME/KEY: modified_base
<222> LOCATION: (2)..(2)
<223> OTHER INFORMATION: locked nucleic acid; phosphorothioated base
<220> FEATURE:
<221> NAME/KEY: modified_base
<222> LOCATION: (3)..(12)
<223> OTHER INFORMATION: phosphorothioated bases
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 107

ccacgcgcga gtaca                                                     15


<210> SEQ ID NO 108
<211> LENGTH: 15
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: locked nucleic acid; phosphorothioated base
<220> FEATURE:
<221> NAME/KEY: modified_base
<222> LOCATION: (2)..(2)
<223> OTHER INFORMATION: locked nucleic acid; phosphorothioated base
<220> FEATURE:
<221> NAME/KEY: modified_base
<222> LOCATION: (3)..(12)
<223> OTHER INFORMATION: phosphorothioated bases
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 108
```

gtataggaac tggca 15

<210> SEQ ID NO 109
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(6)
<223> OTHER INFORMATION: phosphorothioated bases
<220> FEATURE:
<221> NAME/KEY: modified_base
<222> LOCATION: (7)..(7)
<223> OTHER INFORMATION: locked nucleic acid; phosphorothioated base
<220> FEATURE:
<221> NAME/KEY: modified_base
<222> LOCATION: (8)..(12)
<223> OTHER INFORMATION: phosphorothioated bases
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 109
gtggtatagg aactg 15

<210> SEQ ID NO 110
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 110
agaacttgag agcaa 15

<210> SEQ ID NO 111
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)

<223> OTHER INFORMATION: locked nucleic acid; phosphorothioated base
<220> FEATURE:
<221> NAME/KEY: modified_base
<222> LOCATION: (3)..(5)
<223> OTHER INFORMATION: phosphorothioated base
<220> FEATURE:
<221> NAME/KEY: modified_base
<222> LOCATION: (6)..(6)
<223> OTHER INFORMATION: locked nucleic acid; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: locked nucleic acid; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 111
gccagtcaca aattc 15

<210> SEQ ID NO 112
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 112
cacaaattca gatca 15

<210> SEQ ID NO 113
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (7)..(7)
<223> OTHER INFORMATION: locked nucleic acid; phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 113
gtggtatagg aactg 15

<210> SEQ ID NO 114
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 114
gtataggaac tggca 15

<210> SEQ ID NO 115
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(6)
<223> OTHER INFORMATION: phosphorothioated base
<220> FEATURE:
<221> NAME/KEY: modified_base
<222> LOCATION: (7)..(7)
<223> OTHER INFORMATION: locked nucleic acid; phosphorothioated base
<220> FEATURE:
<221> NAME/KEY: modified_base
<222> LOCATION: (8)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 115
gtggtatagg aactg 15

<210> SEQ ID NO 116
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(8)
<223> OTHER INFORMATION: phosphorothioated base
<220> FEATURE:
<221> NAME/KEY: modified_base
<222> LOCATION: (9)..(9)
<223> OTHER INFORMATION: locked nucleic acid; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 116
gccagtcaca aattc 15

<210> SEQ ID NO 117
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 117
cacaaattca gatca 15

<210> SEQ ID NO 118
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:

<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (12)..(13)
<223> OTHER INFORMATION: 2'OXethylxodification; phosphorothioated base
<220> FEATURE:
<221> NAME/KEY: modified_base
<222> LOCATION: (14)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 118
gccagucaca aautc 15

<210> SEQ ID NO 119
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)
<223> OTHER INFORMATION: locked nucleic acid; phosphorothioated base
<220> FEATURE:
<221> NAME/KEY: modified_base
<222> LOCATION: (2)..(5)
<223> OTHER INFORMATION: phosphorothioated base
<220> FEATURE:
<221> NAME/KEY: modified_base
<222> LOCATION: (6)..(6)
<223> OTHER INFORMATION: locked nucleic acid; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: locked nucleic acid; phosphorothioated base
<220> FEATURE:
<221> NAME/KEY: modified_base
<222> LOCATION: (10)..(13)
<223> OTHER INFORMATION: phosphorothioated base
<220> FEATURE:
<221> NAME/KEY: modified_base
<222> LOCATION: (14)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 119
gccagtcaca aattc 15

<210> SEQ ID NO 120
<211> LENGTH: 13
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(3)
<223> OTHER INFORMATION: 2'OXethylxodification; phosphorothioated base
<220> FEATURE:
<221> NAME/KEY: modified_base
<222> LOCATION: (4)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(10)
<223> OTHER INFORMATION: phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
<221> NAME/KEY: modified_base
<222> LOCATION: (12)..(12)
<223> OTHER INFORMATION: locked nucleic acid; phosphorothioated base
<220> FEATURE:
<221> NAME/KEY: modified_base
<222> LOCATION: (13)..(13)
<223> OTHER INFORMATION: locked nucleic acid

<400> SEQUENCE: 120
gccagucaca aat 13

<210> SEQ ID NO 121
<211> LENGTH: 13
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(10)
<223> OTHER INFORMATION: phosphorothioated base
<220> FEATURE:
<221> NAME/KEY: modified_base
<222> LOCATION: (11)..(12)
<223> OTHER INFORMATION: locked nucleic acid; phosphorothioated base
<220> FEATURE:
<221> NAME/KEY: modified_base
<222> LOCATION: (13)..(13)
<223> OTHER INFORMATION: locked nucleic acid

<400> SEQUENCE: 121
gccagtcaca aat 13

<210> SEQ ID NO 122
<211> LENGTH: 11
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)

<223> OTHER INFORMATION: locked nucleic acid; phosphorothioated base
<220> FEATURE:
<221> NAME/KEY: modified_base
<222> LOCATION: (2)..(8)
<223> OTHER INFORMATION: phosphorothioated base
<220> FEATURE:
<221> NAME/KEY: modified_base
<222> LOCATION: (9)..(10)
<223> OTHER INFORMATION: locked nucleic acid; phosphorothioated base
<220> FEATURE:
<221> NAME/KEY: modified_base
<222> LOCATION: (11)..(11)
<223> OTHER INFORMATION: locked nucleic acid

<400> SEQUENCE: 122
gccagtcaca a 11

<210> SEQ ID NO 123
<211> LENGTH: 12
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(9)
<223> OTHER INFORMATION: phosphorothioated base
<220> FEATURE:
<221> NAME/KEY: modified_base
<222> LOCATION: (10)..(11)
<223> OTHER INFORMATION: locked nucleic acid; phosphorothioated base
<220> FEATURE:
<221> NAME/KEY: modified_base
<222> LOCATION: (12)..(12)
<223> OTHER INFORMATION: locked nucleic acid

<400> SEQUENCE: 123
gccagtcaca aa 12

<210> SEQ ID NO 124
<211> LENGTH: 12
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(9)
<223> OTHER INFORMATION: phosphorothioated base
<220> FEATURE:
<221> NAME/KEY: modified_base
<222> LOCATION: (10)..(11)
<223> OTHER INFORMATION: locked nucleic acid; phosphorothioated base
<220> FEATURE:
<221> NAME/KEY: modified_base
<222> LOCATION: (12)..(12)
<223> OTHER INFORMATION: locked nucleic acid

<400> SEQUENCE: 124
attgagccag tc 12

<210> SEQ ID NO 125
<211> LENGTH: 15

<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: locked nucleic acid; phosphorothioated base
<220> FEATURE:
<221> NAME/KEY: modified_base
<222> LOCATION: (3)..(6)
<223> OTHER INFORMATION: phosphorothioated base
<220> FEATURE:
<221> NAME/KEY: modified_base
<222> LOCATION: (7)..(7)
<223> OTHER INFORMATION: locked nucleic acid; phosphorothioated base
<220> FEATURE:
<221> NAME/KEY: modified_base
<222> LOCATION: (8)..(12)
<223> OTHER INFORMATION: phosphorothioated base
<220> FEATURE:
<221> NAME/KEY: modified_base
<222> LOCATION: (13)..(14)
<223> OTHER INFORMATION: locked nucleic acid; phosphorothioated base
<220> FEATURE:
<221> NAME/KEY: modified_base
<222> LOCATION: (15)..(15)
<223> OTHER INFORMATION: locked nucleic acid

<400> SEQUENCE: 125
gtggtatagg aactg 15

<210> SEQ ID NO 126
<211> LENGTH: 17
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:

<221> NAME/KEY: modified_base
<222> LOCATION: (17)..(17)
<223> OTHER INFORMATION: 2'OXethylxodification

<400> SEQUENCE: 126
gccagucaca aautcag 17

<210> SEQ ID NO 127
<211> LENGTH: 15
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(14)
<223> OTHER INFORMATION: 2'OXethylxodification; phosphorothioated base
<220> FEATURE:
<221> NAME/KEY: modified_base
<222> LOCATION: (15)..(15)
<223> OTHER INFORMATION: 2'OXethylxodification

<400> SEQUENCE: 127
gccagucaca aauuc 15

<210> SEQ ID NO 128
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: phosphorothioated base
<220> FEATURE:
<221> NAME/KEY: modified_base

```
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(16)
<223> OTHER INFORMATION: phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (18)..(18)
<223> OTHER INFORMATION: phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 128

gugguauagg aactggcagc a                                            21


<210> SEQ ID NO 129
<211> LENGTH: 21
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(7)
<223> OTHER INFORMATION: phosphorothioated base
<220> FEATURE:
<221> NAME/KEY: modified_base
<222> LOCATION: (8)..(8)
<223> OTHER INFORMATION: 2'OXethylxodification; phosphorothioated base
<220> FEATURE:
<221> NAME/KEY: modified_base
<222> LOCATION: (9)..(9)
<223> OTHER INFORMATION: phosphorothioated base
<220> FEATURE:
<221> NAME/KEY: modified_base
<222> LOCATION: (10)..(10)
<223> OTHER INFORMATION: 2'OXethylxodification; phosphorothioated base
<220> FEATURE:
<221> NAME/KEY: modified_base
<222> LOCATION: (11)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (17)..(18)
<223> OTHER INFORMATION: phosphorothioated base
<220> FEATURE:
<221> NAME/KEY: modified_base
<222> LOCATION: (19)..(20)
<223> OTHER INFORMATION: 2'OXethylxodification; phosphorothioated base
```

<220> FEATURE:
<221> NAME/KEY: modified_base
<222> LOCATION: (21)..(21)
<223> OTHER INFORMATION: 2'OXethylxodification

<400> SEQUENCE: 129
gggagaactu gagagcaaca g 21

<210> SEQ ID NO 130
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(18)
<223> OTHER INFORMATION: phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 130
gccagtcaca aautcagauc a 21

<210> SEQ ID NO 131
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:

<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 131
gugguauagg aactggcagc a 21

<210> SEQ ID NO 132
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(17)
<223> OTHER INFORMATION: phosphorothioated base
<220> FEATURE:
<221> NAME/KEY: modified_base
<222> LOCATION: (18)..(18)
<223> OTHER INFORMATION: 2'OXethylxodification; phosphorothioated base
<220> FEATURE:
<221> NAME/KEY: modified_base
<222> LOCATION: (19)..(20)

<223> OTHER INFORMATION: phosphorothioated base
<220> FEATURE:
<221> NAME/KEY: modified_base
<222> LOCATION: (21)..(21)
<223> OTHER INFORMATION: 2'OXethylxodification; phosphorothioated base
<220> FEATURE:
<221> NAME/KEY: modified_base
<222> LOCATION: (22)..(22)
<223> OTHER INFORMATION: phosphorothioated base
<220> FEATURE:
<221> NAME/KEY: modified_base
<222> LOCATION: (23)..(24)
<223> OTHER INFORMATION: 2'OXethylxodification; phosphorothioated base
<220> FEATURE:
<221> NAME/KEY: modified_base
<222> LOCATION: (25)..(25)
<223> OTHER INFORMATION: 2'OXethylxodification

<400> SEQUENCE: 132
gguauaggaa cuggcagcag uguug 25

<210> SEQ ID NO 133
<211> LENGTH: 22
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (17)..(19)
<223> OTHER INFORMATION: phosphorothioated base
<220> FEATURE:
<221> NAME/KEY: modified_base
<222> LOCATION: (20)..(21)
<223> OTHER INFORMATION: 2'OXethylxodification; phosphorothioated base
<220> FEATURE:
<221> NAME/KEY: modified_base
<222> LOCATION: (22)..(22)
<223> OTHER INFORMATION: 2'OXethylxodification

<400> SEQUENCE: 133
uggtauagga actggcagca gu 22

<210> SEQ ID NO 134
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (2)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(10)
<223> OTHER INFORMATION: phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
<221> NAME/KEY: modified_base
<222> LOCATION: (12)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(17)
<223> OTHER INFORMATION: phosphorothioated base
<220> FEATURE:
<221> NAME/KEY: modified_base
<222> LOCATION: (18)..(18)
<223> OTHER INFORMATION: 2'OXethylxodification; phosphorothioated base
<220> FEATURE:
<221> NAME/KEY: modified_base
<222> LOCATION: (19)..(24)
<223> OTHER INFORMATION: phosphorothioated base
<220> FEATURE:
<221> NAME/KEY: modified_base
<222> LOCATION: (25)..(25)
<223> OTHER INFORMATION: 2'OXethylxodification

<400> SEQUENCE: 134
ggtauaggaa ctggcagcag tgttg 25

<210> SEQ ID NO 135
<211> LENGTH: 24
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(3)
<223> OTHER INFORMATION: phosphorothioated base
<220> FEATURE:
<221> NAME/KEY: modified_base

```
<222> LOCATION: (4)..(4)
<223> OTHER INFORMATION: 2'OXethylxodification; phosphorothioated base
<220> FEATURE:
<221> NAME/KEY: modified_base
<222> LOCATION: (5)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(18)
<223> OTHER INFORMATION: phosphorothioated base
<220> FEATURE:
<221> NAME/KEY: modified_base
<222> LOCATION: (19)..(19)
<223> OTHER INFORMATION: 2'OXethylxodification; phosphorothioated base
<220> FEATURE:
<221> NAME/KEY: modified_base
<222> LOCATION: (20)..(21)
<223> OTHER INFORMATION: phosphorothioated base
<220> FEATURE:
<221> NAME/KEY: modified_base
<222> LOCATION: (22)..(22)
<223> OTHER INFORMATION: 2'OXethylxodification; phosphorothioated base
<220> FEATURE:
<221> NAME/KEY: modified_base
<222> LOCATION: (23)..(23)
<223> OTHER INFORMATION: phosphorothioated base
<220> FEATURE:
<221> NAME/KEY: modified_base
<222> LOCATION: (24)..(24)
<223> OTHER INFORMATION: 2'OXethylxodification

<400> SEQUENCE: 135

aagcggtata ggaactggca gcag                                           24


<210> SEQ ID NO 136
<211> LENGTH: 26
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(7)
<223> OTHER INFORMATION: phosphorothioated base
<220> FEATURE:
<221> NAME/KEY: modified_base
<222> LOCATION: (8)..(8)
<223> OTHER INFORMATION: 2'OXethylxodification; phosphorothioated base
<220> FEATURE:
<221> NAME/KEY: modified_base
<222> LOCATION: (9)..(10)
<223> OTHER INFORMATION: phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
<221> NAME/KEY: modified_base
<222> LOCATION: (12)..(14)
<223> OTHER INFORMATION: phosphorothioated base
```

<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(19)
<223> OTHER INFORMATION: phosphorothioated base
<220> FEATURE:
<221> NAME/KEY: modified_base
<222> LOCATION: (20)..(20)
<223> OTHER INFORMATION: 2'OXethylxodification; phosphorothioated base
<220> FEATURE:
<221> NAME/KEY: modified_base
<222> LOCATION: (21)..(23)
<223> OTHER INFORMATION: phosphorothioated base
<220> FEATURE:
<221> NAME/KEY: modified_base
<222> LOCATION: (24)..(25)
<223> OTHER INFORMATION: 2'OXethylxodification; phosphorothioated base
<220> FEATURE:
<221> NAME/KEY: modified_base
<222> LOCATION: (26)..(26)
<223> OTHER INFORMATION: 2'OXethylxodification

<400> SEQUENCE: 136
gagccaguca caaautcaga tcaccc 26

<210> SEQ ID NO 137
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (2)..(2)
<223> OTHER INFORMATION: phosphorothioated base
<220> FEATURE:
<221> NAME/KEY: modified_base
<222> LOCATION: (3)..(3)
<223> OTHER INFORMATION: 2'OXethylxodification; phosphorothioated base
<220> FEATURE:
<221> NAME/KEY: modified_base
<222> LOCATION: (4)..(10)
<223> OTHER INFORMATION: phosphorothioated base
<220> FEATURE:
<221> NAME/KEY: modified_base
<222> LOCATION: (11)..(13)
<223> OTHER INFORMATION: 2'OXethylxodification; phosphorothioated base
<220> FEATURE:
<221> NAME/KEY: modified_base
<222> LOCATION: (14)..(18)
<223> OTHER INFORMATION: phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 137
aaugggagaa cuugagagca a 21

<210> SEQ ID NO 138
<211> LENGTH: 19
<212> TYPE: DNA
<213> ORGANISM: Artificial Sequence

```
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (19)..(19)
<223> OTHER INFORMATION: 2'OXethylxodification

<400> SEQUENCE: 138

gtgacugtgc ccattgctg                                                19


<210> SEQ ID NO 139
<211> LENGTH: 26
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification; phosphorothioated base
<220> FEATURE:
<221> NAME/KEY: modified_base
<222> LOCATION: (26)..(26)
<223> OTHER INFORMATION: 2'OXethylxodification

<400> SEQUENCE: 139

gacaaccttg cagccactga ugatga                                        26


<210> SEQ ID NO 140
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(3)
<223> OTHER INFORMATION: phosphorothioated base
<220> FEATURE:
<221> NAME/KEY: modified_base
```

<222> LOCATION: (4)..(4)
<223> OTHER INFORMATION: 2'OXethylxodification; phosphorothioated base
<220> FEATURE:
<221> NAME/KEY: modified_base
<222> LOCATION: (5)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: phosphorothioated base
<220> FEATURE:
<221> NAME/KEY: modified_base
<222> LOCATION: (18)..(19)
<223> OTHER INFORMATION: 2'OXethylxodification; phosphorothioated base
<220> FEATURE:
<221> NAME/KEY: modified_base
<222> LOCATION: (20)..(20)
<223> OTHER INFORMATION: 2'OXethylxodification

<400> SEQUENCE: 140
ugguauagga actggcagca 20

<210> SEQ ID NO 141
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(13)
<223> OTHER INFORMATION: phosphorothioated base
<220> FEATURE:
<221> NAME/KEY: modified_base
<222> LOCATION: (14)..(14)
<223> OTHER INFORMATION: 2'OXethylxodification; phosphorothioated base

```
<220> FEATURE:
<221> NAME/KEY: modified_base
<222> LOCATION: (15)..(17)
<223> OTHER INFORMATION: phosphorothioated base
<220> FEATURE:
<221> NAME/KEY: modified_base
<222> LOCATION: (18)..(19)
<223> OTHER INFORMATION: 2'OXethylxodification; phosphorothioated base
<220> FEATURE:
<221> NAME/KEY: modified_base
<222> LOCATION: (20)..(20)
<223> OTHER INFORMATION: 2'OXethylxodification

<400> SEQUENCE: 141

ccagtcacaa autcagauca                                           20


<210> SEQ ID NO 142
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (4)..(4)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (18)..(19)
<223> OTHER INFORMATION: 2'OXethylxodification; phosphorothioated base
<220> FEATURE:
<221> NAME/KEY: modified_base
<222> LOCATION: (20)..(20)
<223> OTHER INFORMATION: 2'OXethylxodification

<400> SEQUENCE: 142

ugguauagga actggcagca                                           20


<210> SEQ ID NO 143
<211> LENGTH: 25
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
```

<221> NAME/KEY: modified_base
<222> LOCATION: (8)..(9)
<223> OTHER INFORMATION: phosphorothioated base
<220> FEATURE:
<221> NAME/KEY: modified_base
<222> LOCATION: (10)..(10)
<223> OTHER INFORMATION: 2'OXethylxodification; phosphorothioated base
<220> FEATURE:
<221> NAME/KEY: modified_base
<222> LOCATION: (11)..(13)
<223> OTHER INFORMATION: phosphorothioated base
<220> FEATURE:
<221> NAME/KEY: modified_base
<222> LOCATION: (14)..(14)
<223> OTHER INFORMATION: 2'OXethylxodification; phosphorothioated base
<220> FEATURE:
<221> NAME/KEY: modified_base
<222> LOCATION: (15)..(18)
<223> OTHER INFORMATION: phosphorothioated base
<220> FEATURE:
<221> NAME/KEY: modified_base
<222> LOCATION: (19)..(19)
<223> OTHER INFORMATION: 2'OXethylxodification; phosphorothioated base
<220> FEATURE:
<221> NAME/KEY: modified_base
<222> LOCATION: (20)..(22)
<223> OTHER INFORMATION: phosphorothioated base
<220> FEATURE:
<221> NAME/KEY: modified_base
<222> LOCATION: (23)..(24)
<223> OTHER INFORMATION: 2'OXethylxodification; phosphorothioated base
<220> FEATURE:
<221> NAME/KEY: modified_base
<222> LOCATION: (25)..(25)
<223> OTHER INFORMATION: 2'OXethylxodification

<400> SEQUENCE: 143
agccagucac aaautcagat caccc 25

<210> SEQ ID NO 144
<211> LENGTH: 17
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (2)..(2)
<223> OTHER INFORMATION: phosphorothioated base
<220> FEATURE:
<221> NAME/KEY: modified_base
<222> LOCATION: (3)..(3)
<223> OTHER INFORMATION: 2'OXethylxodification; phosphorothioated base
<220> FEATURE:
<221> NAME/KEY: modified_base
<222> LOCATION: (4)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(14)

<223> OTHER INFORMATION: phosphorothioated base
<220> FEATURE:
<221> NAME/KEY: modified_base
<222> LOCATION: (15)..(16)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: 2'OXethylxodification

<400> SEQUENCE: 144
uauaggaact ggcagca 17

<210> SEQ ID NO 145
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 145
gugguauagg aactggcagc a 21

<210> SEQ ID NO 146
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(8)
<223> OTHER INFORMATION: phosphorothioated base

```
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(17)
<223> OTHER INFORMATION: phosphorothioated base
<220> FEATURE:
<221> NAME/KEY: modified_base
<222> LOCATION: (18)..(18)
<223> OTHER INFORMATION: 2'OXethylxodification; phosphorothioated base
<220> FEATURE:
<221> NAME/KEY: modified_base
<222> LOCATION: (19)..(20)
<223> OTHER INFORMATION: phosphorothioated base
<220> FEATURE:
<221> NAME/KEY: modified_base
<222> LOCATION: (21)..(21)
<223> OTHER INFORMATION: 2'OXethylxodification; phosphorothioated base
<220> FEATURE:
<221> NAME/KEY: modified_base
<222> LOCATION: (22)..(22)
<223> OTHER INFORMATION: phosphorothioated base
<220> FEATURE:
<221> NAME/KEY: modified_base
<222> LOCATION: (23)..(24)
<223> OTHER INFORMATION: 2'OXethylxodification; phosphorothioated base
<220> FEATURE:
<221> NAME/KEY: modified_base
<222> LOCATION: (25)..(25)
<223> OTHER INFORMATION: 2'OXethylxodification

<400> SEQUENCE: 146

gguauaggaa cuggcagcag uguug                                        25


<210> SEQ ID NO 147
<211> LENGTH: 22
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
```

<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (17)..(19)
<223> OTHER INFORMATION: phosphorothioated base
<220> FEATURE:
<221> NAME/KEY: modified_base
<222> LOCATION: (20)..(21)
<223> OTHER INFORMATION: 2'OXethylxodification; phosphorothioated base
<220> FEATURE:
<221> NAME/KEY: modified_base
<222> LOCATION: (22)..(22)
<223> OTHER INFORMATION: 2'OXethylxodification

<400> SEQUENCE: 147
uggtauagga actggcagca gu 22

<210> SEQ ID NO 148
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (2)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(10)
<223> OTHER INFORMATION: phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
<221> NAME/KEY: modified_base
<222> LOCATION: (12)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(17)
<223> OTHER INFORMATION: phosphorothioated base
<220> FEATURE:
<221> NAME/KEY: modified_base
<222> LOCATION: (18)..(18)
<223> OTHER INFORMATION: 2'OXethylxodification; phosphorothioated base
<220> FEATURE:
<221> NAME/KEY: modified_base
<222> LOCATION: (19)..(24)
<223> OTHER INFORMATION: phosphorothioated base
<220> FEATURE:
<221> NAME/KEY: modified_base
<222> LOCATION: (25)..(25)
<223> OTHER INFORMATION: 2'OXethylxodification

<400> SEQUENCE: 148
ggtauaggaa ctggcagcag tgttg 25

<210> SEQ ID NO 149
<211> LENGTH: 24
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(3)
<223> OTHER INFORMATION: phosphorothioated base
<220> FEATURE:
<221> NAME/KEY: modified_base
<222> LOCATION: (4)..(4)
<223> OTHER INFORMATION: 2'OXethylxodification; phosphorothioated base
<220> FEATURE:
<221> NAME/KEY: modified_base
<222> LOCATION: (5)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(18)
<223> OTHER INFORMATION: phosphorothioated base
<220> FEATURE:
<221> NAME/KEY: modified_base
<222> LOCATION: (19)..(19)
<223> OTHER INFORMATION: 2'OXethylxodification; phosphorothioated base
<220> FEATURE:
<221> NAME/KEY: modified_base
<222> LOCATION: (20)..(21)
<223> OTHER INFORMATION: phosphorothioated base
<220> FEATURE:
<221> NAME/KEY: modified_base
<222> LOCATION: (22)..(22)
<223> OTHER INFORMATION: 2'OXethylxodification; phosphorothioated base
<220> FEATURE:
<221> NAME/KEY: modified_base
<222> LOCATION: (23)..(23)
<223> OTHER INFORMATION: phosphorothioated base
<220> FEATURE:
<221> NAME/KEY: modified_base
<222> LOCATION: (24)..(24)
<223> OTHER INFORMATION: 2'OXethylxodification

<400> SEQUENCE: 149
aagcgguata ggaactggca gcag 24

<210> SEQ ID NO 150
<211> LENGTH: 21
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(3)
<223> OTHER INFORMATION: 2'OXethylxodification; phosphorothioated base
<220> FEATURE:
<221> NAME/KEY: modified_base
<222> LOCATION: (4)..(4)
<223> OTHER INFORMATION: phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(9)
<223> OTHER INFORMATION: phosphorothioated base
<220> FEATURE:
<221> NAME/KEY: modified_base
<222> LOCATION: (10)..(10)
<223> OTHER INFORMATION: 2'OXethylxodification; phosphorothioated base
<220> FEATURE:
<221> NAME/KEY: modified_base
<222> LOCATION: (11)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(16)
<223> OTHER INFORMATION: phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (18)..(18)
<223> OTHER INFORMATION: phosphorothioated base
<220> FEATURE:
<221> NAME/KEY: modified_base
<222> LOCATION: (19)..(20)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification

<400> SEQUENCE: 150
guggcauagg gacgggcagc a 21

<210> SEQ ID NO 151
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(6)

<223> OTHER INFORMATION: 2'OXethylxodification; phosphorothioated base
<220> FEATURE:
<221> NAME/KEY: modified_base
<222> LOCATION: (7)..(19)
<223> OTHER INFORMATION: phosphorothioated base
<220> FEATURE:
<221> NAME/KEY: modified_base
<222> LOCATION: (20)..(24)
<223> OTHER INFORMATION: 2'OXethylxodification; phosphorothioated base
<220> FEATURE:
<221> NAME/KEY: modified_base
<222> LOCATION: (25)..(25)
<223> OTHER INFORMATION: 2'OXethylxodification

<400> SEQUENCE: 151
acaaguggca tagggacggg cagca 25

<210> SEQ ID NO 152
<211> LENGTH: 25
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(12)
<223> OTHER INFORMATION: phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (14)..(16)
<223> OTHER INFORMATION: phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (18)..(20)
<223> OTHER INFORMATION: phosphorothioated base
<220> FEATURE:
<221> NAME/KEY: modified_base
<222> LOCATION: (21)..(21)
<223> OTHER INFORMATION: 2'OXethylxodification; phosphorothioated base
<220> FEATURE:
<221> NAME/KEY: modified_base
<222> LOCATION: (22)..(23)
<223> OTHER INFORMATION: phosphorothioated base
<220> FEATURE:
<221> NAME/KEY: modified_base
<222> LOCATION: (24)..(24)
<223> OTHER INFORMATION: 2'OXethylxodification; phosphorothioated base
<220> FEATURE:

```
<221> NAME/KEY: modified_base
<222> LOCATION: (25)..(25)
<223> OTHER INFORMATION: 2'OXethylxodification

<400> SEQUENCE: 152

acaaguggca tagggacggg cagca                                          25


<210> SEQ ID NO 153
<211> LENGTH: 25
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (2)..(3)
<223> OTHER INFORMATION: phosphorothioated base
<220> FEATURE:
<221> NAME/KEY: modified_base
<222> LOCATION: (4)..(4)
<223> OTHER INFORMATION: 2'OXethylxodification; phosphorothioated base
<220> FEATURE:
<221> NAME/KEY: modified_base
<222> LOCATION: (5)..(6)
<223> OTHER INFORMATION: phosphorothioated base
<220> FEATURE:
<221> NAME/KEY: modified_base
<222> LOCATION: (7)..(7)
<223> OTHER INFORMATION: 2'OXethylxodification; phosphorothioated base
<220> FEATURE:
<221> NAME/KEY: modified_base
<222> LOCATION: (8)..(8)
<223> OTHER INFORMATION: phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (10)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(14)
<223> OTHER INFORMATION: phosphorothioated base
<220> FEATURE:
<221> NAME/KEY: modified_base
<222> LOCATION: (15)..(15)
<223> OTHER INFORMATION: 2'OXethylxodification; phosphorothioated base
<220> FEATURE:
<221> NAME/KEY: modified_base
<222> LOCATION: (16)..(18)
<223> OTHER INFORMATION: phosphorothioated base
<220> FEATURE:
<221> NAME/KEY: modified_base
<222> LOCATION: (19)..(19)
<223> OTHER INFORMATION: 2'OXethylxodification; phosphorothioated base
<220> FEATURE:
<221> NAME/KEY: modified_base
<222> LOCATION: (20)..(21)
<223> OTHER INFORMATION: phosphorothioated base
<220> FEATURE:
<221> NAME/KEY: modified_base
<222> LOCATION: (22)..(22)
<223> OTHER INFORMATION: 2'OXethylxodification; phosphorothioated base
<220> FEATURE:
<221> NAME/KEY: modified_base
<222> LOCATION: (23)..(24)
```

<223> OTHER INFORMATION: phosphorothioated base
<220> FEATURE:
<221> NAME/KEY: modified_base
<222> LOCATION: (25)..(25)
<223> OTHER INFORMATION: 2'OXethylxodification

<400> SEQUENCE: 153
aaguggcaua gggacgggca gcagu 25

<210> SEQ ID NO 154
<211> LENGTH: 20
<212> TYPE: DNA
<213> ORGANISM: Artificial Sequence
<220> FEATURE:
<223> OTHER INFORMATION: synthetic oligonucleotide for upregulation of SCN1A expression
<220> FEATURE:
<221> NAME/KEY: modified_base
<222> LOCATION: (1)..(2)
<223> OTHER INFORMATION: 2'OXethylxodification; phosphorothioated base
<220> FEATURE:
<221> NAME/KEY: modified_base
<222> LOCATION: (3)..(3)
<223> OTHER INFORMATION: phosphorothioated base
<220> FEATURE:
<221> NAME/KEY: modified_base
<222> LOCATION: (4)..(4)
<223> OTHER INFORMATION: 2'OXethylxodification; phosphorothioated base
<220> FEATURE:
<221> NAME/KEY: modified_base
<222> LOCATION: (5)..(5)
<223> OTHER INFORMATION: phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (7)..(11)
<223> OTHER INFORMATION: phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (13)..(15)
<223> OTHER INFORMATION: phosphorothioated base
<220> FEATURE:
<221> NAME/KEY: modified_base
<222> LOCATION: (16)..(16)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: phosphorothioated base
<220> FEATURE:
<221> NAME/KEY: modified_base
<222> LOCATION: (18)..(19)
<223> OTHER INFORMATION: 2'OXethylxodification; phosphorothioated base
<220> FEATURE:
<221> NAME/KEY: modified_base
<222> LOCATION: (20)..(20)
<223> OTHER INFORMATION: 2'OXethylxodification

<400> SEQUENCE: 154
ugguauagga actggcagca 20

<210> SEQ ID NO 155
<211> LENGTH: 24
<212> TYPE: DNA
<213> ORGANISM: Artificial Sequence
<220> FEATURE:
<223> OTHER INFORMATION: synthetic oligonucleotide for upregulation of SCN1A expression

```
<220> FEATURE:
<221> NAME/KEY: modified_base
<222> LOCATION: (1)..(6)
<223> OTHER INFORMATION: 2'OXethylxodification; phosphorothioated base
<220> FEATURE:
<221> NAME/KEY: modified_base
<222> LOCATION: (7)..(18)
<223> OTHER INFORMATION: phosphorothioated base
<220> FEATURE:
<221> NAME/KEY: modified_base
<222> LOCATION: (19)..(23)
<223> OTHER INFORMATION: 2'OXethylxodification; phosphorothioated base
<220> FEATURE:
<221> NAME/KEY: modified_base
<222> LOCATION: (24)..(24)
<223> OTHER INFORMATION: 2'OXethylxodification

<400> SEQUENCE: 155

ccuaucttc cccccctac cuuu                                          24


<210> SEQ ID NO 156
<211> LENGTH: 25
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(5)
<223> OTHER INFORMATION: 2'OXethylxodification; phosphorothioated base
<220> FEATURE:
<221> NAME/KEY: modified_base
<222> LOCATION: (6)..(20)
<223> OTHER INFORMATION: phosphorothioated base
<220> FEATURE:
<221> NAME/KEY: modified_base
<222> LOCATION: (21)..(24)
<223> OTHER INFORMATION: 2'OXethylxodification; phosphorothioated base
<220> FEATURE:
<221> NAME/KEY: modified_base
<222> LOCATION: (25)..(25)
<223> OTHER INFORMATION: 2'OXethylxodification

<400> SEQUENCE: 156

aaguggcata gggacgggca gcagu                                       25


<210> SEQ ID NO 157
<211> LENGTH: 19
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (12)..(12)
<223> OTHER INFORMATION: 2'OXethylxodification; phosphorothioated base
<220> FEATURE:
<221> NAME/KEY: modified_base
<222> LOCATION: (19)..(19)
<223> OTHER INFORMATION: 2'OXethylxodification

<400> SEQUENCE: 157

gtgacugtgc ccattgctg                                              19
```

```
<210> SEQ ID NO 158
<211> LENGTH: 19
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (19)..(19)
<223> OTHER INFORMATION: 2'OXethylxodification

<400> SEQUENCE: 158

gtgactgtgc ccattgctg                                                19


<210> SEQ ID NO 159
<211> LENGTH: 20
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (5)..(5)
<223> OTHER INFORMATION: 2'OXethylxodification; phosphorothioated base
<220> FEATURE:
<221> NAME/KEY: modified_base
<222> LOCATION: (9)..(9)
<223> OTHER INFORMATION: 2'OXethylxodification; phosphorothioated base
<220> FEATURE:
<221> NAME/KEY: modified_base
<222> LOCATION: (13)..(13)
<223> OTHER INFORMATION: 2'OXethylxodification; phosphorothioated base
<220> FEATURE:
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (20)..(20)
<223> OTHER INFORMATION: 2'OXethylxodification

<400> SEQUENCE: 159

cctcuttcug gccttgcttc                                               20


<210> SEQ ID NO 160
<211> LENGTH: 26
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: modified_base
<222> LOCATION: (1)..(1)
<223> OTHER INFORMATION: 2'OXethylxodification; phosphorothioated base
<220> FEATURE:
<221> NAME/KEY: modified_base
<222> LOCATION: (6)..(6)
<223> OTHER INFORMATION: 2'OXethylxodification; phosphorothioated base
<220> FEATURE:
<221> NAME/KEY: modified_base
<222> LOCATION: (11)..(11)
<223> OTHER INFORMATION: 2'OXethylxodification; phosphorothioated base
<220> FEATURE:
```

```
<221> NAME/KEY: modified_base
<222> LOCATION: (17)..(17)
<223> OTHER INFORMATION: 2'OXethylxodification; phosphorothioated base
<220> FEATURE:
<221> NAME/KEY: modified_base
<222> LOCATION: (21)..(21)
<223> OTHER INFORMATION: 2'OXethylxodification; phosphorothioated base
<220> FEATURE:
<221> NAME/KEY: modified_base
<222> LOCATION: (26)..(26)
<223> OTHER INFORMATION: 2'OXethylxodification

<400> SEQUENCE: 160

gacaaccttg cagccactga ugatga                                          26


<210> SEQ ID NO 161
<211> LENGTH: 52
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: misc_feature
<222> LOCATION: (51)..(51)
<223> OTHER INFORMATION: deoxyribonucleotide

<400> SEQUENCE: 161

auuuaaacac ggaagacuuu aguagugcua cuaaagucuu ccguguuuaa at             52


<210> SEQ ID NO 162
<211> LENGTH: 52
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: misc_feature
<222> LOCATION: (51)..(51)
<223> OTHER INFORMATION: deoxyribonucleotide
<220> FEATURE:
<221> NAME/KEY: misc_feature
<222> LOCATION: (52)..(52)
<223> OTHER INFORMATION: deoxyribonucleotide

<400> SEQUENCE: 162

ucacaaauuc agaucaccca ucuucuagaa gaugggugau cugaauuugu ga             52


<210> SEQ ID NO 163
<211> LENGTH: 52
<212> TYPE: DNA
<213> ORGANISM: Artificial Sequence
<220> FEATURE:
<223> OTHER INFORMATION: synthetic oligonucleotide for upregulation of
      SCN1A expression
<220> FEATURE:
<221> NAME/KEY: misc_feature
<222> LOCATION: (51)..(51)
<223> OTHER INFORMATION: deoxyribonucleotide

<400> SEQUENCE: 163

auuuaaacac ggaagacuuu aguagugcua cuaaagucuu ccguguuuaa at             52
```